(12) United States Patent
Tasker et al.

(10) Patent No.: US 7,759,337 B2
(45) Date of Patent: Jul. 20, 2010

(54) PHTHALAZINE COMPOUNDS AND METHODS OF USE

(75) Inventors: Andrew Tasker, Simi Valley, CA (US); Dawei Zhang, Thousand Oaks, CA (US); Guo-Qiang Cao, Thousand Oaks, CA (US); Partha Pratim Chakrabarti, Newbury Park, CA (US); James Richard Falsey, Moorpark, CA (US); Bradley J. Herberich, Newbury Park, CA (US); Randall W. Hungate, Camarillo, CA (US); Liping H. Pettus, Thousand Oaks, CA (US); Anthony Reed, Oxnard, CA (US); Robert M. Rzasa, Ventura, CA (US); Kelvin K. C. Sham, Thousand Oaks, CA (US); Maya C. Thaman, Ventura, CA (US); Shimin Xu, Santa Barbara, CA (US)

(73) Assignee: Amgen Inc., Thousand Oaks, CA (US)

( * ) Notice: Subject to any disclaimer, the term of this patent is extended or adjusted under 35 U.S.C. 154(b) by 971 days.

(21) Appl. No.: 11/367,123

(22) Filed: Mar. 2, 2006

(65) Prior Publication Data

US 2006/0199817 A1 Sep. 7, 2006

Related U.S. Application Data

(60) Provisional application No. 60/659,003, filed on Mar. 3, 2005.

(51) Int. Cl.
C07D 237/34 (2006.01)
C07D 413/12 (2006.01)
C07D 498/08 (2006.01)
C07D 279/12 (2006.01)
C07D 243/08 (2006.01)
A61K 31/498 (2006.01)
A61K 31/5355 (2006.01)
A61K 31/537 (2006.01)
A61K 31/541 (2006.01)
A61K 31/551 (2006.01)
A61P 29/00 (2006.01)
A61P 23/00 (2006.01)
C07D 487/04 (2006.01)
A61K 31/4985 (2006.01)

(52) U.S. Cl. ............... 514/218; 514/234.5; 514/230.5; 514/228.2; 514/248; 540/492; 544/237; 544/119; 544/105; 544/58.2; 544/236

(58) Field of Classification Search ............. 514/234.5, 514/242, 241, 248, 230.5, 228.2, 218; 544/116, 544/182, 180, 237, 119, 105, 582; 540/492

See application file for complete search history.

(56) References Cited

U.S. PATENT DOCUMENTS 4,223,142 A 9/1980 Denzel et al.
5,849,741 A 12/1998 Watanabe et al.
6,288,064 B1 9/2001 Watanabe et al.
6,589,951 B1 * 7/2003 Napoletano et al. ......... 514/248
6,635,644 B2 10/2003 Salituro et al.
6,794,380 B2 9/2004 Brown
2003/0073692 A1 4/2003 Pulici et al.
2004/0018458 A1 1/2004 Nakagawa
2004/0138264 A1 7/2004 Baroni et al.
2004/0176603 A1 9/2004 Priepke et al.

FOREIGN PATENT DOCUMENTS

| WO | WO 97/16442 | | 5/1997 |
|---|---|---|---|
| WO | WO 98/27066 | | 6/1998 |
| WO | WO 00/71129 | | 11/2000 |
| WO | EP 1 057 819 | | 12/2000 |
| WO | WO 02/09681 | | 2/2002 |
| WO | WO 03062209 | * | 1/2003 |
| WO | WO 03/062209 A2 | | 7/2003 |
| WO | WO 2004/010995 | | 2/2004 |
| WO | WO2004099177 | * | 5/2004 |
| WO | WO 2004/054582 | | 7/2004 |

(Continued)

OTHER PUBLICATIONS

Griesser, Chapter 8, The Importance of Solvates (pp. 211-230), in the text, Polymorphism: In the Pharmaceutical Industry, Hilfiker, 2006.*

(Continued)

*Primary Examiner*—James O Wilson
*Assistant Examiner*—Cecilia M Jaisle
(74) *Attorney, Agent, or Firm*—G. Prabhakar Reddy

(57) ABSTRACT

The present invention comprises a new class of compounds useful for the prophylaxis and treatment of protein kinase mediated diseases, including inflammation and related conditions. The compounds have a general Formula I

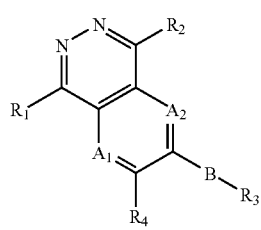

wherein B, $R^1$, $R^2$, $R^3$, $R^4$ and $R^5$ are d.efined herein. The invention also comprises pharmaceutical compositions including one or more compounds of Formula I, uses of such compounds and compositions for treatment of kinase mediated diseases including rheumatoid arthritis, psoriasis and other inflammation disorders, as well as intermediates and processes useful for the preparation of compounds of Formula I.

14 Claims, No Drawings

FOREIGN PATENT DOCUMENTS

| WO | WO 2004054582 | * | 7/2004 |
|----|---------------|---|--------|
| WO | WO 2004/099177 |  | 11/2004 |
| WO | WO 2005/009937 |  | 2/2005 |
| WO | WO 2006/015859 A1 | | 2/2006 |

OTHER PUBLICATIONS

Wikipedia, Derivative (chemistry), http://en.wikipedia.org/wiki/Derivative_(chemistry), downloaded Nov. 22, 2008.*

Oka, et al., Chem. & Pharm. Bull. (1975), 23(10), 2239-50.*

Patani, et al., Chem. Rev., 1996, 96, 3147-3176.*

Emery, et al., BMJ, vol. 324, Feb. 9, 2002, 312-313.*

Pomerantz, et al., J. Drugs in Dermatology, Apr. 2009, http://findarticles.com/p/articles/mi_m0PDG/is_4_8/ai_n31976552/, downloaded Oct. 13, 2009.*

Dayer, et al., N.E. J. Med., vol. 346: 1399-1400, May 2, 2002, #18.*

Baracos, et al., "Stimulation of Muscle Protein Degradation and Prostaglandin $E_2$ Release by Leukocytic Pyrogen (Interleukin-1)", N Eng J Med, 308, 553-558 (1983).

Beutler, et al., "Recombinant Interleukin 1 Suppresses Lipoprotein Lipase Activity in 3T3-L1 Cells", The Journal of Immunology, 135(6), 3969-3971 (1985).

Brahn, et al., "Effects of Tumor Necrosis Factor Alpha (TNF-α) on Collagen Arthritis", Lymphokine and Cytokine Res., 11(5), 253-256 (1992).

Chandrasekhar, et al. "Arthritis Induced by Interleukin-1 Is Dependent on the Site and Frequency of Intraarticular Injection" Clin. Immunol. Immunopathol., 55, 382-400 (1990).

Chapoulaud, et al., "Functionalization by Metalation of the Benzene Moiety of Benzodiazines. Determination of Structures by Long-Range $^1$H-$^{15}$N Correlation at Natural Abundance. Diazines XXV", Tetrahedron, 55, 5389-5404, (1999).

Clouse, et al., "Monokine Regulation of Human Immunodeficiency Virus-1 Expression in a Chronically Infected Human T Cell Clone", The Journal of Immunology, 142, 431-438 (1989).

Cooper, et al., "Acceleration of Onset of Collagen-Induced Arthritis by Intra-articular Injection of Tumour Necrosis Factor or Transforming Growth Factor-Beta", Clin Exp Immunol., 89, 244-250 (1992).

Dinarello, et al., "The Biological Properties of Interleukin-1", Eir. Cytokine Netw., 5, 517-531 (1994).

Firestein, et al., "Stromelysin and Tissue Inhibitor of Metalloproteinases Gene Expression in Rheumatoid Arthritis Synovium", Am J Pathol, 140 (6), 1309-1314 (1992).

Folks, et al., "Susceptibility of Normal Human Lymphocytes to Infection with HTLV-III/LAV", The Journal of Immunology, 136(11), 4049-4053 (1986).

Lähdevirta, et al., "Elevated Levels of Circulating Cachectin/Tumor Necrosis Factor in Patients with Acquired Immunodeficiency Syndrome", The American Journal of Medicine, 85, 289-291 (1988).

Liu, et al., "Cytokine-Induced Neutrophil Chemoattractant mRNA Expressed in Cerebral Ischemia", Neuroscience Letters, 164(1-2), 125-128 (1993).

Maini, et al., "Monoclonal Anti-TNFα Antibody as a Probe of Pathogenesis and Therapy of Rheumatoid Disease", Immunological Reviews, 144, 195-223 (1995).

Miyake, et al., "Syntheses of N-heterocyclic compounds. XXIII. Photochemical Reaction of Polyazanaphthalene Derivatives", Chemical and Pharmaceutical Bulletin, 23(7), 1500-1504, (1975).

Miyake, et al., "Syntheses of N-heterocyclic compounds. XXIV. Oxidation of dihydrotetraazanaphthalene Derivatives", Chemical and Pharmaceutical Bulletin, 23(7), 1505-1510, (1975).

Shohami, et al., "Closed Head Injury Triggers Early Production of TNFα and IL-6 by Brain Tissue", J Cereb Blood Flow Metab, 14: 615-619 (1994).

Yoshikazu, et al., "Syntheses of N-heterocyclic compounds. XXV. Syntheses of pyrido[3,4-d]pyridazine derivatives", Chemical and Pharmaceutical Bulletin, 23(10), 2239-2250, (1975).

* cited by examiner

PHTHALAZINE COMPOUNDS AND METHODS OF USE

This application claims the benefit of U.S. Provisional Application No. 60/659,003, filed Mar. 3, 2005, which is hereby incorporated by reference.

FIELD OF THE INVENTION

The invention relates generally to the field of pharmaceutical agents and, more specifically, to pharmaceutically active compounds, pharmaceutical compositions and methods of use thereof, to treat various disorders, including TNF-α, IL-1β, IL-6 and/or IL-8 mediated diseases and other maladies, such as inflammation and pain. The invention also relates to intermediates and processes useful in the preparation of such compounds.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. For example, protein tyrosine kinases (PTKs) are enzymes, which catalyze the phosphorylation of specific tyrosine residues in cellular proteins. Examples of kinases in the protein kinase family include, without limitation, ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, $FGFR^1$, $FGFR^2$, $FGFR^3$, $FGFR^4$, $FGFR^5$, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Due to their activity in numerous cellular processes, protein kinases have emerged as important therapeutic targets.

Protein kinases play a central role in the regulation and maintenance of a wide variety of cellular processes and cellular function. For example, kinase activity acts as molecular switches regulating inflammatory cytokine production via various pathways. Uncontrolled or excessive cytokine production has been observed in many disease states, and particularly in those related to inflammation.

The p38 protein kinase has been reported to be involved in the regulation of inflammatory cytokines. Interleukin-1 (IL-1) and Tumor Necrosis Factor α (TNF-α) are pro-inflammatory cytokines secreted by a variety of cells, including monocytes and macrophages, in response to many inflammatory stimuli (e.g., lipopolysaccharide—LPS) or external cellular stress (e.g., osmotic shock and peroxide).

Elevated levels of TNF-α over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type II diabetes; bone. resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

TNF-α has been reported to play a role in head trauma, stroke, and ischemia. For instance, in animal models of head trauma (rat), TNF-α levels increased in the contused hemisphere (Shohami et al., J. Cereb. Blood Flow Metab. 14:615 (1994)). In a rat model of ischemia wherein the middle cerebral artery was occluded, the levels of TNF-α mRNA of TNF-α increased (Feurstein et al., Neurosci. Lett. 164:125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, Stroke 25:1481 (1994)).

TNF-α appears to play a role in promoting certain viral life cycles and disease states associated therewith. For instance, TNF-α secreted by monocytes induced elevated levels of HIV expression in a chronically infected T cell clone (Clouse et al., J. Immunol. 142:431 (1989)). Lahdevirta et al., (Am. J. Med. 85:289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8. Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

Antagonism of TNF-α has been reported to be beneficial for treating uveitis (Reiff et al, A&R 44:141-145 (2001)); Sepsis (Abraham, Lancet, 351:929 (1998)); Systemic Lupus Erythrematosis (SLE) (Aringer, A&R, 50:3161 (2004)); Graft vs Host Disease (Couriel, Curr. Opinion Oncology, 12:582 (2000)); Polymyositis and Dermatomyositis (Labiache, Rheumatology, 43:531 (2004)); Type II diabetes (Ruan, Cytokine GF Review, 14:447 (2003)); Sjogren's disease (Marriette, A&R, 50:1270 (2004)), Sarcoidosis (Roberts, Chest, 124:2028 (2003)); Wegener's granulomatosis (WGET, New England J. Med., 352:351 (2005)) and post MI cardiac dysfunction (Sugano et al, Mol. Cell Bioch., 266:127 (2004)). In addition, TNF-α has been reported to play a role in SAPHO, periodic fever, relapsing polychrondritis, multicentric reticulohistiocytosis, macrophage activation syndrome, Hyper IgD syndrome, familial Hibernian fever, Pyoderma gangrenosum, Cochleovestibular disorders, Cicatrical pemphigoid, Herniated intervertebral disc diseases, amyloidosis, CINCA syndrome, myelodisplastic syndrome, alcoholic hepatitis, and endometriosis. Finally, indications which have already been approved for an agent which modulates TNF-α levels in the plasma, and/or other pro-inflammatory cytokines, include without limitation, inflammatory bowel disease (IBD), psoriatis arthritis, ankylosing spondylitis and juvenile RA.

TNF-α and IL-1 appear to play a role in pancreatic β cell destruction and diabetes. pancreatic β cells produce insulin which helps mediate blood glucose homeostasis. Deterioration of pancreatic β cells often accompanies type I diabetes. pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., Clinical Immunol Immunopathol., 55:382 (1990)). In studies using cultured rheumatoid synovial cells, IL-1 is a more potent inducer of stromelysin than is TNF-α (Firestein, Am. J. Pathol., 140: 1309 (1992)). At sites of local injection, neutrophil, lymphocyte, and monocyte emigration has been observed. The emigration is attributed to the induction of chemokines (e.g., L-8), and the up-regulation of adhesion molecules (Dinarello, Eur. Cytokine Netw., 5:517-531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., J. Immunol., 136:40 (1986)). Beutler et al. (J. Immunol., 135:3969 (1985)) discussed the role of IL-1 incachexia. Baracos et al. (New Eng. J. Med., 308:553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., Lymphokine Cytokine Res. 11:253 (1992); and Cooper, Clin. Exp. Immunol., 898:244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-a-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195-223 (1995)). These approaches block the effects of TNF-α and IL-1 by either protein sequestration or receptor antagonism.

Yet another approach to block the effect of TNF-α has been to modulate the activity of the p38 kinase enzyme. For example, the PCT publication, WO 04/010995, published on Feb. 05, 2004, describes fused heteroaryl derivatives for use as P38 kinase inhibitors in the treatment of I.A. rheumatoid arthritis; PCT publication, WO 2005/009937, published on Feb. 03, 2005, describes 5-membered heterocycle-based P38 kinase inhibitors; U.S. Pat. No. 6,635,644, issued Oct. 21, 2003, describes fused nitrogen-containing bicyclic ring systems as P38 inhibitors; and U.S. Pat. No. 6,794,380, issued Sep. 21, 2004, describes amide derivatives as P38 inhibitors.

BRIEF DESCRIPTION OF THE INVENTION

The present invention provides a new class of compounds useful in the prophylaxis and treatment of diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. Accordingly, the invention also comprises pharmaceutical compositions comprising the compounds, methods for the prophylaxis and treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds provided by the invention, including stereoisomers, tautomers, solvates, pharmaceutically acceptable salts, derivatives or prodrugs thereof, are defined by general Formula I

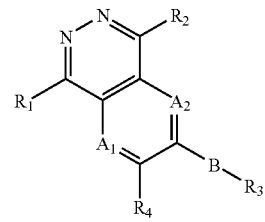

wherein $A^1$, $A^2$, B, $R^1$, $R^2$, $R^3$ and $R^4$ are as described below. The invention also provides procedures for making compounds of Formula I, and intermediates useful in such procedures.

The compounds provided by the invention are capable of modulating various kinase activity. For example, in one embodiment, the compounds are capable of modulating p38 kinase enzyme. To this end, the invention further provides for the use of these compounds for therapeutic, prophylactic, acute and/or chronic treatment of kinase mediated diseases, such as those described herein. For example, the compounds are useful for the prophylaxis and treatment of diseases or conditions involving inflammation.

The invention further provides the preparation of a medicament, containing one or more of the compounds, useful to attenuate, alleviate, or treat disorders through inhibition of such kinase enzymes. For example, and in one embodiment, the invention provides a pharmaceutical composition comprising an effective dosage amount of a compound of Formula I in association with a least one pharmaceutically acceptable carrier.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are defined by general Formula I:

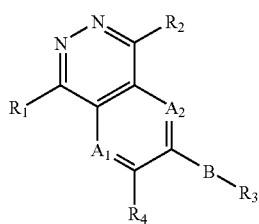

wherein
each of $A^1$ and $A^2$, independently, is $CR^5$ or N;
B is a direct bond, $-(CR^5R^6)_m-$, $-C(=O)-$, $-N(R^6)-$, $-O-$, or $-S(=O)_m-$, wherein m is 0, 1 or 2;
$R^1$ is $-CR^7R^7)_nX$ or $-(CR^7R^8)_nX$, wherein n is 0, 1 or 2 and X is $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)N^7R^7$, $C(O)NR^7R$, $C(S)NR^7R$, $NR^7$ $C(O)R^1$, $NR^7$ $C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2R^8$ or a 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^5$, $R^8$ or $R^9$;
$R^2$ is H, halo, haloalkyl, $NO_2$, CN, $OR^7$, $SR^7$, $NR^7R^8$, $C(O)R^7$, $COOR^7$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $OC(O)NR^7R^8$, $S(O)_2R^7$, $S(O)_2NR^7R^7$, $S(O)_2NR^7R^8$, $NR^7S(O)_2R^7$, $NR^7S(O)_2R^8$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;
$R^3$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said ring system is substituted independently with one or more substituents of $R^{10}$, $R^{11}$, $R^{16}$, $N^{10}NR^{10}$, $R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}$ $(COOR^{10})$, $NR^{10}(COOR^{11})$, $NR^{10}C(O)C(O)R^{10}$, $NR^{10}C(O)$ $C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;
$R^4$ is H, halo, haloalkyl, $NO_2$, CN, $NR^7R^7$, $NR^7R^8$, $OR^7$; $SR^7$, $C(O)R^7$, $OC(O)R^7$, $COOR^7$, $C(O)NRR^7$, $C(O)NR^7R^8$, $NR^7C(O)R^7$, $NR^7C(O)R^8$, $NR^8C(O)NR^7R^8$, $NR^7(COOR^7)$, $OC(O)NR^7R^8$, $S(O)_2R^7$, $S(O)_2NR^7R^8$, $NR^7S(O)_2NR^7R^8$, $NR^7S(O)_2R^7$, $NR^7S(O)_2R^7$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;
$R^5$ is H, halo, haloalkyl, $NO_2$, CN, $SR^7$, $OR^7$, $C(O)R^7$, $COOR^7$, $OC(O)R^7$, $NR^7R^7$, $NR^7R^8$, $C(O)NR^7R^7$, $C(O)NR^7R^8$, $NR^7C(O)R^7$, $NR^7C(O)R^8$, $NR^7C(O)NR^7R^8$, $S(O)NR^7R^8$, $S(O)_2NR^7R^8$, $NR^7S(O)NR^7R^8$, $NR^7S(O)_2NR^7R^8$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;
$R^6$ is H, CN or $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;
$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;
$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$; $SR^9$, $C(O)R^9$, $COOR^9$, $C(O)NR^9R^9$, $NR^9C((O)R^9$, $NR^9C(O)$ $NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;
alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of $R^9$;
$R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{41}$, $R^{15}$ or $R^{16}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{15}$;

$R^{14}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

provided that when B is a direct bond, $R^3$ is an optionally substituted phenyl or an optionally substituted 5- or 6-membered heteroaryl, and X is $NR^7R^8$ wherein $R^7$ is H or $C_{1-10}$-alkyl, then $R^8$ is not an optionally substituted phenyl or an optionally substituted 5- or 6-membered heteroaryl.

In another embodiment, the compounds provided herewith, or stereoisomers, tautomers, solvates, pharmaceutically acceptable salts, derivatives or prodrugs thereof, are generally defined by Formula II

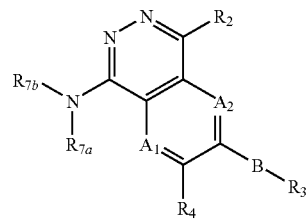

wherein each of $A^1$ and $A^2$, independently, is $CR^5$ or N;

B is a direct bond, $-(CR^5R^6)_m-$, $-C(=O)-$, $-N(R^6)-$, $-O-$, or $-S(=O)_m-$, wherein m is 0, 1 or 2;

$R^2$ is H, halo, haloalkyl, $NO_2$, CN, $OR^{7a}$, $SR^{7a}$, $NR^{7a}R^{7a}$, $C(O)R^{7a}$, $COOR^{7a}$, $C(O)NR^{7a}R^{7a}$, $C(O)NR^{7a}R^{7b}$, $NR^{7a}C(O)R^{7a}$, $NR^{7a}C(O)R^{7b}$, $NR^{7a}C(O)NR^{7a}R^{7a}$, $NR^{7a}C(O)NR^{7a}R^{7b}$, $OC(O)NR^{7a}R^{7b}$, $S(O)_2R^{7a}$, $S(O)_2NR^{7a}R^{7a}$, $S(O)_2NR^{7a}R^{7b}$, $NR^{7a}S(O)_2R^{7a}$, $NR^{7a}S(O)_2R^{7b}$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{7a}$ or $R^9$;

$R^3$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said ring system is substituted independently with one or more substituents of $R^{10}$, $R^{11}$, $R^{16}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)$ $C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, provided that at least one substituent on $R^3$ is $NR^{10}R^{10}$, $NR^{10}R^{11}$, $C(O)R^{10}$, $OC(O)R^{10}$, $COOR^{10}$, $C(O)R^{11}$, $OC(O)R^{11}$, $COOR^{11}$, $C(O)SR^{10}$, $C(O)SR^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $OC(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

$R^4$ is H, halo, haloalkyl, $NO_2$, CN, $NR^7R^7$, $NR^7R^8$, $OR^7$, $SR^7$, $C(O)R^7$, $OC(O)R^7$, $COOR^7$, $C(O)NR^7R^7$, $C(O)NR^7R^8$, $NR^7C(O)R^7$, $NR^7C(O)R^8$, $NR^8C(O)NR^7R^8$, $NR^7(COOR^7)$, $OC(O)NR^7R^8$, $S(O)_2R^7$, $S(O)_2NR^7R^8$, $NR^7S(O)_2NR^7R^8$, $NR^7S(O)_2R^7$, $NR^7S(O)_2R^7$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;

$R^5$ is H, halo, haloalkyl, $NO_2$, CN, $SR^{7a}$, $OR^{7a}$, $C(O)R^{7a}$, $COOR^{7a}$, $OC(O)R^{7a}$, $NR^{7a}R^{7a}$, $NR^{7a}R^{7b}$, $C(O)NR^{7a}R^{7a}$, $C(O)NR^{7a}R^{7b}$, $NR^{7a}C(O)R^{7a}$, $NR^{7a}C(O)R^8$, $NR^7C(O)NR^{7a}R^8$, $S(O)NR^{7a}R^{7b}$, $S(O)_2NR^{7a}R^{7b}$, $NR^{7a}S(O)NR^{7a}R^{7b}$, $NR^{7a}S(O)_2NR^{7a}R^{7b}$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;

$R^6$ is H, CN or $C_{1-10}$-alkyl, $C_{2-10}$-alkenyl, $C_{2-10}$-alkynyl, $C_{3-10}$-cycloalkyl or $C_{4-10}$-cloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;

$R^{7a}$ is H, $C_{1-10}$-alkyl, $C_{2-10}$-alkenyl, $C_{2-10}$-alkynyl, $C_{3-10}$-cycloalkyl, $C_{4-10}$-cycloalkenyl or partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, each of the $C_{1-10}$-alkyl, $C_{2-10}$-alkenyl, $C_{2-10}$-alkynyl, $C_{3-10}$-cycloalkyl, $C_{4-10}$-cycloalkenyl and partially or fully saturated 5-6 membered heterocyclic optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^{7b}$ is H or $C_{1-10}$-alkyl;

alternatively, $R^{7z}$ and $R^{7b}$ taken together with the nitrogen to which they are attached form a saturated or partially or fully unsaturated 5-6 membered monocyclic or 7-10 membered bicyclic heterocyclic ring optionally including 1-3 additional heteroatoms selected from O, N, or S, and optionally substituted independently with 1-5 substituents of $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

$R^9$ is H, halo, haloalkyl, CN, OH, $NO_2$, $NH_2$, oxo, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylanrino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamnino, benzyl or phenyl, provided that when B is a direct bond, $R^3$ is an optionally substituted phenyl or an optionally substituted 5- or 6-membered heteroaryl, and $R^{7b}$ is H or $C_{1-10}$-alkyl, then $R^{7a}$ is not an optionally substituted phenyl or an optionally substituted 5- or 6-membered heteroaryl.

Accordingly, the invention does not include those compounds of Formula I or II in which: (1) B is a direct bond, (2) $R^3$ is an optionally substituted phenyl, an optionally substituted 5-membered heteroaryl (particularly those containing 1-4 heteroatoms selected from O, N and S, with at most one being O or S) or an optionally substituted 6-membered heteroaryl (particularly those containing 1-3 nitrogen atoms), and (3) X is $NR^7R^8$ wherein $R^7$ is H or $C_{1-10}$-alkyl, and $R^8$ is an optionally substituted phenyl or an optionally substituted 5-membered heteroaryl (particularly those containing 1-4 heteroatoms selected from O, N and S, with at most one being O or S) or an optionally substituted 6-membered heteroaryl (particularly those containing 1-3 nitrogen atoms).

In another embodiment, the compounds of Formula I or II include N as $A^1$, in conjunction with any of the above or below embodiments.

In another embodiment, the compounds of Formula I or II include N as $A^2$, in conjunction with any of the above or below embodiments.

In another embodiment, the compounds of Formula I or II include compounds wherein one of $A^1$ and $A^2$ is N, in conjunction with any of the above or below embodiments.

In another embodiment, the compounds of Formula I or II include N, independently, as both $A^1$ and $A^2$, in conjunction with any of the above or below embodiments.

In another embodiment, the compounds of Formula I or II include B as a direct bond, in conjunction with any of the above or below embodiments.

In another embodiment, the compounds of Formula I or II include —$(CR^5R^6)_m$— as B, wherein m is 0, 1 or 2, in conjunction with any of the above or below embodiments.

In another embodiment, the compounds of Formula I or II include —C(=O)— as B, in conjunction with any of the above or below embodiments.

In another embodiment, the compounds of Formula I or II include —$N(R^6)$— as B, in conjunction with any of the above or below embodiments.

In another embodiment, the compounds of Formula I or II include —O— as B, in conjunction with any of the above or below embodiments.

In another embodiment, the compounds of Formula I or II include —$S(=O)_m$— as B, wherein m is 0, 1 or 2, in conjunction with any of the above or below embodiments.

In another embodiment, the compounds of Formula I include —$C(R^7R^7)_nX$ or —$C(R^7R^8)_nX$ as $R^1$, wherein n is 0, 1 or 2 and X is $NR^7R^7$, $NR^7R^8$, $OR^7$; $SR^7$, $OR^8$; $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$, $NR^7S(O)_2R^8$, in conjunction with any of the above or below embodiments.

In another embodiment, the compounds of Formula I include a 5-8 membered monocyclic or 6-12 membered bicyclic ring system as $R^1$, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^5$, $R^8$ or $R^9$, in conjunction with any of the above or below embodiments.

In another embodiment, the compounds of Formula I or II include H, halo, haloalkyl, $NO_2$, CN, $OR^7$, $SR^7$, $NR^7R^8$, $C(O)R^7$, $C_{1-10}$-alkyl, $C_{2-10}$-alkenyl, $C_{2-10}$-alkynyl, $C_{3-10}$-cycloalkyl or $C_{4-10}$-cycloalkenyl as $R^2$, in conjunction with any of the above or below embodiments.

In another embodiment, the compounds of Formula I or II include $COOR^7$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $OC(O)NR^7R^8$, $S(O)_2R^7$, $S(O)_2NR^7R^7$, $S(O)_2NR^7R^8$, $NR^7S(O)_2R^7$ or $NR^7S(O)_2R^8$ as $R^2$, in conjunction with any of the above or below embodiments.

In another embodiment, the compounds of Formula I or II include H or $C_{1-10}$-alkyl as $R^2$, in conjunction with any of the above or below embodiments.

In another embodiment, the compounds of Formula I optionally include one or more substituents of $R^{10}$, $R^{11}$, $R^{16}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$ on $R^3$, in conjunction with any of the above or below embodiments.

In another embodiment, the compounds of Formula II include least one substituent of $NR^{10}R^{10}$, $NR^{10}R^{11}$, $S(O)_2R^{10}$, $S(O)_2R^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $S(O)_2NR^{10}R^{10}$, $S(O)_2NR^{10}R^{11}$, $NR^{10}S(O)_2NR^{10}R^{11}$, $nr^{10}s(o)_2r^{10}$ OR $NR^{10}S(O)_2R^{11}$ on $R^3$, in conjunction with any of the above or below embodiments.

In another embodiment, the compounds of Formula I or II include two substituents on $R^3$, a first substituent of $NR^{10}R^{10}$, $NR^{10}R^{11}$, $S(O)_2R^{10}$, $S(O)_2R^{11}$, $C(O)NR^{10}R^{10}$, $C(O)NR^{10}R^{11}$, $NR^{10}C(O)R^{10}$, $NR^{10}C(O)R^{11}$, $NR^{10}C(O)NR^{10}R^{10}$, $NR^{10}C(O)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$ and a second substituent of $R^{16}$, in conjunction with any of the above or below embodiments.

In another embodiment, the compounds of Formula I or II include phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, dihydrobenzofuranyl, benzothiophenyl, benzoxazolyl, benzopyrazolyl, benzisoxazolyl, benzothiazolyl or benzimidazolyl as $R^3$, each of which has one substituent of $NR^{10}R^{10}$, $NR^{10}R^{11}$, $C(O)R^{10}$, $OC(O)R^{10}$, $COOR^{10}$, $C(O)R^{11}$, $OC(O)R^{11}$, $COOR^{11}$, $C(O)SR^{10}$, $C(O)SR^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $OC(O)NR^{10}R^{11}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, and 1-3 optional substituents of $R^{10}$, $R^{11}$, $R^{16}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR10R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, in conjunction with any of the above or below embodiments.

In another embodiment, the compounds of Formula I or II include one substituent of $NR^{10}R^{10}$, $NR^{10}R^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$ and 0-3 substituents of $R^{16}$, on $R^3$.

In another embodiment, the compounds of Formula I or II include H, halo, haloalkyl, $NO_2$, CN, $NR^7R^7$, $NR^7R^8$, $OR^7$, $SR^7$, $C(O)R^7$, $C_{1-10}$-alkyl, $C_{2-10}$-alkenyl, $C_{2-10}$-alkynyl, $C_{3-10}$-cycloalkyl or $C_{4-10}$-cycloalkenyl as $R^4$, in conjunction with any of the above or below embodiments.

In another embodiment, the compounds of Formula I or II include $OC(O)R^7$, $COOR^7$, $C(O)NR^7R^7$, $C(O)NR^7R^8$, $NR^7C(O)R^7$, $NR^7C(O)R^8$, $NR^8C(O)NR^7R^8$, $NR^7(COOR^7)$, $OC(O)NR^7R^8$, $S(O)_2R^7$, $S(O)_2NR^7R^8$, $NR^7S(O)_2NR^7R^8NR^7S(O)_2R^7$, $NR^7S(O)_2R^7$ as $R^4$, in conjunction with any of the above or below embodiments.

In another embodiment, the compounds of Formula I or II include H or $C_{1-10}$-alkyl as $R^4$, in conjunction with any of the above or below embodiments.

In another embodiment, the compounds of Formula I or II include N or $CR^5$ as $A^1$, $CR^5$ as $A^2$, and phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, dihydrobenzofuranyl, benzothiophenyl, benzisoxazolyl, benzopyrazolyl, benzothiazolyl or benzimidazolyl as $R^3$, in conjunction with any of the above or below embodiments.

In another embodiment, the compounds of Formula I include $NR^7R^7$, $NR^7R^8$, $OR^7$, $SR^7$, $OR^8$, $SR^8$, $C(O)R^7$, $C(O)R^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $S(O)_2NR^7R^7$, $NR^7S(O)_2NR^7R^7$, $NR^7S(O)_2R^7$, $S(O)_2NR^7R^8$, $NR^7S(O)_2R^8$ or a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl as $R^1$ in conjunction with any of the above or below embodiments, wherein said ring system is optionally substituted independently with 1-5 substituents of $R^7$, $R^8$, $R^9$, oxo, $OR^7$, $SR^7$, $C(O)R^7$, $NR^7R^7$, $NR^7R^8$, $OR^8$, $SR^8$, $C(O)R^8$, $COOR^7$, $OC(O)R^7$, $COOR^8$, $OC(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2NR^7R^7$, $S(O)_2NR^7R^8$, $NR^7S(O)_2)NR^7R^7$ or $NR^7S(O)_2NR^7R^8$.

In another embodiment, there are provided compounds of Formula I wherein $A^1$ is $CR^5$ or N;

$A^2$ is $CR^5$;

B is a direct bond;

$R^1$ is $NR^7R^7$, $NR^7R^8$, $OR^7$; $SR^7$, $OR^8$, $SR^8$, $C(O)R^7$, $C(O)R^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $S(O)_2NR^7R^7$, $NR^7S(O)_2NR^7R^7$, $NR^7S(O)_2R^7$, $S(O)_2NR^7R^8$, $NR^7S(O)_2NR^7R^8$, $NR^7S(O)_2R^8$ or a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzothiazolyl, benzisoxazolyl, benzopyrazolyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein the ring system is optionally substituted independently with 1-5 substituents of $R^7$, $R^8$, $R^9$, oxo, $OR^7$, $SR^7$, $C(O)R^7$, $NR^7R^7$, $NR^7R^8$, $OR^8$, $SR^8$, $C(O)R^8$, $COOR^7$, $OC(O)R^7$, $COOR^8$, $OC(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2 NR^7R^7$, $S(O)_2NR^7R^8$, $NR^7S(O)_2)NR^7R^7$ or $NR^7S(O)_2NR^7R^8$;

$R^2$ is H or $C_{1-10}$-alkyl;

$R^3$ is phenyl, naphthyl, pyridyl, pyrimidyl, triazinyl, quinolinyl, isoquinolinyl, quinazolinyl, isoquinazolinyl, thiophenyl, furyl, pyrrolyl, imnidazolyl, triazolyl, thiazolyl, oxazolyl, isoxazolyl, isothiazolyl, indolyl, isoindolyl, benzofuranyl, dihydrobenzofuranyl, benzothiophenyl, benzisoxazolyl, benzopyrazolyl, benzothiazolyl or benzimidazolyl, said $R^3$ substituted with one substituent of $NR^{10}R^{10}$, $NR^{10}R^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{11}$, $NR^{10}C(S)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$ and 0-3 substituents of $R^{16}$;

$R^4$ is H or $C_{1-10}$-alkyl;

$R^5$ is H or $C_{1-10}$-alkyl;

$R^6$ is H or $C_{1-10}$-alkyl;

$R^7$ is H, $C_{1-10}$-alkyl, $C_{2-10}$-alkenyl, $C_{2-10}$-alkynyl or $C_{3-10}$-cycloalkyl, each of the $C_{1-10}$-alklyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2R^8$, $NR^9S(O)_2R^9$, $R^8$ or $R^9$;

$R^8$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzisoxazolyl, benzothiazolyl, benzopyrazolyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-5 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-0}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl or $C_{3-10}$-cycloalkyl, each of the $C_{1-10}$-alkyl, $C_{2-10}$-alkenyl, and $C_{3-10}$-cycloalkyl optionally comprising 1-4 heteroatoms selected from N, O and S and optionally substituted with 1-3 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $C(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{15}$;

$R^{14}$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-3 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds are generally defined by the immediately preceeding embodiment of Formula I, wherein A$^1$ is CR$^5$;

R$^1$ is NR$^7$R$^7$, NR$^7$R$^8$, C(O)R$^7$, C(O)R$^8$, C(O)NR$^7$R$^7$, NR$^7$C(O)R$^7$, C(O)NR$^7$R$^8$, NR$^7$C(O)R$^8$, S(O)$_2$NR$^7$R$^7$, NR$^7$S(O)$_2$R$^7$, S(O)$_2$NR$^7$R$^8$, NR$^7$S(O)$_2$R$^8$ or a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein the ring system is optionally substituted independently with 1-3 substituents of R$^7$, R$^8$, R$^9$, oxo, OR$^1$, SR$^7$, C(O)R$^7$, NR$^7$R$^7$, NR$^7$R$^8$, OR$^8$, SR$^8$, C(O)R$^8$, COOR$^7$, OC(O)R$^7$, COOR$^8$, OC(O)R$^8$, C(O)NR$^7$R$^7$, C(O)NR$^7$R$^8$, NR$^7$C(O)R$^7$, NR$^7$C(O)R$^8$, NR$^7$C(O)NR$^7$R$^7$, NR$^7$C(O)NR$^7$R$^8$, S(O)$_2$NR$^7$R$^7$, S(O)$_2$NR$^7$R$^8$, NR$^7$S(O$_2$)NR$^7$R$^7$ or NR$^7$S(O)$_2$NR$^7$R$^8$;

R$^2$ is H;

R$^3$ is

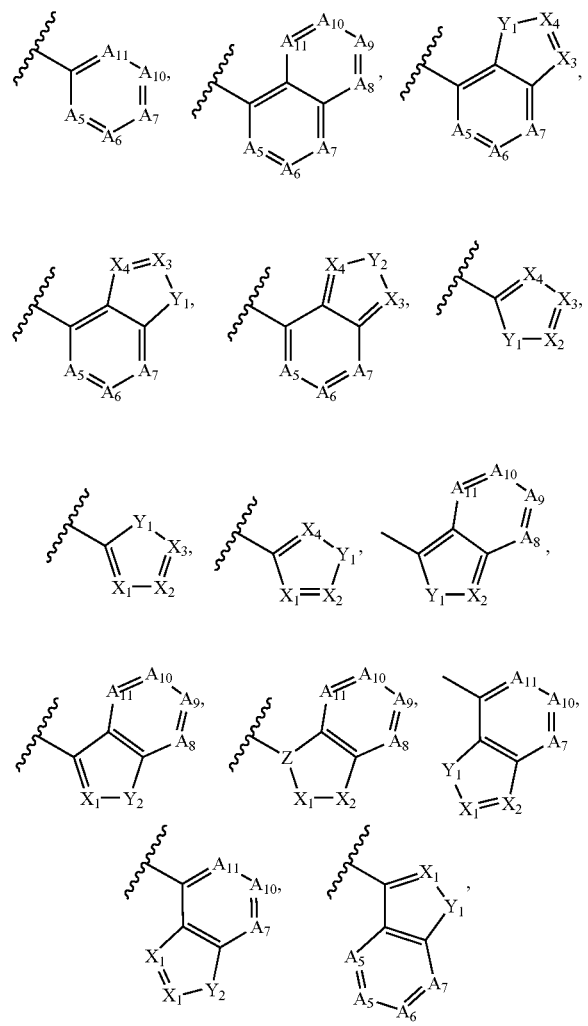

-continued

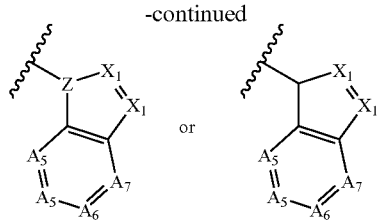

or wherein
one of A$^6$ and A$^7$ is CR$^{3a}$ and the other of A$^6$ and A$^7$ is CR$^{3b}$ or N;
each of A$^5$, A$^8$, A$^9$, A$^{10}$ and A$^{11}$ is, independently, CR$^{3b}$ or N;
X$^2$ is CR$^{3a}$;
each of X$^1$, X$^3$ and X$^4$ is, independently, CR$^{3b}$ or N;
Y$^1$ is CR$^{3b}$R$^{3c}$, NR$^{3c}$, O or S;
Y$^2$ is CR$^{3a}$R$^{3b}$ or NR$^{3a}$; and
Z is CH or N;
R$^{3a}$ is NR$^{10}$R$^{10}$, NR$^{10}$R$^{11}$, C(O)NR$^{10}$R$^{10}$, C(O)NR$^{10}$R$^{11}$, NR$^{10}$C(O)R$^{10}$, NR$^{10}$C(O)R$^{11}$, NR$^{10}$C(O)NR$^{10}$R$^{10}$, NR$^{10}$C(O)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$;
R$^{3b}$ is H, halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl; and
R$^{3c}$ is H, CN or C$_{1-10}$-alkyl;
R$^4$ is H;
R$^5$ is H;
R$^6$ is H;
R$^7$ is H, C$_{1-10}$-alkyl, C$_{2-10}$-alkenyl or C$_{3-6}$-cycloalkyl, each of the C$_{1-10}$-alkyl, C$_{2-10}$-alkenyl and C$_{3-6}$-cycloalkyl optionally substituted with 1-3 substituents of NR$^8$R$^9$, NR$^9$R$^9$OR$^8$, SR$^8$, OR$^9$, SR$^9$, C(O)R$^8$, OC(O)R$^8$, COOR$^8$, C(O)R$^9$, OC(O)R$^9$, COOR$^9$, C(O)NR$^8$R$^9$, C(O)NR$^9$R$^9$, NR$^9$C(O)R$^8$, NR$^9$C(O)R$^9$, NR$^9$C(O)NR$^8$R$^9$, NR$^9$C(O)NR$^9$R$^9$, NR$^9$(COOR$^8$), NR$^9$(COOR$^9$), OC(O)NR$^8$R$^9$, OC(O)NR$^9$R$^9$, S(O)$_2$R$^8$, S(O)$_2$NR$^8$R$^9$, S(O)$_2$R$^9$, S(O)$_2$NR$^9$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$, R$^8$ or R$^9$;
R$^8$ is phenyl, naphthyl, pyridyl, pyrimidyl, quinolinyl, isoquinolinyl, quinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of R$^9$, oxo, NR$^9$R$^9$, OR$^9$; SR$^9$, C(O)R$^9$, COOR$^9$, C(O)NR$^9$R$^9$, NR$^9$C(O)R$^9$, NR$^9$C(O)NR$^9$R$^9$, OC(O)NR$^9$R$^9$, S(O)$_2$R$^9$, S(O)$_2$NR$^9$R$^9$, NR$^9$S(O)$_2$R$^9$, or a partially or fully saturated or unsaturated 5-6 membered ring of carbon atoms optionally including 1-3 heteroatoms selected from O, N, or S, and optionally substituted independently with 1-3 substituents of R$^9$;
alternatively, R$^7$ and R$^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-3 substituents of R$^9$;
R$^9$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl or $C_{3-10}$-cycloalkyl, each of the $C_{1-10}$-alkyl, $C_{2-10}$-alkenyl, and $C_{3-10}$-cycloalkyl optionally substituted with 1-3 substituents of $R^{11}$, $R^{12}$, $R^{16}$, $NR R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{12}$, $NR^{12}S(O)_2R^{11}$ or $NR^{12}S(O)_2R^{12}$; and $R^{11}$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^{12}$, $R^{13}$ or $R^{16}$.

In another embodiment, the compounds are generally defined by Formula I or II above, wherein $R^3$ is

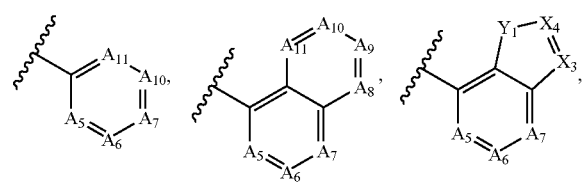

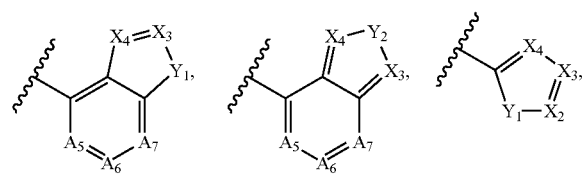

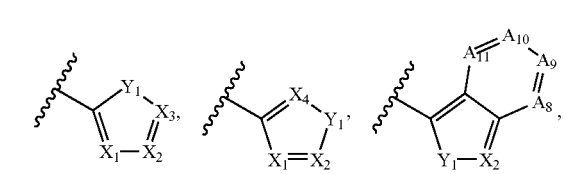

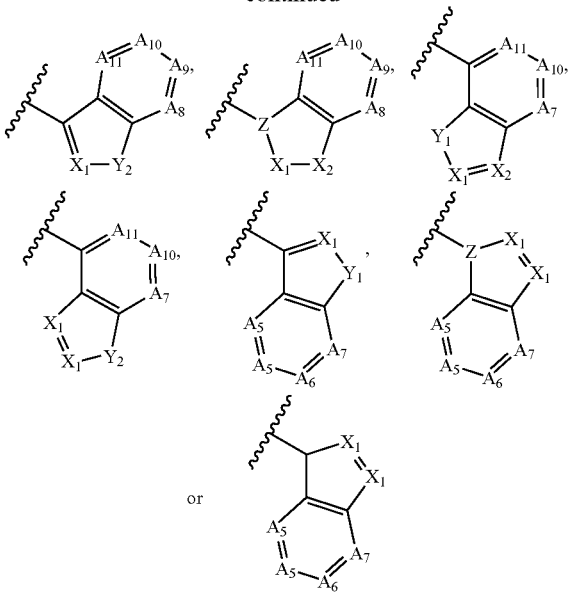

wherein
one of $A^6$ and $A^7$ is $CR^{3a}$ and the other of $A^6$ and $A^7$ is $CR^{3b}$ or N;
each of $A^5$, $A^8$, $A^9$, $A^{10}$ and $A^{11}$ is, independently, $CR^{3b}$ or N;
$X^2$ is $CR^{3a}$;
each of $X^1$, $X^3$ and $X^4$ is, independently, $CR^{3b}$ or N;
$Y^1$ is $CR^{3b}R^{3c}$, $NR^{3c}$, O or S;
$Y^2$ is $CR^{3a}R^{3b}$ or $NR^{3a}$; and
Z is CH or N;
$R^{3a}$ is $NR^{10}R^{10}$, $NR^{10}R^{11}$, $C(O)NR^{10}R^{10}$, $C(O)NR^{10}R^{11}$, $NR^{10}C(O)R^{10}$, $NR^{10}C(O)R^{11}$, $NR^{10}C(O)NR^{10}R^{10}$, $NR^{10}C(O)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;
$R^{3b}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl; and
$R^{3c}$ is H, CN or $C_{1-10}$-alkyl, in conjunction with any of the above or below embodiments of compounds of Formula II.

In another embodiment, the compounds are generally defined by Formula I or II above, wherein $R^3$ is

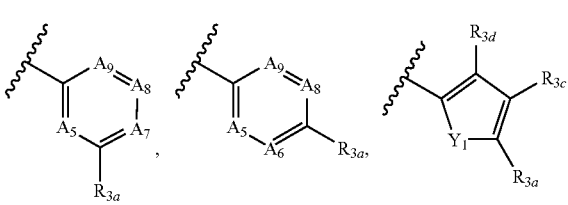

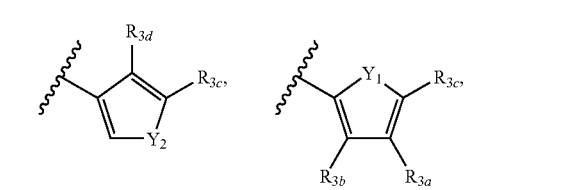

-continued

[chemical structures]

wherein
each of A⁵, A⁶, and A⁷ is, independently, CR$^{3b}$ or N;
A⁸ is CR$^{3c}$ or N; and
A⁹ is CR$^{3d}$ or N;
Y¹ is O or S;
Y² is NR$^{3a}$;
R$^{3a}$ is NR$^{10}$R$^{10}$, NR$^{10}$R$^{11}$, C(O)NR$^{10}$R$^{10}$, C(O)NR$^{10}$R$^{11}$, NR$^{10}$C(O)R$^{10}$, NR$^{10}$C(O)R$^{11}$, NR$^{10}$C(O)NR$^{10}$R$^{10}$, NR$^{10}$C(O)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$;
R$^{3b}$ is H, halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl;
R$^{3c}$ is H, halo, haloalkyl, CN, NO$_2$, NH$_2$, C$_{1-10}$-alkyl, C$_{2-10}$-alkenyl, C$_{2-10}$-alkynyl, or C$_{3-10}$-cycloalkyl;
R$^{3c}$ is H, halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl;
R$^{3d}$ is H, halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl;
alternatively, R$^{3c}$ and R$^{3d}$ taken together with the atoms to which they are attached form a phenyl or tetrahydrofuranyl ring system, optionally substituted with 1-3 substituents of halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl, in conjunction with any of the above or below embodiments of compounds of Formula II.

In another embodiment, the compounds of Formula II include R$^{7z}$ and R$^{7b}$, taken together with the nitrogen to which they are attached, forming a saturated or partially or fully unsaturated 5-6 membered monocyclic or 7-10 membered bicyclic heterocyclic ring optionally including 1-3 additional heteroatoms selected from O, N, or S, and optionally substituted independently with 1-5 substituents of R⁸ or R⁹, in conjunction with any of the above or below embodiments of compounds of Formula II.

In another embodiment, the compounds of Formula II include R$^{7z}$ and R$^{7b}$, taken together with the nitrogen to which they are attached, forming a heterocyclic ring selected from pyrrolidinyl, oxazolinyl, isoxazolinyl, thiazolinyl, pyrazolinyl, morpholinyl, piperidinyl and piperazinyl, wherein said ring is optionally substituted independently with 1-3 substituents of R⁸ or R⁹, in conjunction with any of the above or below embodiments of compounds of Formula II.

In another embodiment, the compounds are generally defined by Formula II, wherein:
A¹ is CR⁵ or N;
A² is CR⁵;
B is a direct bond;
R² is H or C$_{1-10}$-alkyl;

R³ is

[chemical structures]

wherein
one of A⁶ and A⁷ is CR$^{3a}$ and the other of A⁶ and A⁷ is CR$^{3b}$ or N;
each of A⁵, A⁸, A⁹, A$^{10}$ and A$^{11}$ is, independently, CR$^{3b}$ or N;
X² is CR$^{3a}$;
each of X¹, X³ and X⁴ is, independently, CR$^{3b}$ or N;
Y¹ is CR$^{3b}$R$^{3c}$, NR$^{3c}$, or S;
Y² is CR$^{3a}$R$^{3b}$ or NR$^{3a}$; and
Z is CH or N;
wherein R$^{3a}$ is NR$^{10}$R$^{10}$, NR$^{10}$R$^{11}$, C(O)NR$^{10}$R$^{10}$, C(O)NR$^{10}$R$^{11}$, NR$^{10}$C(O)R$^{10}$, NR$^{10}$C(O)R$^{11}$, NR$^{10}$C(O)NR$^{10}$R$^{10}$, NR$^{10}$C(O)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$;
R$^{3b}$ is H, halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl;
R$^{3c}$ is H, halo, haloalkyl, CN, NO$_2$, NH$_2$, C$_{1-10}$-alkyl, C$_{2-10}$-alkenyl, C$_{2-10}$-alkynyl or C$_{2-10}$-cycloalkyl; and
R$^{3c}$ is H, halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl;

$R^4$ is H or $C_{1-10}$-alkyl;

$R^5$ is H or $C_{1-10}$-alkyl;

$R^6$ is H;

$R^{7a}$ is H, $C_{1-10}$-alkyl, $C_{3-6}$-cycloalkyl, or partially or fully saturated 5-6 membered heterocyclic, each of the $C_{1-10}$-alkyl, $C_{3-6}$-cycloalkyl and partially or fully saturated 5-6 membered heterocyclic optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^9$, $R^8$ or $R^9$;

$R^{7b}$ is H or $C_{1-10}$-alkyl;

alternatively, $R^{7a}$ and $R^{7b}$ taken together with the nitrogen to which they are attached form a heterocyclic ring selected from pyrrolidinyl, oxazolinyl, isoxazolinyl, thiazolinyl, pyrazolinyl, morpholinyl, piperidinyl and piperazinyl, wherein said ring is optionally substituted independently with 1-3 substituents of $R^8$ or $R^9$;

$R^8$ is phenyl, naphthyl, pyridyl, pyrimnidyl, quinolinyl, isoquinolinyl, quinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^9$, oxo, $NR^9R^9$, $OR^9$; $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl or a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl and dioxozinyl, each of the $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl and ring system optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl or $C_{3-10}$-cycloalkyl, each of the $C_{1-10}$-alkyl, $C_{2-10}$-alkenyl, and $C_{3-10}$-cycloalkyl optionally substituted with 1-3 substituents of $R^{11}$, $R^2$, $R^{16}$, $NR^{11}R^2$, $NR^{12}R^2$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{12}$, $NR^{12}S(O)_2R^{11}$ or $NR^{12}S(O)_2R^{12}$; and $R^{11}$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^{12}$, $R^{13}$ or $R^{16}$.

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}$, $R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-3 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl or a ring system selected from phenyl, pyridyl, thiophenyl, furyl, tetrahydrofuryl, pyrrolyl, pyrazolyl, thieno-pyrazolyl, imidazolyl, triazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, said ring system optionally substituted independently with 1-3 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In yet another embodiment, the compounds of Formula I include the examples described hereinbelow.

DEFINITIONS

The following definitions should assist in understanding the invention described herein.

The terms "agonist" and "agonistic" when used herein refer to or describe a molecule which is capable of, directly or indirectly, substantially inducing, promoting or enhancing biological activity of a biological molecule, such as an enzyme or receptor, including Tie-2 and Lck.

The term "comprising" is meant to be open ended, including the indicated component(s), but not excluding other elements.

The term "H" denotes a single hydrogen atom. This radical may be attached, for example, to an oxygen atom to form a hydroxyl radical.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$). The term "alkyl" radicals include "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of alkynyl radicals include "lower alkynyl" radicals having two to about six carbon atoms and, for example, lower alkynyl radicals having two to about four carbon atoms. Examples of such radicals include, without limitation, ethynyl, propynyl(propargyl), butynyl, and the like.

The term "alkoxy" or "alkoxyl", when used alone or in combination, embraces linear or branched oxygen-containing radicals each having alkyl portions of one or more carbon atoms. The term alkoxy radicals include "lower alkoxy" radicals having one to six carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. Unless otherwise specified, the "aryl" group may be subsitituted, such as with 1 to 5 substituents including lower alkyl, hydroxyl, halo, haloalkyl, nitro, cyano, alkoxy and lower alkylamino, and the like. Phenyl substituted with —O—$CH_2$—O— or —O—$CH_2$—$CH_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane and partially saturated monocyclic groups such as cyclopentene, cyclohexene or cyclohexadiene. The partially saturated groups are also encompassed in the term "cycloalkenyl" as defined below.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 5-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms and, for example, lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heteroaryl" also embraces bicyclic radicals wherein 5- or 6-membered heteroaryl radicals are fused/condensed with aryl radicals or unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and saturated heterocyclyl include, without limitation, pyrrolidinyl, imnidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N, N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "alkylthio" and "thioalkoxyl" embrace radicals containing a linear or branched alkyl radicA$^1$, of one to ten carbon atoms, attached to a divalent sulfur atom. An example of "alkylthio" is methylthio, (CH$_3$S—).

The term "haloalkylthio" embraces radicals containing a haloalkyl radicA$^1$, of one to ten carbon atoms, attached to a divalent sulfur atom. An example of "haloalkylthio" is trifluoromethylthio.

The term "aminoalkyl" embraces linear or branched alkyl radicals having one to about ten carbon atoms any one of which may be substituted with one or more amino radicals. Examples of aminoalkyl radicals include "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. Examples of alkylaminoalkyl radicals include "lower alkylaminoalkyl" radicals having alkyl radicals of one to six carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. Examples of alkylaminoalkoxy radicals include "lower alkylaminoalkoxy" radicals having alkoxy radicals of one to six carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "Formula I" includes any sub formulas, such as Formula II. Similarly, the term "Formula II" includes any sub formulas.

The term "pharmaceutically-acceptable" when used with reference to a compound of Formulas I or II is intended to refer to a form of the compound that is safe for administration. For example, a free base, a salt form, a solvate, a hydrate, a prodrug or derivative form of a compound of Formula I or of Formula II, which has been approved for mammalian use, via oral ingestion or any other route of administration, by a governing body or regulatory agency, such as the Food and Drug Administration (FDA) of the United States, is pharmaceutically acceptable.

Included in the compounds of Formulas I and II are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I and II may be prepared from an inorganic acid or from an organic acid. Examples of such inorganic acids are hydrochloric, hydrobromic, hydroiodic, hydrofluoric, nitric, carbonic, sulfonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I and II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I or II.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid (HCl), hydrobromic acid (HBr), citric acid, sulphuric acid and phosphoric acid and such organic acids as oxalic acid, stearic and, salicylic acid, pamoic acid, gluconic acid, ethanesulfonic acid, methanesulfonic acid (MSA), benzenesulfonic acid (BSA), toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66, 1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative, which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I. A "pharmaceutically-acceptable prodrug" as used herein, denotes a prodrug, which is pharmaceutically acceptable. Pharmaceutically acceptable modifications to the compounds of Formula I are readily appreciated by those of ordinary skill in the art.

The compound(s) of Formula I or II may be used to treat a subject by administering the compound(s) as a pharmaceutical composition. To this end, the compound(s) can be combined with one or more carriers, diluents or adjuvants to form a suitable composition, which is described in more detail herein.

The term "carrier", as used herein, denotes any pharmaceutically acceptable additive, excipient, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies.

The term "leaving groups" (also denoted as "LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group.

Nucleophiles are known in the art. Examples of nucleophilic groups include, but are not limited to, amines, thiols, alcohols, Grignard reagents, anionic species (e.g., alkoxides, amides, carbanions) and the like.

GENERAL SYNTHETIC PROCEDURES

The present invention further comprises procedures for the preparation of compounds of Formulas I and II.

The compounds of Formulas I and II can be synthesized according to the procedures described in the following Schemes 1-4, wherein the substituents are as defined for Formulas I and II, above, except where further noted. The synthetic methods described below are merely exemplary, and the compounds of the invention may also be synthesized by alternate routes as appreciated by persons of ordinary skill in the art.

The following list of abbreviations used throughout the specification represent the following and should assist in understanding the invention:
ACN, MeCN—acetonitrile
$AgNO_3$—silver nitrate
BSA—bovine serum albumin
BOP—benzotriazol-1-yl-oxy hexafluorophosphate
CDI—carbonyldiimidazole
$Cs_2CO_3$—cesium carbonate
$CHCl_3$—chloroform
$CH_2Cl_2$, DCM—dichloromethane, methylene chloride
DCC—dicyclohexylcarbodiimide
DIC—1,3-diisopropylcarbodiimide
DIEA,$(iPr)_2NEt$—diisopropylethylamine
DME—dimethoxyethane
DMF—dimethylformamide
DMAP—4-dimethylaminopyridine
DMSO—dimethylsulfoxide
EDC—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
$NaOCH_3$—sodium methoxide
NaOH—sodium hydroxide
$Na_2SO_4$—sodium sulfate
NBS—N-bromosuccinimide
$NH_4Cl$—ammonium chloride
$NH_4OH$—ammonium hydroxide
NMP—N-methylpyrrolidinone
$P(t-bu)_3$—tri(tert-butyl)phosphine
PBS—phospate buffered saline
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RT—room temperature
TBTU—O-benzotriazol-1-yl-N,N,N',N'-tetramethyluronium tetrafluoroborate
TEA, $Et_3N$—triethylamine
TFA—trifluoroacetic acid
THF—tetrahydrofuran
UV—ultraviolet light Scheme 1

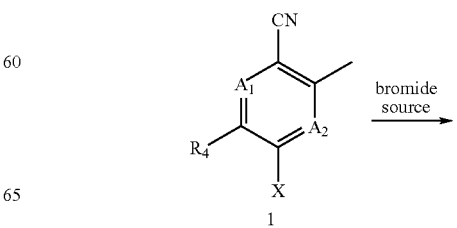

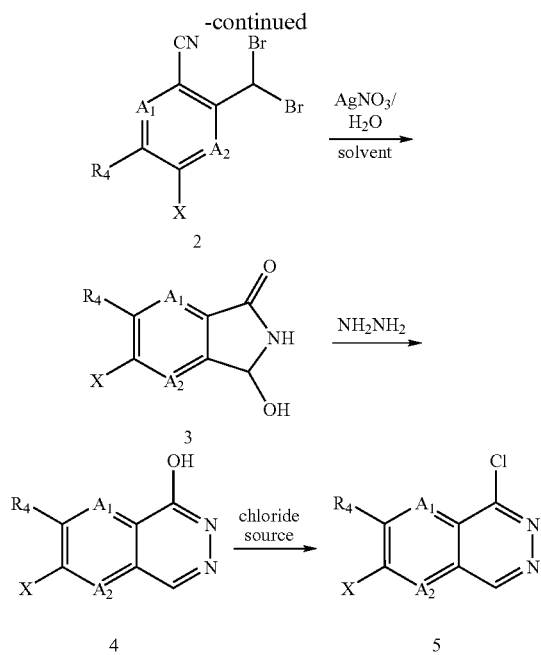

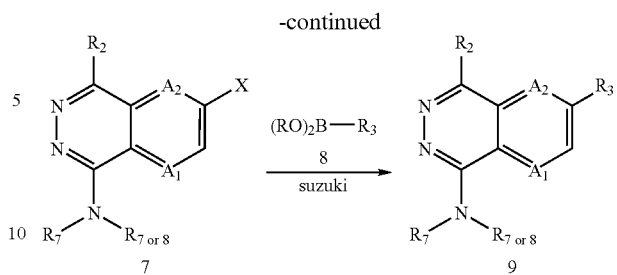

A 1-chloro-6-halo (X=halogen such as Br, I, Cl or F) substituted phthalazine 5, (where both $A_1$ and $A_2$ are each carbon) or aza-phthalazine 5 (where one of $A_1$ or $A_2$ is nitrogen), or diaza-phthalazine 5 (where both $A_1$ and $A_2$ are each nitrogen), and which are generally referred to herein as the C-D ring portion of the compounds of Formulas I and II, can be prepared according to the method generally described in Scheme 1. As shown, a 4-halo-2-methyl cyanobenzene 1 can be treated with a source of bromine under suitable conditions, such as N-bromosuccinimide (commonly referred to as NBS) in the presence of UV light, for a time period to form 2,2-dibromomethyl adduct 2. The 4-cyano-3-di-bromo methylphenyl intermediate 2 can be reacted with silver nitrate, in the presence of a suitable solvent such as acetonitrile, to form the 6-halo-hydroxybenzenesuccinimide compound 3. Formation of compound 3 may require heat, up to and including reflux temperatures depending on the particular solvent and concentration, as appreciated by those skilled in the art. Compound 3 can then be treated with hydrazine to form the corresponding 6-halo-1-hydroxyphthalazine 4. This reaction generally produces reasonable yields of product 4 at room temperature when allowed to react for a prolonged period of time, such as about 24 hours. 4-Hydroxyphthalazine 4 can then be reacted with a suitable chloride source, such as phosphorus oxychloride, in the presence of a suitable solvent, to convert the 2-hydroxy group to the corresponding 1-chloride phthalazine 5. 6-Halo-substituted phthalazine 5 is a useful intermediate for coupling the $R^3$ ring system, with or without a "B" linker, as illustrated in Formulas I and II.

Scheme 2

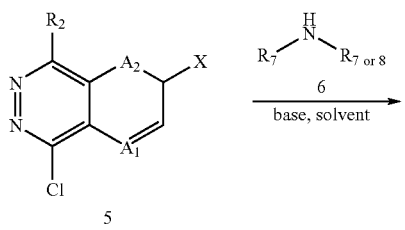

A compound 9 of Formulas I or II can be prepared according to the method generally described in Scheme 2. As shown, 6-halo-substituted phthalazine 5 (see scheme 1 above) can be treated with an $R^1$ group having a suitable nucleophilic species, such as an amino-$R^1$ compound 6 as shown ($R^1$=—$NR^7R^{7\text{ or }8}$), in the presence of a suitable solvent (preferably a high boiling solvent if no base added) and optionally a base to afford the desired 4-amino-phthalazine 7. The nucleophile ($R^1$) may alternatively be an oxygen or sulfur nucleophile ($R^1$=—$OR^{7\text{ or }8}$ or —$SR^{7\text{ or }8}$), which can displace the chloride of the phthalazine in the presence of a suitable base by conventional methods, as appreciated by those skilled in the art. Heat may or may not be required to effect the transformation depending upon the particular substrates involved.

A desired 1-amino-substituted-6-halo-phthalazine 7 can be reacted with a desired $R^3$-substituted boronic acid 8 in a Suzuki-type or Buchwald-type coupling reaction to afford the desired 1-amino-6-$R^3$ substituted phthiazines 9. The Suzuki method is a reaction using a borane reagent, such as a dioxaborolane intermediate 8 (also described in scheme 3 below as a borane B-A intermediate 8), and a suitable leaving group containing reagent, such as the 6-X-phthalazine 5 (X is a leaving group "LG", which may be an I or Br). As appreciated to one of ordinary skill in the art, Suzuki reactions also utilize a palladium catalyst. Suitable palladium catalysts include $Pd(PPh_3)_4$, $Pd(OAc)_2$ or $Pd(dppf)Cl_2$. Where LG is a halide, the halide may be an iodide, a bromide or even a chloride (chloro-pyridyl or chloro-picolinyl B rings undergo Suzuki reactions in the presence of $Pd(OAc)_2$). Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular phthalazine 7 and/or boronic acid 8, as appreciated by those skilled in the art. In addition, where $R^3$ is an aromatic moiety, such as phenyl, the reaction may be complete in a short period of time with heat.

Further, the boronic acid 8 may be any suitable desired boronic acid having the general formula $(RO)_2B—R^3$ (where "B" is a direct bond) or $(RO)_2B—"B"—R^3$, (where "B" is a spacer such as an —$(CR^5R^6)_{0-2}$—, —C(=O)—, —N($R^6$)—, —O— or —S(=O)$_{0-2}$—) as defined in Formulas I and II. The boronic acid may also be a cyclic boronate (not shown). In this fashion, desired $R^1$ groups, such as amino $R^1$ groups, and $R^3$ groups such as aryl or heteroaryl $R^3$ groups, can be installed into the phthalazine core 7. The desired boronic acid compounds 8 may generally be made as illustrated in scheme 3 below.

See also Examples 5 and 6 for methods of installing the boronate on a desired phthalazine ring. Other known metal coupling chemistry, such Stille, Kumada, Negishi coupling methods, and the like, may be employed to couple phthalazines 5 or 7 to desired cyclic $R^3$-substituted moieties.

Alternatively, the coupling method described in Scheme 2 may also be used to couple a C-D ring (phthalazine) to a desired $R^1$ group, such as a B ring, without having an A ring (or an $R^{10}$ or $R^{11}$ substitution) in place (see scheme 3 and Example 2 below). Halo-substituted-$NH_2$-B rings may be coupled via a Suzuki reaction to a dioxaborolane phthalazine 5 or 7, and the amine group may then be converted to an isocyanate, for example, or any other desired group for coupling the A ring (or an $R^{10}$ or $R^{11}$ substitution) via the desired linker.

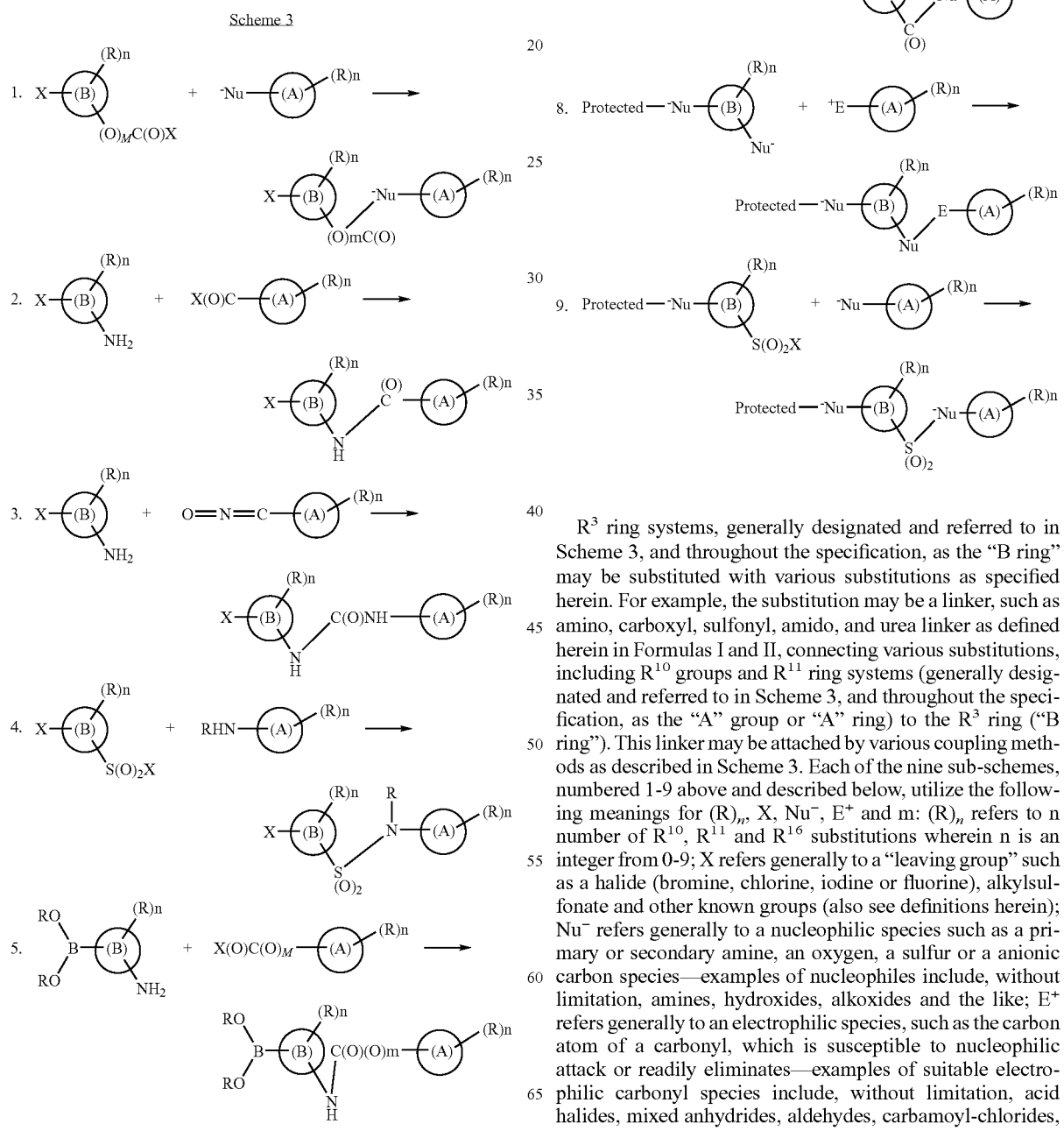

Scheme 3

$R^3$ ring systems, generally designated and referred to in Scheme 3, and throughout the specification, as the "B ring" may be substituted with various substitutions as specified herein. For example, the substitution may be a linker, such as amino, carboxyl, sulfonyl, amido, and urea linker as defined herein in Formulas I and II, connecting various substitutions, including $R^{10}$ groups and $R^{11}$ ring systems (generally designated and referred to in Scheme 3, and throughout the specification, as the "A" group or "A" ring) to the $R^3$ ring ("B ring"). This linker may be attached by various coupling methods as described in Scheme 3. Each of the nine sub-schemes, numbered 1-9 above and described below, utilize the following meanings for $(R)_n$, X, $Nu^-$, $E^+$ and m: $(R)_n$ refers to n number of $R^{10}$, $R^{11}$ and $R^{16}$ substitutions wherein n is an integer from 0-9; X refers generally to a "leaving group" such as a halide (bromine, chlorine, iodine or fluorine), alkylsulfonate and other known groups (also see definitions herein); $Nu^-$ refers generally to a nucleophilic species such as a primary or secondary amine, an oxygen, a sulfur or a anionic carbon species—examples of nucleophiles include, without limitation, amines, hydroxides, alkoxides and the like; $E^+$ refers generally to an electrophilic species, such as the carbon atom of a carbonyl, which is susceptible to nucleophilic attack or readily eliminates—examples of suitable electrophilic carbonyl species include, without limitation, acid halides, mixed anhydrides, aldehydes, carbamoyl-chlorides, sulfonyl chlorides, acids activated with activating reagents such as TBTU, HBTU, HATU, HOBT, BOP, PyBOP and carbodiimides (DCC, EDC, CDI and the like), and other electrophilic species including halides, isocyanates, daizonium ions and the like; and m is either 0 or 1.

The coupling of ring B to A, as shown as products in sub-schemes 1-9, can be brought about using various conventional methods to link ring B and A together. For example, an amide or a sulfonamide linkage, as shown in sub-schemes 2 and 4, and 7 and 9 where the Nu⁻ is an amine, respectively, can be made utilizing an amine on either the B or A groups and an acid chloride or sulfonyl chloride on the other of either the B or A groups. The reaction proceeds generally in the presence of a suitable solvent and/or base.

Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates as illustrated in sub-schemes 5 and 1 where Nu⁻ is an amine, anhydrides as illustrated in sub-scheme 1 where Nu⁻ is an oxygen, reverse amides as generally illustrated in sub-scheme 8 where Nu⁻ is an amine and E⁺ is an acid chloride, ureas as illustrated in sub-scheme 3, thioamides and thioureas where the respective carbonyl oxygen is a sulfur, thiocarbamates where the respective carbonyl oxygen and/or carbamate oxygen is a sulfur, and the like. While the above methods are so described, they are not exhaustive, and other methods for linking groups A and B together may be utilized as appreciated by those skilled in the art.

Although sub-schemes 1-9 are illustrated as having the nucleophilic and electrophilic coupling groups, such as the amino group and acid chloride groups illustrated in sub-scheme 2, directly attached to the substrate, either the A group or B ring, in question, the invention is not so limited. It is contemplated herein that these nucleophilic and/or electrophilic coupling groups may be tethered from their respective ring. For example, the amine group on the B ring, and/or the acid halide group on the A group or ring, as illustrated in sub-scheme 2, may be removed from direct attachment to the ring by a one or more atom spacer, such as by a methylene, ethylene spacer or the like. As appreciated by those skilled in the art, such spacer may or may not affect the coupling reactions described above, and accordingly, such reaction conditions may need to be modified to effect the desired transformation.

The coupling methods described in sub-schemes 1-9 of scheme 3 are also applicable for coupling desired A groups or rings to desired DC—B intermediates, such as to substituted phthalazine benzoic acids (Example 2) or substituted aza- or diazaphthalazine benzoic acids (not shown), to synthesize desired compounds of Formulas I and II. For example, a desirably substituted phthalazine benzoic acid maybe reacted with a desirably substituted primary or secondary amine, such as an $NHR^{10}R^{10}$ or $NHR^{10}R^{11}$ group in the presence of a suitable solvent and a known coupling reagent, such as TBTU, HATU, CDI or others, to prepare the desired A-BCD amide bond, and the final compound of Formulas I or II.

Note that the B-A moiety is connected through a linker "L". "L" may be any linker generally defined by the $R^3$ substitutions in Formulas I and II, and particularly, it includes, without limitation, an amide, a urea, a thiourea, a thioamide, a carbamate, an anhydride, a sulfonamide and the like, allowing for spacer atoms either between ring B and L and/or between ring or group A and L, as described in Scheme 3 above.

Further, the amine may be protected (not shown), such as with BOC—ON, while further substituents are coupled to the B ring, prior to or after coupling the B ring to an A ring or A group to form the desired $R^3$ group.

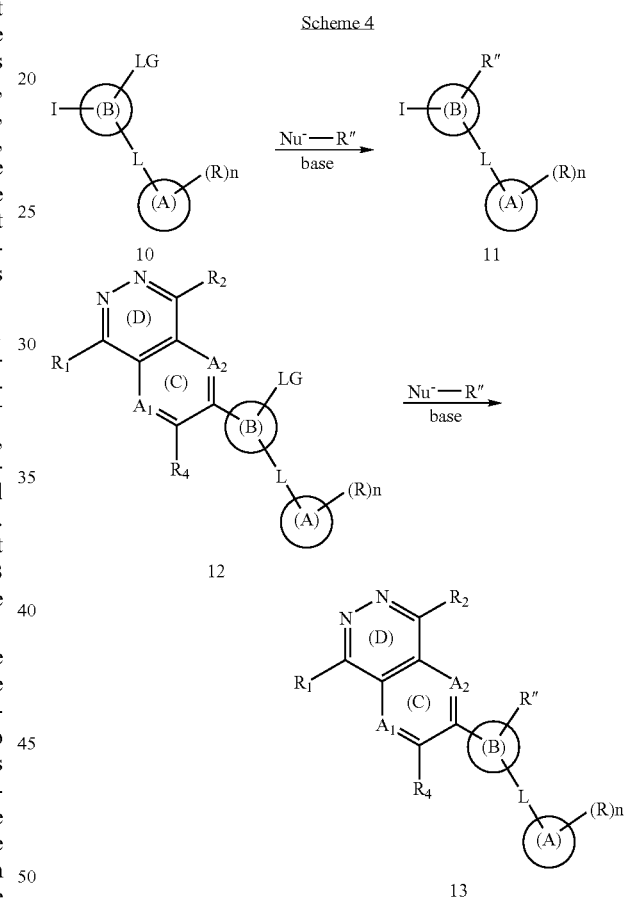

Various $R^{10}$, $R^{11}$ and $R^{16}$ substitutions (designated generally as R" groups in compounds 11 and 13) can be installed on the B ring of Formulas I and II, with or without the C-D ring system attached, as described in Scheme 4. For instance, compounds 11 and 13 may be made by the method described in Scheme 4. As shown, iodinated aryl B ring compounds 10 and compounds 12 may contain suitable leaving groups, such as a fluoride, at a desired position for substitution. These intermediates (compounds 10 and 12) may be reacted with desirable nucleophilic R" groups ($R^{10}$, $R^{11}$ and $R^{16}$ substitutions), such as alkoxides, amines and the like, in the presence of a suitable base, such as a hydride or borohydride, to covalently bind the R" group to the B ring. Alternatively, the B ring may have a nucleophile, such as a hydroxide or an amine, which may be further functionalized as desired via standard chemical methodology, as appreciated by those skilled in the art.

To enhance the understanding and appreciation of the present invention, the following specific examples (starting reagents, intermediates and compounds of Formulas I and II) are set forth. It should be appreciated that the above general methods and specific examples below are merely for illustrative purposes only and are not to be construed as limiting the scope of this invention in any manner. The following analytical methods were used to purify and/or characterize the compounds, and intermediates, described in the examples below.

Analytical Methods:

Unless otherwise indicated, all HPLC analyses were run on a Agilent Model 1100 system with an Agilent Technologies Zorbax SB—$C_8$(5μ) reverse phase column (4.6×150 mm; Part no. 883975-906) run at 30° C. with a flow rate of about 1.50 mL/min. The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Method:

Samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation utilizing one of the following two columns and methods: (A) Using a 50×100 mm column (Waters, Exterra, C18, 5 microns) at 50 mL/min. The mobile phase used was a mixture of solvent A ($H_2O$/10 mM ammonium carbonate at pH about 10, adjusted with conc. NH4OH) and solvent B (85:15 ACN/water, 10 mM ammonium carbonate at pH of about 10 adjusted with conc. $NH_4OH$). Each purification run utilized a 10 minute gradient from 40% to 100% solvent B followed by a 5 minute flow of 100% solvent B. The gradient was followed by a 2 min return to 40% solvent B. (B) Using a 20×50 mm column at 20 mL/min. The mobile phase used was a mixture of solvent A ($H_2O$/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1$H NMR spectra were run on a Varian series Mercury 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

EXAMPLE 1

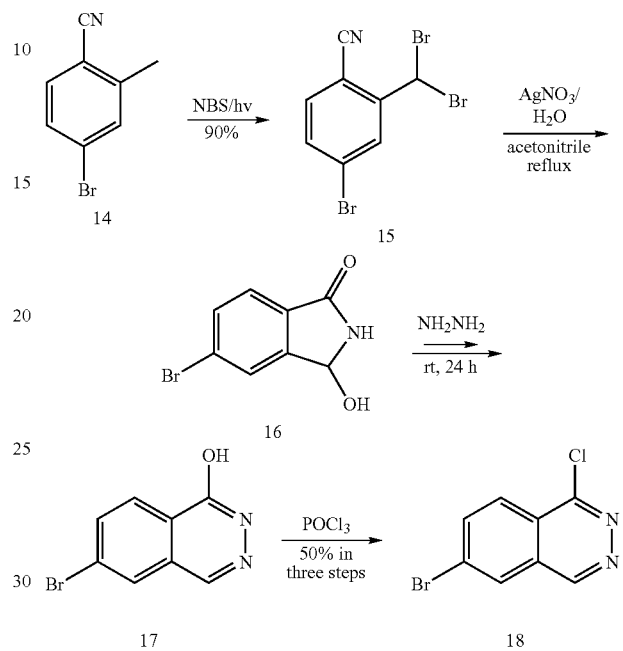

Synthesis of 6-bromo-1-chlorolphthalazine (18)

Step A: A mixture of 4-bromo-2-methylbenzonitrile (14, 22 g, 112 mmol), benzoyl peroxide (2.7 g, 11 mmol) in 400 mL carbon tetrachloride was treated with n-bromosuccimide (21 mL, 247 mmol) at room temperature, then warmed up to 90° C. and stirred for 15 h. After 15 h of reaction, another 20 g of NBS was added and the reaction was stirred at 90° C. for another 10 h. Thin layer chromatography (TLC) revealed that all the starting material had been consumed. The reaction was cooled down to room temperature, filtered, and washed with hexane (100 mL). The filtrate was concentrated in vacou, and the crude product was purified via flash chromatography (silica gel) eluting with a gradient of 4/1 hexanes/EtOAc to 2/1 hexanes/EtOAc, to give as a white solid, 4-bromo-2-(dibromomethyl)benzonitrile 15, 29.6 g. Found MS (ES+): 354 (M+H)$^+$.

Step B: To a solution of silver nitrate (AgNO$_3$, 6.86 mL, 176 mmol) in water (200 mL) refluxed under nitrogen was added 4-bromo-2-(dibromomethyl)benzonitrile (15, 29.6 g, 83.7 mmol) in 750 mL acetonitrile through a dropping funnel slowly in 1 h. The resulting mixture was refluxed under nitrogen and followed by MS periodically for 15 h (M+1=226, 228). As a TLC of the reaction showed some starting material was left, 10 g AgNO$_3$ and 50 mL H$_2$O was added and the reaction was refluxed for 96 h, after which all the starting material was consumed. The mixture was cooled down to room temperature, filtered and the filter cake was washed with 100 mL ethyl acetate. The filtrate was concentrated and neutralized with 1 N NaOH to a pH of about 7. The mixture was extracted with ethyl acetate (3×100 mL). The combined organics were washed with 50 mL brine, dried over anhydrous Na$_2$SO$_4$ and concentrated under reduced pressure. The crude product was purified via flash chromatography (silica gel) eluting with a gradient of 4/1 hexanes/EtOAc to 1/1 hexanes/EtOAc and 10% methanol to give a white solid, 5-bromo-3-hydroxyisoindolin-1-one 16, 17.6 g. Found MS (ES+): 228, 330 (M+H)$^+$.

Step C: A mixture of 5-bromo-3-hydroxyisoindolin-1-one (16, 17.0 g, 75 mmol), and hydrazine, monohydrate (60 mL, 1193 mmol) was stirred at room temperature for 15 h, after which a white solid precipitated out (M+1=225, 227). The mixture was diluted with 100 mL H$_2$O, neutralized with conc. HCl to a PH of about 7. The precipitate was filtrated and washed with 100 mL H$_2$O. The solid was collected, azeotropically dried with toluene (3×50 mL) and further dried in a vacuum oven at 45° C. for 15 h, to yield 6-bromophthalazin-1-ol 17 (16.1 g). Found MS (ES+): 225, 227 (M+H)$^+$.

Step D: A mixture of 6-bromophthalazin-1(2H)-one (17, 2.6 g, 12 mmol) in phosphorous oxychloride (11 mL, 116 mmol) was treated with diisopropylethylamine (2.0 mL, 12 mmol). The mixture was stirred at room temperature for 30 min, then warmed up to a temperature of between about 95-100° C. and stirred under nitrogen. The suspension (reaction) became a deep brown solution in about 30 min, then a yellow solid precipitated out. After about 3 h, all of the starting material was converted, as appeared by TLC, to product (M+1=243, 245). After the mixture was cooled down to room temperature, it was diluted with 50 mL CHCl$_3$ and cooled down to 0° C. The precipitate was filtrated, washed with 10 mL ice cool CHCl$_3$, collected and dried under vacuum, to afford 1.96 g of 6-bromo-1-chlorophthalazine 18, as yellow solid. Found MS (ES+): 243, 245 (M+H)$^+$.

EXAMPLE 2

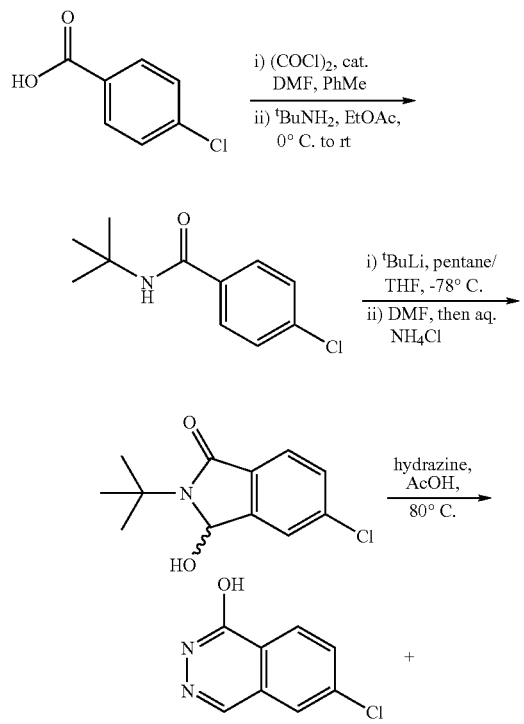

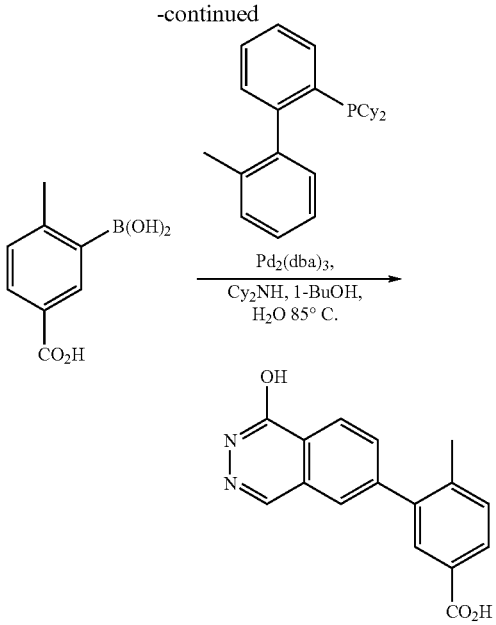

Synthesis of
3-(1-hydroxyphthalazin-6-yl)-4-methylbenzoic acid

Step A: To a stirred suspension of 4-chlorobenzoic acid (31.3 g, 200 mmol) in toluene (200 mL) was added oxalyl chloride (30 mL, 350 mmol) followed by DMF (0.1 mL). The resulting suspension was heated at reflux until all solids dissolved. The solvent was removed under reduced pressure by rotary evaporation. The resulting semi-solid residue was dissolved in ethyl acetate (200 mL) and cooled in an ice bath under nitrogen with mechanical stirring. A solution of tert-butylamine (53 mL, 500 mmol) in ethyl acetate (50 mL) was carefully added to the mixture dropwise keeping the internal temperature below 10° C. During addition the initially clear solution became thick colorless slurry. Ethyl acetate (50 mL) was added followed by sat. aq. NaHCO$_3$ (300 mL) and the resulting mixture was stirred until two clear layers resulted. The biphasic mixture was transferred into a separatory funnel, and the organic layer was separated. The organic layer was then washed with water (100 mL), brine (100 mL), and dried over anhydrous Na$_2$SO$_4$. Recrystallization from ethyl acetate/hexanes afforded N-tert-butyl-4-chlorobenzamide (35.5 g, 84% yield) as colorless needles (mp 136-137° C.).

Step B: A solution of N-tert-butyl4-chlorobenzamide (1.06 g, 5.00 mmol) in anhydrous THF (20 mL) was cooled to −78° C. under nitrogen. To the stirred solution was added dropwise tert-butyllithium solution in pentane (1.7M, 7.3 mL, 12.5 mmol), such that the internal temperature remained below −70° C. The resulting suspension gradually turned from pale to bright yellow. The mixture was stirred for an additional 1 hour at −78° C. DMF (1.5 mL, 19.5 mmol) was added dropwise to the slurry below −70° C. resulting in formation of a clear light yellow solution. The solution was allowed to warm to −20° C. (became colorless) before it was quenched with sat. aq. NH$_4$Cl (10 mL) and allowed to warm to RT. The biphasic mixture was diluted with ethyl acetate (20 mL), and the layers were seperated. The organic layer was washed with water (20 mL), brine (20 mL), and dried over anhydrous MgSO$_4$. The organic solvent was removal under reduced pressure to afford 2-tert-butyl-5-chloro-3-hydroxyisoindolin-1-one (1.18 g, 98% yield) as a colorless solid.

Step C: A suspension of 2-tert-butyl-5-chloro-3-hydroxyisoindolin-1-one (5.26 g, 21.9 mmol) in glacial acetic acid (32 mL) was heated with stirring until the mixture became a clear solution. Anhydrous hydrazine (1.0 mL, 22 mmol) was added dropwise and the resultant solution was stirred at reflux overnight. The reaction mixture was concentrated under reduced pressure. Water was added to the mixture, after which a solid material precipitated out of the solution. The solid was collected by filtration and rinsed thoroughly with water, followed by air-drying to afford 6-chlorophthalazin-1-ol (3.9 g, 98% yield) as an off-white powder (mp 271-273° C.).

Step D: A 10 mL round bottom flask was charged with 6-chlorophthalazin-1-ol (0.35 g, 1.94 mmol), 3-borono-4-methylbenzoic acid (0.42 g, 2.3 mmol), Pd$_2$(dba)$_3$ (9 mg, 9.8 μmol), and 2-(dicyclohexylphosphino)-2'-methylbiphenyl (9 mg, 25 μmol). The flask was evacuated and back-filled with nitrogen. Deoxygenated solvents, 1-butanol (2.0 mL), water (0.5 mL) and dicyclohexylamine (1.5 mL, 7.8 mmol), were added sequentially. The reaction mixture was then heated at 85° C. under nitrogen with efficient stirring overnight. 6 N NaOH aq. (2 mL, 12 mmol) was added and the reaction mixture was stirred until all solids dissolved. The reaction mixture was allowed to warm to RT and water (10 mL) was added. The reaction mixture was transferred into separatory funnel where the layers were separately collected. The aqueous layer was extracted with DCM (2×10 mL). All the organic solutions were discarded. The aqueous layer was adjusted to about pH 6 using 5N HCl. The resulting fine precipitate was collected by filtration, rinsed thoroughly with water, and air-dried. Oven drying of the solid afforded 3-(1-hydroxyphthalazin-6-yl)-4-methylbenzoic acid as a fine off-white powder.

EXAMPLE 3

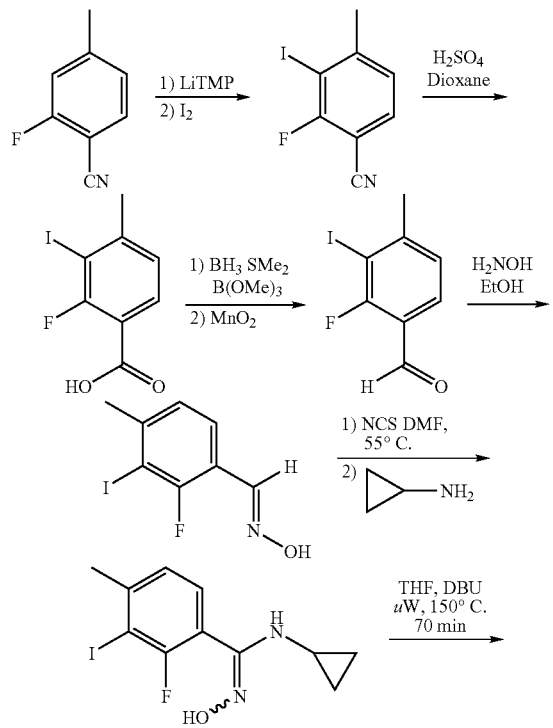

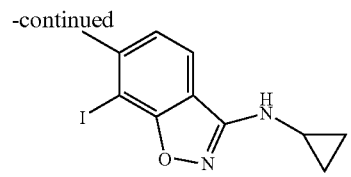

Synthesis of N-cyclopropyl-7-iodo-6-methylbenzo[d]isoxazol-3-amine

Step 1: 2-fluoro-3-iodo-4-methylbenzonitrile

A solution of 2,2,6,6-tetramethyl-4-piperidine (TMP) (45 mL, 267 mmol) in THF (400 mL) was cooled to −78° C. under an atmosphere of nitrogen. n-Butyl lithium (2.5 M in hexane, 110 mL, 275 mmol) was added slowly maintaining the temperature below −70° C. After addition, the reaction mixture was warmed to −50° C. and stirred for 30 minutes. The clear solution became turbid indicating the salt formation. The reaction mixture was recooled to −80° C., and a solution of 2-fluoro-4-methylbenzonitrile (32.4 g, 240 mmol) in THF (150 mL) was slowly added maintaining temperature below −70° C. The mixture was then warmed to −50° C. and stirred for 30 minutes. The mixture was recooled to −70° C. and a saturated solution of iodine (67 g, 264 mmol) in THF (150 mL) was added slowly maintaining the temperature at −70° C. After addition, the mixture was warmed to ambient temperature. The reaction mixture was poured into a solution of Na$_2$S$_2$O$_3$ (160 g in 1.5 L of water) and stirred for 1 h. The organic layer was separated, and the aqueous layer was extracted with ethyl acetate. The organic layers were combined, washed with brine, dried over Na$_2$SO$_4$, and filtered. The volatiles were evaporated under reduced pressure. The crude product was subjected to vacuum distillation, and at about 60° C., the excess TMP was removed, at about 100° C., the starting compound 2-fluoro-4-methylbenzonitrile and a small amount of 2-fluoro-3-iodo-4-methylbenzonitrile were removed and, finally at 115° C., pure 2-fluoro-3-iodo-4-methylbenzonitrile was obtained as an off-white amorphous solid. MS (ESI, pos. ion) m/z: 261.9 (M+1).

Step 2: 2-fluoro-3-iodo-4-methylbenzoic acid

A mixture of 2-fluoro-3-iodo-4-methylbenzonitrile (5.0 g, 19 mmol) in dioxane (10 mL) and 60% H$_2$SO$_4$ (10 mL) was heated at 115° C. in an oil bath for 18 h. After the mixture was cooled to ambient temperature, it was poured onto 30 g ice. The resulting tan solid was filtered, washed with water (2×5 mL) followed by ethyl acetate (2×30 mL), collected and dried to afford 2-fluoro-3-iodo-4-methylbenzoic acid as a tan crystalline solid. The filtrate was transferred to a separatory funnel. The ethyl acetate layer was separated, washed with brine (2×5 mL), dried and concentrated to afford additional 2-fluoro-3-iodo-4-methylbenzoic acid as a tan solid. MS (ESI, pos. ion) m/z: 280.9 (M+1).

Step 3: 2-fluoro-3-iodo-4-methylbenzaldehyde

To a solution of 2-fluoro-3-iodo-4-methylbenzoic acid (2.00 g, 7.1 mmol) in anhydrous THF (10 mL) was added trimethyl borate (0.80 mL, 7.1 mmol) at RT. The resulting mixture was stirred for 15 min, then cooled in an ice bath and treated with borane-dimethyl sulfide (6.4 mL of 2.0 M solution in THF, 12.8 mmol) slowly. The reaction mixture was stirred for 4 h at RT. Methanol (0.5 mL) was added dropwise at RT. After stirring for 30 min, the reaction mixture was concentrated under vacuum. The residue was diluted with of ethyl acetate, washed with a saturated aqueous solution of sodium bicarbonate followed by brine. The resulting organic solution was then dried over magnesium sulfate and concentrated under reduced pressure to give 2-fluoro-3-iodo-4-methylphenyl)methanol as an off-white amorphous solid, which was used without further purification.

Step 4: 2-fluoro-3-iodo-4-methylbenzaldehyde

A solution of (2-fluoro-3-iodo-4-methylphenyl)methanol (1.69 g, 6.35 mmol) in DCM (50 mL) at ambient temperature was treated with $MnO_2$ (5.57 g, 63.5 mmol) and the resulting mixture was stirred overnight. The mixture was filtered through a pad of Celite® eluting with DCM. The filtrate was concentrated and the residue was loaded on an ISCO column (40 g, eluted with 15-35% ethyl acetate in hexanes) to provide 2-fluoro-3-iodo-4-methylbenzaldehyde as an off white solid. MS (ESI, pos. ion) m/z: 264.9 (M+1).

Step) 5: (E)-2-Fluoro-3-iodo-4-methylbenzaldehyde oxime

A solution of 2-fluoro-3-iodo-4-methylbenzaldehyde (1.26 g, 4.77 mmol) in ethanol (5 mL) at RT was treated with hydroxylamine (5 mL) (50% wt. in water) and the reaction stirred for 3 h. The volatiles were removed and the residue was treated with water (5 mL), extracted with ethyl acetate (3×15 mL). The combined ethyl acetate layers were dried and concentrated. Purification on a 40 g ISCO column (eluted with 10-50% ethyl acetate in hexanes) provided the title compound as an off-white crystalline solid. MS (ESI, pos. ion) m/z: 280.0 (M+1).

Step 6: N-cyclopropyl-2-fluoro-N'-hydroxy-3-iodo-4-methylbenzamidine

To a solution of 2-fluoro-3-iodo4-methylbenzaldehyde oxime (0.48 g, 1.7 mmol) in DMF (0.5 mL) was added N-chlorosuccinimide (83 mg, 0.62 mmol) and the mixture was heated at 55° C. for 5 min. The mixture was allowed to cool to <50° C., an additional N-chlorosuccinimide (166 mg, 1.24 mmol) was added, then it was heated at 55° C. for 10 min. The reaction mixture was allowed to cool to RT, treated with water (5 mL), and extracted with ethyl acetate (3×20 mL). The combined ethyl acetate layers were washed with brine, dried and concentrated to afford the intermediate, 2-fluoro-3-iodo-4-methylbenzoyl chloride oxime as a light yellow amorphous solid, which was used without further purification. MS (ESI, pos. ion) m/z: 314.3 (M+1). Cyclopropylamine (0.60 mL, 8.6 mmol) was added dropwise to an ice-cold solution of the above obtained 2-fluoro-3-iodo-4-methylbenzoyl chloride oxime in anhydrous THF (2 mL). The reaction mixture was stirred at ambient for 3 h. The volatiles were removed under reduced pressure and the residue purified on a 40 g ISCO column (eluted with 25-60% ethyl acetate in Hexanes) to provide the title compound as an amorphous off-white solid. MS (ESI, pos. ion) m/z: 335.0 (M+1).

Step 7: N-cyclopropyl-7-iodo-6-methylbenzo[d]isoxazol-3-amine 1,8-Diazabicyclo(5.4.0)-7-undecene (0.25 mL, 1.65 mmol) was added to N-cyclopropyl-2-fluoro-N'-hydroxy-3-iodo-4-methylbenzamidine (500 mg, 1.5 mmol) in anhydrous THF (2.0 mL) then heated in a microwave at 150° C. for 70 min. The solvents were evaporated and the residue was loaded on an ISCO column (40 g, eluted with 25-75% ethyl acetate in Hexanes) to provide the title compound as an off-white crystalline solid. MS (ESI, pos. ion) m/z: 315.0 (M+1).

EXAMPLE 4

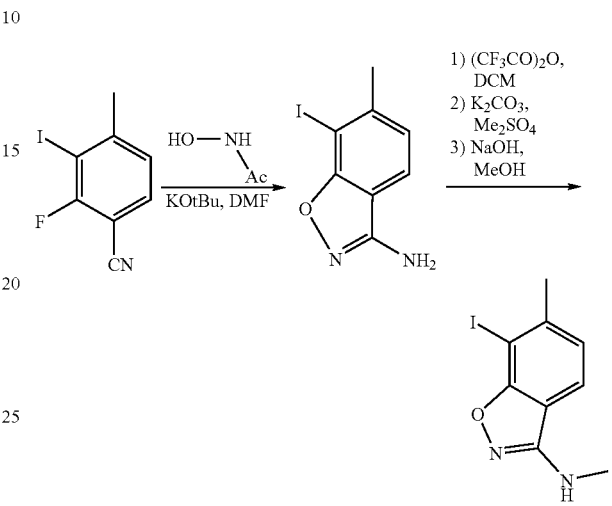

Synthesis of N-Me-7-iodo-6-methylbenzo[d]isoxazol-3-amine

Step 1: 7-Iodo-6-methylbenzo[d]isoxazol-3-amine

To a 250 mL three necked round-bottomed flask equipped with a mechanical stirrer under nitrogen was added anhydrous DMF (100 mL) and acetohydroxamic acid (4.65 g, 62 mmol). After a clear solution was obtained, potassium tert-butoxide (6.94 g, 62 mmol) was added. The cloudy white mixture was allowed to stir for 30 min. 2-Fluoro-3-iodo-4-methylbenzonitrile (8.0 g, 31 mmol) was added and the reaction mixture was allowed to stir at RT for 6 h. Additional acetohydroxarnic acid (1.16 g, 15.5 mmol) and potassium tert-butoxide (1.74 g, 15.5 mmol) were added, and stirring continued for 12 h. The reaction mixture was distilled under reduced pressure to remove most of the DMF and the residue was partitioned between ethyl acetate (250 mL) and sat. aqueous ammonium chloride (50 mL). The aqueous layer was washed with ethyl acetate (2×100 mL). The combined organic layers were washed with brine (50 mL), dried over $MgSO_4$, and then evaporated under reduced pressure. The crude product was loaded on an ISCO column (330 g, eluted with 20-70% ethyl acetate in hexanes) to provide the title compound as an offwhite crystalline solid. MS (ESI, pos. ion) m/z: 275.0 (M+1).

Step 2a: 7-Iodo-N,6-dimethylbenzo[d]isoxazol-3-amine

Trifluoroacetic anhydride (0.63 mL, 4.45 mmol) was added to a solution of 7-iodo-6-methylbenzo[d]isoxazol-3-amine (1.11 g, 4.05 mmol) in 10 mL of DCM. The mixture was stirred for 6 h. The volatiles were removed under reduced pressure to provide 2,2,2-trifluoro-N-(7-iodo-6-methylbenzo[d]isoxazol-3-yl)acetamide as an off white solid, which was used without further purification. MS (ESI, pos. ion) m/z: 370.9 (M+1).

Step 2b: To 2,2,2-trifluoro-N-(7-iodo-6-methylbenzo[d]isoxazol-3-yl)acetamide in acetone (5.0 mL) at RT was added dimethyl sulfate (766 mg, 6.07 mmol) and potassium carbonate (1.40 g, 10.12 mmol). The mixture was heated at 50° C. in an oil bath for 5 h, then cooled to RT, filtered through a pad of Celite and rinsed with additional acetone (2×5 mL). The filtrate was concentrated to dryness to provide 2,2,2-trifluoro-N-(7-iodo-6-methylbenzo[d]isoxazol-3-yl)-N-methylacetamide. MS (ESI, pos. ion) m/z: 385.0 (M+1).

Step 2c: 2,2,2-Trifluoro-N-(7-iodo-6-methylbenzo[d]isoxazol-3-yl)-N-methylacetamide was dissolved in methanol (10 mL) and was treated with of 1 N sodium hydroxide (10 mL). After the mixture was stirred at ambient for 2 h, then the solvents were removed in vacuo. The residue was treated with saturated ammonium chloride aqueous solution (20 mL) and extracted with ethyl acetate (3×50 mL). The combined organic layers were dried over Na$_2$SO$_4$ and concentrated. Purification of the residue on an ISCO (40 g column, eluted with 25-65% ethyl acetate in hexanes) provided title compound as an off white crystalline solid. MS (ESI, pos. ion) m/z: 289.0 (M+1).

EXAMPLE 5

General synthesis (scheme only) of useful Phthalazine Boronic Acid/Ester intermediates

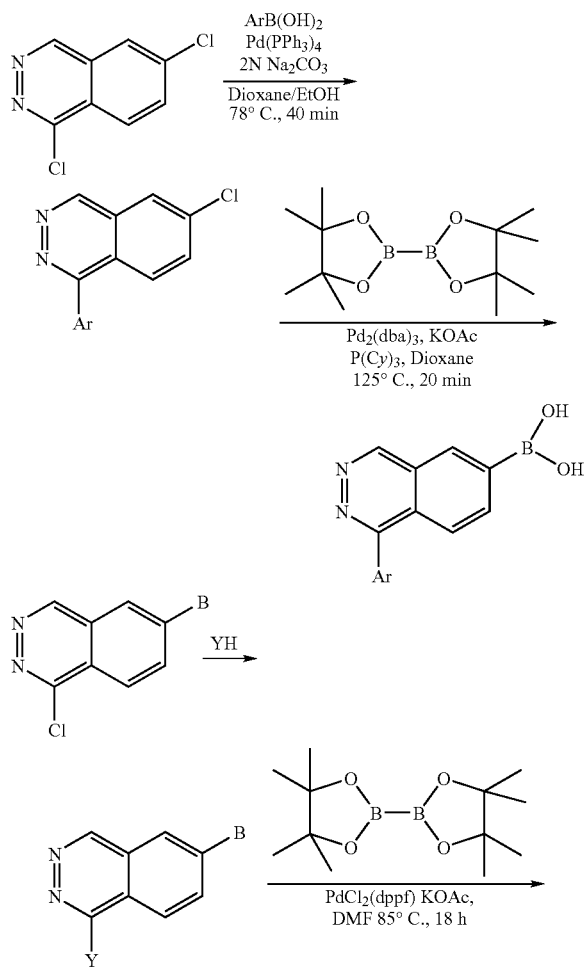

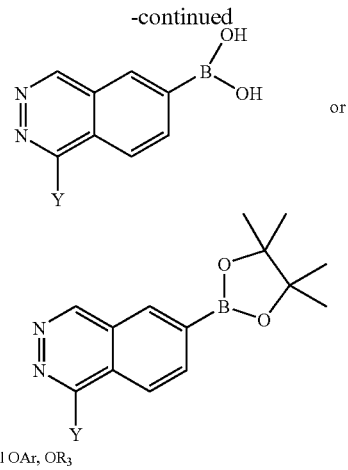

Y = NR$_1$R$_2$, Aryl OAr, OR$_3$

EXAMPLE 6

Synthesis of (S)-1-(3-Methylmorpholino)phthalazin-6-ylboronic acid

Step 1: A mixture of (S)-6-bromo-1-(3-methylmorpholino)phthalazine (1.60 g, 5.2 mmol), bis(pinacolato)diboron (2.0 g, 7.8 mmol) and potassium acetate (2.5 g, 26 mmol) in DMF (25 mL) was degassed with N$_2$ for 20 min. It was then treated with 1,1'-bis(diphenylphosphino)ferrocene-palladium dichloride (0.38 g, 0.52 mmol). The reaction mixture was stirred at 85° C. under nitrogen for 18 h. After cooling to ambient, the reaction mixture was diluted with ethyl acetate (50 mL, and filtered through a Celite® pad, and rinsed with additional ethyl acetate (2×10 mL). The filtrate was concentrated. The residue was treated with diethyl ether (50 mL) and 1 N aqueous HCl (50 mL), and then filtered through a Celite pad. The filtrate was transferred to a separatory funnel, the aqueous phase was separated, concentrated under vacuum and the brown residue was purified on a reversed phased HPLC (5-90% [0.1% TFA in acetonitrile] in [0.1% TFA in water]) to give (S)-1-(3-methylmorpholino)phthalazin-6-ylboronic acid as a light yellow amorphous solid. MS (ESI, pos.ion) m/z: 274.0 (M+1).

EXAMPLE 7

Synthesis of 1-o-Tolylphthalazin-6-ylboronic acid

Step 1: A mixture of 1,6-dichlorophthalazine (1.04 g, 5.21 mmol), tetrakis(triphenylphosphine)palldium (0.30 g, 0.26 mmol), o-tolylboronic acid (0.57 g, 4.2 mmol) in 2 N aq. sodium carbonate (5 mL), 1,4-dioxane (5 mL) and ethanol (2.5 mL) was heated in a Personal Chemistry microwave at 78° C. for 45 min. The mixture was treated with 1 N sodium hydroxide (10 mL), extracted with ethyl acetate (2×35 mL). The combined ethyl acetate layers were dried and concentrated. Purification on an ISCO column (40 g, eluted with 30-75% ethyl acetate in hexanes) provided 6-chloro-1-o-tolylphthalazine as a brown amorphous solid. MS (ESI, pos. ion.) m/z: 255 (M+1).

Step 2: In a sealed glass tube, a mixture of 6-chloro-1-o-tolylphthalazine (127 mg, 0.50 mmol), bis(pinacolato)diboron (146 mg, 0.57 mmol), potassium acetate (98 mg, 1.0 mmol), tris(dibenzylideneacetone)dipalladium (18 mg, 20 µmol) and tricyclohexylphosphine (11 mg, 40 µmol) in 1,4-dioxane (2 mL) was heated in a Personal Chemistry microwave at 125° C. for 30 min. The reaction mixture was filtered through a pad of Celite, and rinsed with ethyl acetate (5 mL). The filtrate was concentrated, then treated with 2 N aq. HCl (2 mL), and extracted with hexanes (5 mL). The acidic layer was diluted with 1 mL of DMSO and put on a reversed phase HPLC (5-90% [0.1% TFA in acetonitrile] in [0.1% TFA in water]) to provide 1-o-tolylphthalazin-6-ylboronic acid as a white fluffy solid. MS (ESI, pos. ion.) m/z: 255 (M+1).

EXAMPLE 8

(Method A)

Synthesis of N-cycloproipyl-4-methyl-3-(1-(4-methylipilerazin-1-yl)phthalazin-6-yl)benzamide Step A: A mixture of 6-bromo-1-chlorophthalazine (0.12 g, 0.5 mmol), 1-methylpiperazine (0.11 mL, 1.0 mmol) and potassium carbonate (0.07 g, 0.5 mmol) in ACN (5 mL) was added to a glass microwave reaction vessel. The reaction mixture was stirred and heated in a Smith Synthesizer® microwave reactor (Personal Chemistry, Inc., Upssala, Sweden) at 180° C. for 20 min. The mixture was concentrated in vacuo, and was purified by flash chromatography (silica gel) eluting with 2% 2 M ammonia in methanol/dichloromethane to 6% 2 M ammonia in MeOH/D)CM to give 6-bromo-1-(4-methylpiperazin-1-yl)phthalazine as yellow solid. MS (ES+): 307, 309 (M+H)$^+$.

Step B: A mixture of 6-bromo-1-(4-methylpiperazin-1-yl) phthalazine (0.13 g, 0.42 mmol), N-cyclopropyl-4-methyl-3-(4,4,5,5-tetramethyl-1,3,2-dioxaborolan-2-yl)benzamide (0.13 g, 0.42 mmol), tetrakis(triphenylphosphine)palladium (24 mg, 0.021 mmol) and 2M aq. potassium carbonate (0.7 mL, 1.4 mmol) in DME/EtOH (4:1) (5 mL) was stirred at 90° C. for 2 h. The mixture was purified via flash chromatography (silica gel) eluting with 2% 2 M ammonia in methanol/dichloromethane to 10% 2 M ammonia in MeOH/DCM to give the title compound 0.15 g as a yellow solid. MS (ES+): 402 (M+H)$^+$.

EXAMPLE 8A (Method A2)

Synthesis of N-cyclopropyl-4-methyl-3-(8-morpholin-4-ylpyrido[2,3-d]pyridazin-3-yl)benzamide Step 1: 5-Bromo-3-methylpicolinonitrile A mixture of 2,5-dibromo-3-methylpyridine (20.17 g, 80.4 mmol) and copper(I) cyanide (7.24 g, 80.8 mmol) in 200 mL DMF was heated to 115° C. overnight. The reaction mixture was cooled to 25° C. and poured into 600 mL of H$_2$O. The solid was filtered, washed with copious amounts of H$_2$O. The filtrate was extracted with EtOAc (4×) and the combined organic layers were washed with H$_2$O and dried over Na$_2$SO$_4$. The solution was filtered, evaporated onto silica gel and purified by flash chromatography eluting with EtOAc:hexane (0:1→1:9) to give the title compound as a white solid. MS m/z: 197.0 [M+1].

Step 2: Methyl 5-bromo-3-methylpicolinate

To a solution of 5-bromo-3-methylpicolinonitrile (2.55 g, 12.9 mmol) in 100 mL of MeOH was bubbled gaseous HCl at 25° C. After 1 h the bubbling was ceased and the reaction was heated at about 64° C. overnight. The reaction was cooled to RT and gaseous HCl was bubbled into the reaction for another 1 h and the mixture was reheated at 64° C. The reaction was monitored by LCMS and when complete, the solvent was removed in vacuo and the residue was dissolved in H$_2$O. The solution was basified with saturated NaHCO$_3$ and extracted with EtOAc (4×). The combined organic layers were evaporated onto silica gel and purified by flash chromatography eluting with EtOAc:hexane (0:1→1:9) to give the title compound as a white amorphous solid. MS m/z: 230.0 [M+1].

Step 3: 3-Bromopyrido[2,3-d]pyridazin-8(7H)-one

To a solution of methyl 5-bromo-3-methylpicolinate (1.785 g, 7.76 mmol) in 30 mL of CCl$_4$ was added N-bromosuccinimide (4.23 g, 23.8 mmol) and benzoyl peroxide (0.199 g, 0.822 mmol). The reaction was heated at 77° C. for 6 h. The reaction mixture was cooled to RT, filtered through a pad of Celite and washed with CCl$_4$. The filtrate was evaporated in vacuo to give a yellow oil. The oil was dissolved in 40 mL MeOH and anhydrous hydrazine (3.00 ml, 95.6 mmol) was added dropwise at 25° C. Upon complete addition the reaction mixture was heated at 78° C. overnight. The reaction mixture was cooled to RT and the solid was filtered, washed with MeOH and CHCl$_3$ and dried by suction. The filtrate was evaporated onto silica gel and purified flash chromatography eluting with 2M NH$_3$ in MeOH:CHCl$_3$ (0:1→3:47) to give the title compound as a light-yellow amorphous solid. MS m/z: 225.9, 227.9 [M+1].

Step 4: 3-Bromo-8-morpholinopyrido[2,3-d]pyridazine

A mixture of 3-bromopyrido[2,3-d]pyridazin-8(7H)-one (0.206 g, 0.91 mmol) and phosphorus oxychloride (5.00 ml, 55 mmol) was heated at 95° C. After 2 h the reaction was cooled to 25° C. and diluted with 30 mL of CHCl$_3$. The solution was cooled to 0° C. and the solid was filtered and washed with CHCl$_3$. The filtrate was concentrated to dryness and azeotroped with toluene (2×). The residue was dissolved in CH$_3$CN and heated with morpholine (0.079 ml, 0.91 mmol) at 190° C. for 15 min in the microwave. The crude material was purified by flash chromatography eluting with 2M NH$_3$ in MeOH:CH$_2$Cl$_2$ (0:1→1:24) to give the title compound as an orange amorphous solid. MS m/z: 295.0 [M+1].

Step 5: N-cyclopropyl-4-methyl-3-(8-morpholin-4-ylpyrido[2,3-d]pyridazin-3-yl)benzamide This title compound by heating a mixture of 3-bromo-8-morpholinopyrido[2,3-d]pyridazine (0.033 g, 0.11 mmol), N-cyclopropyl-4-methyl-3-(4,4,5,5-tetramethyl-1,3,2-dioxaborolan-2-yl)benzamide (0.048 g, 0.16 mmol), sodium carbonate (0.049 g, 0.46 mmol) and trans-dichlorobis(triphenylphosphine)palladium (II) (0.011 g, 0.016 mmol) in DME (2.1 mL)/H$_2$O (0.9 mL)/EtOH (0.6 mL) at 80° C. The mixture was cooled to RT, evaporated onto silica gel and purified flash chromatography eluting with 2M NH$_3$ in MeOH:CH$_2$Cl$_2$ (0:1→1:19) to give the title compound as a tan amorphous solid. MS m/z: 390.2 [M+1].

EXAMPLE 9

(Method B)

Synthesis of 3-(1-chlorophthalazin-6-yl)-N-cyclopropyl-4-methylbenzamide

Step A: A mixture of 6-bromo-1-chlorophthalazine (0.11 g, 0.5 mmol), N-cyclopropyl-4-methyl-3-(4,4,5,5-tetramethyl- 1,3,2-dioxaborolan-2-yl)benzamide (0.1 g, 0.5 mmol), and dichloro[1,1'-bis(diphenylphosphino)ferrocene]dichloride palladium(II) dichloromethane adduct (0.02 g, 0.02 mmol) in toluene (5 mL) was treated with 2 M aq. potassium carbonate (0.7 mL, 1 mmol). The mixture was stirred at 90° C. After about 15 hr, the mixture was cooled to RT and purified by flash chromatography (silica gel) eluting with 1/1 hexanes/ethyl acetate to 6% 2 M ammonia in MeOH/DCM to give the title compound as yellow solid. MS (ES+): 338 (M+H)+.

Step B: A mixture of 3-(1-chlorophthalazin-6-yl)-N-cyclopropyl-4-methylbenzamide (63 mg, 212 μmol) (obtained by method C below), 2-chlorophenylboronic acid (40 mg, 254 μmol) and tetrakis(triphenylphosphine)palladium (12 mg, 11 μmol) in DME/ethanol (4:1) (5 mL) was treated with 2 M aq. potassium carbonate (317 μl, 635 μmol). The mixture was warmed to 85° C. and stirred for 3 h. The mixture was cooled to RT and purified by flash chromatography (silica gel) eluting with 2% 2 M ammonia in MeOH/DCM to 6% 2 M ammonia MeOH/DCM to give N-cyclopropyl-4-methyl-3-(1-o-tolylphthalazin-6-yl)benzamide. MS (ES+): 394 (M+H)+.

EXAMPLE 10

(Method C)

Synthesis of 3-(1-(isopropylamino)phthalazin-6-yl)-N,4-dimethylbenzamide

Step A: To a 250 mL dry flask containing anhydrous ethanol (50 mL) stirred at 0° C. was added dropwise oxalyl chloride (54 mmol). After 5 minutes 3-(1-hydroxyphthalazin-6-yl)-4-methylbenzoic acid (18 mmol) was added in one portion, the suspension was warmed up to reflux and stirred for 3 h. The solvent was evaporated and the residue was vacuum dried at RT for about 2 h to give ethyl 3-(1-hydroxyphthalazin-6-yl)-4-methylbenzoate 5.5 g as an off white solid.

Step B: Ethyl 3-(1-hydroxyphthalazin-6-yl)-4-methylbenzoate (5.5 g) was suspended in acetonitrile (50 mL), and was treated with phosphorus oxychloride (3 mL, 36 mmol). The mixture was stirred at 90° C. for 4 h. The mixture was concentrated to remove all solvent, and redissolved in ethyl acetate (200 mL). The organic solution was washed with water (3×20 mL), brine (20 mL), and was dried over anhydrous Na$_2$SO$_4$, and concentrated in vacuo to give ethyl 3-(1-chlorophthalazin-6-yl)-4-methylbenzoate as a pale yellow solid.

Step C: Ethyl 3-(1-chlorophthalazin-6-yl)-4-methylbenzoate (1.4 g) in acetonitrile (10 mL) was treated with isopropylamine (8 mL, 89 mmol). The mixture was stirred at 140° C. (sealed tube) for 15 h. The mixture was dissolved in 100 mL dichloromethane and was washed with water (20 mL), brine (20 mL), then dried over anhydrous Na$_2$SO$_4$, concentrated in vacuo, and purified by column chromatography eluting with 50% ethyl acetate/DCM to give ethyl 3-(1-(isopropylamino)phthalazin-6-yl)-4-methylbenzoate as a white solid.

Step D: A stirred solution of ethyl 3-(1-(isopropylamino) phthalazin-6-yl)-4-methylbenzoate (4 g, 11 mmol) (obtained by method D below) in ethanol/water (4:1) (50 mL) at RT was treated with potassium hydroxide (1 g, 23 mmol). The mixture was warmed to reflux and stirred for 2 h (M+1=322). The mixture was cooled to RT, then concentrated to remove the organic solvent. The mixture was diluted with 1 N aq. sodium hydroxide (20 mL), extracted with ether (2×50 mL). The combined ether extract was washed with 1N aq. sodium hydroxide (20 mL). The combined water layer was neutralized to pH 7 with conc. HCl. The white precipitate was collected and washed with water (20 mL), azotropically dried with toluene and placed under high vacuum to give 3-(1-(isopropylamino)phthalazin-6-yl)-4-methylbenzoic acid as pale yellow solid.

Step E: A solution of 3-(1-(isopropylamino)phthalazin-6-yl)-4-methylbenzoic acid (0.22 g, 0.7 mmol) in DMF (2 mL) at RT was treated with a 2 M solution of methylamine (2 mL, 3 mmol), and HATU (0.4 g, 1 mmol). The mixture was stirred at RT for 15 h. The mixture was diluted with 100 mL DCM, washed with 20 mL sat. NaHCO$_3$, dried over anhydrous Na$_2$SO$_4$, concentrated in vacuo and purified by column eluting with 2-3% 2M ammonia MeOH/DCM to give the title compound. MS (ES+): 335 (M+H)+.

EXAMPLE 11

(Method D)

Synthesis of 3-(1-(2,4-bis(trifluoromethyl)phenyl) phthalazin-6-yl)-N-cyclopropyl-4-methylbenzamide Step A: A suspension of 3-(1-hydroxyphthalazin-6-yl)-4-methylbenzoic acid (1.0 g, 3.6 mmol) in phosphorous oxychloride (4.9 mL, 54 mmol) was heated at 80° C. for 1 h. The solution was cooled and concentrated. Toluene (10 mL) was added and removed in vacuo. The brown syrup was resuspended in DCM (20 mL) and cooled to 0° C. Diisopropylethylamine (3.1 mL, 18 mmol) followed by cyclopropylamine (3.0 mL, 43 mmol) was added and the mixture was allowed to warm up to RT and stirred for 1 hour. The mixture was concentrated and the crude product was purified by silica gel chromatography (50-100% EtOAc in hexanes) to give 610 mg of 3-(1-chlorophthalazin-6-yl)-N-cyclopropyl-4-methylbenzamide as an off-white solid. MS (ES+)=338.1 (M+H)

Step B: In a microwave tube was placed 3-(1-chlorophthalazin-6-yl)-N-cyclopropyl-4-methylbenzamide (0.097 g, 0.29 mmol), 2,4-bis(trifluoromethyl)benzeneboronic acid (0.074 g, 0.29 mmol), tetrakis(triphenylphosphine) palladium (0) (0.033 g, 0.029 mmol) and 2M potassium carbonate (0.43 mL, 0.86 mmol) in 1.5 mL of DME/EtOH (4/1). The mixture was heated in the microwave at 120° C. for 20 minutes. After cooling, water was added and the mixture was extracted with DCM. The combined organic layers were dried over sodium sulfate, filtered and concentrated. The crude product was purified by HPLC to give 3-(1-(2,4-bis(trifluoromethyl)phenyl)phthalazin-6-yl)-N-cyclopropyl-4-methylbenzamide as an off-white solid. MS (ES+)=516.2 (M+H).

EXAMPLE 12

(Method E)

Synthesis of 1-(2-chlorophenyl)-6-(4-fluorophenoxy)phthalazine

Step A: 6-(4-Fluorophenoxy)phthalazin-1-ol

A 100-mL round-bottom flask under argon was charged with 6-bromophthalazin-1-ol (0.5 g, 2 mmol), 4-fluorophenol (0.4 mL, 4 mmol), 2,2,6,6-tetramethyl-3,5-heptanedione (0.04 mL, 0.2 mmol), cesium carbonate (1 g, 4 mmol), and 1-methyl-2-pyrrolidinone (4 mL), followed by copper (I) chloride (0.1 g, 1 mmol). The reaction mixture was heated at 120° C. for 20 h. The reaction mixture was cooled, diluted with dichloromethane, and washed with water. The pH of the aqueous layer was adjusted to ~7 with saturated aqueous NaHCO$_3$ and extracted with DCM (2×). The combined organic extracts were dried (MgSO$_4$), filtered, and concentrated in vacuo. Flash chromatography eluting with 1%, 2%, 3%, and 5% MeOH/CHCl$_3$ gave the title compound. MS (ES+): 257.1 (M+H)$^+$.

Step B. 1-Chloro-6-(4-fluoroiphenoxy)phthalazine

A solution of 6-(4-fluorophenoxy)phthalazin-1-ol (61.00 mg, 0.24 mmol) in phosphorous oxychloride (1.1 mL, 12 mmol) was heated at 80° C. for 4 h. The reaction mixture was cooled, and concentrated in vacuo. The resulting oil was taken up in chloroform and carefully quenched with ice-cold saturated aqueous NaHCO$_3$, then dried (MgSO$_4$). Flash chromatography eluting with 1%, 2%, 3%, and 5% MeOH/CHCl$_3$ gave the title compound as a light brown glassy foam. MS (ES+): 275.0 (M+H)$^+$.

Step C. 1-(2-Chlorophenyl)-6-(4-fluorophenoxy)phthalazine

A 10 mL round-bottomed flask under argon was charged with 1-chloro-6-(4-fluorophenoxy)phthalazine (42.90 mg, 0.15 mmol), tetrakis(triphenylphosphine)palladium (9 mg, 0.008 mmol), 2-chlorophenylboronic acid (37 mg, 0.23 mmol), ethylene glycol dimethyl ether (1.6 mL), and ethanol (0.4 mL), followed by 2M aqueous sodium carbonate solution (0.23 mL, 0.45 mmol). The reaction was stirred at 90° C. for 3 h. The cooled reaction mixture was diluted with DCM and washed with saturated aqueous NaHCO$_3$ and brine, then dried (MgSO$_4$). Flash chromatography eluting with a gradient of 25:10:65, 40:10:50, 50:10:40, 60:10:30, and 70:10:20 ethyl acetate-dichloromethane-hexanes gave the title compound as a tan amorphous solid. MS (ES+): 351.1 (M+H)$^+$.

EXAMPLE 13

(Method F)

Synthesis of N-Cyclopropyl-3-(1-isopropylphthalazin-6-yl)-4-methylbenzamide

Step A. Ethyl 3-(1-isopropylphthalazin-6-yl)4-methylbenzoate

A 50-mL round-bottom flask under argon was charged with ethyl 3-(1-chlorophthalazin-6-yl)-4-methylbenzoate (106 mg, 0.32 mmol), iron(III) acetylacetonate (5.7 mg, 0.032 mmol), tetrahydrofuran (2.2 mL), and 1-methyl-2-pyrrolidinone (0.22 mL). Isopropylmagnesium chloride (0.24 mL, 0.49 mmol) was added via a syringe to the resulting red solution, causing an immediate color change to brown, and then finally to dark brown. The resulting mixture was stirred for 10 min, and the reaction was diluted with ethyl acetate and carefully quenched with 10% HCl solution. The mixture was washed with saturated aqueous NaHCO$_3$ solution and the organic layer was dried (MgSO$_4$) and concentrated in vacuo. CombiFlash purification (20% to 50% ethyl acetate in hexanes) afforded the title compound as a cream amorphous solid. MS (ES+): 335.2 (M+H)$^+$.

Step B. 3-(1-Isopropylphthalazin-6-yl)4-methylbenzoic acid

A solution of ethyl 3-(1-isopropylphthalazin-6-yl)-4-methylbenzoate (37.5 mg, 0.11 mmol) in tetrahydrofuran (0.3 mL) and methanol (0.15 mL) was treated with 1N aq. sodium hydroxide (0.28 mL, 0.28 mmol) and stirred at RT for 18 h. The reaction mixture was concentrated in vacuo and the residue was taken up in water. The pH was adjusted with 10% HCl solution to ~7. The precipitate formed was collected via filtration and dried under high vacuum to afford the title compound as a maize-colored solid. MS (ES+): 307.2 (M+H)$^+$.

Step C. N-Cyclopropyl-3-(1-isopropylphthalazin-6-yl)-4-methylbenzamide

A 10-mL round-bottom flask was charged with 3-(1-isopropylphthalazin-6-yl)-4-methylbenzoic acid (32 mg, 0.10 mmol), HATU (60 mg, 0.157 mmol), and N,N-dimethylformamide (0.5 mL), followed by cyclopropylamine (0.03 mL, 0.52 mmol). The resulting golden yellow mixture was stirred at RT for 18 h. The reaction mixture was diluted with ethyl acetate and washed with water and brine, then dried (MgSO$_4$) and concentrated in vacuo. CombiFlash purification (20% to 70% ethyl acetate in Hexane) afforded the title compound as an off-white amorphous solid. MS (ES+): 346.2 (M+H)$^+$.

EXAMPLE 14

(Method G)

Synthesis of N-cyclopropyl-6-methyl-7-(1-((S)-3-methylmorpholino)phthalazin-6-yl)benzo[d]isoxazol-3-amine A mixture of (S)-1-(3-methylmorpholino)phthalazin-6-yl-boronic acid (0.11 g, 0.41 mmol), N-cyclopropyl-7-iodo-6-methylbenzo[d]isoxazol-3-amine (0.100 g, 0.32 mmol), tetrakis(triphenylphosphine)palladium (18 mg, 0.016 mmol) in 1,4-dioxane (2.0 mL) and 2 N aqueous sodium carbonate (0.2 mL, 0.4 mmol) in a sealed glass tube was heated in a Personal Chemistry microwave at 130° C. for 20 min. The mixture was diluted with EtOAc (30 mL) and washed with saturated aqueous solution of sodium bicarbonate, and brine. The resulting organic solution was then dried over magnesium sulfate and concentrated under reduced pressure. Flash chromatography on silica gel (ethyl acetate: chloroform 80:20) afforded the titled compound as a yellow solid. MS (ESI, pos.ion) m/z: 416.1 (M+1).

EXAMPLE 15

(Method H)

Synthesis of 6-chloro-N-methyl-7-(1-((S)-3-methylmorpholino)phthalazin-6-yl)benzo[d]isoxazol-3-amine Step 1: (4-Chloro-2-fluorobenzyloxy)(tert-butyl)dimethylsilane To a stirred solution of (4-chloro-2-fluorophenyl)methanol (4.60 g, 28.6 mmol) in THF (100 mL) was added 1H-imidazole (1.95 g, 28.6 mmol) and tert-butylchlorodimethylsilane (4.32 g, 28.6 mmol) at room temperature. The reaction mixture was stirred for 12 h at RT. The white precipitate was filtered and the filtrate was washed with 0.1 N aqueous HCl. The separated aqueous phase was extracted with diethyl ether (2×40 mL). The combined organic phases were washed with saturated aqueous solution of sodium bicarbonate, and brine. The resulting organic solution was dried over magnesium sulfate and concentrated under reduced pressure. Flash chromatography on silica (hexanes) gave (4-chloro-2-fluorobenzyloxy)(tert-butyl)dimethylsilane as colorless oil. $^1$H NMR (300 MHz, CHLOROFORM-d) δ ppm 7.31 (1H, t, J=8.1 Hz), 7.01 (1H, d, J=8.3 Hz), 6.91 (1 H, dd, J=9.9, 1.8 Hz), 4.64 (2H, s), 0.73-0.86 (9H, m), -0.06 (6H, s)

Step 2: (4-Chloro-2-fluoro-3-iodobenzaloxy)(tert-butyl)dimethylsilane

To a stirred solution of diisopropylamine (3.09 mL, 21.8 mmol) in THF (60 mL) under at 0° C. was added n-butyllithium (6.83 mL, 20.0 mmol) dropwise over 5 min. After 10 min, the reaction mixture was cooled to −78° C., and a solution of (4-chloro-2-fluorobenzyloxy)(tert-butyl)dimethylsilane (5.00 g, 18.2 mmol) in THF (15 mL) was added slowly over 5 min. After 2 h at −78° C., a solution of iodine (5.54 g, 21.8 mmol) in THF (25 mL) was added over 10 min. After a further 20 min at −78° C., the reaction mixture was warmed to RT and was quenched with sodium thiosulfate, followed by water (100 mL). The separated aqueous solution was extracted with diethyl ether (2×60 mL). The combined organic phases were washed with saturated aqueous solution of sodium bicarbonate, and brine. The resulting organic solution was then dried over magnesium sulfate and concentrated under reduced pressure. Flash chromatography on silica gel (dichloromethane: hexane=10:90) gave (4-chloro-2-fluoro-3-iodobenzyloxy)(tert-butyl)dimethylsilane as colorless oil. 1H NMR (300 MHz, CDCl$_3$) δ ppm 7.30 (1H, t, J=7.5 Hz), 7.17 (1H, d, J=7.1 Hz), 4.65 (2H, s), 0.75-0.85 (9H, m), 0.01 (6 H, s)

Step 3: (4-Chloro-2-fluoro-3-iodophenyl)methanol

To a solution of (4-chloro-2-fluoro-3-iodobenzyloxy)(tert-butyl)dimethylsilane (6.64 g, 16.6 mmol) in THF (60 mL) was added tetrabutylammonium fluoride, 1.0 M in THF (19.9 mL, 19.9 mmol). The reaction solution was stirred at RT for 1 h. The volatile solvents were removed in vacuo. The residue was diluted with diethyl ether (150 mL), and then washed with saturated aqueous solution of sodium bicarbonate, and brine. The resulting organic solution was then dried over magnesium sulfate and concentrated under reduced pressure. Flash chromatography on silica gel (dichloromethane) gave (4-chloro-2-fluoro-3-iodophenyl)methanol as a colorless oil. 1H NMR (300 MHz, CDCl$_3$) δ ppm 7.16-7.32 (2H, m), 4.66 (2H, d, J=5.7 Hz), 1.90 (1H, t, J=6.0 Hz)

Step 4: 4-Chloro-2-fluoro-3-iodobenzaldehyde

To a solution of (4-chloro-2-fluoro-3-iodophenyl)methanol (4.00 g, 14.0 mmol) in DCM (50 mL) was added manganese oxide (18.2 g, 209 mmol). The reaction mixture was refluxed for 10 h, then filtered through Celite® pad. The filtrate was concentrated under reduced pressure. Flash chromatography on silica gel (dichloromethane:hexane=20:80) gave 4-chloro-2-fluoro-3-iodobenzaldehyde as a white solid. MS (ESI, pos.ion) n/z: 286.2 (M+1)

Step 5: 4-Chloro-2-fluoro-3-iodobenzaldehyde oxime

A solution of 4-chloro-2-fluoro-3-iodobenzaldehyde (4.60 g, 16 mmol) in ethanol (25 mL) at RT was treated with hydroxylamine (4.5 mL, 162 mmol) and the reaction was to stir for 12 h. The volatiles were removed and the residue was treated with water (25 mL), and extracted with ethyl acetate (3×25 mL). The combined ethyl acetate layers were dried over magnesium sulfate and concentrated to provide an off white solid 4-chloro-2-fluoro-3-iodobenzaldehyde oxime. MS (ESI, pos.ion) m/z: 299.9 (M+1)

Step 6: 4-Chloro-2-fluoro-3-iodobenzoyl chloride oxime

To a solution of 4-chloro-2-fluoro-3-iodobenzaldehyde oxime (0.860 g, 2.87 mmol) in DMF (5 mL) at RT was added N-chlorosuccinimide (140 mg). The mixture was heated at 55° C. for 5 min. The mixture was allowed to cool below 50° C. and additional N-chlorosuccinimide (282 mg) was added, and heating continued at 55° C. for 20 min. The resulting reaction mixture was allowed to cool to RT and treated with water (20 mL), and extracted with ethyl acetate (3×30 mL). The combined ethyl acetate layers were washed with brine, dried over magnesium sulfate and concentrated to afford 4-chloro-2-fluoro-3-iodobenzoyl chloride oxime as a light yellow amorphous solid. MS (ESI, pos.ion) m/z: 335 (M+1)

Step 7: 4-chloro-2-fluoro-N'-hydroxy-3-iodo-N-methylbenzamidine

Methylamine (33% wt solution in absolute ethanol, 1.9 mL, 18 mmol) was added dropwise to a solution of 4-chloro-2-fluoro-3-iodobenzoyl chloride oxime (0.600 g, 1.8 mmol) in anhydrous THF (10 mL) at 0° C. The reaction mixture was stirred at RT for 1 h. The volatile solvents were removed under reduced pressure. Flash chromatography on silica gel (dichloromethane:hexane 25:75) gave 4-chloro-2-fluoro-N'-hydroxy-3-iodo-N-methylbenzamidine as an amorphous white solid. MS (ESI, pos.ion) m/z: 330.9 (M+1)

Step 8: 6-chloro-7-iodo-N-methylbenzo[d]isoxazol-3-amine 1,8-diazabicyclo[5.4.0]undec-7-ene (0.102 g, 0.670 mmol) was added to a solution of 4-chloro-2-fluoro-N'-hydroxy-3-iodo-N-methylbenzamidine (0.200 g, 0.609 mmol) in THF (2 mL) in a sealed microwave tube. The reaction mixture was heated in a microwave at 165° C. for 80 min. The resulting mixture was purified by flash chromatography on silica gel (dichloromethane:hexane 10:90) to give 6-chloro-7-iodo-N-methylbenzo[d]isoxazol-3-amine as an off white solid. MS (ESI, pos.ion) m/z: 308.9 (M+1)

Step 9: 6-chloro-N-methyl-7-(1-((S)-3-methylmorpholino)phthalazin-6-yl)benzo[d]isoxazol-3-amine The title compound was prepared according to the procedure described in Example 14, Method G above. MS (ESI, pos.ion) m/z: 410.2 (M+1)

EXAMPLE 16

(Method I)

Synthesis of N-tert-butyl-7-(1-((S)-3-methylmorpholino)phthalazin-6-yl)-4-(trifluoromethyl)benzo[d]isoxazol-3-amine Step 1: 3-bromo-2-fluoro-6-(trifluoromethyl)benzaldehyde To a solution of diisopropylamine (2.01 mL, 14.2 mmol) with THF (20 mL) was added n-butyllithium (4.42 mL, 13.0 mmol) slowly at 0° C. After 10 min, the reaction solution was cooled to −78° C., and 2-bromo-3-fluorobenzotrifluoride (3.00 g, 12.3 mmol) in THF (10 mL) was added dropwise over 5 min. After 1 h at −78° C., anhydrous dimethylformamide (1.14 mL, 14.8 mmol) was added dropwise over 5 min. After further 30 min at −78° C., the reaction mixture was quenched by the rapid addition of acetic acid (4 mL), followed quickly by water (50 mL). The cold solution was quickly extracted with diethyl ether (3×50 mL), and the combined organic extracts were washed with dilute HCl (0.2 M, 40 mL), water (50 mL), brine (50 mL), and dried over MgSO$_4$. Flash chromatography on silica gel (dichloromethane:hexane 10:90) gave 3-bromo-2-fluoro-6-(trifluoromethyl)benzaldehyde (3.22 g, 11.9 mmol, 96.2% yield) as an off white solid. MS (ESI, pos.ion) m/z: 271.0 (M+1)

Step 2: 3-bromo-2-fluoro-6-(trifluoromethyl)benzaldehyde oxime

The title compound was prepared according to the procedure described in Step 5 of Example 15 for 4-chloro-2-fluoro-3-iodobenzaldehyde oxime. MS (ESI, pos.ion) m/z: 287.9 (M+1)

Step 3: 3-bromo-2-fluoro-6-(trifluoromethyl)benzoyl chloride oxime

The title compound was prepared according to the procedure described in Step 6 of Example 15. MS (ESI, pos.ion) m/z: 321 (M+1)

Step 4: 3-bromo-N-tert-butyl-2-fluoro-N'-hydroxy-6-(trifluoromethyl)benzamidine

The title compound was prepared according to the procedure described in described in Step 7 of Example 15. MS (ESI, pos.ion) m/z: 358.1 (M+1)

Step 5: 7-bromo-N-tert-butyl-4-(trifluoromethyl)benzo[d]isoxazol-3-amine

The title compound was prepared according to the procedure described in described in Step 8 of Example 15. MS (ESI, pos.ion) m/z: 338.0 (M+1)

Step 6: N-tert-butyl-7-(1-((S)-3-methylmorpholino)phthalazin-6-yl)-4-(trifluoromethyl)benzo[d]isoxazol-3-amine The title compound was prepared according to the procedure described in Example 14, Method G above. MS (ESI, pos.ion) m/z: 487.2 (M+1)

EXAMPLE 17

(Method J)

Synthesis of 1-(3-(4-chlorophenyl)morpholino)-6-o-tolylphthalazine

Step 1: N,N-diisopropyl 4-(2-methylphenyl)benzamide

To a suspension of 4-(2-methylphenyl)benzoic acid (4.00 g, 18.8 mmol) in DCM (150 mL) was added oxalyl chloride (10.00 g, 78.8 mmol) followed by 5 drops of DMF. The reaction mixture was stirred at RT for 3 h until a clear solution resulted. The solvent was removed in vacuo. The residue was dissolved with DCM (100 mL) and treated with aq. potassium carbonate (3.41 mL, 56.5 mmol). The reaction mixture was cooled to 0° C., and a solution of diisopropylamine (5.33 mL, 37.7 mmol) in DCM (50 mL) was added dropwise. The resulting mixture was stirred at RT over 12 h. The resulting mixture was quenched by the slow addition of saturated aqueous Na$_2$CO$_3$ (100 mL). The organic phase was separated and aqueous phase was extracted with dichloromethane (3×60 mL). The combined organic phases were washed with brine. The resulting organic solution was then dried over magnesium sulfate and concentrated under reduced pressure to give N,N-diisopropyl 4-(2-methylphenyl)benzamide as an off-white solid. MS (ESI, pos.ion) m/z: 296 (M+1)

Step 2: N,N-diisopropyl [2-formyl-4-(2-methylphenyl)benzamide

To a cooled solution of N,N-diisopropyl [4-(2-methylphenyl)benzamide (5.50 g, 19 mmol) in anhydrous THF (50 mL) at −70° C. was added dropwise a solution of tert-butyllithium, 1.7 M in pentane (13 mL, 22 mmol). The yellow mixture was stirred at −78° C. for 30 min, after which dimethylformamide (5.7 mL, 74 mmol) was added dropwise such that the internal temperature was maintained at −70° C. The resultant mixture was stirred at this temperature over 15 min and then was allowed to warm to RT and stood for 40 min. The brown solution was quenched by slow addition of saturated aqueous NH$_4$Cl (100 mL), keeping the internal temperature below 0° C. The resulting mixture was diluted with diethyl ether (100 mL), and stirred at RT for 10 min. The organic phase was separated and aqueous phase was extracted with diethyl ether (3×60 mL). The combined organic phases were washed with brine. The resulting organic solution was then dried over magnesium sulfate and concentrated under reduced pressure to give N,N-diisopropyl 2-formyl-4-(2-methylphenyl)benzamide as a yellow solid. MS (ESI, pos.ion) m/z: 324.2 (M+1)

Step 3: 6-o-tolylphthalazin-1-ol

To a solution of N,N-diisopropyl 2-formyl-4-(2-methylphenyl)benzamide (5.45 g, 12 mmol) in acetic acid (15 mL) was added anhydrous hydrazine (0.56 mL, 18 mmol). The resulting solution was then heated at 110° C. for 16 h. The reaction mixture was cooled to RT, and the volatiles removed in vacuo. The residue was diluted with ethyl acetate (150 mL) and washed with saturated aqueous solution of sodium bicarbonate, and brine. The resulting organic solution was then dried over magnesium sulfate and concentrated under reduced pressure to give 6-o-tolylphthalazin-1-ol as a yellow solid. MS (ESI, pos.ion) m/z: 237.2 (M+1)

Step 4: 1-chloro-6-o-tolylphthalazine

A mixture of 6-o-tolylphthalazin-1-ol (3.65 g, 15 mmol) and phosphorus oxychloride (15 mL, 161 mmol) was stirred at 110° C. for 16 h. After cooling to RT, the phosphorus oxychloride was removed in vacuo. The residue was diluted with ethyl acetate (100 mL) and washed with saturated aqueous Na$_2$O$_3$ and brine. The organic solution was dried over magnesium sulfate, and concentrated under reduced pressure. Flash chromatography on silica gel (ethyl acetate: hexane 60:40) gave 1-chloro-6-o-tolylphthalazine as a yellow solid. MS (ESI, pos.ion) m/z: 255.0 (M+1)

Step 5: 1-(3-(4-chlorophenyl)morpholino)-6-o-tolylphthalazine

A solution of 1-chloro-6-o-tolylphthalazine (0.100 g, 0.393 mmol) in NMP (2 mL) was treated with 3-(4-chlorophenyl)morpholine (0.155 g, 0.785 mmol) and diisopropylethylamine (0.219 mL, 1.26 mmol). The reaction solution was stirred at 120° C. in a sealed tube for 16 hours. After cooling to RT, the reaction solution was treated with saturated aqueous $Na_2CO_3$ (50 mL). The mixture was extracted with ethyl acetate (3×60 mL) and the combined organic phases were washed with brine. The organic solution was dried over magnesium sulfate and concentrated under reduced pressure. Flash chromatography on silica gel (ethyl acetate) gave 1-(3-(4-chlorophenyl)morpholino)-6-o-tolylphthalazine as a yellow solid. MS (ESI, pos.ion) m/z: 416.1 (M+1).

EXAMPLE 18

(Method K)

Synthesis of N-cyclopropyl-3-[1-(2,4-dimethylphenyl)phthalazin-6-yl]-4-methylbenzamide

Step 1: 1,6-dichlorophthalazine

A mixture of 6-chlorophthalazin-1 (2H)-one (10.0 g, 55.4 mmol) and phosphoryl trichloride (50.0 mL, 538 mmol, Aldrich) was heated to 105° C. for 8 h. After cooling to RT, the mixture was concentrated, re-dissolved in $CH_2Cl_2$ and neutralized with sat aq. $NaHCO_3$. After stirring for 3 h, the organic layer was collected and the aqueous layer was extracted with $CH_2Cl_2$ (3×). The combined organics were dried over $Na_2SO_4$, filtered through a $SiO_2$, eluting with EtOAc, and concentrated to give the title compound as a tan solid. MS (ESI, pos. ion) m/z: 199 (M+1).

Step 2: 6-chloro-1-(2.4-dimethylphenyl)phthalazine

A mixture of 1,6-dichlorophthalazine (300 mg, 1507 µmol), 2,4-dimethylphenylboronic acid (249 mg, 1658 µmol), $Pd(PPh_3)_2Cl_2$ (52.9 mg, 75.4 µmol, Strem), and sodium carbonate (479 mg, 4522 µmol) in DME:EtOH:$H_2O$=7:2:3 (5 mL) was heated to 130° C. for 5 min in the Emrys Optimizer microwave. The mixture was diluted with MeOH and $H_2O$ and concentrated over $SiO_2$. The residue was purified with flash chromatography (MeOH/$CH_2Cl_2$=0→2%) to afford the title compound. MS (ESI, pos. ion) m/z: 269 (M+1).

Step 3: N-cyclopropyl-3-(1-(2,4-dimethylphenyl)phthalazin-6-yl)-4-methylbenzamide A mixture of 6-chloro-1-(2,4-dimethylphenyl)phthalazine (150 mg, 558 µmol), N-cyclopropyl-4-methyl-3-(4,4,5,5-tetramethyl-1,3,2-dioxaborolan-2-yl)benzamide (437 mg, 1450 µmol), 2-(dicyclohexylphosphino)-2'-methylbiphenyl (18.3 mg, 50.2 µmol, Strem), $Pd_2(dba)_3$ (15.3 mg, 16.7 µmol, Strem), and potassium carbonate (231 mg, 1674 µmol) in Dioxane:$H_2O$=4:1 (5 mL) was heated to 80° C. for 18 h. After cooling to room temperature, the mixture was diluted with MeOH and concentrated over $SiO_2$. The residue was purified with column chromatography (MeOH/$CH_2Cl_2$=0-4%). The residue was purified with reverse-phase chromatography (Phenomenex Synergi 4m Max RP 80 A column, 150×21 mm, 20 mL/min, 10-95% $CH_3CN/H_2O$, 0.1% TFA, 10.5 min gradient). Yield: 113 mg (50%). MS (ESI, pos. ion) m/z: 408 (M+1).

EXAMPLE 19

Synthesis of 3-(1-(cyclohexylamino)phthalazin-6-yl)-N-cyclopropyl-4-methylbenzamide Step A: A mixture of 6-bromo-I-chlorophthalazine (Example 1, 0.245 g, 1 mmol), cyclohexanamine (0.22 g, 2 mmol) and potassium carbonate (0.14 g, 1 mmol) in 5 mL acetonitrile were added to a glass microwave reaction vessel. The reaction mixture was stirred and heated in a Smith Synthesizer® microwave reactor (Personal Chemistry, Inc., Upssala, Sweden) at 180° C. for 20 min. After 20 min., all starting material was converted to product (M+1=306, 308). The mixture was concentrated under vacuum, and purified via flash chromatography (silica gel) eluting with a gradient of 2% 2 M ammonia in MeOH/DCM to 6% 2 M ammonia in MeOH/DCM to give (0.21 g) 6-bromo-N-cyclohexylphthalazin-1-amine as a yellow solid. Found MS (ES+): 306, 308(M+H)⁺.

Step B: The mixture of 6-bromo-N-cyclohexylphthalazin-1-amine (0.2 g, 0.65 mmol), N-cyclopropyl-4-methyl-3-(4,4,5,5-tetramethyl-1,3,2-dioxaborolan-2-yl)benzamide (0.2 g, 0.65 mmol), tetrakis(triphenylphosphine)palladium (38 mg, 0.0325 mmol) and 2M potassium carbonate (1 mL, 1.95 mmol) in 5 mL DME/EtOH (4:1) was stirred at 90° C. for 2 h. (Product MS found to be M+1=401). The mixture was transferred directly to a column and purified via flash chromatography (silica gel) eluting with a gradient of 2% 2 M ammonia in MeOH/DCM to 10% 2 M ammonia in MeOH/DCM to give the title compound (0.17 g) as a yellow solid. Found MS (ES+): 401(M+H)⁺.

EXAMPLE 20

Synthesis of 3-(1-(2,5-diaza-bicyclo[2.2.1]heptan-2-yl)phthalazin-6-yl)-N-cyclopropyl-4-methylbenzamide Step A: A mixture of 6-bromo-1-chlorophthalazine (Example 1, 0.245 g, 1 mmol), (s,s) tert-butyl 2,5-diaza-bicyclo [2.2.1]heptane-2-carboxylate (0.22 g, 1.1 mmol) and potassium carbonate (0.14 g, 1 mmol) in 5 mL acetonitrile was added to a glass microwave reaction vessel. The reaction mixture was stirred and heated in a Smith Synthesizer® microwave reactor (Personal Chemistry, Inc., Upssala, Sweden) at 180° C. for 20 min. After about 20 min., all starting material was converted to product (M+1=405, 407). The mixture was concentrated under vacuum, and purified via flash chromatography (silica gel) eluting with 1:1 hexane/ethyl acetate to give (0.18 g) tert-butyl 5-(6-bromophthalazin-1-yl)-2,5-diaza-bicyclo[2.2.1]heptane-2-carboxylate as a yellow solid. Found MS (ES+): 405, 407(M+H)⁺.

Step B: A mixture of tert-butyl 5-(6-bromophthalazin-1-yl)-2,5-diaza-bicyclo[2.2.1]heptane-2-carboxylate (0.18 g, 0.44 mmol), N-cyclopropyl-4-methyl-3-(4,4,5,5-tetramethyl-1,3,2-dioxaborolan-2-yl)benzamide (0.14g, 0.44 mmol), tetrakis(triphenylphosphine)palladium (25 mg, 0.022 mmol) and 2 M potassium carbonate (0.66 mL, 1.32 mmol) in 5 mL DME/EtOH (4:1) was stirred at 90° C. for 2 h. The mixture was transferred directly to a column and purified via flash chromatography (silica gel) eluting with a gradient of 2% 2 M ammonia in MeOH/DCM to 10% 2M ammonia in MeOH/DCM to give tert-butyl 5-(6-(5-(cyclopropylcarbamoyl)-2-methylphenyl) phthalazin-1-yl)-2,5-diaza-bicyclo [2.2.1]heptane-2-carboxylate (0.20 g) as a yellow solid. Found MS (ES+): 500(M+H)⁺.

Steps C: A mixture of tert-butyl 5-(6-(5-(cyclopropylcarbamoyl)-2-methylphenyl)phthalazin-1-yl)-2,5-diaza-bicyclo[2.2.1]heptane-2-carboxylate (0.18 g, 360 μmol) in 10 mL methanol stirred at 0° C. under nitrogen was treated with 1 mL of 4 M HCl in dioxane. The mixture was stirred at a temperature of between about 0-22° C. for about 2 h. After 2 h of reacting at 22° C., MS and TLC showed all SM was converted to product (M+1=400). The mixture was concentrated in vacuo, diluted with 100 mL DCM, washed with sat. NaHCO$_3$ 50 mL, dried over anhydrous Na$_2$SO$_4$, filtered and filtrate concentrated via vacou. After purification by column chromatography (eluted with solvent gradient of 5-15% 2 M ammonia in methanol to DCM), the title compound was obtained as a pale yellow solid (46mg). Found MS (ES+): 400(M+H)$^+$.

EXAMPLE 21

Synthesis of N-cyclopropyl-4-methyl-3-(1-(piperazin-1-yl)phthalazin-6-yl)benzamide Step A: A mixture of 6-bromo-1-chlorophthalazine (Example 1, 0.146 g, 0.6 mmol), piperazine (0.1 g, 1.2 mmol) and potassium carbonate (0.08 g, 0.6 mmol) in 5 mL acetonitrile was added to a glass microwave reaction vessel. The reaction mixture was stirred and heated in a Smith Synthesizer® microwave reactor (Personal Chemistry, Inc., Upssala, Sweden) at 180° C. for 20 min. After about 20 min., all starting material was converted to product (M+1=293, 295). The mixture was concentrated under vacuum, and purified via flash chromatography (silica gel) eluting with a gradient of 2% 2M ammonia in MeOH/DCM to 6% 2M ammonia in MeOH/DCM to give (0.113 g) 6-bromo-1-(piperazin-1-yl)phthalazine as a yellow solid. Found MS (ES+): 293, 295(M+H)$^+$.

Step B: A mixture of 6-bromo-1-(piperazin-1-yl)phthalazine (0.12g, 0.41 mmol), N-cyclopropyl-4-methyl-3-(4,4,5,5-tetramethyl-1,3,2-dioxaborolan-2-yl)benzamide (0.12g, 0.41 mmol), tetrakis(triphenylphosphine)palladium (24mg, 0.0205 mmol) and 2 M potassium carbonate (0.7 mL, 1.4 mmol) in 5 mL DME/EtOH (4:1) was stirred at 90° C. for 2 h. The mixture was directly purified via flash chromatography (silica gel) with a gradient of 2% 2 M ammonia in MeOH/DCM to 10% 2 M ammonia in MeOH/DCM to give the title compound (0.14g) as a yellow solid. Found MS (ES+): 388 (M+H)$^+$.

EXAMPLE 22

Synthesis of 3-(1-chlorophthalazin-6-yl)-N-cyclopropyl-4-methylbenzamide

A mixture of 6-bromo-1-chlorophthalazine (Example 1, 0.11 g, 0.5 mmol), N-cyclopropyl-4-methyl-3-(4,4,5,5-tetramethyl-1,3,2-dioxaborolan-2-yl)benzamide (0.1 g, 0.5 mmol), and dichloro[1,1'-bis(diphenylphosphino)ferrocene] dichloride palladium(ii) dichloromethane adduct (0.02 g, 0.02 mmol) in 5 mL toluene was treated with 2 M potassium carbonate (0.7 mL, 1 mmol). The mixture was stirred at 90° C. and followed by MS (product M+1=338) for 15 h. The mixture was cooled down to room temperature and purified directly via flash chromatography (silica gel) eluting with a gradient of 1/1 hexanes/EtOAc to 6% 2M ammonia in MeOH/DCM to give the title compound (0.12 g) as a yellow solid. Found MS (ES+): 338(M+H)$^+$.

EXAMPLE 23

Synthesis of N-cyclopropyl-4-methyl-3-(1-(4-methylpiperazin-1-yl)phthalazin-6-yl)benzamide Step A: A mixture of 6-bromo-1-chlorophthalazine (Example 1, 0.12 g, 0.5 mmol), 1-methylpiperazine (0.11 mL, 1.0 mmol) and potassium carbonate (0.07 g, 0.5 mmol) in 5 mL acetonitrile was added to a glass microwave reaction vessel. The reaction mixture was stirred and heated in a Smith Synthesizer® microwave reactor (Personal Chemistry, Inc., Upssala, Sweden) at 180° C. for about 20 min. After about 20 min. all starting material was converted to product (M+1=307, 309). The mixture was concentrated under vacuum and purified via flash chromatography (silica gel) eluting with a gradient of 2% 2 M ammonia in MeOH/DCM to 6% 2M ammonia in MeOH/DCM to give (0.14 g) 6-bromo-1-(4-methylpiperazin-1-yl)phthalazine as a yellow solid. Found MS (ES+): 307, 309(M+H)$^+$.

Step B: A mixture of 6-bromo-1-(4-methylpiperazin-1-yl)phthalazine (0.13 g, 0.42 mmol), N-cyclopropyl-4-methyl-3-(4,4,5,5-tetramethyl-1,3,2-dioxaborolan-2-yl) benzamide (0.13 g, 0.42 mmol), tetrakis(triphenylphosphine)palladium (24mg, 0.021 mmol) and 2 M potassium carbonate (0.7 mL, 1.4 mmol) in 5 mL DME/EtOH (4:1) was stirred at 90° C. for 2 h. The mixture was directly purified via flash chromatography (silica gel) eluting with a gradient of 2% 2 M ammonia in MeOH/DCM to 10% 2 M ammonia in MeOH/DCM to give the title compound (0.15g) as a yellow solid. Found MS (ES+): 402(M+H)$^+$.

EXAMPLE 24

Synthesis of N-cyclopropyl-3-(1-(3-hydroxypyrolidin-1-yl)phthalazin-6-yl)-4-methylbenzamide Step A: The mixture of 6-bromo-1-chlorophthalazine (Example 1, 0.12 g, 0.5 mmol), pyrrolidin-3-ol (0.08 mL, 1.0 mmol) and potassium carbonate (0.07 g, 0.5 mmol) in 5 mL acetonitrile was added to a glass microwave reaction vessel. The reaction mixture was stirred and heated in a Smith Synthesizer® microwave reactor (Personal Chemistry, Inc., Upssala, Sweden) at 180° C. for 20 min. After about 20 min., all starting material was converted to product (M+1=294, 296). The mixture was concentrated under vacuum and purified via flash chromatography (silica gel) eluting with a gradient of 2% 2 M ammonia in MeOH/DCM to 6% 2M ammonia in MeOH/DCM to give 0.13 1-(6-bromophthalazin-1-yl) pyrrolidin-3-ol as yellow solid. Found MS (ES+): 294, 296 (M+H)$^+$.

Step B: A mixture of 1-(6-bromophthalazin-1-yl)pyrrolidin-3-ol (0.11 g, 0.37 mmol), N-cyclopropyl-4-methyl-3-(4,4,5,5-tetramethyl-1,3,2-dioxaborolan-2-yl)benzamide (0.11 g, 0.37 mmol), tetrakis(triphenylphosphine)palladium (22 mg, 0.019 mmol) and 2M potassium carbonate (0.6 mL, 1.2 mmol) in 5 mL DME/EtOH (4:1) was stirred at 90° C. for 2 h. The mixture was directly purified via flash chromatography (silica gel) eluting with 2% 2M ammonia in MeOH/DCM (0.13 g) to afford the title compound as a yellow solid. Found MS (ES+): 389(M+H)+.

EXAMPLE 25

Synthesis of N-cyclopropyl-4-methyl-3-(1-(piperidin-1-yl)phthalazin-6-yl)benzamide Step A: A mixture of 6-bromo-1-chlorophthalazine (Example 1, 0.1 g, 0.41 mmol), piperidine (0.081 mL, 0.82 mmol) and potassium carbonate (0.056 g, 0.41 mmol) in 5 mL acetonitrile was added to a glass microwave reaction vessel. The reaction mixture was stirred and heated in a Smith Synthesizer® microwave reactor (Personal Chemistry, Inc., Upssala, Sweden) at 180° C. for 20 min. After about 20 min., all starting material was converted to product (M+1=292, 294). The mixture was concentrated under vacuum and purified via flash chromatography (silica gel) eluting with a gradient of 2% 2 M ammonia in MeOH/DCM to 6% 2 M ammonia in MeOH/DCM to give (0.13 g) 6-bromo-1-(piperidin-1-yl)phthalazine as yellow solid. Found MS (ES+): 292, 294 (M+H)+.

Step B: A mixture of 6-bromo-1-(piperidin-1-yl)phthalazine (0.12 g, 0.40 mmol), N-cyclopropyl-4-methyl-3-(4,4,5,5-tetramethyl-1,3,2-dioxaborolan-2-yl)benzamide (0.12 g, 0.4 mmol), tetrakis(triphenylphosphine)palladium (24 mg, 0.02 mmol) and 2M potassium carbonate (0.6 mL, 1.2 mmol) in 5 mL DME/EtOH (4:1) was stirred at 90° C. for 2 h. The mixture was transferred directly to silica gel and purified via flash chromatography (silica gel) eluting with a gradient of 2% 2 M ammonia in MeOH/DCM to 10% 2M ammonia in MeOH/DCM to give the title compound (0.13 g) as yellow solid. Found MS (ES+): 387(M+H)+.

EXAMPLE 26

Synthesis of N-cyclopropyl-3-(1-(5-isopropyl-2,5-diaza-bicyclo[2.2.1]heptan-2-yl)phthalazin-6-yl)-4-methylbenzamide Step A: A mixture of 6-bromo-1-chlorophthalazine (Example 1, 90 mg, 370 µmol), 2-isopropyl-2,5-diaza-bicyclo [2.2.1]heptane dihydrochloride (95 mg, 444 µmol) and potassium carbonate (153 mg, 1109 µmol) in 10 mL acetonitrile was stirred at 130° C. under in a sealed tube. The mixture turned red in about 5 min. The reaction was monitored by MS. After about 1 h at 130° C., MS and TLC showed all starting material was converted to product (M+1=347, 349). The mixture was cooled down to room temperature, and concentrated on a Rotavaporator. After purification by column (eluting with gradient of 2-10% 2M ammonia in methanol to DCM), 2-(6-bromophthalazin-1-yl)-5-isopropyl-2,5-diaza-bicyclo [2.2.1]heptane (60 mg) was obtained as a yellow solid.

Found MS (ES+): 347, 349 (M+H)+.

Step B: A mixture of 2-(6-bromophthalazin-1-yl)-5-isopropyl-2,5-diaza-bicyclo[2.2.1]heptane (60 mg, 173 µmol), N-cyclopropyl-4-methyl-3-(4,4,5,5-tetramethyl-1,3,2-dioxaborolan-2-yl)benzamide (52 mg, 173 µmol) and tetrakis (triphenylphosphine)palladium (10 mg, 9 µmol)in 5 mL DME/EtOH (4:1) was treated with 2M potassium carbonate (0.5 mL, 1 mmol) at 22° C. under nitrogen. The mixture was heated up to 90° C. and stirred for 1 h. The reaction was monitored by MS. After about 1 h at 90° C., MS showed all starting material was converted to product (M+1=442). The mixture was cooled down to room temperature (22° C.). The mixture was transferred directly to silica gel and purified via flash chromatography (silica gel) eluting with a gradient of 2% 2 M ammonia in MeOHIDCM to 6% 2 M ammonia in MeOH/DCM to give the title compound (60 mg). Found MS (ES+): 442(M+H)+.

EXAMPLE 27

Synthesis of 3-(1-(5-oxa-2-aza-bicyclo[2.2.1]heptan-2-yl)phthalazin-6-yl)-N-cyclopropyl-4-methylbenzamide A mixture of 2-oxa-5-aza-bicyclo[2.2.1]heptane hydrochloride (223 mg, 1643 µmol) in 10 mL methanol was treated with MP-carbonate (1 g, 3.2 mmol) at 22° C. for 1 h. The mixture was filtered and concentrated. The residue, 6-bromo-1-chlorophthalazine (Example 1, 100 mg, 411 µmol), potassium carbonate (57 mg, 411 µmol) and 5 mL acetonitrile was added to a glass microwave reaction vessel. The reaction mixture was stirred and heated in a Smith Synthesizer® microwave reactor (Personal Chemistry, Inc., Upssala, Sweden) at 190° C. for 20 min. The mixture was concentrated under vacuum and N-cyclopropyl-4-methyl-3-(4,4,5,5-tetramethyl-1,3,2-dioxaborolan-2-yl)benzamide (124 mg, 411 µmol), tetrakis(triphenylphosphine)palladium (475 mg, 411 µmol), 5 mL DME/EtOH (4:1) and 0.6 mL $H_2O$ were added. The mixture was stirred at 90° C. for 1 h., then directly transferred to silica gel and purified via flash chromatography (silica gel) eluting with a gradient of 2% 2 M ammonia in MeOH/DCM to 10% 2 M ammonia in MeOH/DCM to give the title compound (0.21g) as a yellow solid. Found MS (ES+): 401 (M+H)+.

EXAMPLE 28

Synthesis of 1-(6-(5-(cyclopropylcarbamoyl)-2-methylphenyl)phthalazin-1-yl)piperidine-4-carboxamide Step A: A mixture of the isonipecotamide (71 mg, 554 µmol), 6-bromo-1-chlorophthalazine (Example 1, 90 mg, 370 µmol) and potassium carbonate (51 mg, 370 µmol) in 5 mL acetonitrile was added to a glass microwave reaction vessel. The reaction mixture was stirred and heated in a Smith Synthesizes microwave reactor (Personal Chemistry, Inc., Upssala, Sweden) at 190° C. for about 20 min. at which the starting material was consumed, by TLC, to form product (M+1=335, 337). The mixture was concentrated and purified by column, eluting with a gradient of 2% 2M ammonia in MeOH/DCM to 10% 2M ammonia in MeOH/DCM to give 1-(6-bromophthalazin-1-yl)piperidine-4-carboxamide (0.115g) as a pale yellow solid. Found MS (ES+): 335, 337 (M+H)+.

Step B: A mixture of 1-(6-bromophthalazin-1-yl)piperidine-4-carboxamide,N-cyclopropyl-4-methyl-3-(4,4,5,5-tetramethyl-1,3,2-dioxaborolan-2-yl)benzamide (111 mg, 370 µmol), tetrakis(triphenylphosphine)palladium (21 mg, 18 µmol) and 0.5 mL 2M $K_2CO_3$ in 5 mL DME/EtOH (4:1) was stirred at 90° C. for 1 h. All the starting material was converted to product (M+1=430) by TLC. The mixture was cooled down to room temperature, transferred directly to silica gel and purified via flash chromatography (silica gel) eluting with a gradient of 2% 2 M ammonia in MeOH/DCM to 10% 2 M ammonia in MeOH/DCM to give the title compound (0.11 g) as a pale yellow solid. Found MS (ES+): 430(M+H)+.

EXAMPLE 29

Synthesis of 1-(6-(5-(cyclopropylcarbamoyl)-2-methylphenyl)phthalazin-1-yl)piperidine-3-carboxamide Step A: A glass microwave reaction vessel was charged with nipecotamide (0.17 g, 1.4 mmol), 6-bromo-1-chlorophthalazine (0.110 g, 0.45 mmol), potassium carbonate (0.062g, 0.45 mmol) and 3 mL acetonitrile. The reaction mixture was stirred and heated in a Smith Synthesizer® microwave reactor (Personal Chemistry, Inc., Upssala, Sweden) at 190° C. for 20 min (watts, Powermax feature on, ramp time 1 min). The mixture was purified directly via flash chromatography (silica gel) eluting with 4/1 hexanes/EtOAc to 4/1 hexanes/EtOAc to give (0.15 g) 1-(6-bromophthalazin-1-yl)piperidine-3-carboxamide as a white solid. Found MS (ES+): 335, 337(M+H)+.

Step B: A mixture of 1-(6-bromophthalazin-1-yl)piperidine-3-carboxamide (0.12g, 0.4 mmol), N-cyclopropyl-4-methyl-3-(4,4,5,5-tetramethyl-1,3,2-dioxaborolan-2-yl)benzamide (0.1 g, 0.4 mmol), and tetrakis(triphenylphosphine)palladium (0.02 g, 0.02 mmol) in 5 mL DME/EtOH (4:1) was treated with 2 M potassium carbonate (0.5 mL, 1 mmol). The mixture resulted was warmed up to 90° C. and stirred for 1 h under nitrogen. The mixture was cooled down to room temperature, and the crude product was purified via flash chromatography (silica gel) eluting with a gradient of 4% 2 M ammonia in MeOH/DCM to 6% 2 M ammonia in MeOH/DCM to give (0.11 g) title compound as a pale yellow solid. Found MS (ES+): 430(M+H)+.

EXAMPLE 30

Synthesis of N-cyclopropyl-4-methyl-3-(1-(octahydroisoquinolin-2(1 H)-yl)phthalazin-6-yl)benzamide Step A: A mixture of 6-bromo-1-chlorophthalazine (Example 1, 0.1 g, 411 µmol), decahydroisoquinoline (114 mg, 821 µmol), potassium carbonate (57 mg, 411 µmol) and 5 mL acetonitrile was added to a glass microwave reaction vessel. The reaction mixture was stirred and heated in a Smith Synthesizer® microwave reactor (Personal Chemistry, Inc., Upssala, Sweden) at 180° C. for 20 min. The mixture was concentrated under vacuum and purified via flash chromatography (silica gel) eluting with a gradient of 2% 2 M ammonia in MeOH/DCM to 6% 2M ammonia in MeOH/DCM to give 6-bromo-1-(octahydroisoquinolin-2(1H)-yl)phthalazine (0.15g) as a yellow solid. Found MS (ES+): 346, 348(M+H)+.

Step B: The mixture of 0.15 g 6-bromo-1-(octahydroisoquinolin-2(1 H)-yl)phthalazine, N-cyclopropyl-4-methyl-3-(4,4,5,5-tetramethyl-1,3,2-dioxaborolan-2-yl)benzamide (124 mg, 411 µmol), tetrakis(triphenylphosphine)palladium (24 mg, 21 µmol) and 2 M potassium carbonate (616 µl, 1232 µmol) in 5 mL DME/EtOH (4:1) was stirred at 90° C. for 2 h. The mixture was transferred directly to silica gel and purified via flash chromatography (silica gel) eluting with a gradient of 2% 2 M ammonia in MeOH/DCM to 10% 2M ammonia in MeOH/DCM to give the title compound (0.20g) as a yellow solid. Found MS (ES+):441 (M+H)+.

EXAMPLE 31

Synthesis of N-cyclopropyl-4-methyl-3-(1-(3-oxopiperazin-1-yl)phthalazin-6-yl)benzamide Step A: A glass microwave reaction vessel was charged with 6-bromo-1-chlorophthalazine (Example 1, 0.11 g, 0.45 mmol), piperazin-2-one (0.090 g, 0.90 mmol), potassium carbonate (0.062 g, 0.45 mmol) and 5 mL acetonitrile. The reaction mixture was stirred and heated in a Smith Synthesizer® microwave reactor (Personal Chemistry, Inc., Upssala, Sweden) at 190° C. for about 12 min (watts, Powermax feature on, ramp time 1 min). The mixture was purified directly via flash chromatography (silica gel) eluting with 5% 2 M ammonia methanol/DCM to give the 4-(6-bromophthalazin-1-yl)piperazin-2-one (0.115 g) as a pale yellow solid. Found MS (ES+): 307, 309(M+H)+.

Step B: A mixture of 4-(6-bromophthalazin-1-yl)piperazin-2-one (0.10 g, 326 µmol), N-cyclopropyl-4-methyl-3-(4,4,5,5-tetramethyl-1,3,2-dioxaborolan-2-yl)benzamide (98mg, 326 µmol), and tetrakis(triphenylphosphine)palladium (19 mg, 16 µmol) in 5 mL DME/EtOH (4:1) was treated with 2M potassium carbonate (488 µl, 977 µmol). The resulting mixture was warmed up to 90° C. and stirred for 1 h under nitrogen. The mixture was cooled to room temperature, and the crude product was purified via flash chromatography (silica gel) eluting with a gradient of 4% 2 M ammonia in MeOH/DCM to 6% 2 M ammonia in MeOH/DCM to give the title compound (0.11 g) as a pale yellow solid. Found MS(ES+): 402(M+H)+.

EXAMPLE 32

Synthesis of 4-methyl-3-(1-(3-oxopiperazin-1-yl)phthalazin-6-yl)benzamide

A mixture of 4-(6-bromophthalazin-1-yl)piperazin-2-one (0.1 g, 0.3 mmol), 4-methyl-3-(4,4,5,5-tetramethyl-1,3,2-dioxaborolan-2-yl)benzamide (0.09 g, 0.3 mmol), and tetrakis(triphenylphosphine)palladium (0.02 g, 0.02 mmol) in 5 mL DME/EtOH (4:1) was treated with 2M potassium carbonate (0.5 mL, 1.0 mmol). The mixture resulted was warmed up to 90° C. and stirred for 1 h under nitrogen. The mixture was cooled down to room temperature, and the crude product was purified via flash chromatography (silica gel) eluting with a gradient of 4% 2 M ammonia in MeOH/DCM to 6% 2 M ammonia in MeOH/DCM to give the title compound (60 mg) as a pale yellow solid. Found MS (ES+): 362(M+H)+.

EXAMPLE 33

Synthesis of 3-(1-(2-chlorophenyl)phthalazin-6-yl)-N-cyclopropyl-4-methylbenzamide A mixture of 3-(1-chlorophthalazin-6-yl)-N-cyclopropyl-4-methylbenzamide (0.11 g, 0.327 mmol), 2-chlorophenylboronic acid (51 mg, 329 µmol), 5 mL DME/EtOH (4:1), 0.5 mL 2M $K_2CO_3$ and tetrakis(triphenylphosphine)palladium (20mg) was stirred at 90° C. for 1 h. The reaction mixture was cooled to RT. The crude product was purified via flash chromatography (silica gel) with 2% 2 M ammonia in MeOH/DCM to 6% 2 M ammonia in MeOH/DCM to give the crude compound (120 mg) as a yellow solid. The compound was further purified by HPLC by dissolving the crude product in methanol (~20 mg/mL) and injecting at a rate of about 0.500 mL per injection onto the Gilson preparatory HPLC. Pure product fractions were collected, combined, basefied with sodium bicarbonate (saturated, aqueous), extracted with $CH_2Cl_2$, separated, dried over sodium sulfate, and concentrated via rotary evaporation to give pure title compound (28.8 mg) as a white solid. Found MS (ES+): 414(M+H)$^+$.

EXAMPLE 34

Synthesis of N-cyclopropyl-4-methyl-3-(1-o-tolylphthalazin-6-yl)benzamide

A mixture of 3-(1-chlorophthalazin-6-yl)-N-cyclopropyl-4-methylbenzamide (100 mg, 296 µmol), o-tolylboronic acid (40 mg, 296 µmol) and tetrakis(triphenylphosphine)palladium (17 mg, 15 µmol) in 5 mL DME/EtOH (4:1) was treated with 2M potassium carbonate (444 µl, 888 µmol). The mixture was stirred at 90° C. for 2 h. The mixture was cooled to RT and purified directly without work-up, via flash chromatography (silica gel) eluting with a gradient of 2% 2 M ammonia in MeOH/DCM to 6% 2 M ammonia in MeOH/DCM to give the title compound in (65 mg) as a pale yellow solid. Found MS (ES+): 394(M+H)$^+$.

EXAMPLE 35

Synthesis of N-cyclopropyl-4-methyl-3-(1-p-tolylphthalazin-6-yl)benzamide

A mixture of 3-(1-chlorophthalazin-6-yl)-N-cyclopropyl-4-methylbenzamide (0.1 g, 296 µmol), p-tolyl boronic acid (40 mg, 296 µmol) and tetrakis(triphenylphosphine)palladium (17 mg, 15 µmol) in 5 mL DME/EtOH (4:1) was treated with 2 M potassium carbonate (444 µl, 888 µmol). The mixture was stirred at 90° C. for 2 h. The mixture was cooled to room temperature and purified via flash chromatography (silica gel) eluting with a gradient of 2% 2 M ammonia in MeOH/DCM to 6% 2 M ammonia in MeOH/DCM to give title compound in (95 mg) as a pale yellow solid. Found MS (ES+): 394(M+H)$^+$.

EXAMPLE 36

Synthesis of N-cyclopropyl-3-(1-mesitylphthalazin-6-yl)-4-methylbenzamide

A mixture of 3-(1-chlorophthalazin-6-yl)-N-cyclopropyl-4-methylbenzamide (0.110 g, 326 µmol), 2,4,6-trimethylbenzeneboronic acid (53 mg, 326 µmol) and dichloro[1,1'-bis(diphenylphosphino)ferrocene]dichloride palladium(ii) dichloromethane adduct (12mg, 16 µmol) in 5 mL toluene/ethanol (4:1) was treated with 2 M potassium carbonate (488 µl, 977 µmol). The mixture was stirred at 100° C. under nitrogen and followed by MS for about 15 h. (product MS=422 (M+1)). The mixture was concentrated under vacuum and the crude product was purified via flash chromatography (silica gel) eluting with a gradient of 2% 2 M ammonia in MeOH/DCM to 6% 2 M ammonia in MeOH/DCM to give the title compound (80 mg). Found MS (ES+): 422(M+H)$^+$.

EXAMPLE 37

Synthesis of N-cyclopropyl-4-methyl-3-(1-(1-methylpiperidin-4-yl)phthalazin-6-yl)benzamide Step A: To a mixture of 15 mL LHMDS in 30 mL THF stirred at −78° C. under nitrogen was added a solution of 1-methylpiperidin-4-one (1.22 mL, 10 mmol). The mixture was stirred allowing the temperature to rise from about −78° C. to about −20° C. over a period of about 2 h. The mixture was then cooled to −78° C. again and treated with PhNTf$_2$ (4.2 g, 12 mmol). The mixture was stirred from −78° C. to RT for 2 h. The reaction mixture was quenched with 50 mL sat. NH$_4$Cl and extracted with ethyl acetate (3×50 mL). The combined organic layers were dried over anhydrous Na$_2$SO$_4$ and concentrated via Rotavaporator. The crude product was purified via column eluting with 1:1 hexane/ethyl acetate to yield 1-methyl-1,2,3,6-tetrahydropyridin-4-yl trifluoromethanesulfonate (2.2 g) as a pale yellow oil. Found MS (ES+): 246 (M+H)$^+$.

Step B: A mixture of 1-methyl-1,2,3,6-tetrahydropyridin-4-yl trifluoromethanesulfonate (1.1 g, 4.47 mmol), 4,4,5,5-tetramethyl-2-(4,4,5,5-tetramethyl-1,3,2-dioxaborolan-2-yl)-1,3,2-dioxaborolane (1.24 g, 4.9 mmol), potassium acetate (1.7 mL, 17 mmol), PdCl$_2$(dppf) (0.13 g, 0.15 mmol) and dppf (83 mg, 0.15 mmol) in 50 mL dioxane was degassed by consecutively flushing and evacuating with nitrogen 3 times. The mixture was stirred at 80° C. under nitrogen for 15 h. The reaction mixture was cooled to room temperature, diluted with 100 mL ethyl acetate and washed with H$_2$O (2×25 mL) and brine (20 mL). The organic layer was dried over anhydrous Na$_2$SO$_4$, concentrated and purified via flash chromatography (silica gel) eluting with a gradient of 5/1 hexanes/EtOAc to 4/1 hexanes/EtOAc to give 1-methyl-4-(4,4,5,5-tetramethyl-1,3,2-dioxaborolan-2-yl)-1,2,3,6-tetrahydropyridine as a pale yellow solid (1.1 g). Found MS (ES+): 224 (M+H)$^+$.

Step C: A mixture of 3-(1-chlorophthalazin-6-yl)-N-cyclopropyl-4-methylbenzamide (0.1 g, 0.3 mmol), 1-methyl-4-(4,4,5,5-tetramethyl-1,3,2-dioxaborolan-2-yl)-1,2,3,6-tetrahydropyridine (70 mg, 0.3 mmol) and tetrakis(triphenylphosphine)palladium (0.03 g, 0.03 mmol) in 10 mL DME/EtOH (4:1) was treated with 2 M potassium carbonate (0.6 mL, 1.2 mmol). The mixture was stirred at 90° C. for 2 h. The mixture was cooled to room temperature, diluted with 100 mL DCM, washed with sat. NaHCO$_3$, dried over anhydrous Na$_2$SO$_4$ and concentrated under reduced pressure. The crude product was purified via flash chromatography (silica gel) eluting with a gradient of 2% 2 M ammonia in MeOH/DCM to 6% 2 M ammonia in MeOH/DCM to give N-cyclopropyl-4-methyl-3-(1-(1-methyl-1,2,3,6-tetrahydropyridin-4-yl)phthalazin-6-yl)benzamide (0.10 g) as a pale yellow solid. Found MS (ES+): 399(M+H)$^+$.

Step D: A mixture of N-cyclopropyl-4-methyl-3-(1-(1-methyl-1,2,3,6-tetrahydropyridin-4-yl)phthalazin-6-yl)benzamide (20 mg, 50 µmol), 20 mg 10% palladium on activated carbon in 20 mL ethyl acetate was stirred under 50 psi hydrogen at 22° C. After 2 h reaction, the reaction was monitored for product (MS=401) and starting material (MS=399). The reaction mixture was stirred under 50 psi hydrogen at 22° C. for another 2 h, MS showed all starting material was converted to product. The mixture was filtered and washed with methanol 50 mL. After concentrating the filtrate, the residue was purified by PTLC to obtain the title compound (10 mg) as a pale yellow solid. Found MS (ES+): 401 (M+H)$^+$.

EXAMPLE 38

Synthesis of 4-chloro-N-cyclopropyl-3-(1-morpholinophthalazin-6-yl)benzamide

4-Chloro-N-cyclopropyl-3-iodobenzamide (190 mg, 591 µmol), potassium acetate (174mg, 1773 µmol), bis(pinacolato)diboron (165 mg, 650 µmol), and 1,1'-bis(diphenylphosphino)ferrocene-palladium dichloride (43 mg, 59 µmol) were suspended in dioxane (3.9 mL) and placed in the microwave for 10 min at 180° C. before being added to a mixture of 6-bromo-1-morpholinophthalazine (120 mg, 408 µmol), sodium carbonate-2 M in water (1.2 mL, 2.4 mmol), tetrakis (triphenylphosphine)palladium (68 mg, 59 µmol), and ethyl alcohol (3.9 mL). The combined mixture was heated in the microwave for 10 min at 180° C. The reaction mixture was diluted with 20 mL of EtOAc, added to an addition funnel, and partitioned with sodium bicarbonate (saturated, aqueous). The organic layers were combined, washed 3 times with 20 mL of sodium bicarbonate (saturated, aqueous), separated, combined, dried over sodium sulfate, and concentrated via rotovap to give a crude product. After purification by chromatography, the title compound was obtained. Found MS (ES+): 409 (M+H)$^+$.

EXAMPLE 39

Synthesis of 4-chloro-N-cyclopropyl-3-iodobenzamide

4-Chloro-3-iodobenzoic acid (9.00 g, 31.9 mmol) was heated to 75° C. in thionyl chloride (15 mL) for 4 h. The reaction mixture became homogeneous and was concentrated and dried azeotropically with toluene. The mixture was dissolved in 1,4-dioxane (10 mL), and diisopropylethylamine (11 mL mL, 64 mmol), and cyclopropylamine (2.45 mL, 35 mmol) and stirred at ambient temperature for about 2 h. The reaction was diluted with 50 mL of EtOAc, added to an addition funnel and partitioned with 3 N HCl (aqueous). The organic layers were combined, washed 2 times with 50 mL of 3 N HCl (aqueous), and 2 times with 50 mL of sodium bicarbonate, dried over sodium sulfate, and concentrated via rotovap to give the title compound. Found MS (ES+): 322 (M+H)$^+$.

EXAMPLE 40

Synthesis of N,4-dimethyl-3-(1-morpholinophthalazin-6-yl)benzamide

4-Methyl-3-(1-morpholinophthalazin-6-yl)benzoic acid (100 mg, 286 µmol) was dissolved in thionyl chloride (5.7 mL) and heated to 65° C. for 1 h. The reaction was then concentrated in vacuo, dissolved in tetrahydrofuran 99.9% (5.7 mL) and diisopropylethylamine (150 µL, 859 µmol) and methylamine, 2.0 m solution in THF (0.7 mL) were added. The reaction mixture was stirred for 3 h at ambient temperature. The reaction mixture was diluted with 50 mL of EtOAc, added to an addition funnel and partitioned with sodium bicarbonate (saturated, aqueous). The organic layers were washed 3 times with 50 mL of sodium bicarbonate (saturated, aqueous), dried over sodium sulfate, and concentrated via rotovap to give a crude product. After purification by chromatography, the title compound was obtained. Found MS (ES+): 363(M+H)$^+$.

EXAMPLE 41

Synthesis of N-ethyl-4-methyl-3-(1-morpholinophthalazin-6-yl)benzamide

4-Methyl-3-(1-morpholinophthalazin-6-yl)benzoic acid (100 mg, 286 µmol) was dissolved in thionyl chloride (5.7 mL) and heated to 65° C. for 1 h before being concentrated via rotovap. The crude reaction was dissolved in tetrahydrofuran 99.9% (5.7 mL) and diisopropylethylamine (150 µL, 859 µmol) and ethylamine—2 M in THF (0.71 mL) was added at 0° C. The reaction mixture was warmed to ambient temperature and stirred for 3 h. The reaction mixture was diluted with 50 mL of EtOAc, added to an addition funnel, partitioned with sodium bicarbonate (saturated, aqueous). The organic layers were washed 3 times with 50 mL of sodium bicarbonate (saturated, aqueous), combined, dried over sodium sulfate, and concentrated via rotovap to give a crude product. After purification by chromatography, the title compound was obtained. Found MS (ES+): 377(M+H)$^+$.

EXAMPLE 42

Synthesis of 4-methyl-3-(1-morpholinophthalazin-6-yl)benzamide

4-Methyl-3-(1-morpholinophthalazin-6-yl)benzoic acid (86 mg, 0.25 mmol) was dissolved in thionyl chloride (3.6 mL) and heated to 70° C. for 2 h. The reaction mixture was concentrated in vacuo before ammonia, 0.5 M in 1,4-dioxane (10 mL, 4.9 mmol) and diisopropylethylamine (0.2 mL, 1.2 mmol) were added. The reaction mixture was heated to 50° C. for 5 h and stirred overnight at RT. The reaction was diluted with 100 mL of EtOAc, added to an addition funnel and partitioned with sodium bicarbonate (saturated, aqueous). The organic layers were washed 3 times 75 mL of sodium bicarbonate (saturated, aqueous), combined, dried over sodium sulfate, and concentrated via rotovap to give a crude product. The crude was purified by chromatography to obtain the title compound. Found MS (ES+): 349(M+H)$^+$.

EXAMPLE 43

Synthesis of N-(2-methoxy-5-(trifluoromethyl)phenyl)-4-methyl-3-(1-morpholinophthalazin-6-yl)benzamide 3-Iodo-N-(2-methoxy-5-(trifluoromethyl)phenyl)-4-methylbenzamide (205 mg, 471 µmol), 1,1'-bis(diphenylphosphino)ferrocene-palladium dichloride (34 mg, 47 µmol), bis (pinacolato)diboron (179 mg, 707 µmol), and potassium acetate (118 µL, 1884 µmol) were dissolved/suspended in dimethylformamide (2.4 mL) and placed in the microwave at 160° C. for 10 min. The reaction mixture was then transferred to another vial containing 6-bromo-1-morpholinophthalazine (125mg, 424 µmol), tetrakis(triphenylphosphine) palladium (0)(54 mg, 47 µmol), potassium carbonate-2 M in water (942 µL, 1884 µmol), and ethanol (2.4 mL). The combined mixture was reacted in a microwave oven at 160° C. for 10 min. The reaction mixture was diluted with 50 mL of EtOAc, added to an addition funnel and partitioned with sodium bicarbonate (saturated, aqueous). The organic layer was washed 3 times with 50 mL of sodium bicarbonate (saturated, aqueous), dried over sodium sulfate, and concentrated via rotovap to give a crude product. The crude product was purified by chromatography to obtain the title compound. Found MS (ES+): 523 (M+H)$^+$.

EXAMPLE 44

Synthesis of 4-methyl-3-(1-morpholinophthalazin-6-yl)benzoic acid

6-Bromo-1-morpholinophthalazine (191 mg, 649 µmol), 4-methyl-3-(4,4,5,5-tetramethyl-1,3,2-dioxaborolan-2-yl) benzoic acid (170 mg, 649 µmol), and tetrakis (triphenylphosphine)palladium (75 mg, 65 µmol) were added to a microwave vial before sodium carbonate-2 N in water (1.9 mL, 3892 µmol) and ethanol (3.2 mL) were added. The reaction mixture was reacted in a microwave oven for 10 min at 160° C. The reaction was cooled, diluted with 50 mL of EtOAc, added to an addition funnel and partitioned with sodium bicarbonate (saturated, aqueous). The organic layer was washed 2 times with 50 mL of sodium bicarbonate (saturated, aqueous), and separated. The aqueous layer was acidified to pH 5 with conc. HCl and extracted 4 times with 50 mL of chloroform. The organic layers were combined, dried over sodium sulfate, and concentrated via rotovap to give the title compound. Found MS (ES+): 350 (M+H)$^+$.

EXAMPLE 45

Synthesis of N-cyclopropyl-4-methyl-3-(1-moropholinophthalazin-6-yl)benzamide

Step 1: A mixture of 6-bromo-1-chlorophthalazine (Example 1, 0.1 g, 411 µmol), morpholine (72 mg, 821 µmol) and potassium carbonate (57 mg, 411 µmol) in 5 mL acetonitrile was added to a glass microwave reaction vessel. The reaction mixture was stirred and heated in a Smith Synthesizer® microwave reactor (Personal Chemistry, Inc., Upssala, Sweden) at 180° C. for 20 min. All the starting material was converted to product (M+1=296, 298). The mixture was concentrated under vacuum, and purified via flash chromatography (silica gel) eluting with a gradient of 2% 2 M ammonia in MeOH/DCM to 6% 2 M ammonia in MeOH/DCM to give 6-bromo-1-morpholinophthalazine as yellow solid. Found MS (ES+): 296, 298(M+H)$^+$.

Step 2: A mixture of 6-bromo-1-morpholinophthalazine (0.11 g, 0.37 mmol), N-cyclopropyl-4-methyl-3-(4,4,5,5-tetramethyl-1,3,2-dioxaborolan-2-yl)benzamide (0.11 g, 0.37 mmol), tetrakis(triphenylphosphine)palladium (17 mg, 0.017 mmol) and 2 M potassium carbonate (0.66 mL, 1.32 mmol) in 5 mL DME/EtOH (4:1) was stirred at 90° C. for 2 h. The mixture was transferred directly to a column and purified via flash chromatography (silica gel) eluting with a gradient of 2% 2 M ammonia in MeOH/DCM to 10% 2M ammonia in MeOH/DCM to give the title compound as a yellow solid. Found MS (ES+): 389 (M+H)$^+$.

EXAMPLE 46

Synthesis of N-cyclopropyl-4-methyl-5-(1-morpholinophthalazin-6-yl)thiophene-2-carboxamide 4-Methyl-5-(1-morpholinophthalazin-6-yl)thiophene-2-carboxylic acid (140 mg, 309 µmol) was suspended in thionyl chloride (3.1 mL) and heated to 65° C. for 1 h. The reaction mixture was concentrated in vacuo and azeotropically dried with toluene, before being dissolved/suspended in tetrahydrofuran 99.9% (3.1 mL), diisopropylethylamine (216 µl, 1238 µmol) and cyclopropylamine (71 µl, 1238 µmol). The reaction was stirred at RT for 2 h, diluted with 50 mL of EtOAc, added to an addition funnel and partitioned with sodium bicarbonate (saturated, aqueous). The organic layer was washed 2 times with 50 mL of sodium bicarbonate (saturated, aqueous), dried over sodium sulfate, and concentrated via rotovap to give a crude yellow product. The crude was purified by chromatography, to obtain the title compound. Found MS (ES+): 395(M+H)$^+$.

EXAMPLE 47

Synthesis of 4-methyl-5-(1-morpholinophthalazin-6-yl)thiophene-2-carboxylic acid 6-Bromo-1-morpholinophthalazine (405 mg, 1377 µmol), 4,4,5,5-tetramethyl-2-(4,4,5,5-tetramethyl-1,3,2-dioxaborolan-2-yl)-1,3,2-dioxaborolane (524 mg, 2065 µmol), potassium acetate (541 mg, 5507 µmol), and 1,1'-bis(diphenylphosphino)ferrocene-palladium dichloride (101 mg, 138 µmol) were dissolved in N,N-dimethylformamide (4.6 mL) and placed in the microwave for 10 min at 160° C. The reaction mixture was added to a vial containing methyl 5-bromo-4-methylthiophene-2-carboxylate (388 mg, 1652 µmol), tetrakis(triphenylphosphine)palladium (159 mg, 138 µmol), potassium carbonate-2 M in water (2754 µl, 5507 µmol), and ethanol (4590 µl, 1377 µmol). The vial was placed in the microwave for 10 min at 160° C., cooled, diluted with 75 mL of EtOAc, added to an addition funnel and partitioned with sodium bicarbonate (saturated, aqueous). The organic layer was washed 3× with 50 mL of sodium bicarbonate (saturated, aqueous), and separated. The aqueous layer was acidified to pH 4 with conc. HCl and extracted 3× with 50 mL of chloroform. The combined organic layers were dried over sodium sulfate, and concentrated via rotovap to give a crude product, which was purified by chromatography to obtain the title compound, as the TFA salt. Found MS (ES+): 356(M+H)$^+$.

EXAMPLE 48

Synthesis of N-cyclopropyl-3-(1-(2-(dimethylamino)ethylamino)phthalazin-6-yl)-4-methylbenzamide 6-Bromo-N-(2-(dimethylamino)ethyl)phthalazin-1-amine (115 mg, 390 µmol), potassium acetate (53 mg, 550 µmol), bis(pinacolato)diboron (139 mg, 550 µmol), and 1,1'-bis(diphenylphosphino)ferrocene-palladium dichloride (29 mg, 40 µmol) were suspended in dioxane (4 mL) and placed in the microwave for I 0 min at 160° C. To the reaction was added a mixture of 3-bromo-N-cyclopropyl-4-methylbenzamide (99 mg, 390 µmol), sodium carbonate-2 M in water (0.29 mL, 0.58 mmol), tetrakis(triphenylphosphine)palladium (45 mg, 40 µmol), and ethyl alcohol (5 mL). The reaction was heated in the microwave for 10 min at 160° C. The reaction mixture was diluted with 20 mL of EtOAc, added to an addition funnel and partitioned with sodium bicarbonate (saturated, aqueous). The organic layer was washed 3× with 20 mL of sodium bicarbonate (saturated, aqueous), dried over sodium sulfate, and concentrated via rotovap to give a crude product. The crude product was purified by chromatography to obtain the title compound. Found MS (ES+): 390(M+H)$^+$.

EXAMPLE 49

Synthesis of N-cyclopropyl-3-(1-(2-(diethylamino)ethylamino)phthalazin-6-yl)-4-methylbenzamide 6-Bromo-N-(2-(diethylamino)ethyl)phthalazin-1-amine (140 mg, 430 µmol), potassium acetate (60 mg, 610 µmol), bis(pinacolato)diboron (150 mg, 610 µmol), and 1,1'-bis(diphenylphosphino)ferrocene-palladium dichloride (32 mg, 40 µmol) were suspended in dioxane (4 mL) and heated in the microwave for 10 min at 160° C. The reaction was added to a mixture of 3-bromo-N-cyclopropyl-4-methylbenzamide (110mg, 430 µmol), sodium carbonate-2 M in water (0.33 mL, 0.65 mmol), tetrakis(triphenylphosphine)palladium (50 mg, 40 µmol), and ethyl alcohol (5 mL), the combination of which was heated in the microwave for 10 min at 160° C. The reaction mixture was diluted with 20 mL of EtOAc, added to an addition funnel and partitioned with sodium bicarbonate (saturated, aqueous). The organic layer was washed 3 times with 20 mL of sodium bicarbonate (saturated, aqueous), dried over sodium sulfate, and concentrated via rotovap to give crude product. The crude was purified by chromatography to obtain the title compound. Found MS (ES+): 418(M+H)$^+$.

EXAMPLE 50

Synthesis of 3-bromo-N-cyclopropyl-4-methylbenzamide

3-Bromo-4-methylbenzoic acid (8.35 g, 33 mmol), 1H-benzo[d][1,2,3]triazol-1-ol (4.44 g, 33 mmol), N-(3-dimethylaminopropyl)-N'-ethylcarbodiimide hydrochloride (6.31 g, 33 mmol), and cyclopropylamine (2.5 mL, 36 mmol) were dissolved in dichloromethane (20 mL) and stirred at RT for 16 h. The reaction was diluted with dichloromethane (100 mL), washed 3× with 50 mL of sodium bicarbonate (saturated, aqueous) and 2× with 50 mL of 3 N HCl (aqueous). The organic layer was separated, dried over sodium sulfate, and concentrated via rotovap to give crude product. The crude was purified by chromatography to obtain the title compound. Found MS (ES+): 254(M+H)$^+$.

EXAMPLE 51

Synthesis of 6-bromo-N-(2-(dimethylamino)ethyl)phthalazin-1-amine

6-Bromo-1-chlorophthalazine (0.22 g, 0.91 mmol) was dissolved in N,N-dimethylformamide (3 mL) and potassium carbonate (0.25 g, 1.81 mmol) and N1,N1-dimethylethane-1,2-diamine (0.20 mL, 1.81 mmol) was added. The reaction mixture was heated to 80° C. for 5 h, cooled to ambient temperature and stirred for 16 h. The reaction mixture was diluted with 20 mL of EtOAc, added to an addition funnel and partitioned with sodium bicarbonate (saturated, aqueous). The organic layer was washed 3× with 20 mL of sodium bicarbonate (saturated, aqueous) and once with aqueous brine, separated, dried over sodium sulfate, and concentrated via rotovap to give crude product. The crude was purified by chromatography to obtain the title compound. Found MS (ES+): 295(M+H)$^+$.

EXAMPLE 52

Synthesis of 6-bromo-N-(2-(diethylamino)ethyl)phthalazin-1-amine

6-Bromo-1-chlorophthalazine (0.22 g, 0.91 mmol) was dissolved in N,N-dimethylformamide (3 mL) and potassium carbonate (0.25 g, 1.81 mmol) and N1,N1-diethylethane-1,2-diamine (0.25 mL, 1.81 mmol) were added. The reaction mixture was heated to 80° C. for 5 h, cooled to ambient temperature and stirred for 16 h. The reaction mixture was diluted with 20 mL of EtOAc, added to an addition funnel and partitioned with sodium bicarbonate (saturated, aqueous). The organic layer was washed 3× with 20 mL of sodium bicarbonate (saturated, aqueous) and once with aqueous brine, separated, dried over sodium sulfate, and concentrated via rotovap to give crude product. The crude was purified by chromatography to obtain the title compound. Found MS (ES+): 323(M+H)$^+$.

EXAMPLE 53

Synthesis of (2R)-1-(6-(5-(cyclopropylcarbamoyl)-2-methylphenyl)phthalazin-1-yl)-N-isolpropyl-5-methylpyrrolidine-2-carboxamide N-Cyclopropyl-4-methyl-3-(4,4,5,5-tetramethyl-1,3,2-dioxaborolan-2-yl)benzamide (64 mg, 212 µmol), tetrakis(triphenylphosphine)palladium (18 mg, 16 µmol), and (R)-1-(6-bromophthalazin-1-yl)-N-isopropyl-5-methylpyrrolidine-2-carboxamide (40 mg, 106 µmol) were dissolved/suspended in ethanol (2120 µl, 106 µmol) were placed in a vial and potassium carbonate—1 M in water (424 µl, 424 µmol) was added. The vial was then heated in the microwave for 10 min at 160° C. The reaction mixture was diluted with 75 mL of EtOAc, added to an addition funnel and partitioned with sodium bicarbonate (saturated, aqueous). The organic layer was washed 3 times with 50 mL of sodium bicarbonate (saturated, aqueous), separated, combined, dried over sodium sulfate, and concentrated via rotovap to give crude. The crude was purified by chromatography to obtain the title compound. Found MS (ES+): 472(M+H)$^+$.

EXAMPLE 54

(R)-1-(6-bromophthalazin-1-yl)-N-isopropyl-5-methylpyrrolidine-2-carboxamide

Step A: (R)-1-allyl 2-ethyl 5-hydroxy-5-methylpyrrolidine-1,2-dicarboxylate (R)-1-Allyl 2-ethyl 5-oxopyrrolidine-1,2-dicarboxylate (9.1 g, 38 mmol) was dissolved in dichloromethane (100 mL) and cooled to 0° C. before trimethylaluminum—2 M in toluene (94 mL, 190 mmol) was added. The reaction was stirred at ambient temperature for 16 h. The reaction mixture was quenched with a minimal amount of ammonium chloride (saturated, aqueous) to form a white solid, which was filtered off to give crude product. The crude was purified by chromatography to obtain the title compound. Found MS (ES+): 258(M+H)$^+$.

Step B: (R)-1-(allyloxycarbonyl)-5-methylpyrrolidine-2-carboxylic acid (R)-1-Allyl 2-ethyl 5-hydroxy-5-methylpyrrolidine-1,2-dicarboxylate (3.0g, 12 mmol) was dissolved in trifluoroacetic acid (20 mL) and cooled to 0° C. before borane-pyridine complex (2.9 mL, 23 mmol) was added. The reaction mixture was heated to 90° C. for 3 h, then concentrated in vacuo and NaOH—about 5N (30 mL) was added. The mixture was stirred for 2 h at 60° C., then cooled, washed with EtOAc (30 mL) and acidified to ~pH 5 with conc HCl. The mixture was extracted into dichloromethane, which was separated, dried over sodium sulfate, and concentrated via rotovap to give the title compound. Found MS (ES+): 214 (M+H)$^+$.

Step C: (R)-allyl 2-(isopropylcarbamoyl)-5-methylpyrrolidine-1-carboxylate (R)-1-(Allyloxycarbonyl)-5-methylpyrrolidine-2-carboxylic acid (0.92 g, 4.3 mmol), 1H-benzo[d][1,2,3]triazol-1-ol (0.70 g, 5.2 mmol), N-(3-dimethylaminopropyl)-N'-ethylcarbodiimide hydrochloride (1.0 g, 5.2 mmol), and isopropylamine (0.44 mL, 5.2 mmol) were dissolved in dichloromethane (2 mL) and stirred at ambient temperature for 16 h. The reaction was diluted with dichloromethane (100 mL), washed 3× with 50 mL of sodium bicarbonate (saturated, aqueous), separated, dried over sodium sulfate, and concentrated via rotovap to give crude product. The crude was purified by chromatography to obtain the title compound. Found MS (ES+): 255(M+H)$^+$.

Step D: (R)-N-isopropyl-5-methylpyrrolidine-2-carboxamide (R)-Allyl 2-(isopropylcarbamoyl)-5-methylpyrrolidine-1-carboxylate (450 mg, 1769 µmol) was dissolved in acetonitrile (13 mL) and sodium borohydride (268 mg, 7078 μmol) and tetrakis(triphenylphosphine)palladium(0)(102 mg, 88 μmol) were added at ambient temperature. The reaction mixture was heated to 50° C. for 4 h, then filtered through a pad of silica gel and washed with chloroform to remove impurities. The silica was washed again with methanol to obtain the title compound as a mixture of diastereomers (~60:40). Found MS (ES+): 171(M+H)+.

Step E: 6-Bromo-1-chlorophthalazine (215 mg, 881 μmol), (R)-N-isopropyl-5-methylpyrrolidine-2-carboxamide (150 mg, 881 μmol), and cesium carbonate (1435 mg, 4405 μmol) were added to acetonitrile (4.4 mL) and heated in the microwave oven for 80 min at 200° C. The reaction was diluted with 75 mL of EtOAc, added to an addition funnel and partitioned with sodium bicarbonate (saturated, aqueous). The organic layer was washed 3× with 50 mL of sodium bicarbonate (saturated, aqueous), separated, dried over sodium sulfate, and concentrated via rotovap to give crude. The crude was purified by chromatography to obtain the title compound. Found MS (ES+): 377(M+H)+.

EXAMPLE 55

Synthesis of N-cyclopropyl-3-(1-(ethylthio)phthalazin-6-yl)-4-methylbenzamide

Step A: To a solution of 6-bromo-1-chlorophthalazine (0.22 g, 0.9 mmol) in acetonitile (5 mL) stirred at ambient was added sodium ethanethiolate (0.2 g, 2 mmol), and the mixture was stirred for 1 h. The mixture was diluted with ethyl acetate (100 mL), washed with sat. NH$_4$Cl, dried over anhydrous Na$_2$SO$_4$, and concentrated under reduced pressure. The crude product was purified by chromatography eluting with 1-5% 2 M ammonia methanol/dichloromethane to give the 6-bromo-1-(ethylthio)phthalazine as pale yellow solid.

Step B: A mixture of 6-bromo-1-(ethylthio)phthalazine (1.87 g), N-cyclopropyl-4-methyl-3-(4,4,5,5-tetramethyl-1,3,2-dioxaborolan-2-yl)benzamide (0.3 g, 0.9 mmol), and tetrakis(triphenylphosphine) palladium(0) (0.05 g, 0.05 mmol) in DME/EtOH (4:1) (5 mL) was treated with the 2 M aqueous solution of potassium carbonate (1 mL, 3 mmol). The mixture was heated at 90° C. for 1 h. The mixture was cooled, diluted with ethyl acetate (100 mL), washed with water (3×20 mL), brine 20 mL, dried over anhydrous Na$_2$SO$_4$, and concentrated in vacuo. The crude product was purified by chromatography eluting with 1-5% 2 M ammonia methanol/dichloromethane to give the title compound as pale yellow solid. Found MS(ES+): 364(M+H)+.

EXAMPLE 56

Synthesis of (2R,5S)-2,5-dimethylmoroholine

Step A: To a stirred solution of (S)-2-aminopropan-1-ol (0.2 mmol) in water (200 mL) at 0° C. was added (R)-2-methyloxirane (0.2 mmol) dropwise using a syringe pump over a period of 3 h. The mixture was stirred at 0° C.—RT over 4 h. The mixture was concentrated to remove the water. The mixture was vacuum distilled (110° C. oil bath, collected 55-60° C. fraction) to remove the unreacted alaninol, then collected the 110-115° C. fraction to give the diol product as a pale yellow oil.

Step B: A stirred solution of (S)-2-((R)-2-hydroxypropylamino)propan-1-ol (9.9 g, 74 mmol), N,N-dimethyl-4-aminopyridine (0.91 g, 7.4 mmol) and pyridine (18 g, 223 mmol) in dichloromethane (100 mL) at 0° C. was treated with 4-methylbenzene-1-sulfonyl chloride (30 g, 156 mmol) in 5 portions. The mixture was stirred at 0° C. for 19 h, then at ambient for 2 h. The mixture was quenched with sat. NH$_4$Cl (50 mL), extracted with dichloromethane (3×50 mL). The combined organic layers were washed with brine (50 mL), dried over anhydrous Na$_2$SO$_4$, concentrated and purified by chromatography eluting with 30-70% ethyl acetate/hexane to give (S)-2-(N—((R)-2-hydroxypropyl)-4-methylphenylsulfonamido)propyl-4-methylbenzenesulfonate as a colorless oil.

Step C: A solution of (S)-2-(N—((R)-2-hydroxypropyl)-4-methylphenylsulfonamido) propyl 4-methylbenzenesulfonate (6.7 g, 15 mmol) in THF (50 mL) stirred at 0° C. was treated with 0.5 M solution of potassium bis(trimethylsilyl)amide (30 mL, 15 mmol) in toluene. The mixture was stirred at 0° C. for 1 h, then quenched with 20 mL sat. NH$_4$Cl, and extracted into ethyl acetate (3×50 mL). The combined organic layers were dried over anhydrous Na$_2$SO$_4$, concentrated and purified by column eluting with 10-30% ethyl acetate/hexane to give the (2R,5S)-2,5-dimethyl-4-tosylmorpholine as a colorless oil.

Step, D: To a mixture of (2R,5S)-2,5-dimethyl-4-tosylmorpholine (3.55 g, 13 mmol) in THF (50 mL) stirred at 22° C. was added naphthalene (2.5 g, 20 mmol), and sodium (0.61 g, 26 mmol). The mixture was stirred at 22° C. for 3 h, after which most of starting material was found to be consumed. The mixture was quenched with 20 mL H$_2$O, acidified with concentrated HCl to a pH of about 1, and extracted with ether (3×50 mL). The combined ether layers were washed with 10 mL 2 N HCl. The combined water phase was basified by solid NaOH to pH=14, then extracted with ether (4×20 mL). The combined organics were washed with 20 mL sat. brine, dried over solid KOH, and carefully concentrated using an ice bath. The title compound (2R,5S)-2,5-dimethyl morpholine was obtained as a pale, colorless oil.

EXAMPLE 57

Synthesis of (2R.5R)-2.5-dimethylmorpholine

Step A: To a mixture of (R)-2-aminopropan-1-ol (15 g, 200 mmol) in 200 mL water stirred at 0° C. was added (R)-2-methyloxirane (13 g, 220 mmol) dropwise using a syringe pump over 3 h. The mixture was stirred at 0° C.—RT over 4 h. The mixture was concentrated in vacuo with to remove water. The mixture was vacuum distilled to remove the unreacted alaninol at first (60° C. fraction), then collected the 110-115° C. fraction to give the (R)-2-((R)-2-hydroxypropylamino)propan-1-ol as a sticky pale yellow oil.

Step B: To a mixture of (R)-2-((R)-2-hydroxypropylamino)propan-1-ol (11 g, 83 mmol) in 200 mL dichloromethane stirred at 0° C. was added a sat. solution of sodium bicarbonate (8.3 g, 99 mmol), then added dropwise benzyl chloroformate (15 g, 91 mmol). The mixture was stirred from 0° C. warming to RT over 4 h. The mixture was extracted with dichloromethane (3×100 mL). The combined organics were washed with brine, dried over anhydrous Na$_2$SO$_4$, concentrated in vacuo and purified by column eluting with 20-70% ethyl acetate in hexane to give the benzyl (R)-1-hydroxypropan-2-yl((R)-2-hydroxypropyl)carbamate as a colorless oil.

Step C: To a mixture of benzyl (R)-1-hydroxypropan-2-yl ((R)-2-hydroxypropyl)carbamate (15.5 g, 58 mmol) in 150 mL THF stirred at 0° C. was added triphenyl phosphine (15 mL, 64 mmol) and stirred for 30 min. The mixture was further treated with diethyl azodicarboxylate (10 mL, 64 mmol) dropwise. The mixture was stirred at 0° C.—RT over 15 h. The mixture was concentrated in vacuo, then was treated with 4:1 hexane/ether 300 mL to precipitate the triphenylphosine oxide. The mixture was filtrated and washed with 4:1 hexane/ether 100 mL. The liquid was concentrated and purified by silica gel chromatography eluting with 20% ethyl acetate/hexane to give (2R,5R)-benzyl 2,5-dimethylmorpholine-4-carboxylate as a colorless oil.

Step D: A mixture of (2R,5R)-benzyl 2,5-dimethylmorpholine-4-carboxylate (10.8 g, 43.3 mmol) and Palladium 10% on carbon (1.38 g, 1.30 mmol) in 200 mL ether was stirred under 1 atm hydrogen for 3 h. The mixture was filtered and washed with 20 mL ether. The mixture was dried with anhydrous KOH, then Na and refluxed for 2 h. The mixture was distilled at 130-140° C. to give (2R,5R) 2,5-dimethylmorpholine as colorless oil.

EXAMPLE 58

Synthesis of N-cyclopropyl-4-methyl-3-[1-(4-oxopiperidin-1-yl)phthalazin-6-yl]benzamide To a mixture of N-cyclopropyl-3-(1-(4-ethyleneketal piperidin-1-yl)phthalazin-6-yl)-4-methylbenzamide (0.65 g, 1 mmol) in 100 mL dichloromethane stirred at 0° C. was added Conc. HCl (3 mL, 29 mmol). The mixture was stirred at 0° C. warming to RT over 15 h. The mixture was neutralized with 10% $Na_2CO_3$ to pH=7 and extracted with dichloromethane (3×50 mL). The combined organics were washed with brine, dried over anhydrous $Na_2SO_4$, concentrated and purified by column eluting with 10-50% 2M ammonia methanol/dichloromethane to give the title compound as a pale yellow solid. Found MS(ES+): 401(M+H)$^+$.

EXAMPLE 59

Synthesis of 4-(6-(5-(cyclolpropylcarbamoyl)-2-methylphenyl)phthalazin-1-yl)piperazine-1-carboxamide To a mixture of N-cyclopropyl-4-methyl-3-(1-(piperazin-1-yl)phthalazin-6-yl)benzamide (Method A, 0.1 g, 0.3 mmol) and triethylamine (0.05 g, 0.5 mmol) in 5 mL dichloromethane stirring at RT was added trimethylsilyl isocyanate (0.06 mL, 0.5 mmol). The mixture was stirred at RT for 15 h, and a white solid precipitated out. The mixture was directly purified by silica gel chromatography eluting with 5-10% 2 M ammonia methanol/dichloromethane to yield the title product as a white solid. Found MS(ES+): 431 (M+H)$^+$.

EXAMPLE 60

Synthesis of 4-methyl-3-[1-(1-oxidothiomorpholin-4-yl)phthalazin-6-yl]benzamide

A mixture of 4-methyl-3-[1-(thiomorpholin-4-yl)phthalazin-6-yl]benzamide (0.6 mmol) (Method A) in 10 mL methanol/$H_2O$ (8:2) was stirred at RT was treated with oxone® monopersulfate compound (1 mmol). The mixture was stirred at 0° C.-50° C. over 1h. The mixture was quenched with 20 mL sat. $N_2SO_3$, extracted with dichloromethane (3×50 mL). The combined organic layers were dried over anhydrous $Na_2SO_4$, concentrated in vacuo and purified by silica gel chromatography eluting with 1-5% 2 M ammonia methanol in dichloromethane to give the title compound. Found MS(ES+): 381(M+H)$^+$.

EXAMPLE 61

Synthesis of N-cyclopropyl-3-(1-(4-hydroxy-4-isopropylpiperidin-1-yl)phthalazin-6-yl)-4-methylbenzamide A mixture of N-cyclopropyl-4-methyl-3-(1-(4-oxopiperidin-1-yl)phthalazin-6-yl)benzamide (100 mg, 250 µmol) (Method A, followed by deprotection of the ketal) in 5 mL THF was stirred at −78° C. and treated with isopropylmagnesium chloride (250 µl, 499 µmol). The mixture was stirred at −78° C. warming to RT over 4 h. The mixture was quenched with 5 mL sat $NH_4Cl$ and extracted with dichloromethane (3×50 mL). The combined organics were dried over anhydrous $Na_2SO_4$, concentrated in vacuo and purified by silica gel chromatography eluting with 1-5% 2M ammonia methanol/dichloromethane to give the title compound. Found MS (ES+): 445(M+H)$^+$.

EXAMPLE 62

Synthesis of N-cyclopropyl-4-methyl-3-(1-(1,2,3,6-tetrahydropyridin-4-yl)phthalazin-6-yl)benzamide A mixture of tert-butyl 4-(6-(5-(cyclopropylcarbamoyl)-2-methylphenyl)phthalazin-1-yl)-5,6-dihydropyridine-1(2H)-carboxylate (100 mg, 206 µmol) (Method B) in 2 mL methanol was stirred at RT was treated with 1 mL HBr 48% in $H_2O$. The mixture was stirred for 2 h from 0° C. to RT. The mixture was diluted with 20 mL dichloromethane, washed with 1N NaOH to pH11. The mixture was extracted with dichloromethane (3×20 mL). The combined organics were washed with 20 mL brine, dried over anhydrous $Na_2SO_4$, concentrated via vacuum and purified by silica gel chromatography eluting with 10% 2M ammonia methanol/dichloromethane to give the title compound as a pale yellow solid. Found MS (ES+): 385(M+H)$^+$.

EXAMPLE 63

Synthesis of N-cyclopropyl-4-methyl-3-(1-((S)-2-methylpiperazin-1-yl)phthalazin-6-yl)benzamide (3S)-Tert-butyl 4-(6-(5-(cyclopropylcarbamoyl)-2-methylphenyl)phthalazin-1-yl)-3-methylpiperazine-1-carboxylate (0.2, 0.4 mmol) (Method A) was dissolved in 10 mL MeOH and treated with a 4M solution of HCl (1 mL, 4 mmol) at RT and stirred for 1 h. The mixture was concentrated in vacuo, diluted with 100 mL dichloromethane, washed with sat. $NaHCO_3$, dried over anhydrous $Na_2SO_4$ and concentrated in vacuo. The mixture was purified by silica gel chromatography, eluting with 2 M ammonia MeOH/dichloromethane to give the title compound. Found MS (ES+): 402(M+H)$^+$.

EXAMPLE 64

Synthesis of N-cyclopropyl-4-methyl-3-(1-(piperidin-4-yl)phthalazin-6-yl)benzamide Step A: A mixture of tert-butyl 4-(6-(5-(cyclopropylcarbamoyl)-2-methylphenyl)phthalazin-1-yl)-5,6-dihydropyridine-1 (2H)-carboxylate (1651 µmol, Method B) and palladium, 10 wt. % on activated carbon (825 µmol) in 20 mL EtOH/dichloromethane (5:1) was stirred at 50 psi hydrogen atmosphere at RT for 2 h. The mixture was filtered and washed with 20 mL methanol, concentrated and purified by silica gel chromatography, eluting with 5% 2 M ammonia MeOH/dichloromethane give 0.69 g of a pale yellow solid as a mixture of title compound and the ove-reduced product.

Step B: The product of step A was dissolved in 30 mL EtOH/H$_2$O (2:1), treated with 0.207 g KMnO$_4$ and stirred for 20 min. The mixture was quenched with 10 mL sat. Na$_2$SO$_3$, and extracted with dichloromethane (3×20 mL). The combined organics were dried over anhydrous Na$_2$SO$_4$ and concentrated in vacuo. The crude product was purified by silica gel chromatography, eluting with 5% 2 M ammonia methanol in dichloromethane to give 0.42 g of tert-butyl 4-(6-(5-(cyclopropylcarbamoyl)-2-methylphenyl)phthalazin-1-yl)piperidine-1-carboxylate.

Step C: 0.42 g of Tert-butyl 4-(6-(5-(cyclopropylcarbamoyl)-2-methylphenyl)phthalazin-1-yl)piperidine-1-carboxylate was dissolved in 2 mL methanol, treated with 1 mL 48% HBr at RT and stirred for 1 h. The mixture was quenched with 20 mL 10% Na$_2$CO$_3$ and extracted with dichloromethane (3×50 mL). The combined organic layers were dried over anhydrous Na$_2$SO$_4$ and concentrated in vacuo. The crude product was purified by silica gel chromatography, eluting with 10% -20% 2 M ammonia methanol/dichloromethane to give the title product as pale yellow solid. Found MS (ES+): 387(M+H)$^+$.

EXAMPLE 65

Synthesis of 7-(1-((2R,5R)-2,5-dimethylmorpholino)phthalazin-6-yl)-N,6-dimethylbenzo[d]isoxazol-3-amine Step A: A mixture of 6-bromo-1-((2R,5R)-2,5-dimethylmorpholino)phthalazine (310 µmol) (Method A-Step A), bis(pinacolato)diboron (310 µmol), potassium acetate (6931 µmol) and dichloro[1,1'-bis(diphenylphosphino)ferrocene]palladium (II) dichloromethane adduct (16 µmol) in 15 mL dioxane was stirred at 100° C. for 2 h. The mixture turned dark red. The mixture was cooled to RT quenched with 20 mL 1 N NaOH, and worked up by the conventional base-acid method to afford the boronic acid (0.15 g) as a yellow solid.

Step B: A mixture of the boronic acid (Step A), 7-iodo-N-6-dimethylbenzo[d]isoxazol-3-amine (310 µmol), Tetrakis(triphenylphosphine) palladium(0) (16 µmol) in 5 mL DME/EtOH (4:1) was treated with the 2 M solution of potassium carbonate (466 µl, 931 µmol). The mixture was warmed up to 90° C. and stirred for 30 min, then cooled to RT, diluted with 100 mL dichloromethane and washed with H$_2$O 3×20 mL, brine 20 mL, dried over anhydrous Na$_2$SO$_4$ and concentrated in vacuo. The crude product was purified by silica gel chromatography, eluting with 5% 2 M ammonia methanol/dichloromethane to give the title compound. Found MS(ES+): 404 (M+H)$^+$.

EXAMPLE 66

Synthesis of N-acetyl-3-(1-(4-acetylpiperazin-1-yl)phthalazin-6-yl)-N-cyclopropyl-4-methylbenzamide A mixture of N-cyclopropyl-4-methyl-3-(1-(piperazin-1-yl)phthalazin-6-yl)benzamide (235 µmol), triethylamine (470 µmol) in 5 mL dichloromethane stirring at 0° C. was treated with acetyl chloride (235 µmol) dropwise. The mixture was stirred at 0-22° C. for 1 h, then diluted with 50 mL dichloromethane, washed with 20 mL sat. NH$_4$Cl, dried over anhydrous Na$_2$SO$_4$, concentrated in vacuo and purified by silica gel chromatography, eluting with 50% ethyl acetate/dichloromethane to give the title compound. Found MS(ES+): 472(M+H)$^+$.

EXAMPLE 67

Synthesis of 3-(1-(1-acetylpiperidin-4-yl)phthalazin-6-yl)-N-cyclopropyl-4-methylbenzamide A mixture of N-cyclopropyl-4-methyl-3-(1-(piperidin-4-yl)phthalazin-6-yl)benzamide N-cyclopropyl-4-methyl-3-(1-(piperidin-4-yl)phthalazin-6-yl)benzamide (29 µmol) in 2 mL ethanol was stirred at RT and treated with 2-trifluoromethylamine diacetate (142 µmol). The mixture was stirred at RT for 4 h, then purified directly by silica gel chromatography, eluting with 5% 2 M ammonia methanol/dichloromethane to give the title compound.
Found MS(ES+): 429(M+H)$^+$.

EXAMPLE 68

Synthesis of (2R)-1-(6-(5-(Cyclopropylcarbamoyl)-2-methylphenyl)phthalazin-1-yl)-N-isopropyl-5-methylpyrrolidine-2-carboxamide Step) A: (R)-1-allyl 2-ethyl 5-hydroxy-5-methylpyrrolidine-1,2-dicarboxylate (R)-1-allyl 2-ethyl 5-oxopyrrolidine-1,2-dicarboxylate (9.1 g, 38 mmol) was dissolved in dichloromethane (100 mL) and cooled to 0° C. before trimethylaluminum −2 M in toluene (94 mL, 190 mmol) was added and the mixture was stirred at RT for 16 h. The reaction mixture was quenched with a minimal amount of ammonium chloride (saturated, aqueous) to form a white solid, which was filtered off to give the crude product. After purification by chromatography, the title compound was obtained. MS (ES+): 258 (M+H)$^+$.

Step B: (R)-1-(allyloxycarbonyl)-5-methylpyrrolidine-2-carboxylic acid (R)-1-allyl 2-ethyl 5-hydroxy-5-methylpyrrolidine-1,2-dicarboxylate (3.0 g, 12 mmol) was dissolved in trifluoroacetic acid (20 mL) and cooled to 0° C. before borane-pyridine complex (2.9 mL, 23 mmol) was added. The reaction mixture was heated to 90° C. for 3 h before it was concentrated in vacuo and NaOH −5 N (30 mL) was added. The mixture was stirred for 2 h at 60° C., then cooled, washed with ethyl acetate (30 mL), acidified to ~pH 5 with conc HCl, extracted with dichloromethane, separated, dried over sodium sulfate, and concentrated in vacuo to give the title compound. MS (ES+): 214 (M+H)$^+$.

Step C: (R)-allyl 2-(isopropylcarbamoyl)-5-methylpyrrolidine-1-carboxylate (R)-1-(allyloxycarbonyl)-5-methylpyrrolidine-2-carboxylic acid (0.92 g, 4.3 mmol), 1H-benzo[d][1,2,3]triazol-1-ol (0.70 g, 5.2 mmol), N-(3-dimethylaminopropyl)-N'-ethylcarbodiimide hydrochloride (1.0 g, 5.2 mmol), and isopropylamine (0.44 mL, 5.2 mmol) were dissolved in dichloromethane (2 mL) and stirred at ambient for 16 h before being diluted with dichloromethane (100 mL), washed 3 times with 50 mL of sodium bicarbonate (saturated, aqueous), separated, dried over sodium sulfate, and concentrated in vacuo. The residue was purified by chromatography to obtain the title compound. MS (ES+): 255 (M+H)$^+$.

Step D:
(R)-N-isopropyl-5-methylpyrrolidine-2-carboxamide (R)-allyl 2-(isopropylcarbamoyl)-5-methylpyrrolidine-1-carboxylate (450 mg, 1769 µmol) was dissolved in acetonitrile (13 mL) before sodium borohydride (268 mg, 7078 µmol) and tetrakis(triphenylphosphine)palladium(0) (102 mg, 88 µmol) were added at ambient. The reaction mixture was heated to 50° C. for 4 h then filtered through a pad of silica gel and washed with chloroform to remove impurities. The silica was washed again with methanol to obtain the title compound as a mixture of diastereomers (~60:40). MS (ES+): 171(M+H)$^+$.

Step E: (R)-1-(6-Bromophthalazin-1-yl)-N-isopropyl-5-methylpyrrolidine-2-carboxamide 6-bromo-1-chlorophthalazine (215 mg, 881 µmol), (R)-N-isopropyl-5-methylpyrrolidine-2-carboxamide (150 mg, 881 µmol), and cesium carbonate (1435 mg, 4405 µmol) were added to acetonitrile (4.4 mL) and placed in the microwave for 80 min at 200° C. before being diluted with 75 mL of ethyl acetate, added to a separation funnel, partitioned with sodium bicarbonate (saturated, aqueous), washed 3 times with 50 mL of sodium bicarbonate (saturated, aqueous), separated, dried over sodium sulfate, and concentrated in vacuo to give the crude product. After purification by chromatography, the title compound was obtained. MS (ES+): 377 (M+H)$^+$.

Step F: N-Cyclopropyl-4-methyl-3-(4,4,5,5-tetramethyl-1,3,2-dioxaborolan-2-yl)benzamide (64 mg, 212 µmol), tetrakis(triphenylphosphine)palladium (18 mg, 16 µmol), and (R)-1-(6-bromophthalazin-1-yl)-N-isopropyl-5-methylpyrrolidine-2-carboxamide (40 mg, 106 µmol) were dissolved/suspended in ethanol (2120 µl, 106 µmol) before potassium carbonate –1 M in water (424 µl, 424 µmol) was added to the vial which was then placed in the microwave for 10 min at 160° C. The reaction mixture was diluted with 75 mL of ethyl acetate, added to a separation funnel, partitioned with sodium bicarbonate (saturated, aqueous), washed 3 times with 50 mL of sodium bicarbonate (saturated, aqueous), separated, dried over sodium sulfate, and concentrated in vacuo to give crude. After purification by chromatography, the title compound was obtained. MS (ES+): 472 (M+H)$^+$.

EXAMPLE 69

Synthesis of N-Cyclopropyl-3-(1-morpholin-4-ylphthalazin-6-yl)benzamide

Step A: N-Cyclopropyl-3-iodobenzamide

3-Iodobenzoic acid (4.79 g, 19.3 mmol) was suspended in thionyl chloride (19.3 mL) and stirred for 1 h at 70° C. before it was conc. and azeotropically dried with toluene. The reaction mixture was dissolved in dioxane (19.3 mL) before N-ethyl-N-isopropylpropan-2-amine (13.5 mL, 77.3 mmol) and cyclopropylamine (6.77 mL, 96.6 mmol) were added and stirred for 16 h at ambient temperature. The reaction mixture was diluted with 75 mL of ethyl acetate, added to a separation funnel, partitioned with sodium bicarbonate (saturated, aqueous), washed 2× with 50 mL of 3 N HCl (aqueous), separated, dried over sodium sulfate, and concentrated in vacuo to give the title compound. MS (ES+): 288 (M+H)$^+$.

Step B: To 6-bromo-1-morpholinophthalazine (95 mg, 323 µmol), 1,1'-bis(diphenylphosphino)ferrocene-palladium dichloride (24 mg, 32 µmol), potassium acetate (95 mg, 969 µmol), and 4,4,5,5-tetramethyl-2-(4,4,5,5-tetramethyl-1,3,2-dioxaborolan-2-yl)-1,3,2-dioxaborolane (90 mg, 355 µmol) was added 1,4-dioxane (3.23 mL) before it was heated to 80° C. for 2.5 h. This reaction mixture was added to a mixture of N-cyclopropyl-3-iodobenzamide (111 mg, 388 µmol) and tetrakis(triphenylphosphine) palladium (37 mg, 32 µmol) in ethanol (3.23 mL) and potassium carbonate –1.5 M in water (861 µl, 1292 µmol) and stirred for 2 h at 80° C. The mixture was diluted with 75 mL of ethyl acetate, added to a separation funnel, partitioned with sodium bicarbonate (saturated, aqueous), washed 2× with 50 mL of sodium bicarbonate (saturated, aqueous), separated, dried over sodium sulfate, concentrated in vacuo, and purified by HPLC to give the title compound. MS (ES+): 375 (M+H)$^+$.

EXAMPLE 70

Synthesis of 6-{5-[(Cyclopropylamino)carbonyl]-2-methylphenyl}-N-isopropylphthalazine-1-carboxamide 3-(1-Cyanophthalazin-6-yl)-N-cyclopropyl-4-methylbenzamide (115 mg, 350 µmol) and potassium hydroxide (39 mg, 700 µmol) were dissolved in ethanol/water (1:1) (3.50 mL) before it was placed in the microwave for 10 min at 120° C. The reaction mixture was concentrated before it was dissolved in dimethylformamide (700 µl); HATU (266 mg, 700 µmol) and isopropylamine (150 µl, 1751 µmol) were added. This was stirred at RT for 16 h before more HATU was added, and the reaction mixture was stirred at RT for 7 h. The reaction mixture was diluted with 100 mL of ethyl acetate, added to a separatory funnel, partitioned with water, washed 2× with 50 mL of water, separated, dried over sodium sulfate, concentrated in vacuo, and purified by HPLC to give the title compound.

MS (ES+): 389 (M+H)$^+$.

EXAMPLE 71

Synthesis of N-Cyclopropyl-4-methyl-3-(1-(4-(methylsulfonyl)piperazin-1-yl)phthalazin-6-ylbenzamide Step A: -(Methylsulfonyl)piperazine Benzyl 1-piperazinecarboxylate (2.03 g, 9.22 mmol) was dissolved in pyridine (23.0 mL, 9.22 mmol) and cooled to 0° C. before methanesulfonyl chloride (2.85 mL, 36.9 mmol) was added. The reaction mixture was stirred at 0° C. for 30 minutes and warmed to RT for 2 h. The reaction mixture was diluted with 75 mL of ethyl acetate, added to a separation funnel, partitioned with 3 N HCl (aqueous), washed 3× with 50 mL of 3 N HCl (aqueous), and separated, before the aqueous layer was extracted 3× with chloroform/isopropanol, then dried over sodium sulfate, and concentrated in vacuo to give the title compound. Benzyl 4-(methylsulfonyl)piperazine-1-carboxylate (2.80 g, 9.4 mmol) was dissolved in ethanol (0.43 g, 9.4 mmol) before palladium, 10 wt. % on activated carbon (2.0 g) was added and a hydrogen balloon attached. The reaction mixture was stirred at RT for 2 h before it was filtered through a pad of Celite®, washed with methanol, and concentrated in vacuo to give the title compound. MS (ES+): 165 (M+H)$^+$.

Step B: 6-Bromo-1-(4-(methylsulfonyl)piperazin-1-yl)phthalazine

6-Bromo-1-chlorophthalazine (18 mg, 74 umol) and 1-(methylsulfonyl)piperazine (91 mg, 554 µmol) were dissolved in dichloromethane/methanol when the reaction mixture was concentrated by evaporation under a nitrogen line. The concentrate was heated to 120° C. for 6 h to give the title compound. MS (ES+): 373 (M+H)$^+$.

Step C: To 6-bromo-1-(4-(methylsulfonyl)piperazin-1-yl) phthalazine (122 mg, 329 µmol), N-cyclopropyl-4-methyl-3-(4,4,5,5-tetramethyl-1,3,2-dioxaborolan-2-yl)benzamide (119 mg, 394 µmol), and tetrakis(triphenylphosphine)palladium (38 mg, 33 µmol) was added ethanol (3.29 mL), and potassium carbonate—1.5 M in water (876 µl, 1314 µmol) before it was heated to 80° C. for 1.5 h. The reaction mixture was diluted with 50 mL of ethyl acetate, added to a separation funnel, partitioned with sodium bicarbonate (saturated, aqueous), washed 2× with 20 mL of sodium bicarbonate (saturated, aqueous), separated, dried over sodium sulfate, concentrated in vacuo, and purified by flash chromatography to give the title compound. MS (ES+): 466(M+H)$^+$.

EXAMPLE 72

Synthesis of N-Cyclopropyl-4-fluoro-3-(1-morpholin-4-ylphthalazin-6-yl)benzamide To 4-fluoro-3-(1-morpholinophthalazin-6-yl)benzoic acid (200 mg, 566 µmol) was added thionyl chloride (2.83 mL) before it was heated to 65° C. for 1 h. The reaction mixture was concentrated in vacuo and azeotropically dried with toluene. Dioxane (2.83 mL,), diisopropylethylamine (493 µl, 2830 µmol), and cyclopropylamine (323 µl, 5660 µmol) were added and the mixture was stirred at RT overnight. The reaction mixture was diluted with 50 mL of ethyl acetate, added to a separation funnel, partitioned with sodium bicarbonate (saturated, aqueous), washed 2 times with 20 mL of sodium bicarbonate (saturated, aqueous), separated, dried over sodium sulfate, concentrated in vacuo, and purified by HPLC to give the title compound. MS (ES+): 393 (M+H)$^+$.

EXAMPLE 73

Synthesis of 4-Chloro-3-(1-morpholin-4-ylphthalazin-6-yl)benzamide

Step A: 4-chloro-3-iodobenzamide 4-chloro-3-iodobenzoic acid (2.09 g, 7.40 mmol) was suspended in thionyl chloride (0.540 mL, 7.40 mmol) and heated to 70° C. for 3 h before it was concentrated and azeotropically dried with toluene. The concentrate was dissolved in ammonia, 0.5 M in 1,4-dioxane (92.5 mL, 37.0 mmol) to which diisopropylethylamine (6.44 mL, 37.0 mmol) was added and it was stirred at RT for 3 h. The mixture was diluted with 100 mL of ethyl acetate, added to a separation funnel, partitioned with sodium bicarbonate (saturated, aqueous), washed 4 times with 50 mL of sodium bicarbonate (saturated, aqueous), separated, dried over sodium sulfate, and concentrated in vacuo to give the title compound. MS (ES+): 282 (M+H)$^+$.

Step B: To 6-Bromo-1-morpholinophthalazine (0.20 g, 680 µmol), 1,1'-bis(diphenylphosphino)ferrocene-palladium dichloride (50 mg, 68 µmol), potassium acetate (200 mg, 2040 µmol), and 4,4,5,5-tetramethyl-2-(4,4,5,5-tetramethyl-1,3,2-dioxaborolan-2-yl)-1,3,2-dioxaborolane (207 mg, 816 µmol) was added 1,4-dioxane (6.80 mL) and the mixture was heated to 80° C. for 2 h. The mixture was added to a sealed tube containing 4-chloro-3-iodobenzamide (230 mg, 816 µmol), tetrakis(triphenylphosphine)palladium (79 mg, 68 µmol), potassium carbonate—1.5 M in water (1.81 µl, 2.72 mmol), and ethanol (6.80 mL) and heated to 110° C. for 2 h. After cooling the reaction mixture was diluted with 75 mL of ethyl acetate, added to a separation funnel, partitioned with sodium bicarbonate (saturated, aqueous), washed 3 times with 50 mL of sodium bicarbonate (saturated, aqueous), separated, dried over sodium sulfate, concentrated in vacuo, and purified by HPLC to give the title compound.
MS (ES+): 369(M+H)$^+$.

EXAMPLE 74

Synthesis of N-ethyl-4-methyl-3-(1-morpholin-4-ylphthalazin-6-yl)benzamide

4-Methyl-3-(1-morpholinophthalazin-6-yl)benzoic acid (100 mg, 286 µmol) was dissolved in thionyl chloride (5.7 mL) and heated to 65° C. for 1 h before being concentrated in vacuo. The concentrate was dissolved in THF (5.7 mL), and DIPEA (150 µL, 859 µmol) and ethylamine—2 M in THF (0.71 mL) were added at 0° C. The reaction mixture was warmed to RT and stirred for 3 h, then diluted with 50 mL of ethyl acetate, added to a separation funnel, partitioned with sodium bicarbonate (saturated, aqueous), washed 3× with 50 mL of sodium bicarbonate (saturated, aqueous), separated, dried over sodium sulfate, and concentrated in vacuo to give a crude residue, which was purified by chromatography to afford the title compound. MS (ES+): 377(M+H)$^+$.

EXAMPLE 75

Synthesis of N-Cyclopropyl-4-methyl-3-{1-[(3R)-3-methylmorpholin-4-yl]phthalazin-6-yl}benzamide Step, A: (R)-2-(Benzylamino)propan-1-ol (R)-2-Aminopropan-1-ol (20.00 g, 266.3 mmol) was dissolved in benzene (266 mL) before benzaldehyde (26.91 mL, 266.3 mmol) was added and the reaction refluxed under a Dean-Stark trap for 1.5 h collecting 4.2 mL of water. The reaction mixture was cooled in an ice bath before sodium borohydride (10.07 g, 266.3 mmol) was added. The mixture was warmed to RT and stirred overnight. In an ice bath, methanol was added to the reaction mixture to quench the hydride, then the reaction concentrated, filtered, washed with dichloromethane, concentrated, and purified by flash chromatography to give the title compound. MS (ES+): 166 (M+H)$^+$.

Step B: (R)-N-Benzyl-2-chloro-N-(1-hydroxypropan-2-yl)acetamide (R)-2-(Benzylamino)propan-1-ol (16.58 g, 100 mmol) was dissolved in dichloromethane (125 mL) and TEA (18.1 mL, 130 mmol) before being cooled to −10° C. in a methanol/ice bath. Chloroacetic acid chloride (8.78 mL, 110 mmol) was added dropwise and the mixture was stirred for 1.5 h at −10° C. A small amount of water was then added to remove the amine. The reaction mixture was poured into a separatory funnel, washed 2×50 mL with dichloromethane, separated, organic layers dried over sodium sulfate, concentrated in vacuo, and purified by flash chromatography to give the title compound.
MS(ES+): 242(M+H)$^+$.

Step C: (R)-4-Benzyl-5-methylmorpholin-3-one (R)-N-Benzyl-2-chloro-N-(1-hydroxypropan-2-yl)acetamide (9.49 g, 39.3 mmol) was dissolved in THF (78.5 mL) before NaH—60% in oil (1.73 g, 43.2 mmol) was added and the mixture stirred at reflux for 4 h. The reaction was quenched with a few drops of water, concentrated, diluted with dichloromethane, filtered, and concentrated to give the title compound. MS (ES+): 206(M+H)$^+$.

Step D: (R)-4-Benzyl-3-methylmorpholine (R)-4-Benzyl-5-methylmorpholin-3-one (5.05 g, 24.6 mmol) was dissolved in THF (12.3 mL) before lithium aluminum hydride (1.87 g, 49.2 mmol) was added and the mixture stirred at RT for 1 h. The reaction mixture was quenched with ethyl acetate before a few drops of ammonium chloride was added. The colorless oil was filtered, washed with dichloromethane, concentrated, and purified by flash chromatography to give the title compound. MS (ES+): 192(M+H)$^+$.

Step E: (R)-3-Methylmorpholine (R)-4-Benzyl-3-methylmorpholine (3.16 g, 16521 µmol), was dissolved in ethanol (33.0 mL) to which palladium—10% on carbon (1758 mg, 16521 µmol) was added. The reaction mixture was stirred under 50 psi of hydrogen overnight, then filtered and washed with dichloromethane. The reaction mixture was distilled to remove the solvents before being transferred to a 25 mL flask and distilled under a nitrogen atmosphere in a short path distillation column to give the title compound. MS(ES+): 102 (M+H)$^+$.

Step F: (R)-3-Methylmorpholine (93 mg, 919 µmol) was dissolved in p-xylene (0.460 mL) before 6-bromo-1-chlorophthalazine (112 mg, 460 µmol) was added. The reaction mixture was heated to 165° C. for 1.5 h, then diluted with ethyl alcohol (4.61 mL) before N-cyclopropyl-4-methyl-3-(4,4,5,5-tetramethyl-1,3,2-dioxaborolan-2-yl)benzamide (153 mg, 507 µmol), tetrakis(triphenylphosphine)palladium (27 mg, 23 µmol), and potassium carbonate—1.5 M in water (1229 µl, 1843 µmol) were added. The mixture was heated to 90° C. for 1 h, diluted with 50 mL of ethyl acetate, added to a separatory funnel, partitioned with sodium bicarbonate (saturated, aqueous), washed 2 times with 20 mL of sodium bicarbonate (saturated, aqueous) and separated. The organic layers were dried over sodium sulfate, concentrated, and purified by flash chromatography to give the title compound. MS (ES+): 403(M+H)$^+$.

EXAMPLE 76

Synthesis of N-[2-Methoxy-5-(trifluoromethyl)phenyl]-4-methyl-3-(1-morpholin-4-ylphthalazin-6-yl) benzamide 3-Iodo-N-(2-methoxy-5-(trifluoromethyl)phenyl)-4-methylbenzamide (205 mg, 471 µmol), 1,1'-bis(diphenylphosphino)ferrocene-palladium dichloride (34 mg, 47 µmol), bis(pinacolato)diboron (179 mg, 707 µmol), and potassium acetate (118 µL, 1884 µmol) were dissolved/suspended in DMF (2.4 mL) and heated in the microwave at 160° C. for 10 min. The reaction mixture was transferred to another vial containing 6-bromo-1-morpholinophthalazine (125 mg, 424 µmol), tetrakis(triphenylphosphine)palladium(0) (54 mg, 47 µmol), potassium carbonate-2 M in water (942 µL, 1884 µmol), and ethanol (2.4 mL), and heated in a microwave at 160° C. for 10 min. The reaction mixture was diluted with 50 mL of ethyl acetate, added to a separation funnel, partitioned with sodium bicarbonate (saturated, aqueous), washed 3 times with 50 mL of sodium bicarbonate (saturated, aqueous), separated, dried over sodium sulfate, and concentrated in vacuo to give a crude product, which was purified by chromatography to afford the title compound.

MS (ES+): 523 (M+H)$^+$.

EXAMPLE 77

Synthesis of 6-[2-Methyl-5-(1H-tetraazol-5-yl)phenyl]-1-morpholin-4-ylphthalazine Step A: 5-(4-Methyl-3-(4,4,5,5-tetramethyl-1,3,2-dioxaborolan-2-yl)phenyl)-1H-tetrazole 4-Methyl-3-(4,4,5,5-tetramethyl-1,3,2-dioxaborolan-2-yl)benzamide (0.27 g, 1.0 mmol) and sodium azide (0.20 g, 3.1 mmol) were added to dioxane (5.2 mL, 1.0 mmol) before silicon tetrachloride (0.12 mL, 1.0 mmol) was added. The reaction mixture was heated to 85° C. for 7 h when two spots were observed by tlc. The reaction mixture was stirred at 60° C. overnight. The reaction mixture was diluted with 50 mL chloroform, partitioned with brine (saturated, aqueous), washed 2 times with 50 mL of chloroform, separated, dried over sodium sulfate, and concentrated in vacuo to give the title compound. MS (ES+): 287 (M+H)$^+$.

Step B: 6-Chloro-1-morpholinophthalazine (160 mg, 641 µmol), 5-(4-methyl-3-(4,4,5,5-tetramethyl-1,3,2-dioxaborolan-2-yl)phenyl)-1H-tetrazole (220 mg, 769 µmol), and tetrakis(triphenylphosphine)palladium (74 mg, 64 µmol) were dissolved in ethanol (6408 µl, 641 µmol) and potassium carbonate—2 M in water (1282 µl, 2563 µmol) and heated to 80° C. for 4 h. The reaction mixture was diluted with 20 mL ethyl acetate, partitioned with ammonium chloride (saturated, aqueous), organic layer washed 2 times with 50 mL of ammonium chloride (saturated, aqueous) to give product in the aqueous layer, this was acidified with ca. 3 N HCl to pH 5. The aqueous layer was extracted with chloroform, organic layer separated, dried over sodium sulfate, concentrated in vacuo, and purified via HPLC to give title compound. MS (ES+): 374(M+H)$^+$.

EXAMPLE 78

Synthesis of Methyl 3-(1-cyanophthalazin-6-yl)-4-methylbenzoate

Step A: Methyl 3-(1-hydroxyphthalazin-6-yl)-4-methylbenzoate 3-(1-Hydroxyphthalazin-6-yl)-4-methylbenzoic acid (2.71 g, 9.67 mmol) was suspended in methanol (96.7 mL), thionyl chloride (2.12 mL, 29.0 mmol) was added and the mixture was stirred at 50° C. for 1.5 h and at RT overnight. The mixture was concentrated to give the title compound. MS (ES+): 295(M+H)$^+$.

Step B: Methyl 3-(1-chlorophthalazin-6-yl)-4-methylbenzoate

Methyl 3-(1-hydroxyphthalazin-6-yl)-4-methylbenzoate (2.85 g, 9.68 mmol) was suspended in acetonitrile (19.4 mL), cooled to 0° C. to which phosphorus oxychloride (1.81 mL, 19.4 mmol) was added dropwise. The reaction mixture was warmed to 80° C. for 2.5 h, then concentrated, diluted with 150 mL of ethyl acetate, added to a separatory funnel and partitioned with water. The organics were washed 2×50 mL with water, separated, dried over sodium sulfate, and concentrated in vacuo to give the title compound. MS (ES+): 313 (M+H)$^+$.

Step C: To methyl 3-(1-chlorophthalazin-6-yl)-4-methylbenzoate (2.49 g, 7.96 mmol) and zinc cyanide (1.87 g, 15.9 mmol) was added DMF (39.8 mL). The mixture was sparged with nitrogen for 15 min, and tris(dibenzylideneacetone)dipalladium(0) chloroform adduct (0.330 g, 0.318 mmol) and 1,1'-bis(diphenylphosphino)ferrocene (0.177 g, 0.318 mmol) were added. The reaction was heated to 100° C. for 30 min. The reaction mixture was diluted with 100 mL ethyl acetate, partitioned with sodium bicarbonate (saturated, aqueous), and the organics were washed 3×50 mL with sodium bicarbonate (saturated, aqueous), separated, dried over sodium sulfate, concentrated in vacuo, and purified by flash chromatography to give the title compound. MS (ES+): 304(M+H)$^+$.

EXAMPLE 79

Synthesis of 3-(1-cyanophthalazin-6-yl)-N-cyclopropyl-4-methylbenzamide

To methyl 3-(1-cyanophthalazin-6-yl)-4-methylbenzoate (0.800 g, 2.6 mmol) was added 6N HCl (10.6 mL) and the reaction was heated in a microwave oven for 25 min at 120° C. The reaction was concentrated, dried in vacuo and DMF (5.3 mL) and cyclopropylamine (0.92 mL, 13 mmol) were added. HATU (2.0 g, 5.3 mmol) was added and the reaction mixture was stirred at RT for 1 h, then diluted with 75 mL ethyl acetate, partitioned with sodium bicarbonate (saturated, aqueous), and the organic layers were washed 2×20 mL with sodium bicarbonate (saturated, aqueous), separated, dried over sodium sulfate, concentrated in vacuo, and purified by HPLC to give the title compound. MS (ES+): 329(M+H)$^+$.

EXAMPLE 80

Synthesis of N-Cyclopropyl-5-methyl-4-(1-morpholin-4-ylphthalazin-6-yl)thiophene-2-carboxamide Step A: 4-Bromo-N-cyclopropyl-5-methylthiophene-2-carboxamide 4-Bromo-5-methylthiophene-2-carboxylic acid (1.05 g, 4.75 mmol) was suspended in thionyl chloride (4.75 mL) and heated to 70° C. for 1.5 h. The mixture was concentrated and dried azeotropically with toluene. The reaction mixture was dissolved in dioxane (11.9 mL) to which diisopropylethylamine (4.14 mL, 23.7 mmol) and cyclopropylamine (1.36 mL, 23.7 mmol) were added and stirred at RT for 2 h. The reaction mixture was diluted with 50 mL ethyl acetate, partitioned with sodium bicarbonate (saturated, aqueous), and the organic layers were washed 2×50 mL with sodium bicarbonate (saturated, aqueous), washed with 3 N HCl, separated, dried over sodium sulfate, and concentrated in vacuo to give the title compound. MS (ES+): 262 (M+H)$^+$.

Step B: N-Cyclopropyl-5-methyl-4-(4,4,5,5-tetramethyl-1,3,2-dioxaborolan-2-yl)thiophene-2-carboxamide 4-Bromo-N-cyclopropyl-5-methylthiophene-2-carboxamide (235 mg, 903 μmol), bis(pinacolato)diboron (252 mg, 994 μmol), potassium acetate (266 mg, 2710 μmol), and 1,1'-bis(diphenylphosphino)ferrocene-palladium dichloride (66.1 mg, 90.3 μmol) were dissolved in EtOH/DME (1:4) (4.52 mL) and heated to 90° C. for 1 h. The mixture was cooled to RT, diluted with 50 mL ethyl acetate, partitioned with brine (saturated, aqueous), and the organics were washed 3×20 mL with brine (saturated, aqueous), separated, dried over sodium sulfate, concentrated in vacuo, and purified by flash chromatography to give the title compound. MS (ES+): 308(M+H)$^+$ Step C: A mixture of 6-chloro-1-morpholinophthalazine (200 mg, 801 μmol), N-cyclopropyl-5-methyl-4-(4,4,5,5-tetramethyl-1,3,2-dioxaborolan-2-yl) thiophene-2-carboxamide (205 mg, 667 μmol), and tetrakis (triphenylphosphine)palladium (116 mg, 100 μmol) was charged ethanol (6.67 mL) and potassium carbonate -2 M in water (1335 μl, 2669 μmol), The reaction mixture was heated to 80° C. for 3 h, then diluted with 50 mL ethyl acetate, partitioned with sodium bicarbonate (saturated, aqueous), and the organics were washed 3×20 mL with sodium bicarbonate (saturated, aqueous), separated, dried over sodium sulfate, concentrated in vacuo, and purified by HPLC to give the title compound. MS (ES+): 395 (M+H)$^+$.

EXAMPLE 81

Synthesis of N-Cyclopropyl-4-methyl-5-(1-morpholin-4-ylphthalazin-6-yl)thiophene-2-carboxamide Step A: 4-methyl-5-(1-morpholinophthalazin-6-yl) thiophene-2-carboxylic acid 6-Bromo-1-morpholinophthalazine (405 mg, 1377 μmol), 4,4,5,5-tetramethyl-2-(4,4,5,5-tetramethyl-1,3,2-dioxaborolan-2-yl)-1,3,2-dioxaborolane (524 mg, 2065 μmol), potassium acetate (541 mg, 5507 μmol), and 1,1'-bis(diphenylphosphino)ferrocene-palladium dichloride (101 mg, 138 μmol) were dissolved in N,N-dimethylformamide (4.6 mL) and heated in the microwave oven for 10 minutes at 160° C. To the reaction mixture was added a vial containing a mixture of methyl 5-bromo-4-methylthiophene-2-carboxylate (388 mg, 1652 μmol), tetrakis(triphenylphosphine)palladium (159 mg, 138 μmol), potassium carbonate-2 M in water (2754 μl, 5507 μmol), and ethanol (4590 μl, 1377 μmol). The reaction was heated in the microwave for 10 min at 160° C., then diluted with 75 mL ethyl acetate and partitioned with sodium bicarbonate (saturated, aqueous). The organics were washed 3×50 mL with sodium bicarbonate (saturated, aqueous), and separated before the aqueous layer was acidified to pH 4 with conc. HCl and extracted 3×50 mL with chloroform. The organics were combined and dried over sodium sulfate, and concentrated in vacuo to give the crude product, which was purified by chromatography to afford the title compound as the TFA salt. MS (ES+): 356(M+H)$^+$.

Step B: 4-Methyl-5-(1-morpholinophthalazin-6-yl) thiophene-2-carboxylic acid (140 mg, 309 μmol) was suspended in thionyl chloride (3.1 mL) and the mixture was heated to 65° C. for 1 h. The reaction mixture was concentrated in vacuo and azeotropically dried with toluene, then dissolved/suspended in THF 99.9% (3.1 mL) and DIPEA (216 μl, 1238 μmol) and cyclopropylamine (71 μl, 1238 μmol) were added. The mixture was stirred at RT for 2 h, then diluted with 50 mL ethyl acetate and partitioned with sodium bicarbonate (saturated, aqueous). The organics were washed 2×50 mL with sodium bicarbonate (saturated, aqueous), separated, dried over sodium sulfate, and concentrated in vacuo to give crude yellow product, which was purified by chromatography to afford the title compound. MS (ES+): 395(M+H)$^+$.

EXAMPLE 82

Synthesis of 4-Methyl-3-{1-[(3R)-3-methylmorpholin4-yl]phthalazin-6-yl}benzamide To (R)-3-methylmorpholine (108 mg, 1068 μmol) and 6-bromo-1-chlorophthalazine (130 mg, 534 μmol) was added p-xylene (534 μl) and the mixture was heated to 165° C. for 1.5 h. The reaction mixture was added to 4-methyl-3-(4,4,5,5-tetramethyl-1,3,2-dioxaborolan-2-yl)benzamide (154 mg, 589 μmol), tetrakis(triphenylphosphine)palladium (31 mg, 27 μmol), ethanol (5.35 mL), and potassium carbonate—1.5 M in water (1428 μl, 2142 μmol) and heated to 90° C. for 1 h. It was cooled to RT, diluted with 50 mL of ethyl acetate, partitioned with sodium bicarbonate (saturated, aqueous), and the organics were washed 2×20 mL with sodium bicarbonate (saturated, aqueous), separated, dried over sodium sulfate, concentrated in vacuo, and purified by HPLC to give the title compound.
MS (ES+): 363 (M+H)+.

EXAMPLE 83

Synthesis of 6-{5-[(Cyclopropylamino)carbonyl]-2-methylphenyl}phthalazine-1-carboxamide Methyl 3-(1-cyanophthalazin-6-yl)-4-methylbenzoate (120 mg, 396 μmol) was dissolved in THF/water (4:1) (3.96 mL) and LiOH (19 mg, 791 μmol) was added. The reaction mixture was stirred at 50° C. for 5.5 h, concentrated, and lyophilyzed under house vacuum. The reaction mixture was dissolved in DMF (791 μl) and HATU (301 mg, 791 μmol) and cyclopropylamine (277 μl, 3956 μmol) were added and the mixture was stirred at RT for 16 h. The mixture was diluted with 100 mL ethyl acetate, and partitioned with sodium bicarbonate (saturated, aqueous). The organic layers were washed 3×20 mL with sodium bicarbonate (saturated, aqueous), separated, dried over sodium sulfate, concentrated in vacuo, and purified by HPLC to give the title compound. MS (ES+): 347 (M+H)+.

EXAMPLE 84

Synthesis of 3-(1-Acetyl-4-methylphthalazin-6-yl)-N-cyclopropyl-4-methylbenzamide Step A: 3-(1-Acetyl-4-methyl-3,4-dihydrophthalazin-6-yl)-N-cyclopropyl-4-methylbenzamide 3-(1-Cyanophthalazin-6-yl)-N-cyclopropyl-4-methylbenzamide (177 mg, 539 μmol) was dissolved in THF (5.39 mL) and cooled to 0° C. Methylmagnesium bromide, 1.4 M solution in toluene/THF (75:25) (1925 μl, 2695 μmol) was added, and the reaction mixture was stirred at 0° C., then allowed to warm slowly to RT and stirred for 1 h. The reaction mixture was diluted with 75 mL ethyl acetate, partitioned with water, and the organics were washed 2×20 mL with sodium bicarbonate (saturated, aqueous), separated, dried over sodium sulfate, concentrated in vacuo, and purified by HPLC to give the title compound. MS (ES+): 362 (M+H)+.
Step B: 3-(1-Acetyl-4-methyl-3,4-dihydrophthalazin-6-yl)-N-cyclopropyl-4-methylbenzamide (24 mg, 66 μmol) was dissolved in EtOH/water (2:1) (664 μl) and potassium permanganate (10 mg, 66 μmol) was added. The mixture was stirred at RT for 40 min, quenched with saturated, aqueous sodium thiosulfate and diluted with 50 mL of chloroform. In a separatory funnel, the mixture was washed 2×20 mL with sodium thiosulfate and the organics were separated, dried over sodium sulfate, concentrated in vacuo, and purified by HPLC to give the title compound. MS (ES+): 360 (M+H)+.

EXAMPLE 85

Synthesis of N-Cyclopropyl-4-methyl-3-[1-(morpholin-4-ylcarbonyl)phthalazin-6-yl]benzamide 3-(1-Cyanophthalazin-6-yl)-N-cyclopropyl-4-methylbenzamide (115 mg, 350 μmol) was dissolved in EtOH/water (1:1) (3.50 mL) with potassium hydroxide (39 mg, 700 μmol) and heated in a microwave oven for 15 min at 120° C. The reaction mixture was concentrated in vacuo and dissolved in DMF (700 μl) and morpholine (152 μl, 1751 μmol) to which HATU (399 mg, 1051 μmol) was added. The reaction was stirred at RT for 16 h, then diluted with ethyl acetate, filtered, diluted with 50 mL ethyl acetate, and partitioned with sodium bicarbonate (saturated, aqueous). The organic layers were washed 2×20 mL with sodium bicarbonate (saturated, aqueous), separated, dried over sodium sulfate, concentrated in vacuo, and purified by flash chromatography to give the title compound. MS (ES+): 417 (M+H)+.

EXAMPLE 86

Synthesis of 2-methyl-2-(4-(4,4,5,5-tetramethyl-1,3,2-dioxaborolan-2-yl)phenyl)propanoic acid Step 1: A 250 mL round-bottom flask was charged with ethyl 2-(4-bromophenyl)acetate (5.000 g, 20.6 mmol) in 100 mL of THF. Sodium hydride (95%, 1.48 g, 61.7 mmol) was added at 23° C. The reaction stirred for 1h at RT and then iodomethane (3.21 mL, 51.4 mmol) was added and the reaction was allowed to stir at RT for 2h, then cooled to 0° C. and quenched with EtOH. The mixture was acidified and extracted with dichloromethane (3×100 mL) to give a yellow oil, which was purified by column chromatography (4/1hex/ethyl acetate) to give 3.97 g of ethyl 2-(4-bromophenyl)-2-methylpropanoate as a light yellow oil.
Step 2: A 100 mL round-bottom flask was charged with ethyl 2-(4-bromophenyl)-2-methylpropanoate (0.670 g, 2.47 mmol) in 2.5 mL of MeOH. Potassium hydroxide (2.0 M, 2.47 mL, 4.94 mmol) was added at 0° C. The reaction was heated to reflux for 2 h. After cooling the reaction was extracted with ethyl acetate. The aqueous layer was acidified with 2M HCl and extracted with dichloromethane (3×). The combined organic layers were dried over sodium sulfate, filtered and concentrated to give 464 mg of 2-(4-bromophenyl)-2-methylpropanoic acid as a white solid.
Step 3: A 100 mL round-bottom flask was charged with 2-(4-bromophenyl)-2-methylpropanoic acid (0.48 g, 2.0 mmol), bis(pinacolato)diboron (0.75 g, 3.0 mmol), dichloro[1,1'-bis(diphenylphosphino)ferrocene]dichloride palladium (ii) dichloromethane adduct (0.14 g, 0.20 mmol) and potassium acetate (0.62 mL, 9.9 mmol) in 10 mL of dioxane. The mixture was heated to 80° C. for 18 h, then cooled and concentrated. The residue was dissolved in ethyl acetate and 2 M HCl and filtered. The aqueous layer was extracted with ethyl acetate (2×). The combined organic layers were dried over anhydrous sodium sulfate, filtered and concentrated to give 1.34 g of a red solid. The crude material was purified by column chromatography (1/1 ethyl acetate/hexane) to give 525 mg of 2-methyl-2-(4-(4,4,5,5-tetramethyl-1,3,2-dioxaborolan-2-yl)phenyl)propanoic acid as an off-white solid. ES+=291.2 (M+H).

EXAMPLE 87

Synthesis of 4-methoxypyrimidin-5-ylboronic acid

Step 1: Bromine (2.68 mL, 52.0 mmol) was added to a solution of 4(3H)-pyrimidinone (5.00 g, 52.0 mmol) and potassium acetate (15.3 g, 156 mmol) in 50 mL of acetic acid. The mixture was heated to 80° C. for 2 h and then cooled and concentrated. Water was added to the concentrate and the reaction was extracted with ethyl acetate (3×). The combined organic layers were dried over anhydrous sodium sulfate, filtered and concentrated to give 2.13 g of 5-bromopyrimidin-4(1H)-one as an off-white solid. The aqueous layer was extracted with dichloromethane (3×) to afford an additional 1.22 g of 5-bromopyrimidin-4(1H)-one as a white solid. ES$^+$=175.0 (M+H)

Step 2: A 50 mL round-bottom flask was charged with 5-bromopyrimidin-4(1H)-one (0.882 g, 5.04 mmol) in phosphorus oxychloride (4.61 mL, 50.4 mmol). The reaction was heated to 80° C. for 2 h and then cooled and concentrated. The residue was redissolved in dichloromethane (10 mL), cooled to 0° C. and MeOH (5 mL) was added. The reaction was allowed to warm up to RT and stirred for 1 h. The reaction was concentrated and water and hexanes were added and the layers separated. The hexane layer was dried over sodium sulfate, filtered and concentrated to give 711 mg of 5-bromo-4-methoxypyrimidine as a light yellow solid. ES+=189.0 (M+H)

Step 3: To a solution of 5-bromo-4-methoxypyrimidine (0.460 g, 2.43 mmol) and triisopropyl borate (0.671 mL, 2.92 mmol) in 12 mL of THF at −70° C. was added butyllithium (1.6 m in hexanes, 1.83 mL, 2.92 mmol) dropwise. The addition took 15 minutes and the reaction turned light yellow. The reaction stirred for 30 minutes at −70° C. and was then allowed to warm up to −20° C. The reaction was quenched with ammonium chloride (sat.) and extracted with ethyl acetate. The aqueous layer was concentrated and NaCl (sat.) was added. The aqueous layer was extracted with 3/2 chloroform/iPrOH (3×). The combined organic layers were dried over anhydrous sodium sulfate, filtered and concentrated to give 166 mg of 4-methoxypyrimidin-5-ylboronic acid as a light yellow solid. ES$^+$=155.2 (M+H)

EXAMPLE 88

Synthesis of 2-(dimethylamino)-4-methoxypyrimidin-5-ylboronic acid

Step 1: To a solution of 5-bromo-2,4-dichloropyrimidine (1.000 mL, 7.82 mmol) in MeOH at 0° C. was added sodium methoxide (1.45 mL, 7.82 mmol). The reaction was warmed up to 23° C. and allowed to stir overnight. Water was added and the mixture was extracted with dichloromethane. The combined organic layers were dried over anhydrous sodium sulfate, filtered and concentrated to give 1.73 g of 5-bromo-2-chloro-4-methoxypyrimidine as a white solid. ES$^+$=224.9 (M+H)

Step 2: A solution of dimethylamine (2.0 M solution in THF, 17.2 mL, 34.5 mmol) was added to 5-bromo-2-chloro-4-methoxypyrimidine (1.540 g, 6.89 mmol) at RT. The reaction was heated to 45° C. for 30 min, then cooled and concentrated. The residue was washed and filtered with diethyl ether to give 1.57 g of 5-bromo-4-methoxy-N,N-dimethylpyrimidin-2-amine as a light yellow solid. ES$^+$=232.0 (M+H)

Step 3: To a solution of 5-bromo-4-methoxy-N,N-dimethylpyrimidin-2-amine (0.300 g, 1.29 mmol) and triisopropyl borate (0.416 mL, 1.81 mmol) in 7 mL of THF at −70° C. was added butyllithium (1.6 m in hexanes, 1.13 mL, 1.81 mmol) dropwise. The reaction stirred for 30 min at −70° C. and was allowed to warm up. At −20° C. ammonium chloride (sat.) was added. The mixture was extracted with ethyl acetate (3X). The combined organic layers were dried over anhydrous sodium sulfate, filtered and concentrated to give 250 mg of crude material, which was purified by column chromatography (5% MeOH in dichloromethane) to give 157 mg of 2-(dimethylamino)-4-methoxypyrimidin-5-ylboronic acid as a white solid. ES$^+$=198.1 (M+H).

EXAMPLE 89

Synthesis of 2-methoxy-3-methylphenylboronic Acid

To a solution of 2-bromo-6-methylphenol (0.520 g, 2.78 mmol) in 15 ML of acetone was added iodomethane (0.338 mL, 5.42 mmol) and potassium carbonate (0.768 g, 5.56 mmol). The reaction was heated to reflux and stirred overnight. Ammonium chloride (sat.) was added and the mixture was extracted with diethyl ether. The combined organic layers were dried over anhydrous sodium sulfate, filtered and concentrated to afford 456 mg of 1-bromo-2-methoxy-3-methylbenzene as a clear oil. To a solution of 1-bromo-2-methoxy-3-methylbenzene (0.123 g, 0.61 mmol) in 3 mL of THF at −70° C. was added n-butyllithium (1.6 M in hexanes, 0.46 mL, 0.73 mmol) dropwise. The reaction stirred at −70° C. for 30 minutes and was then allowed to warm up to −20° C. Ammonium chloride (sat.) was added and the mixture was extracted with ethyl acetate, dried over sodium sulfate and filter to give 96 mg crude material. The crude material was purified by column chromatography (3/1 hexanes/ethyl acetate) to afford 40 mg of 2-methoxy-3-methylphenylboronic acid as a white solid. MS(ES+): 167.0 (M+H).

EXAMPLE 90

Synthesis of 6-(dimethylamino)-2-fluoropyridin-3-ylboronic acid

In a microwave tube was placed 2,6-difluoropyridine (0.500 mL, 5.47 mmol), dimethylamine, (2.0 M solution in THF, 4.11 mL, 8.21 mmol). The mixture was heated at 150° C. for 20 min. Water was added and the mixture was extracted with ethyl acetate (3×). The combined organic layers were dried over anhydrous sodium sulfate, filtered and concentrated to give 536 mg of a crude yellow oil, which was purified by column chromatography (3/1 Hex/ethyl acetate) to give 500 mg of 6-fluoro-N,N-dimethylpyridin-2-amine as a light yellow oil. To a solution of diisopropylamine (0.15 mL, 1.1 mmol) in 2 mL of THF at 0° C. was added butyllithium (1.6 M in hexane, 0.69 mL, 1.1 mmol). The reaction stirred for 30 minutes and was then cooled to 60° C. at which time 6-fluoro-N,N-dimethylpyridin-2-amine (0.124 g, 0.88 mmol) was added in 1 mL of THF. The reaction stirred at −60° C. for 45 min. Then triisopropyl borate (0.25 mL, 1.1 mmol) was added and the reaction was allowed to stir for 1 h at 23° C. Ammonium chloride (sat.) was added and the mixture was extracted with ethyl acetate (3×). The combined organic layers were dried over anhydrous sodium sulfate, filtered and concentrated to give 136 mg of a brown oil, which was purified by column chromatography (3/1 hexanes/ethyl acetate to 1/1 EtOAc/hexanes) to give 46 mg of a white solid. ES$^+$=185.1 (M+H)

EXAMPLE 91

Synthesis of 6-((4-methoxybenzyl)(methyl)amino)-2-fluoropyridin-3-ylboronic acid In a microwave tube was placed 2,6-difluoropyridine (0.183 mL, 2.00 mmol) and (4-methoxyphenyl)-N-methylmethanamine (0.604 g, 4.00 mmol) in 2 mL of water. The mixture was heated at 150° C. for 20 min. Water was added and the mixture was extracted with ethyl acetate (3×). The combined organic layer were dried over anhydrous sodium sulfate, filtered and concentrated to give 470 mg of a crude yellow oil, which was purified by column chromatography (3/1 hexanes/ethyl acetate) to give 400 mg of N-(4-methoxybenzyl)-6-fluoro-N-methylpyridin-2-amine as a clear, colorless oil. To a solution of diisopropylamine (1.92 mL, 13.6 mmol) in 25 mL of THF at 0° C. was added butyllithium (1.6 M in hexanes, 8.93 mL, 14.3 mmol). The mixture stirred for 30 minutes and was then cooled to −60° C. and N-(4-methoxybenzyl)-6-fluoro-N-methylpyridin-2-amine (1.760 g, 7.15 mmol) was added dropwise in 10 mL of THF. The reaction stirred for 1 h at −60° C. and then triisopropyl borate (2.88 mL, 12.5 mmol) was added and the reaction allowed to warm up to RT and stirred for 1 h. Ammonium chloride (sat.) was added and the reaction was extracted with ethyl acetate (3×). The combined organic layers were dried over anhydrous sodium sulfate, filtered and concentrated to give 2.13 g of a crude yellow foam, which was purified by column chromatography (3/1 hexanes/ethyl acetate to 1/1 ethyl acetate/hexanes) to give 750 mg of a off-white solid. $ES^+=291.2$ (M+H)

EXAMPLE 92

Synthesis of 2-methylpyridin-3-ylboronic acid

To a solution of 3-bromo-2-methylpyridine (4.00 g, 23 mmol), triisopropyl borate (6.40 mL, 28 mmol) in 50 mL of 4/1 toluene/THF (4/1, 50 mL) at −78° C. was added was added butyllithium (17 mL, 28 mmol), dropwise. The mixture was allowed to warm up to 30 min at −70° C. LCMS and then to 20° C. HCl (2M) was added to bring the solution to pH1. Then water (20 mL) was added and the mixture was extracted with toluene. The aqueous layer was neutralized with 1 M NaOH and extracted with dichloromethane. The aqueous layer was concentrated to dryness and the white solid was washed with dichloromethane. The combined organic layers were dried over sodium sulfate, filtered and concentrated to give 2.10 g of 2-methylpyridin-3-ylboronic acid as a yellow oil.
$ES^+=138.2$ (M+H)

EXAMPLE 93

Synthesis of 4,4,5,5-tetramethyl-2-(2-methyl-5-(methylsulfonyl)phenyl)-1,3,2-dioxaborolane Step 1: To a suspension of iron powder (0.0669 g, 1.20 mmol) in bromine (2.05 mL, 39.9 mmol) at 0° C. was added methyl p-tolyl sulfone (0.340 g, 2.00 mmol). The reaction was warmed up to RT and stirred for 2 h. The mixture was poured into an ice-cold 1 M solution of sodium thiosulfate and ethyl acetate. The layers were separated and the aqueous layer was extracted with ethyl acetate (3×). The combined organic layers were dried over anhydrous sodium sulfate, filtered and concentrated to give 545 mg of crude material. The crude material was purified by column chromatography (3/1 Hex/ethyl acetate to 1/1 ethyl acetate/hexanes) to give 374 mg of 2-bromo-1-methyl-4-(methylsulfonyl)benzene as a white solid. $ES^+=251.0$ (M+H)

Step 2: A flask under nitrogen was charged with 2-bromo-1-methyl-4-(methylsulfonyl)benzene (0.163 g, 0.654 mmol), 4,4,5,5-tetramethyl-2-(4,4,5,5-tetramethyl-1,3,2-dioxaborolan-2-yl)-1,3,2-dioxaborolane (0.249 g, 0.981 mmol), 1,1'-bis(diphenylphosphino)ferrocene]dichloride palladium(II) complex with dichloromethane (0.0479 g, 0.0654 mmol) and potassium acetate (0.321 g, 3.27 mmol) in 4 mL of DMF. The reaction was heated to 80° C. and stirred overnight. The solvent was removed and the residue was taken up in ethyl acetate and 2 M HCl and filtered through Celite®. The organic layer was separated and the aqueous phase was extracted with ethyl acetate (2×). The combined were dried organic layers over anhydrous sodium sulfate, filtered and concentrated to give 415 mg of a crude brown oil, which was purified by column chromatography (3/1 hexanes/ethyl acetate) to afford 125 mg of 4,4,5,5-tetramethyl-2-(2-methyl-5-(methylsulfonyl)phenyl)-1,3,2-dioxaborolane as a white solid. $ES^+=297.1$ (M+H)

EXAMPLE 94

Synthesis of 4-methyl-3-(1-(2-oxopyrrolidine-1-yl) phthalazin-6-yl)benzamide

In a microwave tube was placed 3-(1-chlorophthalazin-6-yl)-4-methylbenzamide (0.150 g, 0.50 mmol), copper (I) iodide (0.0048 g, 0.025 mmol), (1R,2R)-N1,N2-dimethylcyclohexane-1,2-diamine (0.014 g, 0.10 mmol), cesium carbonate (0.34 g, 1.1 mmol) and pyrrolidin-2-one (0.077 mL, 1.0 mmol) in 2 mL of DMF. The mixture was heated at 150°-200° C. for 20 minutes in the microwave. After cooling, the reaction was filtered through Celite®. Water was added to the filtrate and the mixture was extracted with dichloromethane (3×). The organic layer was concentrated and the crude material purified by HPLC to give 4-methyl-3-(1-(2-oxopyrrolidin-1-yl)phthalazin-6-yl)benzamide as white solid. Found MS $(ES^+)=347$ $(M+H^+)$

EXAMPLE 95

Synthesis of N-cyclopropyl-3-(1-(6-methoxy-2-methylpyridin-3-yl)phthalazin-6-yl)-4-methylbenzamide In a microwave tube was placed N-cyclopropyl-3-(1-(6-fluoro-2-methylpyridin-3-yl)phthalazin-6-yl)-4-methylbenzamide (0.060 g, 0.15 mmol, Method D), sodium methoxide (25 wt % solution in methanol, 0.15 mL, 0.70 mmol) and 1.5 mL of NMP. The mixture was heated at 120° C. for 2 min. The crude material was purified HPLC to give N-cyclopropyl-3-(1-(6-methoxy-2-methylpyridin-3-yl)phthalazin-6-yl)-4-methylbenzamide as an off-white solid. Found MS $(ES^+)=425$ $(M+H^+)$

EXAMPLE 96

Synthesis of 4-methyl-3-(1-(2-methyl-4-(methylsulfonyl)phenyl)phthalazin-6-yl)benzamide A solution of 4-methyl-3-(1-(2-methyl-4-(methylthio) phenyl)phthalazin-6-yl)benzamide (170 mg, 0.43 mmol, Method D) in 2 mL of 10/1 methanol/$H_2O$ at 0° C. was treated with oxone (262 mg, 0.43 mmol). The mixture stirred at 0° C. for 1 h and then warmed up to RT for 1 h. The reaction was quenched with 20 mL sodium sulfite (sat.) and extracted with 10% MeOH in dichloromethane. The combined organic layers were dried over anhydrous sodium sulfate, filtered and concentrated. The crude material was purified by HPLC to give 4-methyl-3-(1-(2-methyl-4-(methylsulfonyl)phenyl)phthalazin-6-yl)benzamide as a white solid. Found MS $(ES^+)=432.1$ $(M+H^+)$.

EXAMPLE 97

Synthesis of N-cyclopropyl-4-methyl-3-{1-[(2S)-2-methylpiperidin-1-yl]phthalazin-6-yl}benzamide Step 1: (S)-6-bromo-1-(2-methylpiperidin-1-yl)phthalazine A mixture of 1,6-dichlorophthalazine (0.809 g, 4.06 mmol), (S)-2-methylpiperidine (0.581 g, 5.86 mmol), and N,N-DIPEA (2.00 mL, 11.5 mmol) in 4 mL of NMP was heated at 130° C. After 20 h, the reaction was cooled to RT, concentrated onto silica gel and purified using flash column chromatography eluting with 2M NH$_3$ in MeOH:CH$_2$Cl$_2$ (0:1→3:97) to give a brown liquid. MS m/z: 262.1 [M+1].

Step 2: N-cyclopropyl-4-methyl-3-{1-[(2S)-2-methylpiperidin-1-yl]phthalazin-6-yl}benzamide A mixture of (S)-6-chloro-1-(2-methylpiperidin-1-yl)phthalazine (0.200 g, 0.76 mmol), N-cyclopropyl-4-methyl-3-(4,4,5,5-tetramethyl-1,3,2-dioxaborolan-2-yl)benzamide (0.474 g, 1.6 mmol), potassium carbonate (0.340 g, 2.5 mmol), 2-(dicyclohexylphosphino)-2'-methylbiphenyl (0.054 g, 0.15 mmol) and tris(dibenzylideneacetone)dipalladium (0) (0.045 g, 0.049 mmol) in 5 mL 80% aqueous degassed dioxane was heated at 80° C. for 15 h. The reaction was cooled to RT and partitioned between ethyl acetate/brine. The aqueous layer was extracted with ethyl acetate (3×) and the combined organic layers were concentrated onto silica gel and purified flash chromatography eluting with 2 M NH$_3$ in MeOH:CH$_2$Cl$_2$ (0:1→1:24) to give a brown oil. The material was further purified by reverse-phase HPLC (Prodigy 5u ODS(3), 100A, 250×21.2) with 0.1% formic acid/H$_2$O:0.1% formic acid/CH$_3$CN (3:7→7:3) to give a white amorphous solid. Found MS m/z: 401.2 [M+1].

EXAMPLE 98

Synthesis of 3-(1-(2-(aminocarbonyl)phenyl)-6-phthalazinyl)-N-cyclopropyl-4-methylbenzamide The title compound was prepared by a method analogous to that described in Example 11 (Method D), using a mixture of 3-(1-chlorophthalazin-6-yl)-N-cyclopropyl-4-methylbenzamide (0.111 g, 0.33 mmol), 2-cyanophenylboronic acid (0.211 g, 1.4 mmol), potassium carbonate (0.400 g, 2.9 mmol) and trans-dichlorobis(triphenyl-phosphine)palladium (II) (0.017 g, 0.024 mmol) in 1.4 mL DME/0.6 mL H$_2$O/0.4 mL EtOH, which was heated at 120° C. for 15 min. The mixture was partitioned between ethyl acetate/brine and the aqueous layer was extracted with ethyl acetate (3×). The combined organics were evaporated onto silica gel and purified using flash chromatography eluting with 2M NH$_3$ in MeOH:CH$_2$Cl$_2$ (0:1→7:93) to afford the title compound as an amorphous white solid. Found MS m/z: 423 [M+1].

EXAMPLE 99

Synthesis of 3-{1-[(8aR)-3-oxotetrahydro[1,3]oxazolo[3,4-a]pyrazin-7(1H)-yl]phthalazin-6-yl}-N-cyclopropyl-4-methylbenzamide Step 1: (R)-tert-butyl 3-oxo-tetrahydro-1H-oxazolo[3,4-a]pyrazine-7(3H)-carboxylate A solution of NaOEt was prepared from NaH (60% dispersion in mineral oil) (0.723 g, 19 mmol) and 20 mL EtOH. To this solution was added diethyl carbonate (8.50 mL, 70 mmol) and the mixture was transferred to a solution of (R)-4-N-BOC-2-hydroxymethyl-piperazine (1.523 g, 7.0 mmol) in 80 mL of EtOH and heated at 78° C. After 6.5 h the reaction was cooled to RT and filtered. The filtrate was concentrated to dryness to give an off-white amorphous solid.

Step 2: (R)-tetrahydro-1H-oxazolo[3,4-a]pyrazin-3(5H)-one

To a cooled (0° C.) solution of (R)-tert-butyl 3-oxo-tetrahydro-1H-oxazolo[3,4-a]pyrazine-7(3H)-carboxylate (3.01 g, 12 mmol) in 100 mL CH$_2$Cl$_2$ was added TFA (75 mL, 973 mmol) dropwise. After 2 h the reaction mixture was concentrated to dryness to give a brown semi-crystalline solid, which was purified through a plug of silica gel eluting successively with hexane, Et$_2$O, CH$_2$Cl$_2$ and 10% 2M NH$_3$ in MeOH/CH$_2$Cl$_2$ to give 2.29 g of an orange oil. MS m/z: 143.1 [M+1].

Step 3: (R)-7-(6-chlorophthalazin-1-yl)-tetrahydro-1H-oxazolo[3,4-a]pyrazin-3(5H)-one The title compound was prepared by a method analogous to that described in Example 8 (Method A). A mixture of (R)-tetrahydro-1H-oxazolo[3,4-a]pyrazin-3(5H)-one (0.800 g, 5.63 mmol), 1,6-dichlorophthalazine (0.516 g, 2.59 mmol) and N,N-diisopropylethylamine(1.40 mL, 8.04 mmol) in 3 mL 1-methyl-2-pyrolidone was heated at 140° C. After 4.5 h the reaction was cooled to RT, quenched with H$_2$O and extracted with ethyl acetate (3×). The combined organic layers were dried over Na$_2$SO$_4$, filtered, evaporated onto silica gel and purified by flash chromatography eluting with 2 M NH$_3$ in MeOH/CH$_2$Cl$_2$ (0:1→1:39) to give 1.18 g of a brown liquid. MS m/z: 305.1 [M+1].

Step 4: 3-{1-[(8aR)-3-oxotetrahydro[1,3]oxazolo[3,4-a]pyrazin-7(1 H)-yl]phthalazin-6-yl}-N-cyclopropyl-4-methylbenzamide A stock solution of chloro phthalazine was prepared by dissolving 1.18 g of (R)-7-(6-chlorophthalazin-1-yl)-tetrahydro-1H-oxazolo[3,4-a]pyrazin-3 (5H)-one in 10 mL of n-BuOH. To a 5 mL portion of this stock solution was added 1.25 mL H$_2$O and the solution was bubbled with argon for 20 min. To this solution was added N-cyclopropyl-4-methyl-3-(4,4,5,5-tetramethyl-1,3,2-dioxaborolan-2-yl)benzamide (0.494 g, 1.6 mmol), potassium carbonate (0.354 g, 2.6 mmol), 2-(dicyclohexylphosphino)-2'-methylbiphenyl (0.053 g, 0.15 mmol) and tris(dibenzylideneacetone)dipalladium (0) (0.047 g, 0.051 mmol). The mixture was heated at 80° C. overnight. The reaction mixture was cooled to RT, diluted with MeOH, concentrated onto silica gel and purified flash chromatography eluting with 2 M NH3 in MeOH/CH$_2$Cl$_2$ (0:1→1:39) to give 152 mg of a red-brown tar. The material was further purified by reverse phase HPLC (10→80% CH$_3$CN/H$_2$O) to give the title compound as a yellow tar. Found MS m/z: 444.2 [M+1].

EXAMPLE 100

Synthesis of N-cyclopropyl-4-methyl-3-{1-[(2R)-2-methyl-3-oxopiperazin-1-yl]phthalazin-6-yl}benzamide Step 1: 3-methylpiperazin-2-one To a solution of ethylenediamine (32 mL, 479 mmol) in 300 mL of dry MeOH at RT was added a solution of methyl 2-bromopropionate (13 mL, 120 mmol) in 100 mL dry MeOH over a period of 4 h. After 2 h, the solvent was removed in vacuo. The oily residue was diluted with 200 mL MeOH and heated at 60° C. After 5 h the reaction was cooled to 25° C. and the solvent was removed in vacuo. To the residue was added CHCl$_3$ and the resultant precipitate was filtered. The filtrate was evaporated onto silica gel and purified using flash column chromatography eluting with NH$_4$OH:MeOH:CHCl$_3$ (0:0:1→1:9:90) to give a light yellow amorphous solid. MS m/z: 113.1 [M−1].

Step 2:
4-(6-bromophthalazin-1-yl)-3-methylpiperazin-2-one

In three separate sealed tubes were placed a mixture of 6-bromo-1-chlorophthalazine (0.250 g, 1.03 mmol), 3-methylpiperazin-2-one (0.239 g, 2.09 mmol), K$_2$CO$_3$ (0.155 g, 1.12 mmol) and 5 mL of CH$_3$CN. The three reactions were heated at 190° C. for 15 min in a microwave oven. The reaction mixtures were combined, concentrated onto silica gel and purified using flash chromatography eluting with 2M NH$_3$ in MeOH/CH$_2$Cl$_2$ (0:1→1:19) to give 200 mg (60%) of an orange oil.

Step 3: N-cyclopropyl-4-methyl-3-(1-(2-methyl-3-oxopiperazin-1-yl)phthalazin-6-yl)benzamide This compound was prepared by a method analogous to that described in Example 8 (Method A). A mixture of 4-(6-bromophthalazin-1-yl)-3-methylpiperazin-2-one (0.200 g, 0.62 mmol), N-cyclopropyl-4-methyl-3-(4,4,5,5-tetramethyl-1,3,2-dioxaborolan-2-yl)benzamide (0.245 g, 0.81 mmol), sodium carbonate (0.270 g, 2.5 mmol) and trans-dichlorobis(triphenyl-phosphine)palladium (II) (0.040 g, 0.050 mmol) in DME (7 mL)/H$_2$O (3 mL)/EtOH (2 mL) was heated at 90° C. The reaction was purified by flash chromatography eluting with 2M NH$_3$ in MeOH/CH$_2$Cl$_2$ (0:1-1:19) to give 126 mg of a brown amorphous solid. The material was further purified by reverse phase HPLC (10→100% CH$_3$CN [0.1% TFA]) to give the title compound as a light yellow amorphous solid. Found MS m/z: 416.2 [M+1].

EXAMPLE 101

Synthesis of 3-{1-[(8aS)-3-oxotetrahydro[1,3]oxazolo[3,4-a]pyrazin-7(1H)-yl]phthalazin-6-yl}-N-cyclopropyl-4-methylbenzamide Step 1: (S)-Tert-butyl 3-oxo-tetrahydro-1H-oxazolo[3,4-a]pyrazine-7(3H)-carboxylate A NaOEt solution, prepared from sodium hydride (60% dispersion in mineral oil) (0.990 g, 26 mmol) and 100 mL EtOH, diethyl carbonate (9.00 mL, 74 mmol) and (S)-4-N-BOC-2-hydroxymethyl-piperazine (2.17 g, 10 mmol) was heated at 80° C. The reaction was cooled to RT and filtered. The filtrate was concentrated to dryness to give an off-white amorphous solid.

Step 2:
(S)-tetrahydro-1H-oxazolo[3,4-a]pyrazin-3(5H)-one

Using (S)-Tert-butyl 3-oxo-tetrahydro-1H-oxazolo[3,4-a]pyrazine-7(3H)-carboxylate (2.42 g, 10.000 mmol) in 100 mL CH$_2$Cl$_2$ and TFA (60.000 mL, 779 mmol) in a method analogous to that described in Example 31, the title compound was obtained as a tan oil.

Step 3: (S)-7-(6-chlorophthalazin-1-yl)-tetrahydro-1H-oxazolo[3,4-a]pyrazin-3(5H)-one A mixture of (S)-tetrahydro-1H-oxazolo[3,4-a]pyrazin-3(5H)-one (1.42 g, 10.000 mmol), 1,6-dichlorophthalazine (1.47 g, 7.39 mmol) and N,N-DIPEA (5.00 mL, 30.0 mmol) in 12 mL DMF was heated at 135° C. The crude material was purified by flash chromatography eluting with 2 M NH$_3$ in MeOH/CH$_2$Cl$_2$ (0:1→3:97) to give 1.85 g of a brown oil. MS m/z: 305.1, 307.1 [M+1].

Step 4: 3-{1-[(8aS)-3-oxotetrahydro[1,3]oxazolo[3,4-a]pyrazin-7(1H)-yl]phthalazine-6-yl}-N-cyclopropyl-4-methylbenzamide A mixture of (S)-7-(6-chlorophthalazin-1-yl)-tetrahydro-1H-oxazolo[3,4-a]pyrazin-3(5H)-one (0.600 g, 1.97 mmol), N-cyclopropyl-4-methyl-3-(4,4,5,5-tetramethyl-1,3,2-dioxaborolan-2-yl)benzamide (1.110 g, 3.69 mmol), potassium carbonate (0.875 g, 6.33 mmol), 2-(dicyclohexylphosphino)-2'-methylbiphenyl (0.136 g, 0.373 mmol), and tris(dibenzylideneacetone)dipalladium (0) (0.107 g, 0.117 mmol) in 12 mL of degassed 80% aqueous 1,4-dioxane was heated at 80° C. The crude material was purified flash chromatography eluting with 2 M NH$_3$ in MeOH/CH$_2$Cl$_2$ (0:1→3:97) to give 1.26 g of an orange liquid. The material was further purified by reverse-phase HPLC (Phenomenex Synergi 4u MAX-RP 80, 150×21.2 mM) eluting with 0.1% formic acid-CH$_3$CN: 0.1% formic acid-H$_2$O (1:9→9:1) to give the title compound as a white amorphous solid.
Found MS m/z: 444.2 [M+1].

EXAMPLE 102

Synthesis of 3-{1-[(8aS)-6-oxohexahydropyrrolo[1,2-a]pyrazin-2(1H)-yl]phthalazin-6-yl}-N-cyclopropyl-4-methylbenzamide Step, 1: 2-(6-chlorophthalazin-1-yl)-tetrahydropyrrolo[1,2-a]pyrazin-6(1H,2H,7H)-one A mixture of tetrahydropyrrolo[1,2-a]pyrazin-6(1H,2H,7H)-one (Med. Chem. Res., 7:301 (1997); 0.983 g, 7.01 mmol), 1,6-dichlorophthalazine (1.36 g, 6.83 mmol) and TEA (2.00 mL, 14.3 mmol) in 18 mL of CH$_3$CN was heated at 135° C. for 30 min in a microwave oven. The reaction mixture was concentrated onto silica gel and purified using flash chromatography eluting with 2M NH$_3$ in MeOH:CH$_2$Cl$_2$ (0:1→3:97) to give 404 mg (20%) an orange foam/amorphous solid. MS m/z: 303.1 [M+1].

Step 2: 3-{1-[(8aS)-6-oxohexahydropyrrolo[1,2-a]pyrazin-2(1H-yl]phthalazin-6-yl}-N-cyclopropyl-4-methylbenzamide The title compound was prepared by a method analogous to that described in Example (Method A) using K$_2$CO$_3$ (0.271 g, 2.0 mmol), 2-(6-chlorophthalazin-1-yl)-tetrahydropyrrolo[1,2-a]pyrazin-6(1H,2H,7H)-one (0.185 g, 0.61 mmol), tris(dibenzylideneacetone)dipalladium (0) (0.020 g, 0.022 mmol), N-cyclopropyl-4-methyl-3-(4,4,5,5-tetramethyl-1,3,2-dioxaborolan-2-yl)benzamide (0.447 g, 1.5 mmol) and 2-(dicyclohexylphosphino)-2'-methylbiphenyl (0.020 g, 0.055 mmol). The title compound was purified by flash chromatography eluting with 2M NH$_3$ in MeOH:CH$_2$Cl$_2$ (0:1→1:19) and obtained as an off-white amorphous solid. Found MS m/z: 442.1 [M+1].

EXAMPLE 103

Synthesis of N-cyclopropyl-3-(1-(3-hydroxy-4,5-dihydro-1H-pyrazolo[3,4-c]pyridin-6(7H)-yl)phthalazin-6-yl)-4-methylbenzamide

Step 1: 6-benzyl-4,5,6,7-tetrahydro-1H-pyrazolo[3,4-c]pyridin-3-ol

A mixture of ethyl 1-benzyl-3-oxopiperidine-4-carboxylate hydrochloride (10.0 g, 34 mmol, Aldrich) and hydrazine (30 mL, 824 mmol, Aldrich) was stirred at RT for 48 h. The volatile solvents were removed in vacuo, and the residue was azeotroped with MeOH (1×), then recrystallized from MeOH to obtain the title compound MS (ESI, pos. ion) m/z: 230 (M+1).

Step 2: 4,5,6,7-tetrahydro-1H-pyrazolo[3,4-c]pyridin-3-ol

A mixture of 6-benzyl-4,5,6,7-tetrahydro-1H-pyrazolo[3,4-c]pyridin-3-ol (2.00 g, 8.72 mmol) and palladium on carbon (0.200 g, 1.88 mmol, Aldrich) in MeOH (100 mL) was stirred under $H_2$ atmosphere for 48 h. The mixture was filtered through Celite® and the filter cake was washed with MeOH. The mixture was concentrated in vacuo. The filter cake was washed with water and the filtrate was concentrated in vacuo. Both fractions contained the title compound. MS (ESI, pos. ion) m/z: 140 (M+1).

Step 3: N-cyclopropyl-3-(1-(3-hydroxy-4,5-dihydro-1H-pyrazolo[3,4-c]pyridin-6(7H)-yl)phthalazin-6-yl)-4-methylbenzamide A mixture of 3-(1-chlorophthalazin-6-yl)-N-cyclopropyl-4-methylbenzamide (300 mg, 888 µmol), 4,5,6,7-tetrahydro-1H-pyrazolo[3,4-c]pyridin-3-ol (247 mg, 1776 µmol) and N,N-diisopropylethylamine (310 µl, 1776 µmol) in NMP (3 mL) was heated to 160° C. for 18 h. After cooling to RT, the mixture was diluted with $H_2O$ and extracted with 25% i-PrOH/CHCl$_3$ (3×). The combined organics were dried over $Na_2SO_4$, filtered and concentrated. The residue was purified with reverse-phase chromatography (Phenomenex Synergi 4m Max RP 80 A column, 150×21 mM, 20 mL/min, 10-95% $CH_3CN/H_2O$, 0.1% TFA, 10.5 min gradient) to obtain the title compound. MS (ESI, pos. ion) m/z: 441 (M+1).

EXAMPLE 104

Synthesis of N-cyclopropyl-4-methyl-3-(1-(3-(trifluoromethyl)-5,6-dihydro-[1,2,4]triazolo[4,3-a]pyrazin-7(8H)-yl)phthalazin-6-yl)benzamide

Step 1: 6-chloro-1-(3-(trifluoromethyl)-5,6-dihydro-[1,2,4]triazolo[4,3-a]pyrazin-7(8H)-yl)phthalazine The title compound was prepared according to the method described in Example 19, using 1,6-dichlorophthalazine (400 mg, 2010 µmol), 3-(trifluoromethyl)-5,6,7,8-tetrahydro-[1,2,4]triazolo[4,3-a]pyrazine hydrochloride (Balsells, et. al. Org. Lett., 7:1039-1042 (2005), 689 mg, 3015 µmol) and N,N-diisopropylethylamine (702 µl, 4019 µmol) in NMP (5 mL). MS (ESI, pos. ion) m/z: 355 (M+1).

Step 2: N-cyclopropyl-4-methyl-3-(1-(3-(trifluoromethyl)-5,6-dihydro-[1,2,4]triazolo[4,3-a]pyrazin-7(8H)-yl)phthalazin-6-yl)benzamide The title compound was prepared according to the method described in Example 8 (Method A) using 6-chloro-1-(3-(trifluoromethyl)-5,6-dihydro-[1,2,4]triazolo[4,3-a]pyrazin-7(8H)-yl)phthalazine (350 mg, 987 µmol), N-cyclopropyl-4-methyl-3-(4,4,5,5-tetramethyl-1,3,2-dioxaborolan-2-yl)benzamide (594 mg, 1973 µmol), 2-(dicyclohexylphosphino)-2'-methylbiphenyl (32 mg, 89 µmol), $Pd_2(dba)_3$ (27 mg, 30 µmol, Strem), and potassium carbonate (409 mg, 2960 µmol) in dioxane:$H_2O$=4:1 (5 mL). Found MS (ES+) m/z: 494 (M+1).

EXAMPLE 105

Synthesis of N-cyclopropyl-4-methyl-3-(1-(2-methylpyrrolidin-1-yl)phthalazin-6-yl)benzamide

Step 1: 3-(1-chlorophthalazin-6-yl)-N-cyclopropyl-4-methylbenzamide

A mixture of 3-(1-hydroxyphthalazin-6-yl)-4-methylbenzoic acid (1.08 g, 3.85 mmol) and phosphorus oxychloride (25.0 mL, 268 mmol) was heated to 105° C. for 3 h. After cooling to RT, the solvents were removed in vacuo. The residue was re-dissolved in $CH_2Cl_2$ and treated carefully with cyclopropylamine (1.36 mL, 19.3 mmol) at RT. The mixture was diluted with sat aq. NaHCO$_3$ and $H_2O$ and extracted with $CH_2Cl_2$ (4×). The combined organics were dried over $Na_2SO_4$, filtered and concentrated. The residue was purified using column chromatography (MeOH/$CH_2Cl_2$=0→3%). Found MS (ESI, pos. ion) m/z: 338 (M+1).

Step 2: A mixture of 3-(1-chlorophthalazin-6-yl)-N-cyclopropyl-4-methylbenzamide (300 mg, 888 µmol) and 2-methylpyrrolidine (272 µl, 2664 µmol, Aldrich) in NMP (3 mL) was heated to 160° C. for 18 h. The solution was purified with reverse-phase chromatography (Phenomenex Synergi 4m Max RP 80 A column, 150×21 mM, 20 mL/min, 10-95% $CH_3CN/H_2O$, 0.1% TFA, 10.5 min gradient) to afford the title compound. Found MS (ESI, pos. ion) m/z: 387 (M+1).

EXAMPLE 106

Synthesis of 4-Methyl-3-(1-morpholinophthalazin-6-yl)benzenesulfonamide

Step 1. 3-Bromo-4-methylbenzenesulfonamide

To a mixture of p-toluenesulfonamide (2 g, 1.16 mmol) and iron (0.41 g, 7.36 mmol) was slowly added bromine (6 mL, 116 mmol). The resulting reddish brown solution was stirred at RT for 1 h. The reaction was carefully poured into ice-cold 1 M $Na_2S_2O_3$ aqueous solution and extracted with $CH_2Cl_2$ (2×). The organic extracts were combined and washed with brine, dried (MgSO$_4$), filtered, and concentrated in vacuo. CombiFlash purification (1% to 10% MeOH/$CH_2Cl_2$) afforded the title compound as a white solid. $^1$H NMR (DMSO-d$_6$, 400 MHz): ☐ 7.98 (s, 1H), 7.71 (d, J=8 Hz, 1H), 7.55 (d, J=8 Hz, 1H), 7.54 (br s, 2H), 2.41 (s, 3H).

Step 2. 4-Methyl-3-(4,4,5,5-tetramethyl-1,3,2-dioxaborolan-2-yl)benzenesulfonamide Into a 100-mL flask under argon were added 3-bromo-4-methylbenzenesulfonamide (900 mg, 3.6 mmol), dichloro[1, 1'-bis(diphenylphosphino)ferrocene]palladium (II) dichloromethane adduct (263 mg, 0.36 mmol), bis(pinacolato)diboron (1.371 g, 5.4 mmol), and 1,4-dioxane (18 mL), followed by potassium acetate (1.77 g, 18 mmol). The reaction was heated at 80° C. for 4 h. The cooled reaction was diluted with $CH_2Cl_2$ and washed with saturated aqueous $NaHCO_3$ solution and brine; dried ($MgSO_4$). After filtering via a pad of Celite®, the filtrate was concentrated in vacuo and purified by CombiFlash (25% to 50% ethyl acetate in Hexane) to afford the title compound as a white solid. Found MS (ES+): 298.1 $(M+H)^+$.

Step 3. 4-Methyl-3-(1-morpholinophthalazin-6-yl)benzenesulfonamide

A 50-mL flask under argon were added 6-bromo-1-morpholinophthalazine (150 mg, 0.51 mmol), 4-methyl-3-(4,4,5,5-tetramethyl-1,3,2-dioxaborolan-2-yl)benzenesulfonamide (227 mg, 0.76 mmol), tetrakis(triphenylphosphine)palladium (29 mg, 0.025 mmol), ethyl alcohol (1 mL), and 1,2-dimethoxyethane (4 mL), followed by 2M potassium carbonate aqueous solution (0.77 mL, 1.53 mmol). The reaction was heated at 90° C. for 2 h. The cooled reaction was diluted with $CH_2Cl_2$ and washed with saturated aqueous $NaHCO_3$ and brine; dried ($MgSO_4$) and concentrated in vacuo. Trituration of the resulting crude solid with $CH_2Cl_2$ afforded a pure batch of the title compound as a white solid. Found MS (ES+): 385.1 $(M+H)^+$.

EXAMPLE 107

Synthesis of 7-Iodo-6-methylbenzo[d]isothiazol-3-amine

A mixture of 2-fluoro-3-iodo-4-methylbenzonitrile (130 mg, 0.50 mmol), sulfur (16 mg, 0.50 mmol), ammonium hydroxide (28-30%, 0.25 mL) in 2-methoxyethanol (1.5 mL) was heated in an oil bath at 135° C. for 12 h. The volatile solvents were removed under reduced pressure, and the residue was purified on an ISCO 12 g column (eluted with 25-50% ethyl acetate in hexanes) to provide the title compound as a yellow crystalline solid.
MS (ESI, pos. ion) m/z: 291.0 (M+1).

EXAMPLE 108

Synthesis of N-(Isoxazol-3-yl)-4-methyl-3-(1-morpholinophthalazin-6-yl)benzamide A solution of 4-methyl-3-(1-morpholinophthalazin-6-yl)benzoic acid (Example 8, 160 mg, 0.45 mmol) in thionyl chloride (1.0 mL, 1.37 mmol) was stirred at RT for 1 h. Excess $SOCl_2$ was removed under reduced pressure and the residue was treated with 1 mL of toluene and concentrated under reduced pressure. The residue was dissolved in dichloromethane (3 mL), and isoxazol-3-amine (58 mg, 0.69 mmol) followed by pyridine (72 mg, 0.92 mmol) was added. After the resulting mixture was refluxed for 1 h, cooled to RT, diluted with dichloromethane, and washed with 1 N NaOH. The dichloromethane layer was dried, concentrated, and purified on an ISCO 12 g column (eluted with 5-15% MeOH in ethyl acetate) to provide N-(isoxazol-3-yl)-4-methyl-3-(1-morpholinophthalazin-6-yl)benzamide as an amorphous off-white solid. Found MS (ESI, pos. ion) m/z: 416 (M+1).

EXAMPLE 109

Synthesis of N-Cyclopropyl-4-methyl-3-(1-morpholinophthalazin-6-yl)benzothioamide A mixture of N-cyclopropyl-4-methyl-3-(1-morpholinophthalazin-6-yl)benzamide (85 mg, 0.22 mmol) and Lawesson's reagent (97 mg, 0.24 mmol) in 1 mL THF was heated at 150° C. for 10 min in a microwave oven. Volatile solvents were removed under reduced pressure and the brown residue was purified on an ISCO column (12 g, eluted with 1-10% MeOH in ethyl acetate) to provide N-cyclopropyl-4-methyl-3-(1-morpholinophthalazin-6-yl)benzothioamide as a yellow solid. Found MS ($ESI^+$) m/z: 405.3 (M+1).

The following Examples will further assist in understanding the invention. However, in no way is the following list of compounds intended to limit the scope of the invention. Each compound was named according to the ACD naming convention, as associated with ISIS software. The mass spectral data is recorded $M+H^+$, which is the positive ion as measured by an electrospray ionization method.

TABLE 1

| Ex. No. | Name | MS (M + H+) | Method |
|---|---|---|---|
| 110 | N-cyclopropyl-4-methyl-3-{1-[(2R)-2-methylpiperazin-1-yl]phthalazin-6-yl}benzamide | 402 | A |
| 111 | N-cyclopropyl-4-methyl-3-{1-[(2-morpholin-4-ylethyl)amino]phthalazin-6-yl}benzamide | 432 | A |
| 112 | N-cyclopropyl-3-{1-[(2R,5S)-2,5-dimethylmorpholin-4-yl]phthalazin-6-yl}-4-methylbenzamide | 417 | A |
| 113 | N-cyclopropyl-4-{1-[(2R,5R)-2,5-dimethylmorpholin-4-yl]phthalazin-6-yl}-5-methylpyridine-2-carboxamide | 418 | A |
| 114 | 1-(6-{5-[(cyclopropylamino)carbonyl]-2-methylphenyl}phthalazin-1-yl)piperidine-4-carboxamide | 430 | A |
| 115 | 4-methyl-3-{1-[(1S,4S)-2-oxa-5-azabicyclo[2.2.1]hept-5-yl]phthalazin-6-yl}benzamide | 361 | A |
| 116 | 4-methyl-3-[1-(3-oxopiperazin-1-yl)phthalazin-6-yl]benzamide | 362 | A |
| 117 | N-ethyl-3-[1-(isopropylamino)phthalazin-6-yl]-4-methylbenzamide | 349 | C |
| 118 | 3-(1-methoxyphthalazin-6-yl)-4-methylbenzamide | 294 | A |
| 119 | 3-{1-[(2S,5S)-2,5-dimethylmorpholin-4-yl]phthalazin-6-yl}-4-methylbenzamide | 377 | A |
| 120 | N-cyclopropyl-4-methyl-3-{1-[(1S,4S)-2-oxa-5-azabicyclo[2.2.1]hept-5-yl]phthalazin-6-yl}benzamide | 401 | A |

TABLE 1-continued

| Ex. No. | Name | MS (M + H+) | Method |
|---|---|---|---|
| 121 | N-cyclopropyl-3-(1-mesitylphthalazin-6-yl)-4-methylbenzamide | 422 | B |
| 122 | 3-{1-[(2S,5R)-2,5-dimethylpiperazin-1-yl]phthalazin-6-yl}-4-methylbenzamide | 376 | A |
| 123 | N-cyclopropyl-3-{1-[(2S,5S)-2,5-dimethylmorpholin-4-yl]phthalazin-6-yl}-4-methylbenzamide | 417 | A |
| 124 | 4-(6-{5-[(cyclopropylamino)carbonyl]-2-methylphenyl}phthalazin-1-yl)-N-phenylpiperazine-1-carboxamide | 507 | A |
| 125 | N-cyclopropyl-3-{1-[(1S,4S)-2,5-diazabicyclo[2.2.1]hept-2-yl]phthalazin-6-yl}-4-methylbenzamide | 400 | A |
| 126 | tert-butyl (1S,4S)-5-(6-{5-[(cyclopropylamino)carbonyl]-2-methylphenyl}phthalazin-1-yl)-2,5-diazabicyclo[2.2.1]heptane-2-carboxylate | 500 | A |
| 127 | 3-[1-(1,1-dioxidothiomorpholin-4-yl)phthalazin-6-yl]-4-methylbenzamide | 397 | A |
| 128 | 4-methyl-3-(1-thiomorpholin-4-ylphthalazin-6-yl)benzamide | 365 | A |
| 129 | 4-(6-{5-[(cyclopropylamino)carbonyl]-2-methylphenyl}phthalazin-1-yl)-N-ethylpiperazine-1-carboxamide | 459 | A |
| 130 | N-cyclopropyl-3-{1-[(2R)-2-ethylpiperidin-1-yl]phthalazin-6-yl}-4-methylbenzamide | 415 | A |
| 131 | N-cyclopropyl-4-methyl-3-[1-(4-methylphenyl)phthalazin-6-yl]benzamide | 394 | B |
| 132 | (3R)-1-(6-{5-[(cyclopropylamino)carbonyl]-2-methylphenyl}phthalazin-1-yl)piperidine-3-carboxamide | 430 | A |
| 133 | N-cyclopropyl-3-[1-(1,1-dioxidothiomorpholin-4-yl)phthalazin-6-yl]-4-methylbenzamide | 437 | A |
| 134 | N-cyclopropyl-4-methyl-3-(1-thiomorpholin-4-ylphthalazin-6-yl)benzamide | 405 | A |
| 135 | N-cyclopropyl-5-{1-[(2R,5R)-2,5-dimethylmorpholin-4-yl]phthalazin-6-yl}-2-fluoro-4-methylbenzamide | 435 | A |
| 136 | 3-{1-[(4aR,8aR)-octahydroisoquinolin-2(1H)-yl]phthalazin-6-yl}-N-cyclopropyl-4-methylbenzamide | 441 | A |
| 137 | 6-(2-methyl-5-nitrophenyl)-1-morpholin-4-ylphthalazine | 351 | A |
| 138 | ethyl 3-[1-(isopropylamino)phthalazin-6-yl]-4-methylbenzoate | 350 | C |
| 139 | 4-(6-{5-[(cyclopropylamino)carbonyl]-2-methylphenyl}phthalazin-1-yl)-N-(4-fluorobenzyl)piperazine-1-carboxamide | 539 | A |
| 140 | N-cyclopropyl-4-methyl-3-{1-[(3R)-3-methylpiperazin-1-yl]phthalazin-6-yl}benzamide | 402 | A |
| 141 | 3-(1-aminophthalazin-6-yl)-N-cyclopropyl-4-methylbenzamide | 319 | A |
| 142 | N-cyclopropyl-3-{1-[(2R,6S)-2,6-dimethylmorpholin-4-yl]phthalazin-6-yl}-4-methylbenzamide | 417 | A |
| 143 | 4-methyl-3-{1-[(2R)-2-methylpiperazin-1-yl]phthalazin-6-yl}benzamide | 362 | A |
| 144 | N-cyclopropyl-3-{1-[(1S,4S)-5-isopropyl-2,5-diazabicyclo[2.2.1]hept-2-yl]phthalazin-6-yl}-4-methylbenzamide | 442 | A |
| 145 | 3-(1-chlorophthalazin-6-yl)-4-methylbenzamide | 298 | B |
| 146 | 4-methyl-3-{1-[(2S)-2-methylpiperazin-1-yl]phthalazin-6-yl}benzamide | 362 | A |
| 147 | N-cyclopropyl-3-{1-[(2S,5R)-2,5-dimethylpiperazin-1-yl]phthalazin-6-yl}-4-methylbenzamide | 416 | A |
| 148 | N-cyclopropyl-3-{1-[(3R,5S)-3,5-dimethylpiperazin-1-yl]phthalazin-6-yl}-4-methylbenzamide | 416 | A |
| 149 | N-cyclopropyl-4-methyl-3-{1-[(3S)-3-methylpiperazin-1-yl]phthalazin-6-yl}benzamide | 402 | A |
| 150 | N-cyclopropyl-4-methyl-3-[1-(1-methylpiperidin-4-yl)phthalazin-6-yl]benzamide | 401 | A |
| 151 | N-cyclopropyl-3-{1-[(2S)-2-(hydroxymethyl)pyrrolidin-1-yl]phthalazin-6-yl}-4-methylbenzamide | 403 | A |
| 152 | N-cyclopropyl-3-[1-(4-hydroxy-4-methylpiperidin-1-yl)phthalazin-6-yl]-4-methylbenzamide | 417 | A |
| 153 | tert-butyl 4-(6-{5-[(cyclopropylamino)carbonyl]-2-methylphenyl}phthalazin-1-yl)-3,6-dihydropyridine-1(2H)-carboxylate | 485 | B |
| 154 | 3-{1-[(4aS,8aS)-octahydroquinolin-1(2H)-yl]phthalazin-6-yl}-N-cyclopropyl-4-methylbenzamide | 441 | A |
| 155 | 3-(1-isopropoxyphthalazin-6-yl)-4-methylbenzamide | 322 | A |
| 156 | 3-[1-(2-chlorophenyl)phthalazin-6-yl]-4-methylbenzamide | 374 | B |
| 157 | 3-[1-(4-acetylpiperazin-1-yl)phthalazin-6-yl]-N-cyclopropyl-4-methylbenzamide | 430 | A |
| 158 | 3-[1-(cyclohexylamino)phthalazin-6-yl]-N-cyclopropyl-4-methylbenzamide | 401 | A |
| 159 | N-cyclopropyl-4-methyl-3-(1-piperidin-1-ylphthalazin-6-yl)benzamide | 387 | A |
| 160 | N-cyclopropyl-3-{1-[(2R)-2-(hydroxymethyl)morpholin-4-yl]phthalazin-6-yl}-4-methylbenzamide | 419 | A |

TABLE 1-continued

| Ex. No. | Name | MS (M + H+) | Method |
|---|---|---|---|
| 161 | N-cyclopropyl-4-methyl-3-[1-(2-methyl-5-N-cyclopropylamido-phenyl)phthalazin-6-yl]benzamide | 477 | B |
| 162 | N-cyclopropyl-3-{1-[4-(2,6-dimethylphenyl)piperazin-1-yl]phthalazin-6-yl}-4-methylbenzamide | 492 | A |
| 163 | N-cyclopropyl-4-methyl-3-[1-(3-oxopiperazin-1-yl)phthalazin-6-yl]benzamide | 402 | A |
| 164 | 3-(1-chlorophthalazin-6-yl)-N-cyclopropyl-4-methylbenzamide | 338 | B |
| 165 | N-cyclopropyl-4-methyl-3-(1-piperazin-1-ylphthalazin-6-yl)benzamide | 388 | A |
| 166 | N-cyclopropyl-3-{1-[(3R)-3-hydroxypyrrolidin-1-yl]phthalazin-6-yl}-4-methylbenzamide | 389 | A |
| 167 | N-cyclopropyl-3-[1-(1,4-dioxa-8-azaspiro[4.5]dec-8-yl)phthalazin-6-yl]-4-methylbenzamide | 445 | A |
| 168 | N-cyclopropyl-3-(1-isopropoxyphthalazin-6-yl)-4-methylbenzamide | 362 | A |
| 169 | N-cyclopropyl-3-(1-methoxyphthalazin-6-yl)-4-methylbenzamide | 334 | A |
| 170 | 3-[1-(2-chlorophenyl)phthalazin-6-yl]-N-cyclopropyl-4-methylbenzamide | 414 | B |
| 171 | 3-{1-[(2R,5R)-2,5-dimethylmorpholin-4-yl]phthalazin-6-yl}-4-methylbenzamide | 377 | A |
| 172 | N-cyclopropyl-3-[1-(isopropylamino)phthalazin-6-yl]-4-methylbenzamide | 361 | C |
| 173 | N-cyclopropyl-3-{1-[(2S,5R)-2,5-dimethylmorpholin-4-yl]phthalazin-6-yl}-4-methylbenzamide | 417 | A |
| 174 | N-cyclopropyl-3-{1-[(2R,5R)-2,5-dimethylmorpholin-4-yl]phthalazin-6-yl}-4-methylbenzamide | 417 | A |
| 175 | 4-methyl-3-(1-morpholin-4-ylphthalazin-6-yl)benzamide | 349 | A |
| 176 | 4-methyl-3-[1-(2-methylphenyl)phthalazin-6-yl]benzamide | 354 | B |
| 177 | 4-fluoro-3-(1-morpholin-4-ylphthalazin-6-yl)benzamide | 353 | A |
| 178 | N-cyclopropyl-4-methyl-3-{1-[(3S)-3-methylmorpholin-4-yl]phthalazin-6-yl}benzamide | 403 | A |
| 179 | 3-[1-(isopropylamino)phthalazin-6-yl]-4-methylbenzamide | 321 | A |
| 180 | N-cyclopropyl-4-methyl-3-{1-[(2R)-2-methylpiperidin-1-yl]phthalazin-6-yl}benzamide | 401 | A |
| 181 | N,4-dimethyl-3-(1-morpholin-4-ylphthalazin-6-yl)benzamide | 362 | C |
| 182 | 4-methyl-3-{1-[(2R)-2-methylpiperidin-1-yl]phthalazin-6-yl}benzamide | 361 | A |
| 183 | N-cyclopropyl-3-(1-{[2-(dimethylamino)ethyl]amino}phthalazin-6-yl)-4-methylbenzamide | 390 | A |
| 184 | 4-methyl-3-{1-[(3S)-3-methylmorpholin-4-yl]phthalazin-6-yl}benzamide | 363 | A |
| 185 | 3-(1-{[(1R)-2-hydroxy-1-methylethyl]amino}phthalazin-6-yl)-4-methylbenzamide | 337 | A |
| 186 | N-cyclopropyl-3-(1-{[2-(diethylamino)ethyl]amino}phthalazin-6-yl)-4-methylbenzamide | 418 | A |
| 187 | N-cyclopropyl-3-[1-(dimethylamino)phthalazin-6-yl]-4-methylbenzamide | 347 | A |
| 188 | N-cyclopropyl-3-{1-[(2-methoxyethyl)(methyl)amino]phthalazin-6-yl}-4-methylbenzamide | 391 | A |
| 189 | 3-{1-[(2-methoxyethyl)amino]phthalazin-6-yl}-4-methylbenzamide | 337.2 | A |
| 190 | 3-(1-{[(1S)-2-methoxy-1-methylethyl]amino}phthalazin-6-yl)-4-methylbenzamide | 351.2 | A |
| 191 | tert-butyl N-(6-{5-[(cyclopropylamino)carbonyl]-2-methylphenyl}phthalazin-1-yl)-L-alaninate | 447.3 | A |
| 192 | N-cyclopropyl-3-(1-{[(1S)-2-methoxy-1-methylethyl]amino}phthalazin-6-yl)-4-methylbenzamide | 391.2 | A |
| 193 | N-cyclopropyl-4-methyl-3-(1-{[(1R)-1-phenylethyl]amino}phthalazin-6-yl)benzamide | 423.2 | A |
| 194 | N-cyclopropyl-3-{1-[(2-methoxyethyl)amino]phthalazin-6-yl}-4-methylbenzamide | 277.2 | A |
| 195 | 6-[2-methyl-5-(methylsulfonyl)phenyl]-1-morpholin-4-ylphthalazine | 384.1 | A |
| 196 | 3-[1-(4-methoxypyrimidin-5-yl)phthalazin-6-yl]-4-methylbenzamide | 372.2 | D |
| 197 | N-cyclopropyl-3-{1-[2-(dimethylamino)-4-methoxypyrimidin-5-yl]phthalazin-6-yl}-4-methylbenzamide | 455.2 | D |
| 198 | 3-[1-(2,3-dimethoxyphenyl)phthalazin-6-yl]-4-methylbenzamide | 400.2 | D |
| 199 | 3-{1-[2-chloro-4-(trifluoromethyl)phenyl]phthalazin-6-yl}-4-methylbenzamide | 442.1 | D |
| 200 | 3-{1-[2,4-bis(trifluoromethyl)phenyl]phthalazin-6-yl}-N-cyclopropyl-4-methylbenzamide | 516.2 | D |

TABLE 1-continued

| Ex. No. | Name | MS (M + H+) | Method |
|---|---|---|---|
| 201 | N-cyclopropyl-3-[1-(2-methoxy-3-methylphenyl)phthalazin-6-yl]-4-methylbenzamide | 424.2 | D |
| 202 | 3-[1-(4-methoxy-2-methylphenyl)phthalazin-6-yl]-4-methylbenzamide | 384.2 | D |
| 203 | 4-methyl-3-{1-[4-(morpholin-4-ylmethyl)phenyl]phthalazin-6-yl}benzamide | 439.2 | D |
| 204 | 3-[1-(2-methoxy-3-methylphenyl)phthalazin-6-yl]-4-methylbenzamide | 384.2 | D |
| 205 | 2-[4-(6-{5-[(cyclopropylamino)carbonyl]-2-methylphenyl}phthalazin-1-yl)phenyl]-2-methylpropanoic acid | 466.2 | D |
| 206 | N-cyclopropyl-3-{1-[2-methoxy-6-(methylamino)pyridin-3-yl]phthalazin-6-yl}-4-methylbenzamide | 440.2 | D |
| 207 | N-cyclopropyl-3-[1-(6-methoxy-2-methylpyridin-3-yl)phthalazin-6-yl]-4-methylbenzamide | 425.2 | D |
| 208 | 3-[1-(4'-chloro-1,1'-biphenyl-4-yl)phthalazin-6-yl]-N-cyclopropyl-4-methylbenzamide | 490.2 | D |
| 209 | 3-[1-(4-chlorophenyl)phthalazin-6-yl]-N-cyclopropyl-4-methylbenzamide | 414.2 | D |
| 210 | 3-{1-[4-chloro-2-(trifluoromethyl)phenyl]phthalazin-6-yl}-N-cyclopropyl-4-methylbenzamide | 482.2 | D |
| 211 | 3-[1-(2-chloro-6-methylpyridin-3-yl)phthalazin-6-yl]-4-methylbenzamide | 389.1 | D |
| 212 | 3-[1-(2-chloro-6-methylpyridin-3-yl)phthalazin-6-yl]-N-cyclopropyl-4-methylbenzamide | 429.2 | D |
| 213 | 3-[1-(4-fluoro-2-methoxyphenyl)phthalazin-6-yl]-4-methylbenzamide | 388.2 | D |
| 214 | 4-methyl-3-{1-[4-(methylsulfonyl)phenyl]phthalazin-6-yl}benzamide | 418.2 | D |
| 215 | 4-methyl-3-(1-pyrimidin-5-ylphthalazin-6-yl)benzamide | 342.2 | D |
| 216 | 3-[1-(1H-indol-2-yl)phthalazin-6-yl]-4-methylbenzamide | 379.2 | D |
| 217 | 3-[1-(4-fluoro-2-methylphenyl)phthalazin-6-yl]-4-methylbenzamide | 372.2 | D |
| 218 | 3-{1-[4-(aminosulfonyl)-2-methylphenyl]phthalazin-6-yl}-N-cyclopropyl-4-methylbenzamide | 473.2 | D |
| 219 | 3-{1-[2-chloro-4-(trifluoromethyl)phenyl]phthalazin-6-yl}-N-cyclopropyl-4-methylbenzamide | 482.1 | D |
| 220 | 4-methyl-3-{1-[2-(trifluoromethyl)phenyl]phthalazin-6-yl}benzamide | 408.1 | D |
| 221 | 3-[1-(2-chloro-4-methylphenyl)phthalazin-6-yl]-4-methylbenzamide | 388.1 | D |
| 222 | 3-[1-(2-chloro-4-fluorophenyl)phthalazin-6-yl]-4-methylbenzamide | 392.1 | D |
| 223 | 3-[1-(2,4-dichlorophenyl)phthalazin-6-yl]-4-methylbenzamide | 408.1 | D |
| 224 | 3-[1-(4-chloro-2-methoxyphenyl)phthalazin-6-yl]-N-cyclopropyl-4-methylbenzamide | 444.2 | D |
| 225 | 3-[1-(2,4-dimethoxypyrimidin-5-yl)phthalazin-6-yl]-4-methylbenzamide | 402.2 | D |
| 226 | 3-[1-(2,4-dimethoxyphenyl)phthalazin-6-yl]-4-methylbenzamide | 400.2 | D |
| 227 | 3-[1-(4-isopropoxy-2-methylphenyl)phthalazin-6-yl]-4-methylbenzamide | 412.2 | D |
| 228 | 3-[1-(2-methoxypyridin-3-yl)phthalazin-6-yl]-4-methylbenzamide | 371.2 | D |
| 229 | 3-[1-(2-chloro-4-methoxyphenyl)phthalazin-6-yl]-4-methylbenzamide | 404 | D |
| 230 | N-cyclopropyl-3-[1-(2-methoxypyridin-3-yl)phthalazin-6-yl]-4-methylbenzamide | 411.2 | D |
| 231 | 3-[1-(2-chloro-4-ethoxyphenyl)phthalazin-6-yl]-4-methylbenzamide | 418.1 | D |
| 232 | 3-[1-(4-chloro-2-methylphenyl)phthalazin-6-yl]-4-methylbenzamide | 388.1 | D |
| 233 | 3-[1-(2-chloropyridin-3-yl)phthalazin-6-yl]-N-cyclopropyl-4-methylbenzamide | 415.2 | D |
| 234 | N-cyclopropyl-3-[1-(2,4-dimethoxypyrimidin-5-yl)phthalazin-6-yl]-4-methylbenzamide | 442.2 | D |
| 235 | 3-[1-(2-chloro-4-methylphenyl)phthalazin-6-yl]-N-cyclopropyl-4-methylbenzamide | 428.2 | D |
| 236 | 3-{1-[4-(aminosulfonyl)-2-methylphenyl]phthalazin-6-yl}-4-methylbenzamide | 433.1 | D |
| 237 | 3-{1-[4-methoxy-2-(trifluoromethyl)phenyl]phthalazin-6-yl}-4-methylbenzamide | 438.2 | D |
| 238 | 3-[1-(4-chloro-2-ethoxyphenyl)phthalazin-6-yl]-4-methylbenzamide | 418 | D |
| 239 | N-cyclopropyl-3-[1-(4-fluorophenyl)phthalazin-6-yl]-4-methylbenzamide | 398.2 | D |

TABLE 1-continued

| Ex. No. | Name | MS (M + H+) | Method |
|---|---|---|---|
| 240 | [4-(6-{5-[(cyclopropylamino)carbonyl]-2-methylphenyl}phthalazin-1-yl)phenyl]acetic acid | 438.2 | D |
| 241 | N-cyclopropyl-4-methyl-3-[1-(2-methylpyridin-3-yl)phthalazin-6-yl]benzamide | 395.2 | D |
| 242 | N-cyclopropyl-3-[1-(4-methoxy-2-methylphenyl)phthalazin-6-yl]-4-methylbenzamide | 424.2 | D |
| 243 | 4-methyl-3-{1-[2-methyl-4-(methylsulfinyl)phenyl]phthalazin-6-yl}benzamide | 416.2 | D |
| 244 | N-cyclopropyl-4-methyl-3-(1-thien-2-ylphthalazin-6-yl)benzamide | 386.1 | D |
| 245 | N-cyclopropyl-4-methyl-3-{1-[4-(trifluoromethoxy)phenyl]phthalazin-6-yl}benzamide | 464.2 | D |
| 246 | N-cyclopropyl-3-[1-(2-fluorophenyl)phthalazin-6-yl]-4-methylbenzamide | 398.2 | D |
| 247 | N,6-dimethyl-7-[1-(2-methylpyridin-3-yl)phthalazin-6-yl]-1,2-benzisoxazol-3-amine | 382.2 | G |
| 248 | N-cyclopropyl-3-[1-(3-fluoro-2-methoxyphenyl)phthalazin-6-yl]-4-methylbenzamide | 428.2 | D |
| 249 | N-cyclopropyl-4-methyl-3-{1-[4-(trifluoromethyl)phenyl]phthalazin-6-yl}benzamide | 448.2 | D |
| 250 | N-cyclopropyl-4-methyl-3-(1-phenylphthalazin-6-yl)benzamide | 380.2 | D |
| 251 | N-cyclopropyl-3-[1-(2-ethylphenyl)phthalazin-6-yl]-4-methylbenzamide | 408.2 | D |
| 252 | 3-[1-(2-methoxy-5-methylpyridin-4-yl)phthalazin-6-yl]-4-methylbenzamide | 385.2 | D |
| 253 | 3-[1-(4-tert-butylphenyl)phthalazin-6-yl]-N-cyclopropyl-4-methylbenzamide | 436.2 | D |
| 254 | N-cyclopropyl-4-methyl-3-{1-[2-(trifluoromethyl)phenyl]phthalazin-6-yl}benzamide | 448.2 | D |
| 255 | 4-methyl-3-[1-(2-methylpyridin-3-yl)phthalazin-6-yl]benzamide | 255.2 | D |
| 256 | N-cyclopropyl-4-methyl-3-{1-[2-methyl-4-(methylsulfonyl)phenyl]phthalazin-6-yl}benzamide | 472.2 | D |
| 257 | 3-[1-(4-chloro-2-methylphenyl)phthalazin-6-yl]-N-cyclopropyl-4-methylbenzamide | 428.2 | D |
| 258 | N-cyclopropyl-3-{1-[4-methoxy-2-(trifluoromethyl)phenyl]phthalazin-6-yl}-4-methylbenzamide | 478.2 | D |
| 259 | 3-[1-(2-fluoro-5-methylpyridin-4-yl)phthalazin-6-yl]-4-methylbenzamide | 373.1 | D |
| 260 | 4-methyl-3-{1-[2-methyl-4-(methylsulfanyl)phenyl]phthalazin-6-yl}benzamide | 400.1 | D |
| 261 | N-cyclopropyl-4-methyl-3-{1-[2-methyl-4-(methylsulfanyl)phenyl]phthalazin-6-yl}benzamide | 440.1 | D |
| 262 | N-cyclopropyl-3-[1-(4-fluoro-2-methoxyphenyl)phthalazin-6-yl]-4-methylbenzamide | 428.2 | D |
| 263 | N-cyclopropyl-4-methyl-3-[1-(3-methylpyridin-4-yl)phthalazin-6-yl]benzamide | 395.2 | D |
| 264 | N-cyclopropyl-3-[1-(2-methoxypyrimidin-5-yl)phthalazin-6-yl]-4-methylbenzamide | 412.2 | D |
| 265 | N,N,4-trimethyl-3-(1-morpholin-4-ylphthalazin-6-yl)benzamide | 377.1 | A |
| 266 | N-cyclopropyl-4-methyl-3-[1-(1,4-oxazepan-4-yl)phthalazin-6-yl]benzamide | 403.2 | A |
| 267 | 3-{1-[(8aR)-6-oxohexahydropyrrolo[1,2-a]pyrazin-2(1H)-yl]phthalazin-6-yl}-N-cyclopropyl-4-methylbenzamide | 442.3 | A |
| 268 | N-cyclopropyl-4-methyl-3-{1-[(2R)-2-methyl-3-oxopiperazin-1-yl]phthalazin-6-yl}benzamide | 416.2 | A |
| 269 | 3-{1-[(8aS)-3-oxotetrahydro[1,3]oxazolo[3,4-a]pyrazin-7(1H)-yl]phthalazin-6-yl}-N-cyclobutyl-4-methylbenzamide | 458.2 | A |
| 270 | 4-methyl-3-[1-(1,4-oxazepan-4-yl)phthalazin-6-yl]benzamide | 363.1 | A |
| 271 | N-cyclopropyl-4-methyl-3-{1-[(2S)-2-methyl-3-oxopiperazin-1-yl]phthalazin-6-yl}benzamide | 416.1 | A |
| 272 | 3-{1-[(8aS)-6-oxohexahydropyrrolo[1,2-a]pyrazin-2(1H)-yl]phthalazin-6-yl}-N-cyclopropyl-4-methylbenzamide | 442.3 | A |
| 273 | N-cyclopropyl-4-methyl-3-{1-[(2S)-2-(trifluoromethyl)pyrrolidin-1-yl]phthalazin-6-yl}benzamide | 441.2 | A |
| 274 | 3-{1-[(8aS)-hexahydropyrrolo[1,2-a]pyrazin-2(1H)-yl]phthalazin-6-yl}-N-cyclopropyl-4-methylbenzamide | 428.3 | A |
| 275 | N-cyclopropyl-4-methyl-3-[1-(5-oxo-1,4-diazepan-1-yl)phthalazin-6-yl]benzamide | 416.1 | A |
| 276 | N-cyclopropyl-4-methyl-3-(8-morpholin-4-ylpyrido[2,3-d]pyridazin-3-yl)benzamide | 390.2 | A2 |
| 277 | 4-methyl-3-[1-(5-oxo-1,4-diazepan-1-yl)phthalazin-6-yl]benzamide | 376.1 | A |

TABLE 1-continued

| Ex. No. | Name | MS (M + H+) | Method |
|---|---|---|---|
| 278 | N-methoxy-4-methyl-3-(1-morpholin-4-ylphthalazin-6-yl)benzamide | 379.2 | A |
| 279 | 3-[1-(isopropylamino)phthalazin-6-yl]-N-methoxy-4-methylbenzamide | 351.2 | A |
| 280 | 3-{1-[(8aS)-3-oxotetrahydro[1,3]oxazolo[3,4-a]pyrazin-7(1H)-yl]phthalazin-6-yl}-4-methylbenzamide | 404.2 | A |
| 281 | 3-[1-(dimethylamino)phthalazin-6-yl]-4-methylbenzamide | 307.2 | A |
| 282 | 3-{1-[(8aS)-hexahydropyrrolo[1,2-a]pyrazin-2(1H)-yl]phthalazin-6-yl}-4-methylbenzamide | 388.1 | A |
| 283 | N-cyclobutyl-3-[1-(dimethylamino)phthalazin-6-yl]-4-methylbenzamide | 361.2 | A |
| 284 | 3-{1-[(8aR)-3-oxotetrahydro[1,3]oxazolo[3,4-a]pyrazin-7(1H)-yl]phthalazin-6-yl}-4-methylbenzamide | 404.1 | A |
| 285 | 3-{1-[(8aS)-6-oxohexahydropyrrolo[1,2-a]pyrazin-2(1H)-yl]phthalazin-6-yl}-4-methylbenzamide | 402.1 | A |
| 286 | N-cyclopropyl-3-[1-(4-fluoro-2-methylphenyl)phthalazin-6-yl]-4-methylbenzamide | 412 | K |
| 287 | N-cyclopropyl-4-methyl-3-[1-(4-methyl-6-oxo-1,6-dihydropyridin-3-yl)phthalazin-6-yl]benzamide | 411 | K |
| 288 | N-cyclopropyl-3-(1-hydroxyphthalazin-6-yl)-4-methylbenzamide | 320 | K |
| 289 | 3-{1-[cyclohexyl(methyl)amino]phthalazin-6-yl}-N-cyclopropyl-4-methylbenzamide | 415 | A |
| 290 | N-cyclopropyl-3-{1-[isopropyl(methyl)amino]phthalazin-6-yl}-4-methylbenzamide | 375 | A |
| 291 | 3-{1-[cyclohexyl(methyl)amino]phthalazin-6-yl}-4-methylbenzamide | 375 | A |
| 292 | 3-{1-[isopropyl(methyl)amino]phthalazin-6-yl}-4-methylbenzamide | 335 | A |
| 293 | N-cyclopropyl-3-{1-[(2S)-2-isopropylpyrrolidin-1-yl]phthalazin-6-yl}-4-methylbenzamide | 415 | A |
| 294 | 4-methyl-3-{1-[3-(trifluoromethyl)-5,6-dihydro[1,2,4]triazolo[4,3-a]pyrazin-7(8H)-yl]phthalazin-6-yl}benzamide | 454 | A |
| 295 | N-cyclopropyl-4-methyl-3-{1-[(2S)-2-methylpyrrolidin-1-yl]phthalazin-6-yl}benzamide | 387 | D |
| 296 | N-cyclopropyl-4-methyl-3-{1-[(2R)-2-methylpyrrolidin-1-yl]phthalazin-6-yl}benzamide | 387 | D |
| 297 | N-cyclopropyl-4-methyl-3-(1-{[(2R)-tetrahydrofuran-2-ylmethyl]amino}phthalazin-6-yl)benzamide | 403.2 | A |
| 298 | N-cyclopropyl-4-methyl-3-(1-{[(1S)-1-methylpropyl]amino}phthalazin-6-yl)benzamide | 375.2 | A |
| 299 | 4-methyl-3-[1-(2-methylphenoxy)phthalazin-6-yl]benzamide | 370.1 | A |
| 300 | 4-methyl-3-{1-[(2-methylpyridin-3-yl)oxy]phthalazin-6-yl}benzamide | 371.1 | A |
| 301 | 3-[1-(4-fluorophenoxy)phthalazin-6-yl]-4-methylbenzamide | 374.1 | A |
| 302 | N-cyclopropyl-4-methyl-3-(1-{[(1S)-1-methylpropyl]oxy}phthalazin-6-yl)benzamide | 376.2 | A |
| 303 | 4-methyl-3-(1-{[(1S)-1-methylpropyl]amino}phthalazin-6-yl)benzamide | 335.2 | A |
| 304 | 3-[1-(2,4-difluorophenoxy)phthalazin-6-yl]-4-methylbenzamide | 392.1 | A |
| 305 | N-cyclopropyl-3-[1-(4-fluoro-2-methylphenoxy)phthalazin-6-yl]-4-methylbenzamide | 428.2 | A |
| 306 | 3-[1-(2-methoxyphenoxy)phthalazin-6-yl]-4-methylbenzamide | 386.1 | A |
| 307 | 3-[1-(3-chlorophenoxy)phthalazin-6-yl]-4-methylbenzamide | 390.1 | A |
| 308 | N-cyclopropyl-4-methyl-3-{1-[(2-methylpyridin-3-yl)oxy]phthalazin-6-yl}benzamide | 411.2 | A |
| 309 | N-cyclopropyl-4-methyl-3-(1-{[(2S)-tetrahydrofuran-2-ylmethyl]amino}phthalazin-6-yl)benzamide | 403.3 | A |
| 310 | N-cyclopropyl-4-methyl-3-(1-{[3-(2-oxopyrrolidin-1-yl)propyl]amino}phthalazin-6-yl)benzamide | 444.2 | A |
| 311 | 3-[1-(cyclohexyloxy)phthalazin-6-yl]-4-methylbenzamide | 362.1 | A |
| 312 | N-cyclopropyl-3-{1-[(4-hydroxycyclohexyl)amino]phthalazin-6-yl}-4-methylbenzamide | 417.2 | A |
| 313 | N-cyclopropyl-3-(1-{[(1S)-2-methoxy-1-methylethyl]amino}phthalazin-6-yl)-4-methylbenzamide | 391.2 | A |
| 314 | N-cyclopropyl-4-methyl-3-(1-{[(1R)-1-methylpropyl]amino}phthalazin-6-yl)benzamide | 375.2 | A |
| 315 | 4-methyl-3-[1-(neopentyloxy)phthalazin-6-yl]benzamide | 350.1 | A |
| 316 | 4-methyl-3-{1-[(1-methylpiperidin-3-yl)oxy]phthalazin-6-yl}benzamide | 377.1 | A |
| 317 | N-cyclopropyl-4-methyl-3-{1-[(1-methylpiperidin-3-yl)oxy]phthalazin-6-yl}benzamide | 417.2 | A |
| 318 | N-cyclopropyl-6-methyl-7-[1-(2-methylphenoxy)phthalazin-6-yl]-1,2-benzisoxazol-3-amine | 423.2 | A |

TABLE 1-continued

| Ex. No. | Name | MS (M + H+) | Method |
|---|---|---|---|
| 319 | N-cyclopropyl-4-methyl-3-{1-[(1-methylpiperidin-4-yl)oxy]phthalazin-6-yl}benzamide | 417.2 | A |
| 320 | 3-[1-(4-fluoro-2-methylphenoxy)phthalazin-6-yl]-4-methylbenzamide | 388.1 | A |
| 321 | 3-[1-(2,4-dimethylphenoxy)phthalazin-6-yl]-4-methylbenzamide | 384.1 | A |
| 322 | 4-methyl-3-(1-{[(1S)-1-methylpropyl]oxy}phthalazin-6-yl)benzamide | 336.1 | A |
| 323 | 3-[1-(cyclopentylamino)phthalazin-6-yl]-4-methylbenzamide | 347.1 | A |
| 324 | 4-methyl-3-(1-{[(1R)-1-methylpropyl]oxy}phthalazin-6-yl)benzamide | 336.1 | A |
| 325 | 3-[1-(cyclopentylamino)phthalazin-6-yl]-N-cyclopropyl-4-methylbenzamide | 387.2 | A |
| 326 | N-cyclopropyl-4-methyl-3-[1-(neopentyloxy)phthalazin-6-yl]benzamide | 390.2 | A |
| 327 | 3-[1-(tert-butylamino)phthalazin-6-yl]-N-cyclopropyl-4-methylbenzamide | 375.2 | A |
| 328 | N-cyclopropyl-4-methyl-3-(1-{[(1R)-1-methylpropyl]oxy}phthalazin-6-yl)benzamide | 376.2 | A |
| 329 | N-cyclopropyl-4-methyl-3-[1-(tetrahydro-2H-pyran-4-ylamino)phthalazin-6-yl]benzamide | 403.3 | A |
| 330 | N,6-dimethyl-7-(1-(((1S)-1-methyl-2-(methyloxy)ethyl)oxy)-6-phthalazinyl)-1,2-benzisoxazol-3-amine | 379.1 | A |
| 331 | N,6-dimethyl-7-(1-((1-methylethyl)oxy)-6-phthalazinyl)-1,2-benzisoxazol-3-amine | 349.2 | A |
| 332 | 6-(4-methylphenoxy)-1-(2-methylphenyl)phthalazine | 327.1 | E |
| 333 | 6-(4-fluorophenoxy)-1-[4-(morpholin-4-ylmethyl)phenyl]phthalazine | 416.2 | E |
| 334 | 1-(2-methoxyphenyl)-6-(4-methylphenoxy)phthalazine | 343.1 | E |
| 335 | 6-(4-fluorophenoxy)-1-[4-(methylsulfonyl)phenyl]phthalazine | 395 | E |
| 336 | 6-(4-fluorophenoxy)-1-morpholin-4-ylphthalazine | 326.1 | E |
| 337 | 6-(4-fluorophenoxy)-1-thien-3-ylphthalazine | 323 | E |
| 338 | 6-(3-chlorophenoxy)-1-(2-methylphenyl)phthalazine | 347 | E |
| 339 | 6-(4-fluorophenoxy)-1-[2-(trifluoromethyl)phenyl]phthalazine | 385 | E |
| 340 | 6-(4-fluorophenoxy)-1-(2-methylphenyl)phthalazine | 331.1 | E |
| 341 | 1-(4-fluoro-2-methylphenyl)-6-(4-fluorophenoxy)phthalazine | 349 | E |
| 342 | methyl 2-{[1-(2-methylphenyl)phthalazin-6-yl]oxy}benzoate | 371.1 | E |
| 343 | N-cyclopropyl-2-{[1-(2-methylphenyl)phthalazin-6-yl]oxy}benzamide | 396.1 | E |
| 344 | 6-(4-fluorophenoxy)-1-(1H-pyrazol-4-yl)phthalazine | 307.1 | E |
| 345 | 6-(2,4-difluorophenoxy)-1-(2-methylphenyl)phthalazine | 349.1 | E |
| 346 | 1-(2-chlorophenyl)-6-(4-methylphenoxy)phthalazine | 347.1 | E |
| 347 | 1-(4-fluoro-2-methylphenyl)-6-phenoxyphthalazine | 331 | E |
| 348 | {4-[6-(4-fluorophenoxy)phthalazin-1-yl]phenyl}acetic acid | 375 | E |
| 349 | 6-(4-fluorophenoxy)-1-(2-methoxypyridin-3-yl)phthalazine | 348.1 | E |
| 350 | (1S,4S)-5-[6-(4-fluorophenoxy)phthalazin-1-yl]-2-oxa-5-azabicyclo[2.2.1]heptane | 338.1 | E |
| 351 | 6-(4-fluorophenoxy)-1-pyrimidin-5-ylphthalazine | 319.1 | E |
| 352 | N-cyclopropyl-3-{[1-(2-methylphenyl)phthalazin-6-yl]oxy}benzamide | 396.1 | E |
| 353 | 6-(4-fluorophenoxy)-1-[4-(methylsulfonyl)piperazin-1-yl]phthalazine | 403.1 | E |
| 354 | 3-{[1-(2-methylphenyl)phthalazin-6-yl]oxy}benzoic acid | 357.1 | E |
| 355 | 6-(3-fluorophenoxy)-1-(2-methylphenyl)phthalazine | 331.1 | E |
| 356 | 6-(2,4-difluorophenoxy)-1-morpholin-4-ylphthalazine | 344.1 | E |
| 357 | 3-[1-(isopropylamino)phthalazin-6-yl]-4-methylbenzenesulfonamide | 357.2 | A |
| 358 | 3-[1-(isopropylamino)phthalazin-6-yl]-N,4-dimethylbenzenesulfonamide | 371 | A |
| 359 | N-cyclopropyl-3-[1-(isopropylamino)phthalazin-6-yl]-4-methylbenzenesulfonamide | 397.2 | A |
| 360 | N-cyclopropyl-4-methyl-3-(1-morpholin-4-ylphthalazin-6-yl)benzenesulfonamide | 425.2 | A |
| 361 | N-ethyl-3-(1-isobutylphthalazin-6-yl)-4-methylbenzamide | 348.2 | F |
| 362 | ethyl 3-(1-isopropylphthalazin-6-yl)-4-methylbenzoate | 335.2 | F |
| 363 | N-ethyl-3-(1-isopropylphthalazin-6-yl)-4-methylbenzamide | 334.2 | F |
| 364 | 4-[6-(4-fluorophenoxy)phthalazin-1-yl]-3-methylbenzenesulfonamide | 410.1 | E |
| 365 | 6-[6-methyl-3-(methylamino)-1,2-benzisoxazol-7-yl]-N-[(1S)-1-methylpropyl]phthalazin-1-amine | 362.2 | G |
| 366 | 6-[6-methyl-3-(methylamino)-1,2-benzisoxazol-7-yl]-N-[(1R)-1-methylpropyl]phthalazin-1-amine | 362.2 | G |
| 367 | 6-methyl-7-{1-[(3S)-3-methylmorpholin-4-yl]phthalazin-6-yl}-1,2-benzisothiazol-3-amine | 392.2 | G |
| 368 | 3-{1-[(2R,5S)-2,5-dimethyl-4-(2,2,2-trifluoroethyl)piperazin-1-yl]phthalazin-6-yl}-4-methylbenzamide | 458.2 | A |

TABLE 1-continued

| Ex. No. | Name | MS (M + H+) | Method |
|---|---|---|---|
| 369 | N-cyclopropyl-4-methyl-3-{1-[(1-pyridin-2-ylethyl)amino]phthalazin-6-yl}benzamide | 424.3 | A |
| 370 | 6-[3-(cyclopropylamino)-6-methyl-1,2-benzisoxazol-7-yl]-N-isopropylphthalazin-1-amine | 374.2 | G |
| 371 | 3-{1-[(2S)-4-acetyl-2-methylpiperazin-1-yl]phthalazin-6-yl}-N-cyclopropyl-4-methylbenzamide | 444.3 | A |
| 372 | N-isopropyl-6-[6-methyl-3-(methylamino)-1,2-benzisoxazol-7-yl]phthalazin-1-amine | 348.2 | G |
| 373 | N,6-dimethyl-7-{1-[(3R)-3-methylmorpholin-4-yl]phthalazin-6-yl}-1,2-benzisoxazol-3-amine | 390.2 | G |
| 374 | N-cyclopropyl-6-methyl-7-[1-(2-methylphenyl)phthalazin-6-yl]-1,2-benzisoxazol-3-amine | 407.2 | G |
| 375 | 1,6-bis(2-methoxypyridin-3-yl)phthalazine | 345.1 | K |
| 376 | N-cyclopropyl-3-{1-[(2R,5S)-2,5-dimethyl-4-(2,2,2-trifluoroethyl)piperazin-1-yl]phthalazin-6-yl}-4-methylbenzamide | 498.3 | A |
| 377 | N-cyclopropyl-7-[1-(4-fluoro-2-methylphenyl)phthalazin-6-yl]-6-methyl-1,2-benzisoxazol-3-amine | 425.2 | G |
| 378 | N-cyclopropyl-2-hydroxy-4-methyl-3-[1-(2-methylphenyl)phthalazin-6-yl]benzenecarboximidamide | 409.3 | G |
| 379 | ethyl(3S)-4-(6-{5-[(cyclopropylamino)carbonyl]-2-methylphenyl}phthalazin-1-yl)-3-methylpiperazine-1-carboxylate | 474.3 | A |
| 380 | 4-methyl-N-(5-methylisoxazol-3-yl)-3-(1-morpholin-4-ylphthalazin-6-yl)benzamide | 430.2 | A |
| 381 | N-(tert-butyl)-6-methyl-7-{1-[(3S)-3-methylmorpholin-4-yl]phthalazin-6-yl}-1,2-benzisoxazol-3-amine | 432.3 | G |
| 382 | 4-chloro-N-cyclopropyl-7-[1-(4-fluoro-2-methylphenyl)phthalazin-6-yl]-1,2-benzisoxazol-3-amine | 445.7 | G |
| 383 | 3-{1-[(2S)-4-acetyl-2-methylpiperazin-1-yl]phthalazin-6-yl}-4-methylbenzamide | 404.2 | A |
| 384 | N-ethyl-6-methyl-7-{1-[(3S)-3-methylmorpholin-4-yl]phthalazin-6-yl}-1,2-benzisoxazol-3-amine | 404.2 | G |
| 385 | 6-(3-amino-6-methyl-1,2-benzisoxazol-7-yl)-N-isopropylphthalazin-1-amine | 334.2 | G |
| 386 | 1,6-bis(2-methylphenyl)phthalazine | 311.2 | K |
| 387 | 6-methyl-7-{1-[(3S)-3-methylmorpholin-4-yl]phthalazin-6-yl}-1,2-benzisoxazol-3-amine | 376.2 | G |
| 388 | N-cyclopropyl-6-methyl-7-(1-morpholin-4-ylphthalazin-6-yl)-1,2-benzisoxazol-3-amine | 401.2 | G |
| 389 | 6-[3-(ethylamino)-6-methyl-1,2-benzisoxazol-7-yl]-N-isopropylphthalazin-1-amine | 362.2 | G |
| 390 | 7-{1-[(2S)-4-acetyl-2-methylpiperazin-1-yl]phthalazin-6-yl}-N-cyclopropyl-6-methyl-1,2-benzisoxazol-3-amine | 457.3 | G |
| 391 | 6-methyl-7-{1-[(3S)-3-methylmorpholin-4-yl]phthalazin-6-yl}-1H-indazol-3-amine | 375.2 | G |
| 392 | N-cyclopropyl-3-{1-[(2R,5S)-2,5-dimethyl-4-(2,2,2-trifluoroethyl)piperazin-1-yl]phthalazin-6-yl}-4-methylbenzamide | 498.2 | A |
| 393 | N-cyclopropyl-3-{1-[(2S,5R)-2,5-dimethyl-4-(2,2,2-trifluoroethyl)piperazin-1-yl]phthalazin-6-yl}-4-methylbenzamide | 498.2 | A |
| 394 | 3-{1-[(2R,5R)-2,5-dimethylpyrrolidin-1-yl]phthalazin-6-yl}-4-methylbenzamide | 361.2 | A |
| 395 | N-cyclopropyl-3-{1-[(2R,5R)-2,5-dimethylpyrrolidin-1-yl]phthalazin-6-yl}-4-methylbenzamide | 401.2 | A |
| 396 | N,6-dimethyl-7-[1-(2-methylphenyl)phthalazin-6-yl]-1,2-benzisoxazol-3-amine | 381.2 | G |
| 397 | N,6-dimethyl-7-(1-((S)-3-methylmorpholino)phthalazin-6-yl)benzo[d]isoxazol-3-amine | 390.2 | G |
| 398 | 1-[3-(4-fluorophenyl)morpholin-4-yl]-6-(2-methylphenyl)phthalazine | 400.5 | J |
| 399 | N-[(1S)-2-methoxy-1-methylethyl]-6-[6-methyl-3-(methylamino)-1,2-benzisoxazol-7-yl]phthalazin-1-amine | 378 | G |
| 400 | 6-chloro-7-{1-[(3S)-3-methylmorpholin-4-yl]phthalazin-6-yl}-N-(2,2,2-trifluoroethyl)-1,2-benzisoxazol-3-amine | 479 | H |
| 401 | 6-chloro-N-cyclopropyl-7-{1-[(3S)-3-methylmorpholin-4-yl]phthalazin-6-yl}-1,2-benzisoxazol-3-amine | 437 | H |
| 402 | 6-chloro-N-isopropyl-7-{1-[(3S)-3-methylmorpholin-4-yl]phthalazin-6-yl}-1,2-benzisoxazol-3-amine | 439.2 | H |
| 403 | N-(6-methyl-7-{1-[(3S)-3-methylmorpholin-4-yl]phthalazin-6-yl}-1,2-benzisoxazol-3-yl)acetamide | 418.5 | G |
| 404 | N-isopropyl-3-[1-(isopropylamino)phthalazin-6-yl]-4-methylbenzamide | 363 | D |
| 405 | N-isopropyl-4-methyl-3-(1-morpholin-4-ylphthalazin-6-yl)benzamide | 391 | D |

TABLE 1-continued

| Ex. No. | Name | MS (M + H+) | Method |
|---|---|---|---|
| 406 | 4-methyl-3-(1-phenoxyphthalazin-6-yl)benzamide | 356 | A |
| 407 | 3-{1-[(2-hydroxyethyl)amino]phthalazin-6-yl}-4-methylbenzamide | 323 | A |

The following compounds in Tables 2 and 3 are additional representative examples of Formula I, as provided by the present invention.

TABLE 2

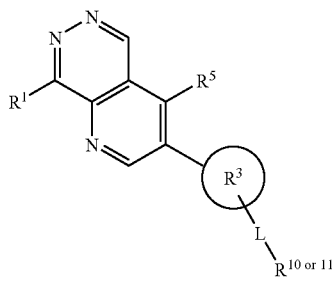

| Ex. No. | $R^1$ | $R^3$ | $R^5$ | L | $R^{10}$ or $R^{11}$ |
|---|---|---|---|---|---|
| 408 | 1-morpholinyl | 2-$CH_3$-phenyl | H | m-C(O)NH— | Methyl or cyclopropyl |
| 409 | 1-piperazinyl | 4-$CH_3$-phenyl | H | m-C(O)NH— | Methyl or cyclopropyl |
| 410 | 1-piperidinyl | phenyl | H | m-C(O)NH— | Methyl or cyclopropyl |
| 411 | cyclohexyl-N— | 6-$CH_3$-phenyl | H | m-C(O)NH— | Methyl or cyclopropyl |
| 412 | morpholine-$(CH_2)_2$—N— | 2-$OCH_3$-phenyl | H | m-C(O)NH— | Methyl or cyclopropyl |
| 413 | $(CH_3)_2$N—$(CH_2)_2$—N— | 4-$OCH_3$-phenyl | H | m-C(O)NH— | Methyl or cyclopropyl |
| 414 | $(C_2H_5)_2$N—$(CH_2)_2$—N— | phenyl | H | m-C(O)NH— | Methyl or cyclopropyl |
| 415 | 3-OH-1-pyrrolidinyl | 6-$OCH_3$-phenyl | H | m-C(O)NH— | Methyl or cyclopropyl |
| 416 | 3-amido-1-pyrrolidinyl | 6-$OCH_3$-phenyl | H | m-C(O)NH— | Methyl or cyclopropyl |
| 417 | 4-amido-1-piperidinyl | 2-F-phenyl | H | m-C(O)NH— | Methyl or cyclopropyl |
| 418 | 3-amido-1-piperidinyl | 2-F-phenyl | H | m-C(O)NH— | Methyl or cyclopropyl |
| 419 | 4N-$CH_3$-1-piperizinyl | 4-F-phenyl | H | m-C(O)NH— | Methyl or cyclopropyl |
| 420 | 2-cl-phenyl | phenyl | H | m-C(O)NH— | Methyl or cyclopropyl |
| 421 | 2-$CH_3$-phenyl | 6-F-phenyl | H | m-C(O)NH— | Methyl or cyclopropyl |
| 422 | 4-$CH_3$-phenyl | 2-thiophene | H | m-C(O)NH— | Methyl or cyclopropyl |
| 423 | 4-cl-phenyl | 3-thiophene | H | m-C(O)NH— | Methyl or cyclopropyl |
| 424 | 3-cl-phenyl | 2-pyridine | H | m-C(O)NH— | Methyl or cyclopropyl |
| 425 | 3-$CH_3$-phenyl | 3-pyridine | H | m-C(O)NH— | Methyl or cyclopropyl |
| 426 | 2-thiophene | 2-$CH_3$-phenyl | H | m-C(O)NH— | Methyl or cyclopropyl |
| 427 | 3-thiophene | 4-$CH_3$-phenyl | H | m-C(O)NH— | Methyl or cyclopropyl |

TABLE 2-continued

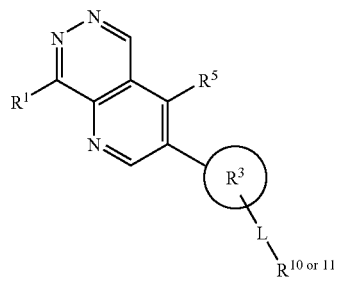

| Ex. No. | $R^1$ | $R^3$ | $R^5$ | L | $R^{10}$ or $R^{11}$ |
|---|---|---|---|---|---|
| 428 | 2-pyridine | phenyl | H | m-C(O)NH— | Methyl or cyclopropyl |
| 429 | 1-morpholinyl | 2-CH$_3$-phenyl | H | m-C(O)NH— | ethyl |
| 430 | 1-piperazinyl | 4-CH$_3$-phenyl | H | m-C(O)NH— | ethyl |
| 431 | 1-piperidinyl | phenyl | H | m-C(O)NH— | ethyl |
| 432 | cyclohexyl-N— | 6-CH$_3$-phenyl | H | m-C(O)NH— | ethyl |
| 433 | morpholine-(CH$_2$)$_2$—N— | 2-OCH$_3$-phenyl | H | m-C(O)NH— | ethyl |
| 434 | (CH$_3$)$_2$N—(CH$_2$)$_2$—N— | 4-OCH$_3$-phenyl | H | m-C(O)NH— | ethyl |
| 435 | (C$_2$H$_5$)$_2$N—(CH$_2$)$_2$—N— | phenyl | H | m-C(O)NH— | ethyl |
| 436 | 3-OH-1-pyrrolidinyl | 6-OCH$_3$-phenyl | H | m-C(O)NH— | ethyl |
| 437 | 3-amido-1-pyrrolidinyl | 6-OCH$_3$-phenyl | H | m-C(O)NH— | ethyl |
| 438 | 3-amido-1-piperidinyl | 2-F-phenyl | H | m-C(O)NH— | ethyl |
| 439 | 4-amido-1-piperidinyl | 2-F-phenyl | H | m-C(O)NH— | ethyl |
| 440 | 4N-CH$_3$-1-piperizinyl | 4-F-phenyl | H | m-C(O)NH— | ethyl |
| 441 | 2-cl-phenyl | phenyl | H | m-C(O)NH— | ethyl |
| 442 | 2-CH$_3$-phenyl | 6-F-phenyl | H | m-C(O)NH— | ethyl |
| 443 | 4-CH$_3$-phenyl | 2-thiophene | H | m-C(O)NH— | ethyl |
| 444 | 4-cl-phenyl | 3-thiophene | H | m-C(O)NH— | ethyl |
| 445 | 3-cl-phenyl | 2-pyridine | H | m-C(O)NH— | ethyl |
| 446 | 3-CH$_3$-phenyl | 3-pyridine | H | m-C(O)NH— | ethyl |
| 447 | 2-thiophene | 2-CH$_3$-phenyl | H | m-C(O)NH— | ethyl |
| 448 | 3-thiophene | 4-CH$_3$-phenyl | H | m-C(O)NH— | ethyl |
| 449 | 2-pyridine | phenyl | H | m-C(O)NH— | ethyl |
| 450 | 1-morpholinyl | 2-CH$_3$-phenyl | H | m-C(O)NH— | propyl |
| 451 | 1-piperazinyl | 4-CH$_3$-phenyl | H | m-C(O)NH— | propyl |
| 452 | 1-piperidinyl | phenyl | H | m-C(O)NH— | propyl |
| 453 | cyclohexyl-N— | 6-CH$_3$-phenyl | H | m-C(O)NH— | propyl |
| 454 | morpholine-(CH$_2$)$_2$—N— | 2-OCH$_3$-phenyl | H | m-C(O)NH— | propyl |
| 455 | (CH$_3$)$_2$N—(CH$_2$)$_2$—N— | 4-OCH$_3$-phenyl | H | m-C(O)NH— | propyl |
| 456 | (C$_2$H$_5$)$_2$N—(CH$_2$)$_2$—N— | phenyl | H | m-C(O)NH— | propyl |
| 457 | 3-OH-1-pyrrolidinyl | 6-OCH$_3$-phenyl | H | m-C(O)NH— | propyl |
| 458 | 3-amido-1-pyrrolidinyl | 6-OCH$_3$-phenyl | H | m-C(O)NH— | propyl |
| 459 | 3-amido-1-piperidinyl | 2-F-phenyl | H | m-C(O)NH— | propyl |
| 460 | 4-amido-1-piperidinyl | 2-F-phenyl | H | m-C(O)NH— | propyl |
| 461 | 4N-CH$_3$-1-piperizinyl | 4-F-phenyl | H | m-C(O)NH— | propyl |
| 462 | 2-cl-phenyl | phenyl | H | m-C(O)NH— | propyl |
| 463 | 2-CH$_3$-phenyl | 6-F-phenyl | H | m-C(O)NH— | propyl |
| 464 | 4-CH$_3$-phenyl | 2-thiophene | H | m-C(O)NH— | propyl |
| 465 | 4-cl-phenyl | 3-thiophene | H | m-C(O)NH— | propyl |
| 466 | 3-cl-phenyl | 2-pyridine | H | m-C(O)NH— | propyl |
| 467 | 3-CH$_3$-phenyl | 3-pyridine | H | m-C(O)NH— | propyl |
| 468 | 2-thiophene | 2-CH$_3$-phenyl | H | m-C(O)NH— | propyl |
| 469 | 3-thiophene | 4-CH$_3$-phenyl | H | m-C(O)NH— | propyl |
| 470 | 2-pyridine | phenyl | H | m-C(O)NH— | propyl |
| 471 | 4-F-phenyl | H | CH$_3$ | m-C(O)NH— | cyclopropyl |

TABLE 3

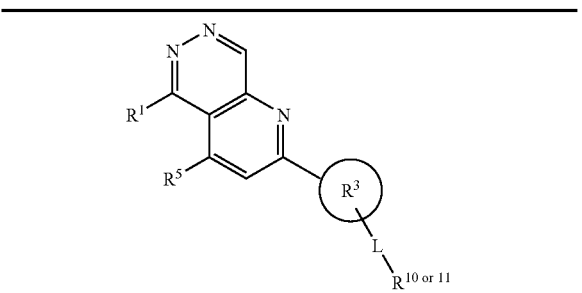
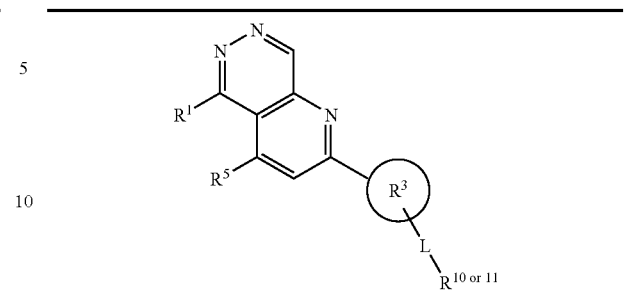

| Ex. No. | R¹ | R³ | R⁵ | L | R¹⁰ or R¹¹ |
|---|---|---|---|---|---|
| 472 | 1-morpholinyl | 2-$CH_3$-phenyl | H | m-C(O)NH— | Methyl or cyclopropyl |
| 473 | 1-piperazinyl | 4-$CH_3$-phenyl | H | m-C(O)NH— | Methyl or cyclopropyl |
| 474 | 1-piperidinyl | phenyl | H | m-C(O)NH— | Methyl or cyclopropyl |
| 475 | cyclohexyl-N— | 6-$CH_3$-phenyl | H | m-C(O)NH— | Methyl or cyclopropyl |
| 476 | morpholine-$(CH_2)_2$—N— | 2-$OCH_3$-phenyl | H | m-C(O)NH— | Methyl or cyclopropyl |
| 477 | $(CH_3)_2$N—$(CH_2)_2$—N— | 4-$OCH_3$-phenyl | H | m-C(O)NH— | Methyl or cyclopropyl |
| 478 | $(C_2H_5)_2$N—$(CH_2)_2$—N— | phenyl | H | m-C(O)NH— | Methyl or cyclopropyl |
| 479 | 3-OH-1-pyrrolidinyl | 6-$OCH_3$-phenyl | H | m-C(O)NH— | Methyl or cyclopropyl |
| 480 | 3-amido-1-pyrrolidinyl | 6-$OCH_3$-phenyl | H | m-C(O)NH— | Methyl or cyclopropyl |
| 481 | 4-amido-1-piperidinyl | 2-F-phenyl | H | m-C(O)NH— | Methyl or cyclopropyl |
| 482 | 3-amido-1-piperidinyl | 2-F-phenyl | H | m-C(O)NH— | Methyl or cyclopropyl |
| 483 | 4N-$CH_3$-1-piperizinyl | 4-F-phenyl | H | m-C(O)NH— | Methyl or cyclopropyl |
| 484 | 2-cl-phenyl | phenyl | H | m-C(O)NH— | Methyl or cyclopropyl |
| 485 | 2-$CH_3$-phenyl | 6-F-phenyl | H | m-C(O)NH— | Methyl or cyclopropyl |
| 486 | 4-$CH_3$-phenyl | 2-thiophene | H | m-C(O)NH— | Methyl or cyclopropyl |
| 487 | 4-cl-phenyl | 3-thiophene | H | m-C(O)NH— | Methyl or cyclopropyl |
| 488 | 3-cl-phenyl | 2-pyridine | H | m-C(O)NH— | Methyl or cyclopropyl |
| 489 | 3-$CH_3$-phenyl | 3-pyridine | H | m-C(O)NH— | Methyl or cyclopropyl |
| 490 | 2-thiophene | 2-$CH_3$-phenyl | H | m-C(O)NH— | Methyl or cyclopropyl |
| 491 | 3-thiophene | 4-$CH_3$-phenyl | H | m-C(O)NH— | Methyl or cyclopropyl |
| 492 | 2-pyridine | phenyl | H | m-C(O)NH— | Methyl or cyclopropyl |
| 493 | 1-morpholinyl | 2-$CH_3$-phenyl | H | m-C(O)NH— | ethyl |
| 494 | 1-piperazinyl | 4-$CH_3$-phenyl | H | m-C(O)NH— | ethyl |
| 495 | 1-piperidinyl | phenyl | H | m-C(O)NH— | ethyl |
| 496 | cyclohexyl-N— | 6-$CH_3$-phenyl | H | m-C(O)NH— | ethyl |
| 497 | morpholine-$(CH_2)_2$—N— | 2-$OCH_3$-phenyl | H | m-C(O)NH— | ethyl |
| 498 | $(CH_3)_2$N—$(CH_2)_2$—N— | 4-$OCH_3$-phenyl | H | m-C(O)NH— | ethyl |
| 499 | $(C_2H_5)_2$N—$(CH_2)_2$—N— | phenyl | H | m-C(O)NH— | ethyl |
| 500 | 3-OH-1-pyrrolidinyl | 6-$OCH_3$-phenyl | H | m-C(O)NH— | ethyl |
| 501 | 3-amido-1-pyrrolidinyl | 6-$OCH_3$-phenyl | H | m-C(O)NH— | ethyl |
| 502 | 3-amido-1-piperidinyl | 2-F-phenyl | H | m-C(O)NH— | ethyl |
| 503 | 4-amido-1-piperidinyl | 2-F-phenyl | H | m-C(O)NH— | ethyl |
| 504 | 4N-$CH_3$-1-piperizinyl | 4-F-phenyl | H | m-C(O)NH— | ethyl |
| 505 | 2-cl-phenyl | phenyl | H | m-C(O)NH— | ethyl |
| 506 | 2-$CH_3$-phenyl | 6-F-phenyl | H | m-C(O)NH— | ethyl |
| 507 | 4-$CH_3$-phenyl | 2-thiophene | H | m-C(O)NH— | ethyl |
| 508 | 4-cl-phenyl | 3-thiophene | H | m-C(O)NH— | ethyl |
| 509 | 3-cl-phenyl | 2-pyridine | H | m-C(O)NH— | ethyl |
| 510 | 3-$CH_3$-phenyl | 3-pyridine | H | m-C(O)NH— | ethyl |
| 511 | 2-thiophene | 2-$CH_3$-phenyl | H | m-C(O)NH— | ethyl |
| 512 | 3-thiophene | 4-$CH_3$-phenyl | H | m-C(O)NH— | ethyl |
| 513 | 2-pyridine | phenyl | H | m-C(O)NH— | ethyl |
| 514 | 1-morpholinyl | 2-$CH_3$-phenyl | H | m-C(O)NH— | propyl |
| 515 | 1-piperazinyl | 4-$CH_3$-phenyl | H | m-C(O)NH— | propyl |
| 516 | 1-piperidinyl | phenyl | H | m-C(O)NH— | propyl |
| 517 | cyclohexyl-N— | 6-$CH_3$-phenyl | H | m-C(O)NH— | propyl |

TABLE 3-continued

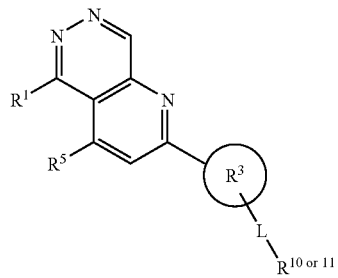

| Ex. No. | R$^1$ | R$^3$ | R$^5$ | L | R$^{10}$ or R$^{11}$ |
|---|---|---|---|---|---|
| 518 | morpholine-(CH$_2$)$_2$—N— | 2-OCH$_3$-phenyl | H | m-C(O)NH— | propyl |
| 519 | (CH$_3$)$_2$N—(CH$_2$)$_2$—N— | 4-OCH$_3$-phenyl | H | m-C(O)NH— | propyl |
| 520 | (C$_2$H$_5$)$_2$N—(CH$_2$)$_2$—N— | phenyl | H | m-C(O)NH— | propyl |
| 521 | 3-OH-1-pyrrolidinyl | 6-OCH$_3$-phenyl | H | m-C(O)NH— | propyl |
| 522 | 3-amido-1-pyrrolidinyl | 6-OCH$_3$-phenyl | H | m-C(O)NH— | propyl |
| 523 | 3-amido-1-piperidinyl | 2-F-phenyl | H | m-C(O)NH— | propyl |
| 524 | 4-amido-1-piperidinyl | 2-F-phenyl | H | m-C(O)NH— | propyl |
| 525 | 4N-CH$_3$-1-piperizinyl | 4-F-phenyl | H | m-C(O)NH— | propyl |
| 526 | 2-cl-phenyl | phenyl | H | m-C(O)NH— | propyl |
| 527 | 2-CH$_3$-phenyl | 6-F-phenyl | H | m-C(O)NH— | propyl |
| 528 | 4-CH$_3$-phenyl | 2-thiophene | H | m-C(O)NH— | propyl |
| 529 | 4-cl-phenyl | 3-thiophene | H | m-C(O)NH— | propyl |
| 530 | 3-cl-phenyl | 2-pyridine | H | m-C(O)NH— | propyl |
| 531 | 3-CH$_3$-phenyl | 3-pyridine | H | m-C(O)NH— | propyl |
| 532 | 2-thiophene | 2-CH$_3$-phenyl | H | m-C(O)NH— | propyl |
| 533 | 3-thiophene | 4-CH$_3$-phenyl | H | m-C(O)NH— | propyl |
| 534 | 2-pyridine | phenyl | H | m-C(O)NH— | propyl |
| 535 | 4-F-phenyl | H | CH$_3$ | m-C(O)NH— | cyclopropyl |

While the examples described above provide processes for synthesizing compounds of Formulas I and II, it should be appreciated that other methods may be utilized to prepare such compounds. Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. The specialist knows, or can easily establish, which protecting groups are suitable with the reactions described herein.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, N.Y. (1981), in The Peptides, Volume 3, E. Gross and J. Meienhofer editors, Academic Press, London and New York (1981), in Methoden der Organischen Chemie (Methods of Organic Chemistry), Houben Weyl, 4$^{th}$ edition, Volume 15/1, georg Thieme Verlag, Stuttgart (1974), in H.-D. Jakubke and H. Jescheit, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H+form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., ethyl acetate; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine;

carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

In synthesizing a compound of formulas I and II according to a desired procedure, the steps may be performed in an order suitable to prepare the compound, including a procedure described herein or by an alternate order of steps described herein, and may be preceded, or followed, by additional protection/deprotection steps as necessary. The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

In one embodiment, the present invention provides a method of making a compound of Formula I or II, the method comprising the step of reacting a compound 7

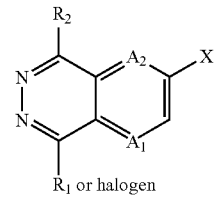

7

, wherein $A^1$, $A^2$, $R^1$ and $R^2$ are as defined herein in Formulas I or II and X is a halogen, with a boronic acid having a general formula $(RO)_2B-R^3$, wherein $R^3$ is defined herein and R is H or an optionally substituted ethyl group forming a cyclic borolane reagent, to make a compound of claim 1.

Compounds of the present invention can possess, in general, one or more asymmetric carbon atoms and are thus capable of existing in the form of optical isomers including, without limitation, racemates and racemic mixtures, scalemic mixtures, single enantiomers, individual diastereomers and diastereomeric mixtures. All such isomeric forms of these compounds are expressly included in the present invention. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

The compounds of the invention may be modified by appending appropriate fanctionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

These detailed descriptions fall within the scope, and serve to exemplify, the above-described General Synthetic Procedures which form part of the invention. These detailed descriptions are presented for illustrative purposes only and are not intended as a restriction on the scope of the invention.

Although the pharmacological properties of the compounds of the invention (Formulas I and II) vary with structural change, in general, activity possessed by compounds of Formulas I and II may be demonstrated both in vitro as well as in vivo. Particularly, the pharmacological properties of the compounds of this invention may be confirmed by a number of pharmacological in vitro assays. The following exemplified pharmacological assays have been carried out with the compounds according to the invention. Compounds of the invention were found to inhibit the activity of various kinase enzymes, including, without limitation, p38 receptor kinase at doses less than 25 µM.

BIOLOGICAL EVALUATION

The following assays were used to characterize the ability of compounds of the invention to inhibit the production of TNF-α and interleukin cytokines, including IL-1, IL-1-β, I1-6 and IL-8. The second assay can be used to measure the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a cyclooxygenase enzyme (COX-1 and COX-2) inhibition activity in vitro assay, can be used to characterize the ability of compounds of the invention to inhibit COX-1 and/or COX-2.

Lipopolysaccharide-Activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2 \times 10^6$/mL in DMEM supplemented to contain 2% FCS, 10 mM, 0.3 mg/mL glutamate, 100 U/mL penicillin G and 100 mg/mL streptomycin sulfate (complete media). Cells were plated into Falcon flat bottom, 96 well culture plates (200 µL/well) and cultured overnight at 37° C. and 6% $CO_2$.

Non-adherent cells were removed by washing with 200 µl/well of fresh medium. Wells containing adherent cells (~70% monocytes) were replenished with 100 µL of fresh medium.

Preparation of Test Compound Stock Solutions

Test compounds were dissolved in DMZ. Compound stock solutions were prepared to an initial concentration of 10-50 µM. Stocks were diluted initially to 20-200 µM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 µL complete medium. Monocytes were cultured with test compounds for 60 min at which time 25 µL of complete medium containing 30 ng/mL lipopolysaccharide from *E. coli* K532 were added to each well. Cells were cultured an additional 4 hrs. Culture supernatants were then removed and TNF presence in the supernatants was quantified using an ELISA.

TNF Elisa

Flat bottom, 96 well Corning High Binding ELISA plates were coated overnight (4° C.) with 150 µL/well of 3 µg/mL murine anti-human TNF-α MAb (R&D Systems #MAB210). Wells were then blocked for 1 h at room temperature with 200 µL/well of $CaCl_2$-free ELISA buffer supplemented to contain 20 mg/mL BSA (standard ELISA buffer: 20 mM, 150 mM NaCl, 2 mM $CaCl_2$, 0.15 mM thimerosal, pH 7.4). Plates were washed and replenished with 100 µL of test supernatants (diluted 1:3) or standards. Standards consisted of eleven 1.5-fold serial dilutions from a stock of I ng/mL recombinant human TNF (R&D Systems). Plates were incubated at room temperature for 1 h on orbital shaker (300 rpm), washed and replenished with 100 µL/well of 0.5 µg/mL goat anti-human TNF-α (R&D systems #AB-210-NA) biotinylated at a 4:1 ratio. Plates were incubated for 40 min, washed and replenished with 100 µL/well of alkaline phosphatase-conjugated streptavidin (Jackson ImmunoResearch #016-050-084) at 0.02 µg/mL. Plates were incubated 30 min, washed and replenished with 200 µL/well of 1 mg/mL of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production. The compounds of Examples 8-38, 40-43, 45-49, 55, 58-77, 79-85, 94-106 and 108-407 exhibited activities in the whole blood monocyte assay (LPS induced TNF release) with $IC_{50}$ values of 5 µM or less.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Lipopolysaccharide-Activated THP1 Cell TNF Production Assay

THP1 cells are resuspended in fresh THP1 media (RPMI 1640, 10% heat-inactivated FBS, 1×PGS, 1×NEAA, plus 30 μM βME) at a concentration of 1E6/mL. One hundred microliters of cells per well are plated in a polystyrene 96-well tissue culture. One microgram per mL of bacterial LPS is prepared in THP1 media and is transferred to the wells. Test compounds are dissolved in 100% DMSO and are serially diluted 3-fold in a polypropylene 96-well microtiter plate (drug plate). HI control and LO control wells contain only DMSO. One microliter of test compound from the drug plate followed by 10 μL of LPS are transferred to the cell plate. The treated cells are induced to synthesize and secrete TNF-α at 37° C. for 3 h. Forty microliters of conditioned media are transferred to a 96-well polypropylene plate containing 110 μL of ECL buffer (50 mM Tris-HCl pH 8.0, 100 mM NaCl, 0.05% Tween 20, 0.05% NaN$_3$ and 1%FBS) supplemented with 0.44 nM MAB610 monoclonal Ab (R&D Systems), 0.34 nM ruthenylated AF210NA polyclonal Ab (R&D Systems) and 44 μg/mL sheep anti-mouse M280 Dynabeads (Dynal). After a 2 h incubation at room temperature with shaking, the reaction is read on the ECL M8 Instrument (IGEN Inc.). A low voltage is applied to the ruthenylated TNF-α immune complexes, which in the presence of TPA (the active component in Origlo), results in a cyclical redox reaction generating light at 620 nM. The amount of secreted TNF-α in the presence of compound compared with that in the presence of DMSO vehicle alone (HI control) is calculated using the formula: % control (POC)=(cpd−average LO)/(average HI−average LO) 100. Data (consisting of POC and inhibitor concentration in μM) is fitted to a 4-parameter equation (y=A+((B-A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm.

Inhibition of LPS-Induced TNF-α Production in Mice

Male DBA/1LACJ mice are dosed with vehicle or test compounds in a vehicle (the vehicle consisting of 0.5% tragacanth in 0.03 N HC1) 30 min prior to lipopolysaccharide (2 mg/Kg, I.V.) injection. Ninety minutes after LPS injection, blood is collected and the serum is analyzed by ELISA for TNF-α levels.

Compounds of the invention may be shown to have anti-inflammatory properties in animal models of inflammation, including carageenan paw edema, collagen induced arthritis and adjuvant arthritis, such as the carageenan paw edema model (C. A. Winter et al., Proc. Soc. Exp. Biol. Med., 111: 544 (1962); K. F. Swingle, in R. A. Scherrer and M. W. Whitehouse, Eds., Anti-inflammatory Agents, Chemistry and Pharmacology, 13(II):33, Academic, New York (1974) and collagen induced arthritis (D. E. Trentham et al., J. Exp. Med., 146:857 (1977); J. S. Courtenay, Nature (New Biol.), 283:666 (1980)).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/mL ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per mL DMSO and store aliquots at −20° C.; (d) 250 μM human glucagon (Peninsula): solubilize 0.5 mg vial in 575 μl 0.1N acetic acid (1 μL yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μL 10% BSA (heat-inactivated) and 990 μL Assay Buffer; (g) $^{125}$I-Glucagon (NEN, receptor-grade, 2200 Ci/mmol): dilute to 50,000 cpm/25 μL in assay buffer with BSA (about 50 μM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).
2. Add 10 mL Enzyme-free Dissoc. Fluid and hold for about 4 min at 37° C.
3. gently tap cells free, triturate, take aliquot for counting and centrifuge remainder for 5 min at 1000 rpm.
4. Resuspend pellet in Assay Buffer at 75000 cells per 100 μL.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of I$^{125}$-glucagon binding in the presence of compounds of Formula I. The reagents are combined as follows:

| | Compound/ Vehicle | 250 μM Glucagon | $^{125}$I-Glucagon | CHO/ hGLUR Cells |
|---|---|---|---|---|
| Total Binding | —/5 μl | — | 25 μL | 100 μL |
| + Compound | 5 μl/— | — | 25 μL | 100 μL |
| Nonspecific Binding | —/5 μl | 1 μl | 25 μL | 100 μL |

The mixture is incubated for 60 min at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10%FBS); all cell incubations are at 37° C. in a humidified environment containing 5% CO$_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 h on a shaker to prevent attachment. Cells are pelleted and resuspended in Hank's Buffered Saline (HBS) at a concentration of $2.5\times10^6$ cells/mL and plated in 96-well culture plates at a density of $5\times10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3\times10^6$ cells/mL in MEM-FBS containing 1 ng human IL-1b/mL, plated in 96-well tissue culture plates at a density of $3\times10^4$ cells per well, incubated on a shaker for 1 hour to evenly distribute cells, followed by an additional 2 hour static incubation to allow attachment. The media is then replaced with MEM containing 2% FBS (MEM-2%FBS) and 1 ng human IL-lb/miL, and the cells incubated for 18-22 h. Following replacement of media with 190 mL MEM, 10 mL of test compound diluted in HBS is added to achieve the desired concentration and the cells incubated for 4 h. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1N HCl, followed by neutralization with 1N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls. Various compounds of the invention may be shown to inhibit the COX-1 and/or COX-2 activity.

INDICATIONS

Accordingly, compounds of the invention are useful for, but not limited to, the prevention or treatment of inflammation, pro-inflammatory cytokines levels including, without limitation, TNF, IL-1, IL-2, IL-6 and/or IL-8, and disease associated therewith. The compounds of the invention have kinase modulatory activity in general, and p38 kinase modulatory activity in particular. In one embodiment of the invention, there is provided a method of treating a disorder related to the activity of p38 enzyme in a subject, the method comprising administering to the subject an effective dosage amount of a compound of a compound of Formulas I or II.

Accordingly, the compounds of the invention would be useful in therapy as anti-inflammatory agents in treating inflammation, or to minimize deleterious effects of p38. Based on the ability to modulate pro-inflammatory cytokine production, the compounds of the invention are also useful in treatment and therapy of cytokine-mediated diseases. Particularly, these compounds can be used for the treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection, or any combination thereof, in a subject.

An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further applicable to the treatment of inflammation, e.g. inflammatory disease or condition, of connective tissues including dermatomyositis and myositis.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration.

The compounds of the invention are also useful in the treatment of diabetic conditions such as diabetic retinopathy and microangiopathy.

The compounds of the present invention are also useful for treating ankylosing spondylitis, inflammatory bowel disease, inflammatory pain, ulcerative colitis, asthma, chronic obstructive pulmonary disease, myelodysplastic syndrome, endotoxic shock, chronic hepatitis C or a combination thereof.

The present invention also provides methods for the treatment of protein tyrosine kinase-associated disorders, comprising the step of administering to a subject in need thereof at least one compound of the Formula I or of Formula II in an amount effective therefore. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compound(s) of the present invention in treating protein tyrosine kinase-associated disorders is exemplified by, but is not limited to, treating a range of disorders such as:

The present invention also provides for a method for treating the aforementioned disorders such as atopic dermatitis by administration of a therapeutically effective amount of a compound of the present invention, which is an inhibitor of protein tyrosine kinase, to a patient, whether or not in need of such treatment.

In yet another embodiment, the compounds are useful for decreasing the level of, or lowering plasma concentrations of, one or more of TNF-α, IL-1β, IL-6 and IL-8 in a subject, generally a mammal and typically a human.

In yet another embodiment, the compounds are useful for treating a pain disorder in a subject, which is typically a human by administering to the subject an effective dosage amount of a compound according to formulas I or II.

In yet another embodiment, the compounds are useful for treating diabetes in a subject, which is typically a human, by administering to the subject an effective dosage amount of a compound according to formulas I or II, to produce a glucagon antagonist effect.

In yet another embodiment, the compounds are useful for decreasing prostaglandin production in a subject, which is typically a human, by administering to the subject an effective dosage amount of a compound according to formulas I or II.

In yet another embodiment, the compounds are useful for decreasing cyclooxygenase enzyme activity in a subject, which is typically a human, by administering to the subject an effective amount of a compound according to formulas I or II.

In yet another embodiment, the cyclooxygenase enzyme is COX-2.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating TNF-α, IL-1, IL-6, and IL-8 mediated diseases, cancer, and/or hyperglycemia with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg, and even more advantageously between about 0.25 and about 1 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment of the present invention, there is provided a method of manufacturing a medicament, the method comprising combining an amount of a compound according to Formulas I or II with a pharmaceutically acceptable carrier to manufacture the medicament.

In yet another embodiment, there is provided a method of manufacturing a medicament for the treatment of inflammation, the method comprising combining an amount of a compound according to Formulas I or II with a pharmaceutically acceptable carrier to manufacture the medicament.

COMBINATIONS

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of TNF-α, IL-1, IL-6, and IL-8 mediated diseases, cancer, and/or hyperglycemia.

If formulated as a fixed dose, such combination products employ the compounds of this invention within the accepted dosage ranges. Compounds of Formulas I and II may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The compounds of the invention may also be used in co-therapies with anti-neoplastic agents such as other kinase inhibitors, including CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I:

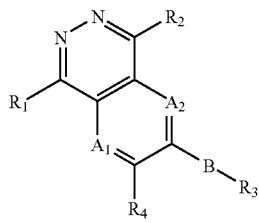

or a stereoisomer or pharmaceutically acceptable salt thereof, wherein each of $A^1$ and $A^2$, independently, is $CR^5$;

B is a direct bond, —N($R^6$)— or —O—;

$R^1$ is —$(CR^7R^7)_nX$ or —$(CR^7R^8)_nX$, wherein n is 0, 1 or 2 and X is $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)$ $NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$, $NR^7S(O)_2R^8$; or $R^1$ is a 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^5$, $R^8$ or $R^9$;

$R^2$ is H, halo, haloalkyl, $NO_2$, CN, —OH, —$OC_{1-3}$-alkyl, —$SC_{1-3}$-alkyl, or $C_{1-3}$-alkyl;

$R^3$ is phenyl, naphthyl, 3-pyridyl, pyrimidyl, triazinyl, quinolinyl, isoquinolinyl, quinazolinyl, isoquinazolinyl, thienyl, furyl, pyrrolyl, pyrazolyl, imidazolyl, triazolyl, thiazolyl, oxazolyl, isoxazolyl, isothiazolyl, indolyl, isoindolyl, benzofuranyl, dihydrobenzofuranyl, benzothienyl, benzisoxazolyl, benzisothiazolyl, benzopyrazolyl, benzothiazolyl or benzimidazolyl, each of which is substituted independently with one or more substituents of $R^{16}$, $NR^{10}R^{10}$, $NR^{10}R^{11}$, $COOR^{10}$, $COOR^{11}$, $C(O)NR^{10}R^{10}$, $C(O)NR^{10}R^{11}$, $NR^{10}C(O)R^{10}$, $NR^{10}C(O)R^{11}$, $NR^{10}C(O)NR^{10}R^{10}$, $NR^{10}C(O)NR^{10}R^{11}$, $NR^{10}(COOR^{10})$, $NR^{10}(COOR^{11})$, $S(O)_2NR^{10}R^{10}$ $S(O)_2NR^{10}R^{11}$, $NR^{10}S(O)_2NR^{10}R^{11}$, $NR^{10}S(O)_2R^{10}$ or $NR^{10}S(O)_2R^{11}$;

$R^4$ is H, halo, haloalkyl, $NO_2$, CN, —OH, —$OC_{1-3}$-alkyl, —$SC_{1-3}$-alkyl, or $C_{1-3}$-alkyl;

$R^5$ is H or $C_{1-3}$-alkyl;

$R^6$ is H or $CH_3$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)$ $R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)$ $NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$; $SR^9$, $C(O)R^9$, $COOR^8$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of $R^9$;

$R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$alkylamino-, $C_{1-10}$-dialkylamino-, $C_{1-10}$-alkoxyl or $C_{1-10}$-thioalkyl, each of which is optionally substituted independently with 1-5 substituents of e, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$; $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

provided that when B is a direct bond, $R^3$ is an optionally substituted phenyl or an optionally substituted 5- or 6-membered heteroaryl, and X is $NR^7R^8$ wherein $R^7$ is H or $C_{1-10}$-alkyl, then $R^8$ is not an optionally substituted phenyl or an optionally substituted 5- or 6-membered heteroaryl.

2. The compound of claim 1 wherein B is a direct bond.

3. The compound of claim 1 wherein at least one substituent on $R^3$ is $NR^{10}R^{10}$, $NR^{10}R^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}C(S)NR^{10}R^{11}S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$.

4. The compound of claim 1 wherein
$A^1$ is CH;
$A^2$ is CH;
B is a direct bond;
$R^1$ is $NR^7R^7$, $NR^7R^8$, $OR^7$, $SR^7$, $OR^8$, $SR^8$, $C(O)R^7$, $C(O)R^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $S(O)_2NR^7R^7$, $NR^7S(O)_2NR^7R^7$, $NR^7S(O)_2R^7$, $S(O)_2NR^7R^8$, $NR^7S(O)_2NR^7R^8$, $NR^7S(O)_2R^8$ or $R^1$ is a ring system selected from phenyl, naphthyl, pyridyl, pyrimidyl, triazinyl, quinolinyl, isoquinolinyl, quinazolinyl, isoquinazolinyl, thienyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, benzodioxolyl, cyclopropyl, cyclobutyl, cyclopentyl, cyclohexyl and cycloheptyl, wherein said ring system is optionally substituted independently with 1-3 substituents of $R^7$, $R^8$, $R^9$, oxo, $OR^7$, $SR^7$, $C(O)R^7$, $NR^7R^7$, $NR^7R^8$, $OR^8$, $SR^8$, $C(O)R^8$, $COOR^7$, $OC(O)R^7$, $COOR^8$, $OC(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2NR^7R^7$, $S(O)_2NR^7R^8$, $NR^7S(O_2)NR^7R^7$ or $NR^7S(O)_2NR^7R^8$, $R^2$ is H;

$R^3$ is phenyl, naphthyl, pyridyl, pyrimidyl, quinolinyl, isoquinolinyl, quinazolinyl, isoquinazolinyl, thienyl, furyl, pyrrolyl, imidazolyl, triazolyl, thiazolyl, oxazolyl, isoxazolyl, isothiazolyl, indolyl, isoindolyl, benzofuranyl, dihydrobenzofuranyl, benzothienyl, benzoxazolyl, benzopyrazolyl, benzisoxazolyl, benzisothiazolyl, benzothiazolyl or benzimidazolyl, said $R^3$ substituted with one substituent of $NR^{10}R^{10}$, $NR^{10}R^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $-S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$ and 0-3 substituents of $R^{16}$;

$R^4$ is H;

$R^5$ is H;

$R^7$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkynyl and $C_{3-10}$-cycloalkyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^8$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a ring selected from phenyl, naphthyl, pyridyl, pyrimidyl, triazinyl, quinolinyl, isoquinolinyl, quinazolinyl, isoquinazolinyl, thienyl,furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, benzodioxolyl, cyclopropyl, cyclobutyl, cyclopentyl, cyclohexyl and cycloheptyl, each of which is optionally substituted independently with 1-3 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl or $C_{3-10}$-cycloalkyl, each of the $C_{1-10}$-alkyl, $C_{2-10}$-alkenyl, and $C_{3-10}$-cycloalkyl optionally comprising 1-4 heteroatoms selected from N, O and S and opionally sibstitued with 1-3 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a ring selected from phenyl, naphthyl, pyridyl, pyrimidyl, triazinyl, quinolinyl, isoquinolinyl, quinazolinyl, isoquinazolinyl, thienyl,furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, benzodioxolyl, cyclopropyl, cyclobutyl, cyclopentyl, cyclohexyl and cycloheptyl, each of which is optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a ring selected from phenyl, naphthyl, pyridyl, pyrimidyl, triazinyl, quinolinyl, isoquinolinyl, quinazolinyl, isoquinazolinyl, thienyl,furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, benzodioxolyl, cyclopropyl, cyclobutyl, cyclopentyl, cyclohexyl and cycloheptyl, each of which is optionally substituted independently with 1-3 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino, $C_{1-10}$-dialkylamino-, $C_{1-10}$-alkoxyl or $C_{1-10}$-thioalkoxyl, each of which is optionally substituted independently with 1-3 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

5. The compound of claim 4 wherein $R^1$ is $NR^7R^7$, $NR^7R^8$, $C(O)R^7$, $C(O)R^8$, $C(O)NR^7R^7$, $NR^7C(O)R^7$, $C(O)NR^7R^8$, $NR^7C(O)R^8$, $S(O)_2NR^7R^7$, $NR^7S(O)_2R^7$, $S(O)_2NR^7R^8$, $NR^7S(O)_2R^8$ or a ring system selected from phenyl, naphthyl, pyridyl, pyrimidyl, triazinyl, quinolinyl, isoquinolinyl, quinazolinyl, isoquinazolinyl, thienyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, benzodioxolyl, cyclopropyl, cyclobutyl, cyclopentyl, cyclohexyl and cycloheptyl, wherein the ring system is optionally substituted independently with 1-3 substituents of $R^7$, $R^8$, $R^9$, oxo, $OR^7$, $SR^7$, $C(O)R^7$, $NR^7R^7$, $NR^7R^8$, $OR^8$, $SR^8$, $C(O)R^8$, $COOR^7$, $OC(O)R^7$, $COOR^8$, $OC(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2NR^7R^7$, $S(O)_2NR^7R^8$, $NR^7S(O_2)NR^7R^7$ or $NR^7S(O)_2NR^7R^8$;

$R^2$ is H;

$R^3$ is

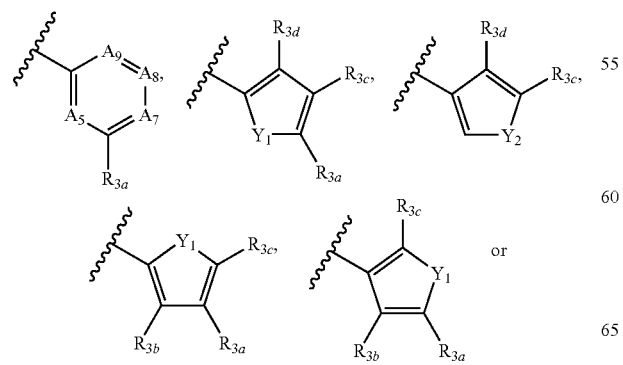

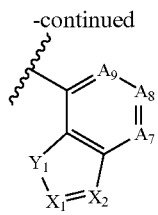

wherein each of $A^5$ and $A^9$ is, independently, $CR^{3b}$;

each of $A^7$ and $A^8$ is, independently, $CR^{3b}$ or N, provided no more than one of $A^7$ and $A^8$ is N;

$X^2$ is $CR^{3a}$;

$X^1$ is N; and $Y^1$ is $CR^{3b}R^{3c}$, $NR^{3c}$, O or S;

$R^{3a}$ is $NR^{10}R^{10}$, $NR^{10}R^{11}$, $C(O)NR^{10}R^{10}$, $C(O)NR^{10}R^{11}$, $NR^{10}C(O)R^{10}$, $NR^{10}C(O)R^{11}$, $NR^{10}C(O)NR^{10}R^{10}$, $NR^{10}C(O)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

$R^{3b}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl; and $R^{3c}$ is H, CN or $C_{1-10}$-alkyl; and $R^{3d}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl;

$R^4$ is H;

$R^7$ is H, $C_{1-10}$-alkyl, $C_{2-10}$-alkenyl or $C_{3-6}$-cycloalkyl, each of the $C_{1-10}$-alkyl, $C_{2-10}$-alkenyl and $C_{3-6}$-cycloalkyl optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a ring selected from phenyl, naphthyl, pyridyl, pyrimidyl, quinolinyl, isoquinolinyl, quinazolinyl, thienyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^9$, oxo, $NR^9R^9$, $OR^9$; $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl or $C_{3-10}$-cycloalkyl, each of the $C_{1-10}$-alkyl, $C_{2-10}$-alkenyl, and $C_{3-10}$-cycloalkyl optionally substituted with 1-3 substituents of $R^{16}$; and $R^{11}$ is a ring selected from phenyl, naphthyl, pyridyl, pyrimidyl, triazinyl, quinolinyl, isoquinolinyl, quinazolinyl, isoquinazolinyl, thienyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl and cycloheptyl, each of which is optionally substituted independently with 1-3 substituents of $R^{16}$.

6. A compound of formula II

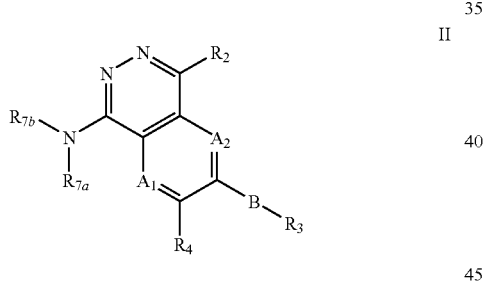

II or a stereoisomer or pharmaceutically acceptable salt thereof, wherein each of $A^1$ and $A^2$, independently, is CH;

B is a direct bond;

$R^2$ is H, halo, haloalkyl, CN or $C_{1-4}$-alkyl;

$R^3$ is a ring selected from phenyl, 3-pyridyl, pyrimidyl, pyridazinyl, thienyl, furyl, pyrolyl, imidazolyl, thiazolyl, oxazolyl, isoxazolyl, benzisoxazolyl and benisothizolyl, said ring substituted independently with one substituent of $NR^{10}R^{10}$, $NR^{10}R^{11}$, $C(O)NR^{10}$ $R^{10}$, $NR^{10}C(O)R^{11}$, $S(O)_2NR^{10}R^{10}$, $S(O)_2NR^{10}R^{11}$, $NR^{10}S(O)_2R^{10}$ or $NR^{10}S(O)_2R^{11}$ and 0-3 substituents of $R^{16}$;

$R^4$ is H;

$R^{7a}$ is H, $C_{1-10}$-alkyl, $C_{2-10}$-alkenyl, $C_{2-10}$-alkynyl, $C_{3-10}$-cycloalkyl, $C_{4-10}$-cycloalkenyl or partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, each of the $C_{1-10}$-alkyl, $C_{2-10}$-alkenyl, $C_{2-10}$-alkynyl, $C_{3-10}$-cycloalkyl, $C_{4-10}$-cycloalkenyl and partially or fully saturated 5-6 membered heterocyclic optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^{7b}$ is H or $C_{1-10}$-alkyl;

alternatively, $R^{7a}$ and $R^{7b}$ taken together with the nitrogen to which they are attached form a saturated or partially or fully unsaturated 5-6 membered monocyclic or 7-10 membered bicyclic heterocyclic ring optionally including 1-3 additional heteroatoms selected from O, N, or S, and optionally substituted independently with 1-5 substituents of $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

$R^9$ is H, halo, haloalkyl, CN, OH, $NO_2$, $NH_2$, oxo, acetyl, $C_{1-10}$-alkyl, $C_{2-10}$-alkenyl, $C_{2-10}$-alkenyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally substituted with 1-5 substituents of $R^{16}$;

$R^{11}$ is a ring selected from phenyl, naphthyl, pyridyl, pyrimidyl, triazinyl, quinolinyl, isoquinolinyl, quinazolinyl, isoquinazolinyl, thienyl, furyl, pyrrolyl, imidazolyl, triazolyl, thiazolyl, oxazolyl, isoxazolyl, isothiazolyl, indolyl, isoindolyl, benzofuranyl, benzothiolphenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl and cycloheptyl, said ring optionally substituted independently with 1-3 substituents of $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl, provided that when B is a direct bond, $R^3$ is an optionally substituted phenyl or an optionally substituted 5- or 6-membered heteroaryl, and $R^{7b}$ is H or $C_{1-10}$-alkyl, then $R^{7a}$ is not an optionally substituted phenyl or an optionally substituted 5- or 6-membered heteroaryl.

7. The compound of claim 1, or a pharmaceutically acceptable salt thereof, selected from:

N-cyclopropyl-4-methyl-3-{1-[(2R)-2-methylpiperazin-1-yl]phthalazin-6-yl}benzamide;
N-cyclopropyl-4-methyl-3-{1-[(2-morpholin-4-ylethyl)amino]phthalazin-6-yl}benzamide;
N-cyclopropyl-3-{1-[(2R,5S)-2,5-dimethylmorpholin-4-yl]phthalazin-6-yl}-4-methylbenzamide;
N-cyclopropyl-4-{1-[(2R,5R)-2,5-dimethylmorpholin-4-yl]phthalazin-6-yl}-5-methylpyridine-2-carboxamide;
1-(6-{5-[(cyclopropylamino)carbonyl]-2-methylphenyl}phthalazin-1-yl)piperidine-4-carboxamide;
4-methyl-3-{1-[(1S,4S)-2-oxa-5-azabicyclo[2.2.1]hept-5-yl]phthalazin-6-yl}benzamide;
4-methyl-3-[1-(3-oxopiperazin-1-yl)phthalazin-6-yl]benzamide;
N-ethyl-3-[1-(isopropylamino)phthalazin-6-yl]-4-methylbenzamide;
3-(1-methoxyphthalazin-6-yl)-4-methylbenzamide;
3-{1-[(2S,5S)-2,5-dimethylmorpholin-4-yl]phthalazin-6-yl}-4-methylbenzamide;
N-cyclopropyl-4-methyl-3-{1-[(1S,4S)-2-oxa-5-azabicyclo[2.2.1]hept-5-yl]phthalazin-6-yl}benzamide;
N-cyclopropyl-3-(1-mesitylphthalazin-6-yl)-4-methylbenzamide;
3-{1-[(2S,5R)-2,5-dimethylpiperazin-1-yl]phthalazin-6-yl}-4-methylbenzamide;
N-cyclopropyl-3-{1-[(2S,5S)-2,5-dimethylmorpholin-4-yl]phthalazin-6-yl}-4-methylbenzamide;
4-(6-{5-[(cyclopropylamino)carbonyl]-2-methylphenyl}phthalazin-1-yl)-N-phenylpiperazine-1-carboxamide;
N-cyclopropyl-3-{1-[(1S,4S)-2,5-diazabicyclo[2.2.1]hept-2-yl]phthalazin-6-yl}-4-methylbenzamide;
tert-butyl (1S,4S)-5-(6-{5-[(cyclopropylamino)carbonyl]-2-methylphenyl}phthalazin-1-yl)-2,5-diazabicyclo[2.2.1]heptane-2-carboxylate;
3-[1-(1,1-dioxidothiomorpholin-4-yl)phthalazin-6-yl]-4-methylbenzamide;
4-methyl-3-(1-thiomorpholin-4-ylphthalazin-6-yl)benzamide;
4-(6-{5-[(cyclopropylamino)carbonyl]-2-methylphenyl}phthalazin-1-yl)-N-ethylpiperazine-1-carboxamide;
N-cyclopropyl-3-{1-[(2R)-2-ethylpiperidin-1-yl]phthalazin-6-yl}-4-methylbenzamide;
N-cyclopropyl-4-methyl-3-[1-(4-methylphenyl)phthalazin-6-yl]benzamide;
(3R)-1-(6-{5-[(cyclopropylamino)carbonyl]-2-methylphenyl}phthalazin-1-yl)piperidine-3-carboxamide;
N-cyclopropyl-3-[1-(1,1-dioxidothiomorpholin-4-yl)phthalazin-6-yl]-4-methylbenzamide;
N-cyclopropyl-4-methyl-3-(1-thiomorpholin-4-ylphthalazin-6-yl)benzamide;
N-cyclopropyl-5-{1-[(2R,5R)-2,5-dimethylmorpholin-4-yl]phthalazin-6-yl}-2-fluoro-4-methylbenzamide;
3-{1-[(4aR,8aR)-octahydroisoquinolin-2(1H)-yl]phthalazin-6-yl}-N-cyclopropyl-4-methylbenzamide;
6-(2-methyl-5-nitrophenyl)-1-morpholin-4-ylphthalazine;
ethyl 3-[1-(isopropylamino)phthalazin-6-yl]-4-methylbenzoate;
4-(6-{5-[(cyclopropylamino)carbonyl]-2-methylphenyl}phthalazin-1-yl)-N-(4-fluorobenzyl)piperazine-1-carboxamide;
N-cyclopropyl-4-methyl-3-{1-[(3R)-3-methylpiperazin-1-yl]phthalazin-6-yl}benzamide;
3-(1-aminophthalazin-6-yl)-N-cyclopropyl-4-methylbenzamide;
N-cyclopropyl-3-{1-[(2R,6S)-2,6-dimethylmorpholin-4-yl]phthalazin-6-yl}-4-methylbenzamide;
4-methyl-3-{1-[(2R)-2-methylpiperazin-1-yl]phthalazin-6-yl}benzamide;
N-cyclopropyl-3-{1-[(1S,4S)-5-isopropyl-2,5-diazabicyclo[2.2.1]hept-2-yl]phthalazin-6-yl}-4-methylbenzamide;
4-methyl-3-{1-[(2S)-2-methylpiperazin-1-yl]phthalazin-6-yl}benzamide;
N-cyclopropyl-3-{1-[(2S,5R)-2,5-dimethylpiperazin-1-yl]phthalazin-6-yl}-4-methylbenzamide;
N-cyclopropyl-3-{1-[(3R,5S)-3,5-dimethylpiperazin-1-yl]phthalazin-6-yl}-4-methylbenzamide;
N-cyclopropyl-4-methyl-3-{1-[(3S)-3-methylpiperazin-1-yl]phthalazin-6-yl}benzamide;
N-cyclopropyl-4-methyl-3-[1-(1-methylpiperidin-4-yl)phthalazin-6-yl]benzamide;
N-cyclopropyl-3-{1-[(2S)-2-(hydroxymethyl)pyrrolidin-1-yl]phthalazin-6-yl}-4-methylbenzamide;
N-cyclopropyl-3-[1-(4-hydroxy-4-methylpiperidin-1-yl)phthalazin-6-yl]-4-methylbenzamide;
tert-butyl 4-(6-{5-[(cyclopropylamino)carbonyl]-2-methylphenyl}phthalazin-1-yl)-3,6-dihydropyridine-1(2H)-carboxylate;
3-{1-[(4aS,8aS)-octahydroquinolin-1(2H)-yl]phthalazin-6-yl}-N-cyclopopyl-4-methylbenzamide;
3-(1-isopropoxyphthalazin-6-yl)-4-methylbenzamide;
3-[1-(2-chlorophenyl)phthalazin-6-yl]-4-methylbenzamide;
3-[1-(4-acetylpiperazin-1-yl)phthalazin-6-yl]-N-cyclopropyl-4-methylbenzamide;
3-[1-(cyclohexylamino)phthalazin-6-yl]-N-cyclopropyl-4-methylbenzamide;

N-cyclopropyl-4-methyl-3-(1-piperidin-1-ylphthalazin-6-yl)benzamide;
N-cyclopropyl-3-{1-[(2R)-2-(hydroxymethyl)morpholin-4-yl]phthalazin-6-yl}-4-methylbenzamide;
N-cyclopropyl-3-{1-[4-(2,6-dimethylphenyl)piperazin-1-yl]phthalazin-6-yl}-4-methylbenzamide;
N-cyclopropyl-4-methyl-3-[1-(3-oxopiperazin-1-yl)phthalazin-6-yl]benzamide;
3-(1-chlorophthalazin-6-yl)-N-cyclopropyl-4-methylbenzamide;
N-cyclopropyl-4-methyl-3-(1-piperazin-1-ylphthalazin-6-yl)benzamide;
N-cyclopropyl-3-{1-[(3R)-3-hydroxypyrrolidin-1-yl]phthalazin-6-yl}-4-methylbenzamide;
N-cyclopropyl-3-[1-(1,4-dioxa-8-azaspiro[4.5]dec-8-yl)phthalazin-6-yl]-4-methylbenzamide;
N-cyclopropyl-3-(1-isopropoxyphthalazin-6-yl)-4-methylbenzamide;
N-cyclopropyl-3-(1-methoxyphthalazin-6-yl)-4-methylbenzamide;
3-[1-(2-chlorophenyl)phthalazin-6-yl]-N-cyclopropyl-4-methylbenzamide;
3-{1-[(2R,5R)-2,5-dimethylmorpholin-4-yl]phthalazin-6-yl}-4-methylbenzamide;
N-cyclopropyl-3-[1-(isopropylamino)phthalazin-6-yl]-4-methylbenzamide;
N-cyclopropyl-3-{1-[(2S,5R)-2,5-dimethylmorpholin-4-yl]phthalazin-6-yl}-4-methylbenzamide;
N-cyclopropyl-3-{1-[(2R,5R)-2,5-dimethylmorpholin-4-yl]phthalazin-6-yl}-4-methylbenzamide;
4-methyl-3-(1-morpholin-4-ylphthalazin-6-yl)benzamide;
4-methyl-3-[1-(2-methylphenyl)phthalazin-6-yl]benzamide;
4-fluoro-3-(1-morpholin-4-ylphthalazin-6-yl)benzamide;
N-cyclopropyl-4-methyl-3-{1-[(3S)-3-methylmorpholin-4-yl]phthalazin-6-yl}benzamide;
3-[1-(isopropylamino)phthalazin-6-yl]-4-methylbenzamide;
N-cyclopropyl-4-methyl-3-{1-[(2R)-2-methylpiperidin-1-yl]phthalazin-6-yl}benzamide;
N,4-dimethyl-3-(1-morpholin-4-ylphthalazin-6-yl)benzamide;
4-methyl-3-{1-[(2R)-2-methylpiperidin-1-yl]phthalazin-6-yl}benzamide;
N-cyclopropyl-3-(1-{[2-(dimethylamino)ethyl]amino}phthalazin-6-yl)-4-methylbenzamide;
4-methyl-3-{1-[(3S)-3-methylmorpholin-4-yl]phthalazin-6-yl}benzamide;
3-(1-{[(1R)-2-hydroxy-1-methylethyl]amino}phthalazin-6-yl)-4-methylbenzamide;
N-cyclopropyl-3-(1-{[2-(diethylamino)ethyl]amino}phthalazin-6-yl)-4-methylbenzamide;
N-cyclopropyl-3-[1-(dimethylamino)phthalazin-6-yl]-4-methylbenzamide;
N-cyclopropyl-3-{1-[(2-methoxyethyl)(methyl)amino]phthalazin-6-yl}-4-methylbenzamide;
3-{1-[(2-methoxyethyl)amino]phthalazin-6-yl}-4-methylbenzamide;
3-(1-{[(1S)-2-methoxy-1-methylethyl]amino}phthalazin-6-yl)-4-methylbenzamide;
tert-butyl N-(6-{5-[(cyclopropylamino)carbonyl]-2-methylphenyl}phthalazin-1-yl)-L-alaninate;
N-cyclopropyl-3-(1-{[(1S)-2-methoxy-1-methylethyl]amino}phthalazin-6-yl)-4-methylbenzamide;
N-cyclopropyl-4-methyl-3-(1-{[(1R)-1-phenylethyl]amino}phthalazin-6-yl)benzamide;
N-cyclopropyl-3-{1-[(2-methoxyethyl)amino]phthalazin-6-yl}-4-methylbenzamide;
6-[2-methyl-5-(methylsulfonyl)phenyl]-1-morpholin-4-ylphthalazine;
3-[1-(4-methoxypyrimidin-5-yl)phthalazin-6-yl]-4-methylbenzamide;
N-cyclopropyl-3-{1-[2-(dimethylamino)-4-methoxypyrimidin-5-yl]phthalazin-6-yl}-4-methylbenzamide;
3-[1-(2,3-dimethoxyphenyl)phthalazin-6-yl]-4-methylbenzamide;
3-{1-[2-chloro-4-(trifluoromethyl)phenyl]phthalazin-6-yl}-4-methylbenzamide;
3-{1-[2,4-bis(trifluoromethyl)phenyl]phthalazin-6-yl}-N-cyclopropyl-4-methylbenzamide;
N-cyclopropyl-3-[1-(2-methoxy-3-methylphenyl)phthalazin-6-yl]-4-methylbenzamide;
3-[1-(4-methoxy-2-methylphenyl)phthalazin-6-yl]-4-methylbenzamide;
4-methyl-3-{1-[4-(morpholin-4-ylmethyl)phenyl]phthalazin-6-yl}benzamide;
3-[1-(2-methoxy-3-methylphenyl)phthalazin-6-yl]-4-methylbenzamide;
2-[4-(6-{5-[(cyclopropylamino)carbonyl]-2-methylphenyl}phthalazin-1-yl)phenyl]-2-methylpropanoic acid;
N-cyclopropyl-3-{1-[2-methoxy-6-(methylamino)pyridin-3-yl]phthalazin-6-yl}-4-methylbenzamide;
N-cyclopropyl-3-[1-(6-methoxy-2-methylpyridin-3-yl)phthalazin-6-yl]-4-methylbenzamide;
3-[1-(4'-chloro-1,1'-biphenyl-4-yl)phthalazin-6-yl]-N-cyclopropyl-4-methylbenzamide;
3-[1-(4-chlorophenyl)phthalazin-6-yl]-N-cyclopropyl-4-methylbenzamide;
3-{1-[4-chloro-2-(trifluoromethyl)phenyl]phthalazin-6-yl}-N-cyclopropyl-4-methylbenzamide;
3-[1-(2-chloro-6-methylpyridin-3-yl)phthalazin-6-yl]-4-methylbenzamide;
3-[1-(2-chloro-6-methylpyridin-3-yl)phthalazin-6-yl]-N-cyclopropyl-4-methylbenzamide;
3-[1-(4-fluoro-2-methoxyphenyl)phthalazin-6-yl]-4-methylbenzamide;
4-methyl-3-{1-[4-(methylsulfonyl)phenyl]phthalazin-6-yl}benzamide;
4-methyl-3-(1-pyrimidin-5-ylphthalazin-6-yl)benzamide;
3-[1-(1H-indol-2-yl)phthalazin-6-yl]-4-methylbenzamide;
3-[1-(4-fluoro-2-methylphenyl)phthalazin-6-yl]-4-methylbenzamide;
3-{1-[4-(aminosulfonyl)-2-methylphenyl]phthalazin-6-yl}-N-cyclopropyl-4-methylbenzamide;
3-{1-[2-chloro-4-(trifluoromethyl)phenyl]phthalazin-6-yl}-N-cyclopropyl-4-methylbenzamide;
4-methyl-3-{1-[2-(trifluoromethyl)phenyl]phthalazin-6-yl}benzamide;
3-[1-(2-chloro-4-methylphenyl)phthalazin-6-yl]-4-methylbenzamide;
3-[1-(2-chloro-4-fluorophenyl)phthalazin-6-yl]-4-methylbenzamide;
3-[1-(2,4-dichlorophenyl)phthalazin-6-yl]-4-methylbenzamide;
3-[1-(4-chloro-2-methoxyphenyl)phthalazin-6-yl]-N-cyclopropyl-4-methylbenzamide;
3-[1-(2,4-dimethoxypyrimidin-5-yl)phthalazin-6-yl]-4-methylbenzamide;
3-[1-(2,4-dimethoxyphenyl)phthalazin-6-yl]-4-methylbenzamide;

3-[1-(4-isopropoxy-2-methylphenyl)phthalazin-6-yl]-4-methylbenzamide;
3-[1-(2-methoxypyridin-3-yl)phthalazin-6-yl]-4-methylbenzamide;
3-[1-(2-chloro-4-methoxyphenyl)phthalazin-6-yl]-4-methylbenzamide;
N-cyclopropyl-3-[1-(2-methoxypyridin-3-yl)phthalazin-6-yl]-4-methylbenzamide;
3-[1-(2-chloro-4-ethoxyphenyl)phthalazin-6-yl]-4-methylbenzamide;
3-[1-(4-chloro-2-methylphenyl)phthalazin-6-yl]-4-methylbenzamide;
3-[1-(2-chloropyridin-3-yl)phthalazin-6-yl]-N-cyclopropyl-4-methylbenzamide;
N-cyclopropyl-3-[1-(2,4-dimethoxypyrimidin-5-yl)phthalazin-6-yl]-4-methylbenzamide;
3-[1-(2-chloro-4-methylphenyl)phthalazin-6-yl]-N-cyclopropyl-4-methylbenzamide;
3-{1-[4-(aminosulfonyl)-2-methylphenyl]phthalazin-6-yl}-4-methylbenzamide;
3-{1-[4-methoxy-2-(trifluoromethyl)phenyl]phthalazin-6-yl}-4-methylbenzamide;
3-[1-(4-chloro-2-ethoxyphenyl)phthalazin-6-yl]-4-methylbenzamide;
N-cyclopropyl-3-[1-(4-fluorophenyl)phthalazin-6-yl]-4-methylbenzamide;
[4-(6-{5-[(cyclopropylamino)carbonyl]-2-methylphenyl}phthalazin-1-yl)phenyl]acetic acid;
N-cyclopropyl-4-methyl-3-[1-(2-methylpyridin-3-yl)phthalazin-6-yl]benzamide;
N-cyclopropyl-3-[1-(4-methoxy-2-methylphenyl)phthalazin-6-yl]-4-methylbenzamide;
4-methyl-3-{1-[2-methyl-4-(methylsulfinyl)phenyl]phthalazin-6-yl}benzamide;
N-cyclopropyl-4-methyl-3-(1-thien-2-ylphthalazin-6-yl)benzamide;
N-cyclopropyl-4-methyl-3-{1-[4-(trifluoromethoxy)phenyl]phthalazin-6-yl}benzamide;
N-cyclopropyl-3-[1-(2-fluorophenyl)phthalazin-6-yl]-4-methylbenzamide;
N,6-dimethyl-7-[1-(2-methylpyridin-3-yl)phthalazin-6-yl]-1,2-benzisoxazol-3-amine;
N-cyclopropyl-3-[1-(3-fluoro-2-methoxyphenyl)phthalazin-6-yl]-4-methylbenzamide;
N-cyclopropyl-4-methyl-3-{1-[4-(trifluoromethyl)phenyl]phthalazin-6-yl}benzamide;
N-cyclopropyl-4-methyl-3-(1-phenylphthalazin-6-yl)benzamide;
N-cyclopropyl-3-[1-(2-ethylphenyl)phthalazin-6-yl]-4-methylbenzamide;
3-[1-(2-methoxy-5-methylpyridin-4-yl)phthalazin-6-yl]-4-methylbenzamide;
3-[1-(4-tert-butylphenyl)phthalazin-6-yl]-N-cyclopropyl-4-methylbenzamide;
N-cyclopropyl-4-methyl-3-{1-[2-(trifluoromethyl)phenyl]phthalazin-6-yl}benzamide;
4-methyl-3-[1-(2-methylpyridin-3-yl)phthalazin-6-yl]benzamide;
N-cyclopropyl-4-methyl-3-{1-[2-methyl-4-(methylsulfonyl)phenyl]phthalazin-6-yl}benzamide;
3-[1-(4-chloro-2-methylphenyl)phthalazin-6-yl]-N-cyclopropyl-4-methylbenzamide;
N-cyclopropyl-3-{1-[4-methoxy-2-(trifluoromethyl)phenyl]phthalazin-6-yl}-4-methylbenzamide;
3-[1-(2-fluoro-5-methylpyridin-4-yl)phthalazin-6-yl]-4-methylbenzamide;
4-methyl-3-{1-[2-methyl-4-(methylsulfanyl)phenyl]phthalazin-6-yl}benzamide;
N-cyclopropyl-4-methyl-3-{1-[2-methyl-4-(methylsulfanyl)phenyl]phthalazin-6-yl}benzamide;
N-cyclopropyl-3-[1-(4-fluoro-2-methoxyphenyl)phthalazin-6-yl]-4-methylbenzamide;
N-cyclopropyl-4-methyl-3-[1-(3-methylpyridin-4-yl)phthalazin-6-yl]benzamide;
N-cyclopropyl-3-[1-(2-methoxypyrimidin-5-yl)phthalazin-6-yl]-4-methylbenzamide;
N,N,4-trimethyl-3-(1-morpholin-4-ylphthalazin-6-yl)benzamide;
N-cyclopropyl-4-methyl-3-[1-(1,4-oxazepan-4-yl)phthalazin-6-yl]benzamide;
3-{1-[(8aR)-6-oxohexahydropyrrolo[1,2-a]pyrazin-2(1H)-yl]phthalazin-6-yl}-N-cyclopropyl-4-methylbenzamide;
N-cyclopropyl-4-methyl-3-{1-[(2R)-2-methyl-3-oxopiperazin-1-yl]phthalazin-6-yl}benzamide;
3-{1-[(8aS)-3-oxotetrahydro[1,3]oxazolo[3,4-a]pyrazin-7(1H)-yl]phthalazin-6-yl}-N-cyclobutyl-4-methylbenzamide;
4-methyl-3-[1-(1,4-oxazepan-4-yl)phthalazin-6-yl]benzamide;
N-cyclopropyl-4-methyl-3-{1-[(2S)-2-methyl-3-oxopiperazin-1-yl]phthalazin-6-yl}benzamide;
3-{1-[(8aS)-6-oxohexahydropyrrolo[1,2-a]pyrazin-2(1H)-yl]phthalazin-6-yl}-N-cyclopropyl-4-methylbenzamide;
N-cyclopropyl-4-methyl-3-{1-[(2S)-2-(trifluoromethyl)pyrrolidin-1-yl]phthalazin-6-yl}benzamide;
3-{1-[(8aS)-hexahydropyrrolo[1,2-a]pyrazin-2(1H)-yl]phthalazin-6-yl}-N-cyclopropyl-4-methylbenzamide;
N-cyclopropyl-4-methyl-3-[1-(5-oxo-1,4-diazepan-1-yl)phthalazin-6-yl]benzamide;
N-cyclopropyl-4-methyl-3-(8-morpholin-4-ylpyrido[2,3-d]pyridazin-3-yl)benzamide;
4-methyl-3-[1-(5-oxo-1,4-diazepan-1-yl)phthalazin-6-yl]benzamide;
N-methoxy-4-methyl-3-(1-morpholin-4-ylphthalazin-6-yl)benzamide;
3-[1-(isopropylamino)phthalazin-6-yl]-N-methoxy-4-methylbenzamide;
3-{1-[(8aS)-3-oxotetrahydro[1,3]oxazolo[3,4-a]pyrazin-7(1H)-yl]phthalazin-6-yl}-4-methylbenzamide;
3-[1-(dimethylamino)phthalazin-6-yl]-4-methylbenzamide;
3-{1-[(8aS)-hexahydropyrrolo[1,2-a]pyrazin-2(1H)-yl]phthalazin-6-yl}-4-methylbenzamide;
N-cyclobutyl-3-[1-(dimethylamino)phthalazin-6-yl]-4-methylbenzamide;
3-{1-[(8aR)-3-oxotetrahydro[1,3]oxazolo[3,4-a]pyrazin-7(1H)-yl]phthalazin-6-yl}-4-methylbenzamide;
3-{1-[(8aS)-6-oxohexahydropyrrolo[1,2-a]pyrazin-2(1H)-yl]phthalazin-6-yl}-4-methylbenzamide;
N-cyclopropyl-3-[1-(4-fluoro-2-methylphenyl)phthalazin-6-yl]-4-methylbenzamide;
N-cyclopropyl-4-methyl-3-[1-(4-methyl-6-oxo-1,6-dihydropyridin-3-yl)phthalazin-6-yl]benzamide;
N-cyclopropyl-3-(1-hydroxyphthalazin-6-yl)-4-methylbenzamide;
3-{1-[cyclohexyl(methyl)amino]phthalazin-6-yl}-N-cyclopropyl-4-methylbenzamide;
N-cyclopropyl-3-{1-[isopropyl(methyl)amino]phthalazin-6-yl}-4-methylbenzamide;
3-{1-[cyclohexyl(methyl)amino]phthalazin-6-yl}-4-methylbenzamide;

3-{1-[isopropyl(methyl)amino]phthalazin-6-yl}-4-methylbenzamide;
N-cyclopropyl-3-{1-[(2S)-2-isopropylpyrrolidin-1-yl]phthalazin-6-yl}-4-methylbenzamide;
4-methyl-3-{1-[3-(trifluoromethyl)-5,6-dihydro[1,2,4]triazolo[4,3-a]pyrazin-7(8H)-yl]phthalazin-6-yl}benzamide;
N-cyclopropyl-4-methyl-3-{1-[(2S)-2-methylpyrrolidin-1-yl]phthalazin-6-yl}benzamide;
N-cyclopropyl-4-methyl-3-{1-[(2R)-2-methylpyrrolidin-1-yl]phthalazin-6-yl}benzamide;
N-cyclopropyl-4-methyl-3-(1-{[(2R)-tetrahydrofuran-2-ylmethyl]amino}phthalazin-6-yl)benzamide;
N-cyclopropyl-4-methyl-3-(1-{[(1S)-1-methylpropyl]amino}phthalazin-6-yl)benzamide;
4-methyl-3-[1-(2-methylphenoxy)phthalazin-6-yl]benzamide;
4-methyl-3-{1-[(2-methylpyridin-3-yl)oxy]phthalazin-6-yl}benzamide;
3-[1-(4-fluorophenoxy)phthalazin-6-yl]-4-methylbenzamide;
N-cyclopropyl-4-methyl-3-(1-{[(1S)-1-methylpropyl]oxy}phthalazin-6-yl)benzamide;
4-methyl-3-(1-{[(1S)-1-methylpropyl]amino}phthalazin-6-yl)benzamide;
3-[1-(2,4-difluorophenoxy)phthalazin-6-yl]-4-methylbenzamide;
N-cyclopropyl-3-[1-(4-fluoro-2-methylphenoxy)phthalazin-6-yl]-4-methylbenzamide;
3-[1-(2-methoxyphenoxy)phthalazin-6-yl]-4-methylbenzamide;
3-[1-(3-chlorophenoxy)phthalazin-6-yl]-4-methylbenzamide;
N-cyclopropyl-4-methyl-3-{1-[(2-methylpyridin-3-yl)oxy]phthalazin-6-yl}benzamide;
N-cyclopropyl-4-methyl-3-(1-{[(2S)-tetrahydrofuran-2-ylmethyl]amino}phthalazin-6-yl)benzamide;
N-cyclopropyl-4-methyl-3-(1-{[3-(2-oxopyrrolidin-1-yl)propyl]amino}phthalazin-6-yl)benzamide;
3-[1-(cyclohexyloxy)phthalazin-6-yl]-4-methylbenzamide;
N-cyclopropyl-3-{1-[(4-hydroxycyclohexyl)amino]phthalazin-6-yl}-4-methylbenzamide;
N-cyclopropyl-3-(1-{[(1S)-2-methoxy-1-methylethyl]amino}phthalazin-6-yl)-4-methylbenzamide;
N-cyclopropyl-4-methyl-3-(1-{[(1R)-1-methylpropyl]amino}phthalazin-6-yl)benzamide;
4-methyl-3-[1-(neopentyloxy)phthalazin-6-yl]benzamide;
4-methyl-3-{1-[(1-methylpiperidin-3-yl)oxy]phthalazin-6-yl}benzamide;
N-cyclopropyl-4-methyl-3-{1-[(1-methylpiperidin-3-yl)oxy]phthalazin-6-yl}benzamide;
N-cyclopropyl-6-methyl-7-[1-(2-methylphenoxy)phthalazin-6-yl]-1,2-benzisoxazol-3-amine;
N-cyclopropyl-4-methyl-3-{1-[(1-methylpiperidin-4-yl)oxy]phthalazin-6-yl}benzamide;
3-[1-(4-fluoro-2-methylphenoxy)phthalazin-6-yl]-4-methylbenzamide;
3-[1-(2,4-dimethylphenoxy)phthalazin-6-yl]-4-methylbenzamide;
4-methyl-3-(1-{[(1S)-1-methylpropyl]oxy}phthalazin-6-yl)benzamide;
3-[1-(cyclopentylamino)phthalazin-6-yl]-4-methylbenzamide;
4-methyl-3-(1-{[(1R)-1-methylpropyl]oxy}phthalazin-6-yl)benzamide;
3-[1-(cyclopentylamino)phthalazin-6-yl]-N-cyclopropyl-4-methylbenzamide;
N-cyclopropyl-4-methyl-3-[1-(neopentyloxy)phthalazin-6-yl]benzamide;
3-[1-(tert-butylamino)phthalazin-6-yl]-N-cyclopropyl-4-methylbenzamide;
N-cyclopropyl-4-methyl-3-(1-{[(1R)-1-methylpropyl]oxy}phthalazin-6-yl)benzamide;
N-cyclopropyl-4-methyl-3-[1-(tetrahydro-2H-pyran-4-ylamino)phthalazin-6-yl]benzamide;
N,6-dimethyl-7-(1-(((1S)-1-methyl-2-(methyloxy)ethyl)oxy)-6-phthalazinyl)-1,2-benzisoxazol-3-amine;
N,6-dimethyl-7-(1-((1-methylethyl)oxy)-6-phthalazinyl)-1,2-benzisoxazol-3-amine;
6-(4-methylphenoxy)-1-(2-methylphenyl)phthalazine;
6-(4-fluorophenoxy)-1-[4-(morpholin-4-ylmethyl)phenyl]phthalazine;
1-(2-methoxyphenyl)-6-(4-methylphenoxy)phthalazine;
6-(4-fluorophenoxy)-1-[4-(methylsulfonyl)phenyl]phthalazine;
6-(4-fluorophenoxy)-1-morpholin-4-ylphthalazine;
6-(4-fluorophenoxy)-1-thien-3-ylphthalazine;
6-(3-chlorophenoxy)-1-(2-methylphenyl)phthalazine;
6-(4-fluorophenoxy)-1-[2-(trifluoromethyl)phenyl]phthalazine;
6-(4-fluorophenoxy)-1-(2-methylphenyl)phthalazine;
1-(4-fluoro-2-methylphenyl)-6-(4-fluorophenoxy)phthalazine;
methyl 2-{[1-(2-methylphenyl)phthalazin-6-yl]oxy}benzoate;
N-cyclopropyl-2-{[1-(2-methylphenyl)phthalazin-6-yl]oxy}benzamide;
6-(4-fluorophenoxy)-1-(1H-pyrazol-4-yl)phthalazine;
6-(2,4-difluorophenoxy)-1-(2-methylphenyl)phthalazine;
1-(2-chlorophenyl)-6-(4-methylphenoxy)phthalazine;
1-(4-fluoro-2-methylphenyl)-6-phenoxyphthalazine;
6-(4-fluorophenoxy)-1-(2-methoxypyridin-3-yl)phthalazine;
(1S,4S)-5-[6-(4-fluorophenoxy)phthalazin-1-yl]-2-oxa-5-azabicyclo[2.2.1]heptane;
6-(4-fluorophenoxy)-1-pyrimidin-5-ylphthalazine;
N-cyclopropyl-3-{[1-(2-methylphenyl)phthalazin-6-yl]oxy}benzamide;
6-(4-fluorophenoxy)-1-[4-(methylsulfonyl)piperazin-1-yl]phthalazine;
3-{[1-(2-methylphenyl)phthalazin-6-yl]oxy}benzoic acid;
6-(3-fluorophenoxy)-1-(2-methylphenyl)phthalazine;
6-(2,4-difluorophenoxy)-1-morpholin-4-ylphthalazine;
3-[1-(isopropylamino)phthalazin-6-yl]-4-methylbenzenesulfonamide;
3-[1-(isopropylamino)phthalazin-6-yl]-N,4-dimethylbenzenesulfonamide;
N-cyclopropyl-3-[1-(isopropylamino)phthalazin-6-yl]-4-methylbenzenesulfonamide;
N-cyclopropyl-4-methyl-3-(1-morpholin-4-ylphthalazin-6-yl)benzenesulfonamide;
N-ethyl-3-(1-isobutylphthalazin-6-yl)-4-methylbenzamide;
ethyl 3-(1-isopropylphthalazin-6-yl)-4-methylbenzoate;
N-ethyl-3-(1-isopropylphthalazin-6-yl)-4-methylbenzamide;
4-[6-(4-fluorophenoxy)phthalazin-1-yl]-3-methylbenzenesulfonamide;
6-[6-methyl-3-(methylamino)-1,2-benzisoxazol-7-yl]-N-[(1S)-1-methylpropyl]phthalazin-1-amine;

6-[6-methyl-3-(methylamino)-1,2-benzisoxazol-7-yl]-N-[(1R)-1-methylpropyl]phthalazin-1-amine;
6-methyl-7-{1-[(3S)-3-methylmorpholin-4-yl]phthalazin-6-yl}-1,2-benzisothiazol-3-amine;
3-{1-[(2R,5S)-2,5-dimethyl-4-(2,2,2-trifluoroethyl)piperazin-1-yl]phthalazin-6-yl}-4-methylbenzamide;
N-cyclopropyl-4-methyl-3-{1-[(1-pyridin-2-ylethyl)amino]phthalazin-6-yl}benzamide;
6-[3-(cyclopropylamino)-6-methyl-1,2-benzisoxazol-7-yl]-N-isopropylphthalazin-1-amine;
3-{1-[(2S)-4-acetyl-2-methylpiperazin-1-yl]phthalazin-6-yl}-N-cyclopropyl-4-methylbenzamide;
N-isopropyl-6-[6-methyl-3-(methylamino)-1,2-benzisoxazol-7-yl]phthalazin-1-amine;
N,6-dimethyl-7-{1-[(3R)-3-methylmorpholin-4-yl]phthalazin-6-yl}-1,2-benzisoxazol-3-amine;
N-cyclopropyl-6-methyl-7-[1-(2-methylphenyl)phthalazin-6-yl]-1,2-benzisoxazol-3-amine;
1,6-bis(2-methoxypyridin-3-yl)phthalazine;
N-cyclopropyl-3-{1-[(2R,5S)-2,5-dimethyl-4-(2,2,2-trifluoroethyl)piperazin-1-yl]phthalazin-6-yl}-4-methylbenzamide;
N-cyclopropyl-7-[1-(4-fluoro-2-methylphenyl)phthalazin-6-yl]-6-methyl-1,2-benzisoxazol-3-amine;
N-cyclopropyl-2-hydroxy-4-methyl-3-[1-(2-methylphenyl)phthalazin-6-yl]benzenecarboximidamide;
ethyl(3S)-4-(6-{5-[(cyclopropylamino)carbonyl]-2-methylphenyl}phthalazin-1-yl)-3-methylpiperazine-1-carboxylate;
4-methyl-N-(5-methylisoxazol-3-yl)-3-(1-morpholin-4-ylphthalazin-6-yl)benzamide;
N-(tert-butyl)-6-methyl-7-{1-[(3S)-3-methylmorpholin-4-yl]phthalazin-6-yl}-1,2-benzisoxazol-3-amine;
4-chloro-N-cyclopropyl-7-[1-(4-fluoro-2-methylphenyl)phthalazin-6-yl]-1,2-benzisoxazol-3-amine;
3-{1-[(2S)-4-acetyl-2-methylpiperazin-1-yl]phthalazin-6-yl}-4-methylbenzamide;
N-ethyl-6-methyl-7-{1-[(3S)-3-methylmorpholin-4-yl]phthalazin-6-yl}-1,2-benzisoxazol-3-amine;
6-(3-amino-6-methyl-1,2-benzisoxazol-7-yl-isopropylphthalazin-1-amine;
1,6-bis(2-methylphenyl)phthalazine;
6-methyl-7-{1-[(3S)-3-methylmorpholin-4-yl]phthalazin-6-yl}-1,2-benzisoxazol-3-amine;
N-cyclopropyl-6-methyl-7-(1-morpholin-4-ylphthalazin-6-yl)-1,2-benzisoxazol-3-amine;
6-[3-(ethylamino)-6-methyl-1,2-benzisoxazol-7-yl]-N-isopropylphthalazin-1-amine;
7-{1-[(2S)-4-acetyl-2-methylpiperazin-1-yl]phthalazin-6-yl}-N-cyclopropyl-6-methyl-1,2-benzisoxazol-3-amine;
6-methyl-7-{1-[(3S)-3-methylmorpholin-4-yl]phthalazin-6-yl}-1H-indazol-3-amine;
N-cyclopropyl-3-{1-[(2R,5S)-2,5-dimethyl-4-(2,2,2-trifluoroethyl)piperazin-1-yl]phthalazin-6-yl}-4-methylbenzamide;
N-cyclopropyl-3-{1-[(2S,5R)-2,5-dimethyl-4-(2,2,2-trifluoroethyl)piperazin-1-yl]phthalazin-6-yl}-4-methylbenzamide;
3-{1-[(2R,5R)-2,5-dimethylpyrrolidin-1-yl]phthalazin-6-yl}-4-methylbenzamide;
N-cyclopropyl-3-{1-[(2R,5R)-2,5-dimethylpyrrolidin-1-yl]phthalazin-6-yl}-4-methylbenzamide;
N,6-dimethyl-7-[1-(2-methylphenyl)phthalazin-6-yl]-1,2-benzisoxazol-3-amine;
N,6-dimethyl-7-(1-((S)-3-methylmorpholino)phthalazin-6-yl)benzo[d]isoxazol-3-amine;
1-[3-(4-fluorophenyl)morpholin-4-yl]-6-(2-methylphenyl)phthalazine;
N-[(1S)-2-methoxy-1-methylethyl]-6-[6-methyl-3-(methylamino)-1,2-benzisoxazol-7-yl]phthalazin-1-amine;
6-chloro-7-{1-[(3S)-3-methylmorpholin-4-yl]phthalazin-6-yl}-N-(2,2,2-trifluoroethyl)-1,2-benzisoxazol-3-amine;
6-chloro-N-cyclopropyl-7-{1-[(3S)-3-methylmorpholin-4-yl]phthalazin-6-yl}-1,2-benzisoxazol-3-amine;
6-chloro-N-isopropyl-7-{1-[(3S)-3-methylmorpholin-4-yl]phthalazin-6-yl}-1,2-benzisoxazol-3-amine;
N-(6-methyl-7-{1-[(3S)-3-methylmorpholin-4-yl]phthalazin-6-yl}-1,2-benzisoxazol-3-yl)acetamide;
N-isopropyl-3-[1-(isopropylamino)phthalazin-6-yl]-4-methylbenzamide;
N-isopropyl-4-methyl-3-(1-morpholin-4-ylphthalazin-6-yl)benzamide;
4-methyl-3-(1-phenoxyphthalazin-6-yl)benzamide;
3-{1-[(2-hydroxyethyl)amino]phthalazin-6-yl}-4-methylbenzamide;
N-cyclopropyl-4-methyl-3-(1-((2-(4-morpholinyl)ethyl)amino)-6-phthalazinyl)benzamide;
N-cyclopropyl-4-methyl-3-(1-(4-morpholinyl)-6-phthalazinyl)benzamide;
N-cyclopropyl-3-(1-((2-(diethylamino)ethyl)amino)-6-phthalazinyl)-4-methylbenzamide;
N-cyclopropyl-3-(1-((2-(dimethylamino)ethyl)amino)-6-phthalazinyl)-4-methylbenzamide;
3-(1-(cyclohexylamino)-6-phthalazinyl)-N-cyclopropyl-4-methylbenzamide;
N-cyclopropyl-4-methyl-3-(1-(1-piperazinyl)-6-phthalazinyl)benzamide;
N-cyclopropyl-3-(1-((S)-3-hydroxypyrrolidin-1-yl)phthalazin-6-yl)-4-methylbenzamide;
N-cyclopropyl-3-(1-((R)-3-hydroxypyrrolidin-1-yl)phthalazin-6-yl)-4-methylbenzamide;
N-cyclopropyl-4-methyl-3-(1-(4-methyl-1-piperazinyl)-6-phthalazinyl)benzamide;
N-cyclopropyl-4-methyl-3-(1-(piperidin-1-yl)phthalazin-6-yl)benzamide;
(1S,4S)-tert-butyl 5-(6-(5-(cyclopropylcarbamoyl)-2-methylphenyl)phthalazin-1-yl)-2,5-diaza-bicyclo[2.2.1]heptane-2-carboxylate;
4-methyl-3-(1-morpholinophthalazin-6-yl)benzamide;
(2R,5R)-1-(6-(5-(cyclopropylcarbamoyl)-2-methylphenyl)phthalazin-1-yl)-N-isopropyl-5-methylpyrrolidine-2-carboxamide;
(2R,5S)-1-(6-(5-(cyclopropylcarbamoyl)-2-methylphenyl)phthalazin-1-yl)-N-isopropyl-5-methylpyrrolidine-2-carboxamide;
3-(1-((1S,4S)-2,5-diaza-bicyclo[2.2.1]heptan-2-yl)phthalazin-6-yl)-N-cyclopropyl-4-methylbenzamide;
4-methyl-5-(1-(4-morpholinyl)-6-phthalazinyl)-2-thiophenecarboxylic acid;
ethyl 4-methyl-5-(1-(4-morpholinyl)-6-phthalazinyl)-2-thiophenecarboxylate;
N,4-dimethyl-3-(1-(4-morpholinyl)-6-phthalazinyl)benzamide;
N-ethyl-4-methyl-3-(1-(4-morpholinyl)-6-phthalazinyl)benzamide;
N-cyclopropyl-4-methyl-3-(1-(1-methyl-4-piperidinyl)-6-phthalazinyl)benzamide;
N-cyclopropyl-4-methyl-5-(1-morpholinophthalazin-6-yl)thiophene-2-carboxamide;
N-(2-methoxy-5-(trifluoromethyl)phenyl)-4-methyl-3-(1-morpholinophthalazin-6-yl)benzamide;

3-(1-(2-chlorophenyl)phthalazin-6-yl)-N-cyclopropyl-4-methylbenzamide;

N-cyclopropyl-3-(1-((1S,4S)-5-isopropyl-2,5-diaza-bicyclo[2.2.1]heptan-2-yl)phthalazin-6-yl)-4-methylbenzamide;

3-(1-((1S,4S)-5-oxo-2-aza-bicyclo[2.2.1]heptan-2-yl)phthalazin-6-yl)-N-cyclopropyl-4-methylbenzamide;

1-(6-(5-(cyclopropylcarbamoyl)-2-methylphenyl)phthalazin-1-yl)piperidine-4-carboxamide;

N-cyclopropyl-4-methyl-3-(1-((4aR,8aS)-octahydroisoquinolin-2(1H)-yl)phthalazin-6-yl)benzamide;

N-cyclopropyl-4-methyl-3-(1-((4aR,8aR)-octahydroisoquinolin-2(1H)-yl)phthalazin-6-yl)benzamide;

N-cyclopropyl-4-methyl-3-(1-((4aS,8aS)-octahydroisoquinolin-2(1H)-yl)phthalazin-6-yl)benzamide;

N-cyclopropyl-4-methyl-3-(1-((4aS,8aR)-octahydroisoquinolin-2(1H)-yl)phthalazin-6-yl)benzamide;

N-cyclopropyl-4-methyl-3-(1-p-tolylphthalazin-6-yl)benzamide;

N-cyclopropyl-4-methyl-3-(1-o-tolylphthalazin-6-yl)benzamide;

6-(4-methylpyridin-3-yl)-1-morpholinophthalazine;

(3S)-1-(6-(5-(cyclopropylcarbamoyl)-2-methylphenyl)phthalazin-1-yl)piperidine-3-carboxamide;

(3R)-1-(6-(5-(cyclopropylcarbamoyl)-2-methylphenyl)phthalazin-1-yl)piperidine-3-carboxamide;

N-sec-butyl-4-chloro-3-(1-morpholinophthalazin-6-yl)benzamide;

N-cyclopropyl-4-methyl-3-(1-(3-oxopiperazin-1-yl)phthalazin-6-yl)benzamide;

4-methyl-3-(1-(3-oxopiperazin-1-yl)phthalazin-6-yl)benzamide; and

N-cyclopropyl-3-(1-mesitylphthalazin-6-yl)-4-methylbenzamide.

8. A pharmaceutical compositon comprising a pharmaceutically acceptable carrier and a compound according to claim 6.

9. A pharmaceutical compositon comprising a pharmaceutically acceptable carrier and a compound according to claim 7.

10. The compound of claim 1, or a pharmaceutically acceptable salt thereof, having a formula

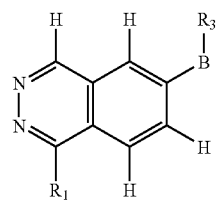

wherein,

B is O or NH;

$R^1$ is $NR^7R^7$, $NR^7R^8$, $OR^7$, $SR^7$, $OR^8$, $SR^8$ or a ring selected from phenyl, pyridyl, pyrimidyl, pyridazinyl, triazinyl, thienyl, furyl, pyrrolyl, pyrazolyl, imidazolyl, triazolyl, tetrazolyl, thiazolyl, oxazolyl, isoxazolyl, isothiazolyl, indolyl, isoindolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl and cycloheptyl, wherein said ring system is optionally substituted independently with 1-3 substituents of halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl;

$R^3$ is phenyl, naphthyl, pyridyl, pyrimidyl, triazinyl, quinolinyl, isoquinolinyl, quinazolinyl, isoquinazolinyl, thienyl, furyl, pyrrolyl, pyrazolyl, imidazolyl, triazolyl, thiazolyl, oxazolyl, isoxazolyl, isothiazolyl, indolyl, isoindolyl, benzofuranyl, dihydrobenzofuranyl, benzothienyl, benzisoxazolyl, benzisothiazolyl, benzopyrazolyl, benzothiazolyl or benzimidazolyl, each of which is optionally substituted independently with 1-3 substituents of halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl;

each $R^7$, independently, is H, $C_{1-10}$-alkyl, $C_{2-10}$-alkenyl, $C_{2-10}$-alkenyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^8$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a ring selected from phenyl, naphthyl, pyridyl, pyrimidyl, triazinyl, quinolinyl, isoquinolinyl, quinazolinyl, isoquinazolinyl, thienyl, furyl, pyrrolyl, imidazolyl, triazolyl, thiazolyl, oxazolyl, isoxazolyl, isothiazolyl, indolyl, isoindolyl, benzofuranyl, benzothienyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, benzodioxolyl, cyclopropyl, cyclobutyl, cyclopentyl, cyclohexyl and cycloheptyl, each of which is optionally substituted independently with 1-3 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-3 substituents of $R^9$; and $R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

11. A compound, or a pharmaceutically acceptable salt thereof, selected from:

N-cyclopropyl-4-methyl-3-{1-[(2R)-2-methylpiperazin-1-yl]phthalazin-6-yl}benzamide;
N-cyclopropyl-4-methyl-3-{1-[(2-morpholin-4-ylethyl)amino]phthalazin-6-yl}benzamide;
N-cyclopropyl-3-{1-[(2R,5S)-2,5-dimethylmorpholin-4-yl]phthalazin-6-yl}-4-methylbenzamide;
N-cyclopropyl-3-(1-mesitylphthalazin-6-yl)-4-methylbenzamide;
N-cyclopropyl-3-{1-[(2S,5S)-2,5-dimethylmorpholin-4-yl]phthalazin-6-yl}-4-methylbenzamide;
N-cyclopropyl-3-{1-[(2R)-2-ethylpiperidin-1-yl]phthalazin-6-yl}-4-methylbenzamide;
N-cyclopropyl-4-methyl-3-[1-(4-methylphenyl)phthalazin-6-yl]benzamide;
N-cyclopropyl-4-methyl-3-(1-thiomorpholin-4-ylphthalazin-6-yl)benzamide;
N-cyclopropyl-5-{1-[(2R,5R)-2,5-dimethylmorpholin-4-yl]phthalazin-6-yl}-2-fluoro-4-methylbenzamide;
N-cyclopropyl-4-methyl-3-{1-[(3R)-3-methylpiperazin-1-yl]phthalazin-6-yl}benzamide;
N-cyclopropyl-3-{1-[(2R,6S)-2,6-dimethylmorpholin-4-yl]phthalazin-6-yl}-4-methylbenzamide;
N-cyclopropyl-3-{1-[(2S,5R)-2,5-dimethylpiperazin-1-yl]phthalazin-6-yl}-4-methylbenzamide;
N-cyclopropyl-3-{1-[(3R,5S)-3,5-dimethylpiperazin-1-yl]phthalazin-6-yl}-4-methylbenzamide;
N-cyclopropyl-4-methyl-3-{1-[(3S)-3-methylpiperazin-1-yl]phthalazin-6-yl}benzamide;
N-cyclopropyl-4-methyl-3-[1-(1-methylpiperidin-4-yl)phthalazin-6-yl]benzamide;
N-cyclopropyl-3-{1-[(2S)-2-(hydroxymethyl)pyrrolidin-1-yl]phthalazin-6-yl}-4-methylbenzamide;
N-cyclopropyl-3-[1-(4-hydroxy-4-methylpiperidin-1-yl)phthalazin-6-yl]-4-methylbenzamide;
3-(1-isopropoxyphthalazin-6-yl)-4-methylbenzamide;
3-[1-(2-chlorophenyl)phthalazin-6-yl]-4-methylbenzamide;
3-[1-(4-acetylpiperazin-1-yl)phthalazin-6-yl]-N-cyclopropyl-4-methylbenzamide;
3-[1-(cyclohexylamino)phthalazin-6-yl]-N-cyclopropyl-4-methylbenzamide;
N-cyclopropyl-4-methyl-3-(1-piperidin-1-ylphthalazin-6-yl)benzamide;
N-cyclopropyl-3-{1-[(2R)-2-(hydroxymethyl)morpholin-4-yl]phthalazin-6-yl}-4-methylbenzamide;
N-cyclopropyl-3-{1-[4-(2,6-dimethylphenyl)piperazin-1-yl]phthalazin-6-yl}-4-methylbenzamide;
N-cyclopropyl-4-methyl-3-[1-(3-oxopiperazin-1-yl)phthalazin-6-yl]benzamide;
N-cyclopropyl-4-methyl-3-(1-piperazin-1-ylphthalazin-6-yl)benzamide;
N-cyclopropyl-3-{1-[(3R)-3-hydroxypyrrolidin-1-yl]phthalazin-6-yl}-4-methylbenzamide;
N-cyclopropyl-3-[1-(1,4-dioxa-8-azaspiro[4.5]dec-8-yl)phthalazin-6-yl]-4-methylbenzamide;
N-cyclopropyl-3-(1-isopropoxyphthalazin-6-yl)-4-methylbenzamide;
N-cyclopropyl-3-(1-methoxyphthalazin-6-yl)-4-methylbenzamide;
3-{1-[(2R,5R)-2,5-dimethylmorpholin-4-yl]phthalazin-6-yl}-4-methylbenzamide;
N-cyclopropyl-3-[1-(isopropylamino)phthalazin-6-yl]-4-methylbenzamide;
N-cyclopropyl-3-{1-[(2S,5R)-2,5-dimethylmorpholin-4-yl]phthalazin-6-yl}-4-methylbenzamide;
N-cyclopropyl-3-{1-[(2R,5R)-2,5-dimethylmorpholin-4-yl]phthalazin-6-yl}-4-methylbenzamide;
4-methyl-3-(1-morpholin-4-ylphthalazin-6-yl)benzamide;
4-fluoro-3-(1-morpholin-4-ylphthalazin-6-yl)benzamide;
N-cyclopropyl-4-methyl-3-{1-[(3S)-3-methylmorpholin-4-yl]phthalazin-6-yl}benzamide;
N-cyclopropyl-4-methyl-3-{1-[(2R)-2-methylpiperidin-1-yl]phthalazin-6-yl}benzamide;
4-methyl-3-{1-[(2R)-2-methylpiperidin-1-yl]phthalazin-6-yl}benzamide;
N-cyclopropyl-3-(1-{[2-(dimethylamino)ethyl]amino}phthalazin-6-yl)-4-methylbenzamide;
4-methyl-3-{1-[(3S)-3-methylmorpholin-4-yl]phthalazin-6-yl}benzamide;
3-(1-{[(1R)-2-hydroxy-1-methylethyl]amino}phthalazin-6-yl)-4-methylbenzamide;
N-cyclopropyl-3-(1-{[2-(diethylamino)ethyl]amino}phthalazin-6-yl)-4-methylbenzamide;
N-cyclopropyl-3-[1-(dimethylamino)phthalazin-6-yl]-4-methylbenzamide;
N-cyclopropyl-3-{1-[(2-methoxyethyl)(methyl)amino]phthalazin-6-yl}-4-methylbenzamide;
3-{1-[(2-methoxyethyl)amino]phthalazin-6-yl}-4-methylbenzamide;
3-(1-{[(1S)-2-methoxy-1-methylethyl]amino}phthalazin-6-yl)-4-methylbenzamide;
N-cyclopropyl-3-(1-{[(1S)-2-methoxy-1-methylethyl]amino}phthalazin-6-yl)-4-methylbenzamide;
N-cyclopropyl-4-methyl-3-(1-{[(1R)-1-phenylethyl]amino}phthalazin-6-yl)benzamide;
N-cyclopropyl-3-{1-[(2-methoxyethyl)amino]phthalazin-6-yl}-4-methylbenzamide;
N-cyclopropyl-3-{1-[2-(dimethylamino)-4-methoxypyrimidin-5-yl]phthalazin-6-yl}-4-methylbenzamide;
3-{1-[2,4-bis(trifluoromethyl)phenyl]phthalazin-6-yl}-N-cyclopropyl-4-methylbenzamide;
N-cyclopropyl-3-[1-(2-methoxy-3-methylphenyl)phthalazin-6-yl]-4-methylbenzamide;
3-[1-(4-methoxy-2-methylphenyl)phthalazin-6-yl]-4-methylbenzamide;
4-methyl-3-{1-[4-(morpholin-4-ylmethyl)phenyl]phthalazin-6-yl}benzamide;
3-[1-(2-methoxy-3-methylphenyl)phthalazin-6-yl]-4-methylbenzamide;
N-cyclopropyl-3-{1-[2-methoxy-6-(methylamino)pyridin-3-yl]phthalazin-6-yl}-4-methylbenzamide;
N-cyclopropyl-3-[1-(6-methoxy-2-methylpyridin-3-yl)phthalazin-6-yl]-4-methylbenzamide;
3-[1-(4-chlorophenyl)phthalazin-6-yl]-N-cyclopropyl-4-methylbenzamide;
3-{1-[4-chloro-2-(trifluoromethyl)phenyl]phthalazin-6-yl}-N-cyclopropyl-4-methylbenzamide;
3-[1-(2-chloro-6-methylpyridin-3-yl)phthalazin-6-yl]-N-cyclopropyl-4-methylbenzamide;
3-{1-[4-(aminosulfonyl)-2-methylphenyl]phthalazin-6-yl}-N-cyclopropyl-4-methylbenzamide;
3-{1-[2-chloro-4-(trifluoromethyl)phenyl]phthalazin-6-yl}-N-cyclopropyl-4-methylbenzamide;
3-[1-(4-chloro-2-methoxyphenyl)phthalazin-6-yl]-N-cyclopropyl-4-methylbenzamide;
3-[1-(4-isopropoxy-2-methylphenyl)phthalazin-6-yl]-4-methylbenzamide;
N-cyclopropyl-3-[1-(2-methoxypyridin-3-yl)phthalazin-6-yl]-4-methylbenzamide;
3-[1-(2-chloropyridin-3-yl)phthalazin-6-yl]-N-cyclopropyl-4-methylbenzamide;

N-cyclopropyl-3-[1-(2,4-dimethoxypyrimidin-5-yl)phthalazin-6-yl]-4-methylbenzamide;
3-[1-(2-chloro-4-methylphenyl)phthalazin-6-yl]-N-cyclopropyl-4-methylbenzamide;
3-{1-[4-(aminosulfonyl)-2-methylphenyl]phthalazin-6-yl}-4-methylbenzamide;
3-{1-[4-methoxy-2-(trifluoromethyl)phenyl]phthalazin-6-yl}-4-methylbenzamide;
N-cyclopropyl-3-[1-(4-fluorophenyl)phthalazin-6-yl]-4-methylbenzamide;
N-cyclopropyl-4-methyl-3-[1-(2-methylpyridin-3-yl)phthalazin-6-yl]benzamide;
N-cyclopropyl-3-[1-(4-methoxy-2-methylphenyl)phthalazin-6-yl]-4-methylbenzamide;
N-cyclopropyl-4-methyl-3-(1-thien-2-ylphthalazin-6-yl)benzamide;
N-cyclopropyl-4-methyl-3-{1-[4-(trifluoromethoxy)phenyl]phthalazin-6-yl}benzamide;
N-cyclopropyl-3-[1-(2-fluorophenyl)phthalazin-6-yl]-4-methylbenzamide;
N,6-dimethyl-7-[1-(2-methylpyridin-3-yl)phthalazin-6-yl]-1,2-benzisoxazol-3-amine;
N-cyclopropyl-3-[1-(3-fluoro-2-methoxyphenyl)phthalazin-6-yl]-4-methylbenzamide;
N-cyclopropyl-4-methyl-3-{1-[4-(trifluoromethyl)phenyl]phthalazin-6-yl}benzamide;
N-cyclopropyl-4-methyl-3-(1-phenylphthalazin-6-yl)benzamide;
N-cyclopropyl-3-[1-(2-ethylphenyl)phthalazin-6-yl]-4-methylbenzamide;
3-[1-(2-methoxy-5-methylpyridin-4-yl)phthalazin-6-yl]-4-methylbenzamide;
3-[1-(4-tert-butylphenyl)phthalazin-6-yl]-N-cyclopropyl-4-methylbenzamide;
N-cyclopropyl-4-methyl-3-{1-[2-(trifluoromethyl)phenyl]phthalazin-6-yl}benzamide;
4-methyl-3-[1-(2-methylpyridin-3-yl)phthalazin-6-yl]benzamide;
N-cyclopropyl-4-methyl-3-{1-[2-methyl-4-(methylsulfonyl)phenyl]phthalazin-6-yl}benzamide;
3-[1-(4-chloro-2-methylphenyl)phthalazin-6-yl]-N-cyclopropyl-4-methylbenzamide;
N-cyclopropyl-3-{1-[4-methoxy-2-(trifluoromethyl)phenyl]phthalazin-6-yl}-4-methylbenzamide;
N-cyclopropyl-4-methyl-3-{1-[2-methyl-4-(methylsulfanyl)phenyl]phthalazin-6-yl}benzamide;
N-cyclopropyl-3-[1-(4-fluoro-2-methoxyphenyl)phthalazin-6-yl]-4-methylbenzamide;
N-cyclopropyl-4-methyl-3-[1-(3-methylpyridin-4-yl)phthalazin-6-yl]benzamide;
N-cyclopropyl-3-[1-(2-methoxypyrimidin-5-yl)phthalazin-6-yl]-4-methylbenzamide;
N-cyclopropyl-4-methyl-3-{1-[(2R)-2-methyl-3-oxopiperazin-1-yl]phthalazin-6-yl}benzamide;
N-cyclopropyl-4-methyl-3-{1-[(2S)-2-methyl-3-oxopiperazin-1-yl]phthalazin-6-yl}benzamide;
N-cyclopropyl-4-methyl-3-{1-[(2S)-2-(trifluoromethyl)pyrrolidin-1-yl]phthalazin-6-yl}benzamide;
N-cyclopropyl-4-methyl-3-[1-(5-oxo-1,4-diazepan-1-yl)phthalazin-6-yl]benzamide;
N-cyclopropyl-4-methyl-3-(8-morpholin-4-ylpyrido[2,3-d]pyridazin-3-yl)benzamide;
N-cyclobutyl-3-[1-(dimethylamino)phthalazin-6-yl]-4-methylbenzamide;
N-cyclopropyl-3-[1-(4-fluoro-2-methylphenyl)phthalazin-6-yl]-4-methylbenzamide;
N-cyclopropyl-4-methyl-3-[1-(4-methyl-6-oxo-1,6-dihydropyridin-3-yl)phthalazin-6-yl]benzamide;
3-{1-[cyclohexyl(methyl)amino]phthalazin-6-yl}-N-cyclopropyl-4-methylbenzamide;
N-cyclopropyl-3-{1-[isopropyl(methyl)amino]phthalazin-6-yl}-4-methylbenzamide;
3-{1-[cyclohexyl(methyl)amino]phthalazin-6-yl}-4-methylbenzamide;
3-{1-[isopropyl(methyl)amino]phthalazin-6-yl}-4-methylbenzamide;
N-cyclopropyl-3-{1-[(2S)-2-isopropylpyrrolidin-1-yl]phthalazin-6-yl}-4-methylbenzamide;
N-cyclopropyl-4-methyl-3-{1-[(2S)-2-methylpyrrolidin-1-yl]phthalazin-6-yl}benzamide;
N-cyclopropyl-4-methyl-3-{1-[(2R)-2-methylpyrrolidin-1-yl]phthalazin-6-yl}benzamide;
N-cyclopropyl-4-methyl-3-(1-{[(2R)-tetrahydrofuran-2-ylmethyl]amino}phthalazin-6-yl)benzamide;
N-cyclopropyl-4-methyl-3-(1-{[(1S)-1-methylpropyl]amino}phthalazin-6-yl)benzamide;
4-methyl-3-[1-(2-methylphenoxy)phthalazin-6-yl]benzamide;
4-methyl-3-{1-[(2-methylpyridin-3-yl)oxy]phthalazin-6-yl}benzamide;
3-[1-(4-fluorophenoxy)phthalazin-6-yl]-4-methylbenzamide;
N-cyclopropyl-4-methyl-3-(1-{[(1S)-1-methylpropyl]oxy}phthalazin-6-yl)benzamide;
4-methyl-3-(1-{[(1S)-1-methylpropyl]amino}phthalazin-6-yl)benzamide;
N-cyclopropyl-3-[1-(4-fluoro-2-methylphenoxy)phthalazin-6-yl]-4-methylbenzamide;
N-cyclopropyl-4-methyl-3-{1-[(2-methylpyridin-3-yl)oxy]phthalazin-6-yl}benzamide;
N-cyclopropyl-4-methyl-3-(1-{[(2S)-tetrahydrofuran-2-ylmethyl]amino}phthalazin-6-yl)benzamide;
N-cyclopropyl-4-methyl-3-(1-{[3-(2-oxopyrrolidin-1-yl)propyl]amino}phthalazin-6-yl)benzamide;
N-cyclopropyl-3-{1-[(4-hydroxycyclohexyl)amino]phthalazin-6-yl}-4-methylbenzamide;
N-cyclopropyl-3-(1-{[(1S)-2-methoxy-1-methylethyl]amino}phthalazin-6-yl)-4-methylbenzamide;
N-cyclopropyl-4-methyl-3-(1-{[(1R)-1-methylpropyl]amino}phthalazin-6-yl)benzamide;
N-cyclopropyl-4-methyl-3-{1-[(1-methylpiperidin-3-yl)oxy]phthalazin-6-yl}benzamide;
N-cyclopropyl-6-methyl-7-[1-(2-methylphenoxy)phthalazin-6-yl]-1,2-benzisoxazol-3-amine;
N-cyclopropyl-4-methyl-3-{1-[(1-methylpiperidin-4-yl))oxy]phthalazin-6-yl}benzamide;
3-[1-(cyclopentylamino)phthalazin-6-yl]-N-cyclopropyl-4-methylbenzamide;
N-cyclopropyl-4-methyl-3-[1-(neopentyloxy)phthalazin-6-yl]benzamide;
3-[1-(tert-butylamino)phthalazin-6-yl]-N-cyclopropyl-4-methylbenzamide;
N-cyclopropyl-4-methyl-3-(1-{[(1R)-1-methylpropyl]oxy}phthalazin-6-yl)benzamide;
N-cyclopropyl-4-methyl-3-[1-(tetrahydro-2H-pyran-4-ylamino)phthalazin-6-yl]benzamide;
N,6-dimethyl-7-(1-(((1S)-1-methyl-2-(methyloxy)ethyl)oxy)-6-phthalazinyl)-1,2-benzisoxazol-3-amine;
N,6-dimethyl-7-(1-((1-methylethyl)oxy)-6-phthalazinyl)-1,2-benzisoxazol-3-amine;
6-(4-fluorophenoxy)-1-[4-(morpholin-4-ylmethyl)phenyl]phthalazine;

N-cyclopropyl-2-{[1-(2-methylphenyl)phthalazin-6-yl]oxy}benzamide;
N-cyclopropyl-3-{[1-(2-methylphenyl)phthalazin-6-yl]oxy}benzamide;
3-[1-(isopropylamino)phthalazin-6-yl]-4-methylbenzenesulfonamide;
3-[1-(isopropylamino)phthalazin-6-yl]—N,4-dimethylbenzenesulfonamide;
N-cyclopropyl-3-[1-(isopropylamino)phthalazin-6-yl]-4-methylbenzenesulfonamide;
N-cyclopropyl-4-methyl-3-(1-morpholin-4-ylphthalazin-6-yl)benzenesulfonamide;
N-ethyl-3-(1-isopropylphthalazin-6-yl)-4-methylbenzamide;
N-cyclopropyl-4-methyl-3-{1-[(1-pyridin-2-ylethyl)amino]phthalazin-6-yl}benzamide;
3-{1-[(2S)-4-acetyl-2-methylpiperazin-1-yl]phthalazin-6-yl}-N-cyclopropyl-4-methylbenzamide;
N-cyclopropyl-3-{1-[(2R,5S)-2,5-dimethyl-4-(2,2,2-trifluoroethyl)piperazin-1-yl]phthalazin-6-yl}-4-methylbenzamide;
4-methyl-N-(5-methylisoxazol-3-yl)-3-(1-morpholin-4-ylphthalazin-6-yl)benzamide;
N-(tert-butyl)-6-methyl-7-{1-[(3S)-3-methylmorpholin-4-yl]phthalazin-6-yl}-1,2-benzisoxazol-3-amine;
N-cyclopropyl-3-{1-[(2R,5S)-2,5-dimethyl-4-(2,2,2-trifluoroethyl)piperazin-1-yl]phthalazin-6-yl}-4-methylbenzamide;
N-cyclopropyl-3-{1-[(2S,5R)-2,5-dimethyl-4-(2,2,2-trifluoroethyl)piperazin-1-yl]phthalazin-6-yl}-4-methylbenzamide;
N-cyclopropyl-3-{1-[(2R,5R)-2,5-dimethylpyrrolidin-1-yl]phthalazin-6-yl}-4-methylbenzamide;
N-[(1S)-2-methoxy-1-methylethyl]-6-[6-methyl-3-(methylamino)-1,2-benzisoxazol-7-yl]phthalazin-1-amine;
N-isopropyl-3-[1-(isopropylamino)phthalazin-6-yl]-4-methylbenzamide;
N-isopropyl-4-methyl-3-(1-morpholin-4-ylphthalazin-6-yl)benzamide;
N-cyclopropyl-4-methyl-3-(1-((2-(4-morpholinyl)ethyl)amino)-6-phthalazinyl)benzamide;
N-cyclopropyl-4-methyl-3-(1-(4-morpholinyl)-6-phthalazinyl)benzamide;
N-cyclopropyl-4-methyl-3-(1-morpholinophthalazin-6-yl)benzamide;
N-cyclopropyl-3-(1-((2-(diethylamino)ethyl)amino)-6-phthalazinyl)-4-methylbenzamide;
3-(1-(cyclohexylamino)-6-phthalazinyl)-N-cyclopropyl-4-methylbenzamide;
N-cyclopropyl-4-methyl-3-(1-(1-piperazinyl)-6-phthalazinyl)benzamide;
N-cyclopropyl-3-(1-((S)-3-hydroxypyrrolidin-1-yl)phthalazin-6-yl)-4-methylbenzamide;
N-cyclopropyl-3-(1-((R)-3-hydroxypyrrolidin-1-yl)phthalazin-6-yl)-4-methylbenzamide;
N-cyclopropyl-4-methyl-3-(1-(4-methyl-1-piperazinyl)-6-phthalazinyl)benzamide;
N-cyclopropyl-4-methyl-3-(1-(piperidin-1-yl)phthalazin-6-yl)benzamide;
4-methyl-3-(1-morpholinophthalazin-6-yl)benzamide;
N,4-dimethyl-3-(1-(4-morpholinyl)-6-phthalazinyl)benzamide;
N-ethyl-4-methyl-3-(1-(4-morpholinyl)-6-phthalazinyl)benzamide;
N-cyclopropyl-4-methyl-3-(1-(1-methyl-4-piperidinyl)-6-phthalazinyl)benzamide;
N-(2-methoxy-5-(trifluoromethyl)phenyl)-4-methyl-3-(1-morpholinophthalazin-6-yl)benzamide;
3-(1-(2-chlorophenyl)phthalazin-6-yl)-N-cyclopropyl-4-methylbenzamide;
N-cyclopropyl-3-(1-((1S,4S)-5-isopropyl-2,5-diaza-bicyclo[2.2.1]heptan-2-yl)phthalazin-6-yl)-4-methylbenzamide;
N-cyclopropyl-4-methyl-3-(1-p-tolylphthalazin-6-yl)benzamide;
N-cyclopropyl-4-methyl-3-(1-o-tolylphthalazin-6-yl)benzamide;
N-cyclopropyl-4-methyl-3-(1-(3-oxopiperazin-1-yl)phthalazin-6-yl)benzamide; and
N-cyclopropyl-3-(1-mesitylphthalazin-6-yl)-4-methylbenzamide.

12. A pharmaceutical composition comprising a pharmaceutically acceptable carrier and a compound according to claim 11.

13. The compound, N-cyclopropyl-4-methyl-3-(1-morpholinophthalazin-6-yl)benzamide, or a pharmaceutically acceptable salt thereof.

14. A pharmaceutical compositon comprising a pharmaceutically acceptable carrier and a compound according to claim 13.

* * * * *